(12) United States Patent
Chen et al.

(10) Patent No.: US 10,722,484 B2
(45) Date of Patent: Jul. 28, 2020

(54) METHODS OF CANCER TREATMENT

(71) Applicant: K-Gen, Inc., Burlingame, CA (US)

(72) Inventors: Ruihong Chen, Burlingame, CA (US); Chun Jiang, Hillsborough, CA (US)

(73) Assignee: K-Gen, Inc., Burlingame, CA (US)

( * ) Notice: Subject to any disclaimer, the term of this patent is extended or adjusted under 35 U.S.C. 154(b) by 0 days.

(21) Appl. No.: 16/083,806

(22) PCT Filed: Mar. 9, 2017

(86) PCT No.: PCT/US2017/021695
§ 371 (c)(1),
(2) Date: Sep. 10, 2018

(87) PCT Pub. No.: WO2017/156350
PCT Pub. Date: Sep. 14, 2017

(65) Prior Publication Data
US 2019/0298679 A1    Oct. 3, 2019

Related U.S. Application Data

(60) Provisional application No. 62/306,030, filed on Mar. 9, 2016.

(51) Int. Cl.
| | |
|---|---|
| *A61K 31/22* | (2006.01) |
| *A61K 31/225* | (2006.01) |
| *A61K 31/23* | (2006.01) |
| *A61K 31/285* | (2006.01) |
| *A61K 31/19* | (2006.01) |
| *A61P 35/00* | (2006.01) |
| *A61K 33/243* | (2019.01) |
| *A61K 31/122* | (2006.01) |
| *A61K 31/282* | (2006.01) |
| *A61K 31/336* | (2006.01) |
| *A61K 31/365* | (2006.01) |
| *A61K 31/436* | (2006.01) |
| *A61K 31/4375* | (2006.01) |
| *A61K 31/4402* | (2006.01) |
| *A61K 31/502* | (2006.01) |
| *A61K 31/519* | (2006.01) |
| *A61K 31/52* | (2006.01) |
| *A61K 31/551* | (2006.01) |
| *A61K 45/06* | (2006.01) |
| *A61K 31/337* | (2006.01) |

(52) U.S. Cl.
CPC ............ *A61K 31/22* (2013.01); *A61K 31/122* (2013.01); *A61K 31/282* (2013.01); *A61K 31/336* (2013.01); *A61K 31/337* (2013.01); *A61K 31/365* (2013.01); *A61K 31/436* (2013.01); *A61K 31/4375* (2013.01); *A61K 31/4402* (2013.01); *A61K 31/502* (2013.01); *A61K 31/519* (2013.01); *A61K 31/52* (2013.01); *A61K 31/551* (2013.01); *A61K 33/243* (2019.01); *A61K 45/06* (2013.01); *A61P 35/00* (2018.01)

(58) Field of Classification Search
CPC ...... A61K 31/22; A61K 31/225; A61K 31/23; A61K 31/385
USPC ........ 514/546, 547, 549, 550, 551, 557, 561
See application file for complete search history.

(56) References Cited

U.S. PATENT DOCUMENTS

| | | | |
|---|---|---|---|
| 4,716,179 A | 12/1987 | Hecker | |
| 5,145,842 A * | 9/1992 | Driedger | ................. C07C 69/00 514/63 |
| 5,716,968 A * | 2/1998 | Driedger | ................. C07C 69/00 514/323 |
| 5,756,510 A | 5/1998 | Griffin | |
| 5,869,485 A | 2/1999 | Missbach | |
| 5,886,017 A * | 3/1999 | Driedger | .............. C07D 209/08 514/410 |
| 6,054,470 A | 4/2000 | Betageri | |
| 6,268,395 B1 | 7/2001 | Hattori | |
| 6,337,335 B1 | 1/2002 | Hutchings | |
| 6,432,452 B1 | 8/2002 | Aylward | |
| 6,495,541 B1 | 12/2002 | Webber | |
| 6,506,769 B2 | 1/2003 | Snow | |
| 6,509,365 B1 | 1/2003 | Lubisch | |
| 6,596,746 B1 | 7/2003 | Das | |
| 6,608,053 B2 | 8/2003 | Hayakawa | |
| 6,689,778 B2 | 2/2004 | Bemis | |
| 6,903,098 B1 | 6/2005 | Lubisch | |
| 7,091,345 B2 | 8/2006 | Cai | |
| 7,122,679 B2 | 10/2006 | Ator | |
| 7,153,856 B2 | 12/2006 | Barrish | |
| 7,163,941 B2 | 1/2007 | Honold | |
| 7,268,138 B2 | 9/2007 | Kalish | |
| 7,285,556 B2 | 10/2007 | Benish | |
| 7,351,701 B2 | 4/2008 | Helleday | |
| 7,381,730 B2 | 6/2008 | Gungor | |

(Continued)

FOREIGN PATENT DOCUMENTS

| | | |
|---|---|---|
| WO | WO 2007/076704 A1 | 7/2007 |
| WO | WO 2010/101849 A1 | 9/2010 |

(Continued)

OTHER PUBLICATIONS

US 8,450,329 B2, 05/2013, Ren (withdrawn)

(Continued)

*Primary Examiner* — Raymond J Henley, III

(74) *Attorney, Agent, or Firm* — Dechert LLP

(57) ABSTRACT

This present disclosure is directed to a method of treating a subject with cancer with a combination of a protein kinase C (PKC) activator and a second therapeutic agent.

27 Claims, 56 Drawing Sheets

(56) References Cited

U.S. PATENT DOCUMENTS

| | | |
|---|---|---|
| 7,417,148 B2 | 8/2008 | Boschelli |
| 7,449,464 B2 | 11/2008 | Martin |
| 7,462,623 B2 | 12/2008 | Ple |
| 7,491,725 B2 | 2/2009 | Lajeunesse |
| 7,494,997 B2 | 2/2009 | Asaki |
| 7,528,142 B2 | 5/2009 | Binch |
| 7,534,797 B2 | 5/2009 | Arnold |
| 7,576,209 B2 | 8/2009 | Kelly, III |
| 7,652,014 B2 | 1/2010 | Mabire |
| 7,691,888 B2 | 4/2010 | Betzemeier |
| 7,692,006 B2 | 4/2010 | Menear |
| 7,700,594 B2 | 4/2010 | Chen |
| 7,728,131 B2 | 6/2010 | Asaki |
| 7,781,596 B1 | 8/2010 | Lubisch |
| 7,803,795 B2 | 9/2010 | Mevellec |
| 7,812,164 B2 | 10/2010 | Austad |
| 7,875,621 B2 | 1/2011 | Van Der |
| 7,879,857 B2 | 2/2011 | Mabire |
| 7,888,344 B2 | 2/2011 | Alexander |
| 7,910,598 B2 | 3/2011 | Kompella |
| 7,928,104 B2 | 4/2011 | Mabire |
| 7,998,977 B2 | 8/2011 | Joseph |
| 8,003,651 B2 | 8/2011 | Mitchell |
| 8,022,103 B2 | 9/2011 | Xu |
| 8,053,574 B2 | 11/2011 | Bruce |
| 8,067,632 B2 | 11/2011 | Wender |
| 8,071,623 B2 | 12/2011 | Jones |
| 8,080,557 B2 | 12/2011 | Kennis |
| 8,097,622 B2 | 1/2012 | Nakayama |
| 8,101,622 B2 | 1/2012 | Baik |
| 8,106,092 B2 | 1/2012 | Ogbourne |
| 8,110,578 B2 | 2/2012 | Perrin-Ninkovic |
| 8,114,874 B2 | 2/2012 | Zou |
| 8,119,649 B2 | 2/2012 | Donato |
| 8,242,116 B2 | 8/2012 | Alexander |
| 8,273,782 B2 | 9/2012 | Seefeld |
| 8,299,090 B2 | 10/2012 | Pellicciari |
| 8,329,701 B2 | 12/2012 | Mitchell |
| 8,377,937 B2 | 2/2013 | Bencsik |
| 8,431,612 B2 | 4/2013 | Xu |
| 8,440,829 B2 | 5/2013 | Barda |
| 8,486,936 B2 | 7/2013 | Khvat |
| 8,536,378 B2 | 9/2013 | Wender |
| 8,546,399 B2 | 10/2013 | Bruncko |
| 8,557,814 B2 | 10/2013 | Castelhano |
| 8,580,815 B2 | 11/2013 | Yasri |
| 8,618,097 B2 | 12/2013 | Bencsik |
| 8,658,659 B2 | 2/2014 | Grierson |
| 8,722,661 B2 | 5/2014 | Haynes |
| 8,778,927 B2 | 7/2014 | Dorsch |
| 8,791,131 B2 | 7/2014 | Cheng |
| 8,802,866 B2 | 8/2014 | Emde |
| 8,816,122 B2 | 8/2014 | Wender |
| 8,822,524 B2 | 9/2014 | Sebti |
| 8,841,299 B2 | 9/2014 | Hermann |
| 8,853,216 B2 | 10/2014 | Bencsik |
| 8,895,559 B2 | 11/2014 | Klein |
| 8,895,744 B2 | 11/2014 | Gambacorti Passerini |
| 8,901,356 B2 | 12/2014 | Högberg |
| 8,921,336 B2 | 12/2014 | Gray |
| 8,921,361 B2 | 12/2014 | Cmiljanovic |
| 8,940,752 B2 | 1/2015 | Li |
| 9,062,061 B2 | 6/2015 | Honda |
| 9,102,687 B2 | 8/2015 | Grue-Søtensen |
| 9,120,805 B2 | 9/2015 | Dorsch |
| 9,150,579 B2 | 10/2015 | Vakkalanka |
| 9,156,853 B2 | 10/2015 | Harrison |
| 9,163,003 B2 | 10/2015 | Chen |
| 9,174,949 B2 | 11/2015 | Vernier |
| 9,174,995 B2 | 11/2015 | Dorsch |
| 9,181,266 B2 | 11/2015 | Cheung |
| 9,227,982 B2 | 1/2016 | Cheung |
| 9,242,993 B2 | 1/2016 | Lynch |
| 9,255,106 B2 | 2/2016 | Zhang |
| 9,255,107 B2 | 2/2016 | Wang |
| 9,273,052 B2 | 3/2016 | Tang |
| 9,284,334 B2 | 3/2016 | Pastor Fernández |
| 9,290,460 B2 | 3/2016 | Cai |
| 9,303,040 B2 | 4/2016 | Mitchell |
| 9,315,491 B2 | 4/2016 | Kuo |
| 9,339,503 B2 | 5/2016 | Buchstaller |
| 9,340,549 B2 | 5/2016 | Bregman |
| 9,376,433 B2 | 6/2016 | Dorsch |
| 9,388,142 B2 | 7/2016 | Dorsch |
| 9,416,133 B2 | 8/2016 | Staehle |
| 9,475,812 B2 | 10/2016 | Wu |
| 9,505,749 B2 | 11/2016 | Bregman |
| 9,522,881 B2 | 12/2016 | Zhang |
| 9,556,203 B2 | 1/2017 | Cmiljanovic |
| 9,579,319 B2 | 2/2017 | Armer |
| 2003/0207873 A1 | 11/2003 | Harrington |
| 2008/0069809 A1 | 3/2008 | Ogbourne |
| 2009/0187046 A1 | 7/2009 | Wender |
| 2010/0068204 A1 | 3/2010 | Tsou |
| 2010/0092536 A1* | 4/2010 | Hunter .................. A61K 38/17  424/423 |
| 2010/0099710 A1 | 4/2010 | Jensen |
| 2010/0204318 A1 | 8/2010 | Ogbourne |
| 2011/0014699 A1 | 1/2011 | Wender |
| 2011/0112110 A1 | 5/2011 | Gambacorti Passerini |
| 2011/0178070 A1 | 7/2011 | Gong |
| 2011/0224297 A1 | 9/2011 | Brown |
| 2012/0101283 A1 | 4/2012 | Wender |
| 2012/0309739 A1 | 12/2012 | Bell |
| 2013/0065908 A1 | 3/2013 | Mitchell |
| 2013/0090323 A1 | 4/2013 | Dransfield |
| 2013/0274233 A1 | 10/2013 | Wang |
| 2013/0324600 A1 | 12/2013 | Grue-Sørensen |
| 2013/0331446 A1 | 12/2013 | Grue-Sørensen |
| 2013/0345215 A1 | 12/2013 | Feng |
| 2014/0066431 A1 | 3/2014 | Rice |
| 2014/0080810 A1 | 3/2014 | Rice |
| 2014/0107100 A1 | 4/2014 | Rice |
| 2014/0121231 A1 | 5/2014 | Bolin |
| 2014/0371311 A1 | 12/2014 | Oh |
| 2015/0051217 A1 | 2/2015 | Bencsik |
| 2015/0051242 A1 | 2/2015 | Zhao |
| 2015/0175622 A1 | 6/2015 | Liang |
| 2015/0274751 A1 | 10/2015 | Kouji |
| 2015/0368274 A1 | 12/2015 | Shen |
| 2016/0090386 A1 | 3/2016 | Ho |
| 2016/0115177 A1 | 4/2016 | Lum |
| 2016/0244424 A1 | 8/2016 | Jean |

FOREIGN PATENT DOCUMENTS

| | | | |
|---|---|---|---|
| WO | WO 2011/014888 A1 | 2/2011 | |
| WO | WO 2013/052162 A1 | 4/2013 | |
| WO | WO 2013/177349 A1 | 11/2013 | |
| WO | WO 2013/182546 A1 | 12/2013 | |
| WO | WO 2013/182688 A1 | 12/2013 | |
| WO | WO 2014/045101 A1 | 3/2014 | |
| WO | WO 2014/066967 A1 | 5/2014 | |
| WO | WO 2014/087165 A1 | 6/2014 | |
| WO | WO 2014/206524 A1 | 12/2014 | |
| WO | WO2015/014442 A1 | 2/2015 | |
| WO | WO 2015/018475 A1 | 2/2015 | |
| WO | WO 2015/042029 A1 | 3/2015 | |
| WO | WO 2015/069512 A1 | 5/2015 | |
| WO | WO 2015/074135 A1 | 5/2015 | |
| WO | WO 2015/083008 A1 | 6/2015 | |
| WO | WO 2015/096884 A1 | 7/2015 | |
| WO | WO 2015/144021 A1 | 10/2015 | |
| WO | WO 2015/154630 A1 | 10/2015 | |
| WO | WO 2015/169421 A1 | 11/2015 | |
| WO | WO 2016/055786 A1 | 4/2016 | |
| WO | WO 2016/055790 A1 | 4/2016 | |
| WO | WO 2016/141312 A1 | 9/2016 | |
| WO | WO 2016/165205 A1 | 10/2016 | |
| WO | WO 2016/179066 A1 | 11/2016 | |

(56) References Cited

FOREIGN PATENT DOCUMENTS

WO    WO 2017/083783 A2    5/2017
WO    WO 2018/046933 A1    3/2018

OTHER PUBLICATIONS

Ali, et al., 2009 "Protein kinases C isozymes are differentially eypressed in human breast carcinomas," Life Sci 84(21-22):766-71.
Antal et al., 2015 "Cancer-Associated Protein Kinase C Mutations Reveal Kinase's Role as Tumor Suppressor," Cell 160:489-502.
Barcelo et al., 2014 "Phosphorylation at Ser-181 of Oncogenic KRAS Is Required for Tumor Growth," Cancer Res 74(4):1190-99.
Barton et al., 2013 "Prospects for treatment of latent HIV," Clin Pharmacol Ther 93(1):46-56.
Beans et al., 2013 Highly potent, synthetically accessible prostratin analogs induce latent HIV expression in vitro and ex vivo, Proc Natl Acad Sci USA 110(29):11698-703.
Benhadji et al.. 2008 "Antiproliferative activity of PEP005, a novel ingenol angelate that modulates PKC functions, alone and in combination with cytotoxic agents in human colon cancer cells," British Journal of Cancer. 99:1808-1815.
Boone et al., 2016 "Targeting the Wnt/β-catenin pathway in primary ovarian cancer with the porcupine inhibitor WNT974," Lab Invest 96(2):249-59.
Brooks et al., 1989 "Tumour-promoting and hyperplastic effects of phorbol and daphnane esters in CD-1 mouse skin and a synergistic effect of calcium ionophore with the non-promoting activator of protein kinase C, sapintoxin A," Carcinogenesis 10(2):283-88.
Clark, et al., 2003 "Altered protein kinase C (PKC) isoforms in non-small cell lung cancer cells: PKCdelta promotes cellular survival and chemotherapeutic resistance," Cancer Res 63(4):780-86.
Darcis et al., 2015 "An In-Depth Comparison of Latency-Reversing Agent Combinations in Various in Vitro and Ex Vivo HIV-1 Latency Models Identified Bryostatin-1+JQ1 and Ingenol-B+JQ1 to Potently Reactivate Viral Gene Expression," PloS Pathog 11(7):e1005063.
De Lichterveide et al., 2012 "Euphohelioscopin a is a PKC activator capable of inducing macrophage differentiation," Chem Biol 19(8):994-1000.
Duran-Pena et al., 2014 "Biologically active diterpenes containing a gem-dimethylcyclopropane subunit: an intriguing source of PKC modulators," The Royal Society of Chemistry, ESI for Nat Prod Rep S1-2-38.
Ethier et al., 2012 PARP-1 Modulation of mTOR Signaling in Response to a DNA Alkylating Agent, PloS One, 7(10):e47978 (17 pages).
Garczarczyk et al., 2010 "Protein kinase Cγin colon cancer cells: Expression, Thr$^{514}$ " phophorylation and sensitivity to butyrate-mediated upregulation as related to the degree of differentiation, Chem Biol Interact 185(1):25-32.
Han, et al., 2002 "Expression and function of classical protein kinase C isoenzymes in gastric cancer cell line and its drug-resistant sublines," World J Gastroenterol 8(3):441-45.
Dissanayake et al., 2008 "Detecting PKC phosphorylation as part of the Wnt/calcium pathway in cutaneous melanoma," Methods Mol Biol 468:157 (15 pages).
Ibrahim et al., 2012 "P13K Inhibition Impairs BRCA1/2 Expression and Sensitizes BRCA-Proficient Triple-Negative Breast Cancer to PARP Inhibition," Cancer Discovery 2:1036-1047.
Iori et al., 2003 "In situ protein Kinase C activity is increased in cultured fibroblasts from Type I diabetic patients with nephropathy," Diabetolgia 46(4):511-30.
Jiang et al., 2015 "Synergistic Reactivation of Latent HIV Expression by Ingenol-3-Angelate, PEP005, Targeted NF-kB Signaling in Combination with JQ1 Induced p-TETb Activation," PloS Pathog 11(7):e1005066 (17 pages).
Kawamura et al., 2016 "Nineteen-step total synthesis of (+)-phorbol," Nature 532:90-93.

Kazanietz et al., 1995 "Residues in the Second Cysteine-rich Region of Protein Kinase C δ Relevant to Phorbol Ester Binding as Revealed by Site-directed Mutagenesis," J Biol Chem 270(37):21852-59.
Kornev et al., 2006 "Surface comparison of active and inactive protein kinases identifies a conserved activation mechanism," Proc Natl Acad Sci USA 103(47): 17783-88.
Lau et al., 2013 "A novel tankyrase small-molecule inhibitor suppresses APC mutation-driven colorectal tumor growth," Cancer Res 73(10):3132-44.
Lu et al., 1997 "Tumor Promotion by Depleting Cells of Protein Kinase Cδ," Mol Cell Biol 17(6):3418-28.
Manzow, et al., 2000 "Evidence against a role of general protein kinase C downreguiation in skin tumor promotion," Int J Cancer 85(4): 503-07.
Margolis et al., 2013 "Combined approaches for HIV cure," Curr Opin HIV AIDS 8(3):230-35.
Miyata et al. 2015 "Mechanism of the inhibition of leukemia cell growth and induction of apoptosis through the activation of ATR and PTEN by the topoisomerase inhibitor 3EZ, 20Ac-ingenol," Leukemia Rsearch. 39, p. 927-932.
Mullin et al., 2000 "Increased Tight Junction Permeability Can Result from Protein Kinase C Activation/Translocation and Act as a Tumor Promotional Event in Epithelial Cancers," Adv Drug Deliv Rev; Annals of the New York Academy of Sciences 915(1):231-36.
Newton, 2010 "Protein kinase C: poised to signal," Am J Physiol Endocrinol Metab 298:E395-E402.
Nishikawa et al., 1997 "Determination of the Specific Substrate Sequence Motifs of Protein Kinase C Isozymes," J Biol Chem 272(2):952-60.
Okada-Iwaski et al., 2016 "The Discovery and Characterization of K-756, a Novel WNT/β-Catenin Pathway Inhibitor Targeting Tankyrase," Mol Cancer Ther 15(7):1525-34.
Porta et al., 2014 "Targeting PI3K/Akt/mTOR signaling in cancer," Front Oncol. 4(64):1-11.
Prior et al., 2012 "A comprehensive survey of Ras mutations in cancer," Cancer Res 72(10):2457-67.
Pusztai et al., 2007 "Macrocyclic Lathyrane Diterpenes as Antitumor Promoters," Anticancer Res 27(1A):201-06.
Raynauld, et al., 2007 "Pharmacologic Characterization of a Potent Inhibitor of Class I Phosphatidylinositide 3-Kinases," Cancer Res 67(12):5840-50.
Ruano et al., 1989 "Direct haplotyping of chromosomal segments from multiple heterozygotes via a allele-specific PCR amplificaiion," Nucleic Acids Res 17(20):8392.
Scarborough, et al., 2017 "AZ1366: An Inhibitor of Tankyrase and the Canonical Wnt Pathway that Limits the Persistence of Non-Small Cell Lung Cancer Cells Following EGFR Inhibition," Clin Cancer Res CCR-16-1179.
Serova et al, 2008 "Effects of protein kinase C modulation by PEP005, a novel ingenol angelate, on mitogen-activated protein kinase and phosphatidylinositol 3-kinase signaling in cancer cells," Molecular Cancer Therapeutics. 7:915-922.
Shen et al., 2015 "The protein kinase C agonist prostratin induces differentiation of human myeloid leukemia cells and enhances cellular differentiation by chemotherapeutic agents," Cancer Letters 356:686-696.
Steinberg, 2008 "Structural Basis of Protein Kinase C Isoform Function," Physiol Rev 88(4): 1341-78.
Thiel et al., 2005 "Expression of Cyclooxygenase-2 Is Regulated by Glycogen Synthase Kinase-3 beta 3 in Gastric Cancer Cells" J Biol Chem. 281:4564-4569.
Van De Stolpe et al., 2011 "Circulating tumor cell isolation and diagnostics: toward routine clinical use," Cancer Res 71(18):5955-60.
Wang et al., 2001 Role of Hydrophobic Residues in the C1b Domain of Protein Kinase C δ on Ligand and Phospholipid Interactions, J Biol Chem 276(22):19580-87.
Wang et al., 2012 "Substrate Recognition Mechanism of Atypical Protein Kinase Cs Revealed by the Structure of PKC$_\iota$ in Complex with a Substrate Peptide from Par-3," Structure 20(6):791-801.

(56) References Cited

OTHER PUBLICATIONS

Wang et al., 2016, "Effective use of PI3K Inhibitor BKM120 and PARP inhibitor Olaparib to treat PIK3CA mutant ovarian cancer," Oncotarget 7(11):13153-66.

Weer et al., 2011 "A Gateway Synthesis, PKC Affinities and Cell Growth Activities of Daphnane Congeners," Nat Chem 3(8):615-19.

Yang et al., 2013 "The Noncoding RNA Expression Profile and the Effect of lncRNA AK126698 on Cisplatin Resistance in Non-Small-Cell Lung Cancer Cell", PloS One 8(5):e65309 (12 pages).

Yin et al., 2013 "Tumor-Initiating Cells and FZD8 Play a Major Role in Drug Resistance in Triple-Negative Breast Cancer," Mol Cancer Ther 2013 12(4):491-98.

You et al., 2016 "Development of a triazole class of highly potent Porcn inhibitors," Bioorg Med Chem Lett 26(24):5891-95.

Yoshida et al., 1996 "Antitumor activity of daphnane-type diterpene gnidimacrin isolated from *Stellera chamaejasme* L" Int J Cancer 66(2):268-73.

Zhang et al., 2002 "Phosphoprotein analysis using antibodies broadly reactive against phosphorylated motifs," J Biol Chem. 277(42):39379-87.

International Preliminary Report on Patentability for International Application PCT/US2017/021695, dated Sep. 11, 2018.

International Search Report for International Application PCT/US2017/021695, dated Jul. 20, 2017.

* cited by examiner (PART 1)

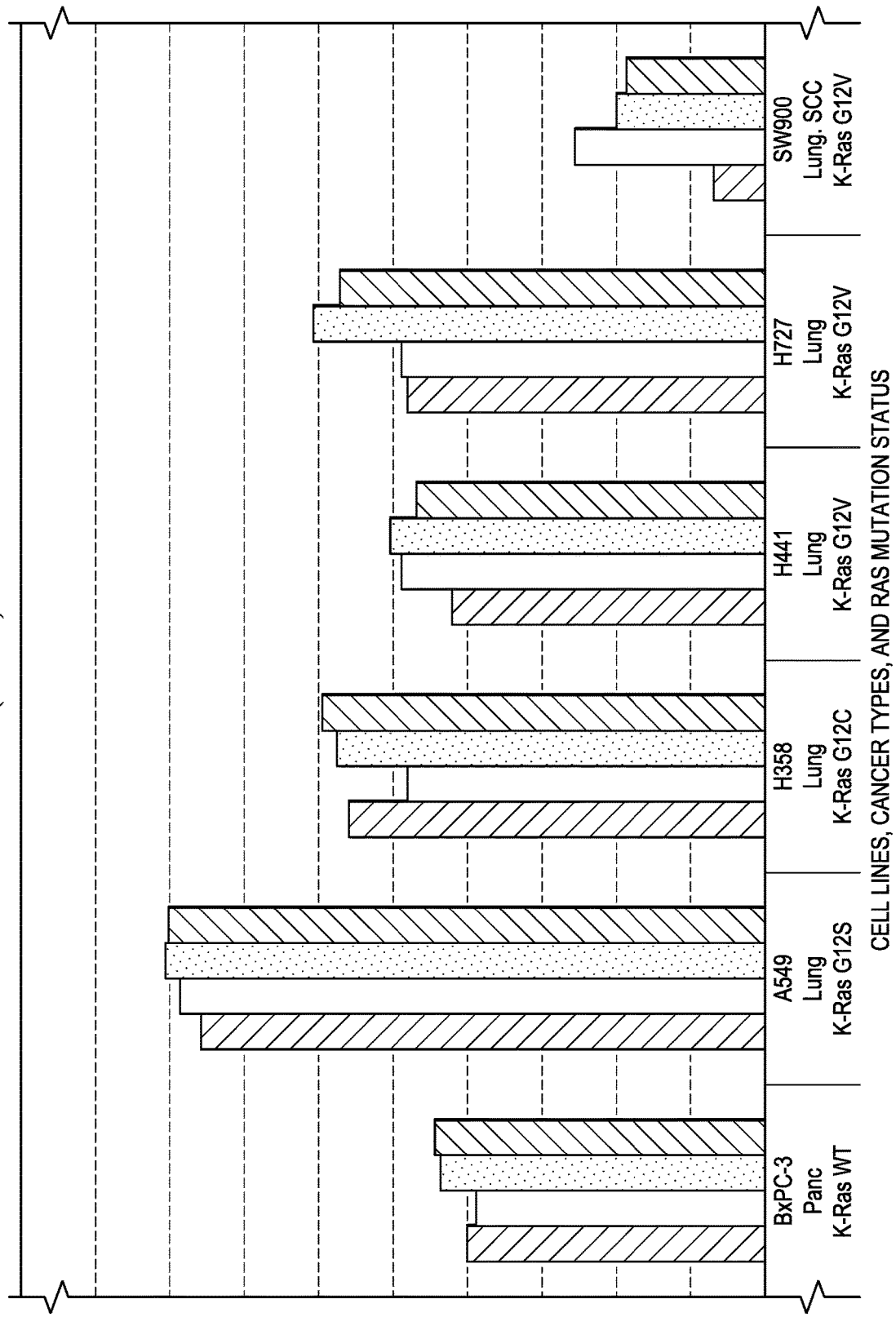
FIG. 1 (PART 2)

(PART 3)

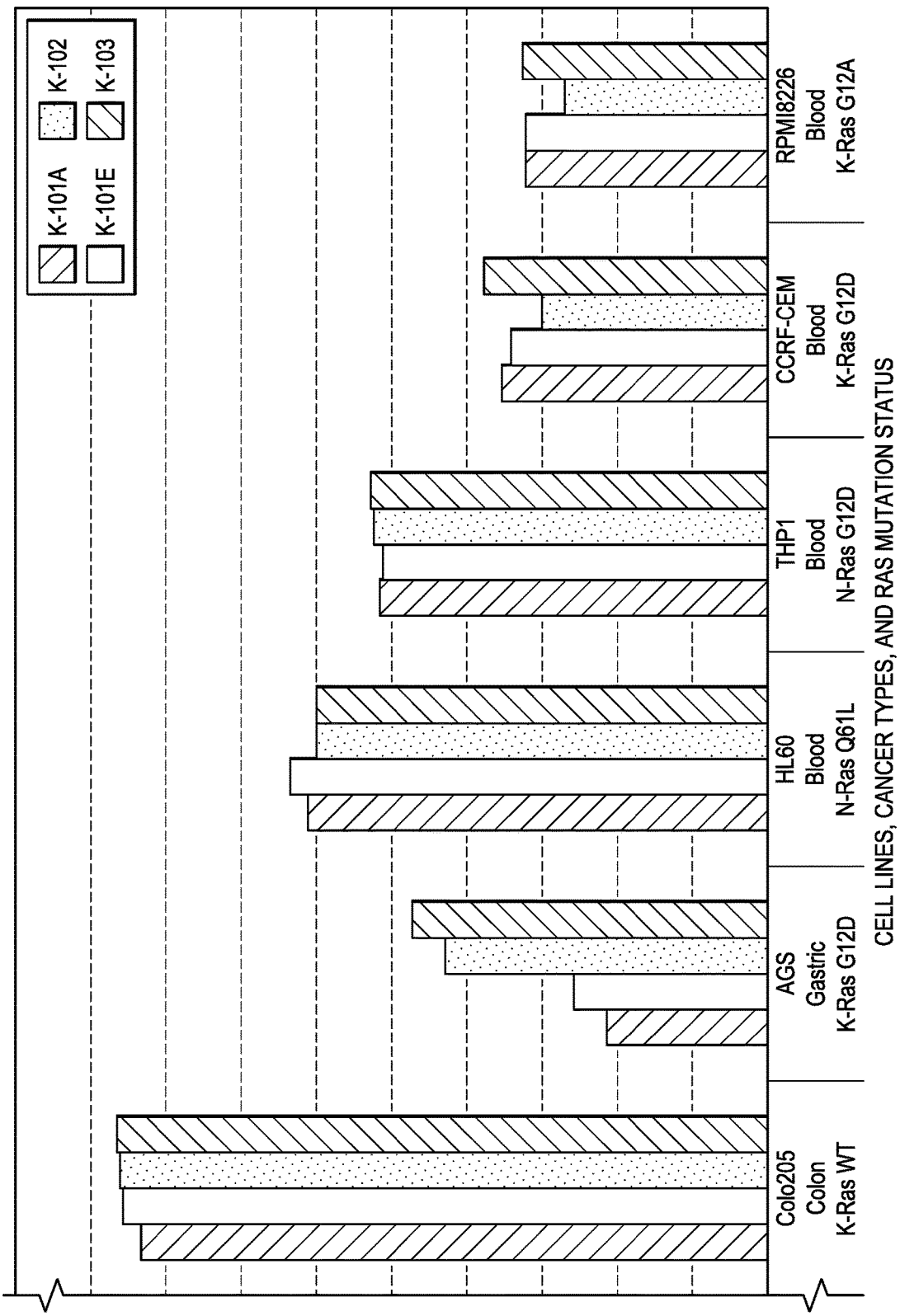
FIG. 1 (PART 4)

MacSynergy II SYNERGY VOLUMES: 140

MacSynergy II SYNERGY VOLUMES: 295

MacSynergy II SYNERGY VOLUMES: 59
MacSynergy II ANTAGONISM VOLUMES: -39

MacSynergy II SYNERGY VOLUMES: 4
MacSynergy II ANTAGONISM VOLUMES: -16

METHODS OF CANCER TREATMENT

1. CROSS-REFERENCE TO RELATED APPLICATIONS

This application is a National Stage of International Application No. PCT/US2017/021695, filed Mar. 9, 2017, which claims the benefit under 35 U.S.C. § 119(e) of U.S. Provisional Application No. 62/306,030, filed Mar. 9, 2016, the contents of all of which are is incorporated herein in their entirety.

2. BACKGROUND

Cancer is a disease of abnormal and uncontrolled cell growth. Cancer cells are also genetically unstable and subject to frequent mutations, resulting in a heterogeneous mixture of cancer cells, some of which are resistant to chemotherapeutic treatments. While rounds of chemotherapy may eliminate most of the cancer cells in a patient, the chemotherapy also becomes a selection mechanism for chemo-resistant cancer cells. Relapses in cancer patients are thought to occur because a small number of cancer cells survive by accumulating mutations that make them resistant to the chemotherapeutic agent being used.

Combination chemotherapy combines two or more chemotherapeutic agents to attack cancer cells by targeting different physiological targets (e.g., mechanisms of action) and/or life cycles of the cancer cell, with minimal cross resistance between the agents in order to decrease the likelihood that the cancer cells can survive the combination therapy. One primary rationale for combination chemotherapy in cancer treatment is that the probability of developing all of the mutations that confer resistance in a single cancer cell to all of the chemotherapeutic agents of the combination is much lower than the probability of accumulating mutations conferring resistance to a single chemotherapeutic agent. Combination therapy can also allow use of lower doses of a chemotherapeutic agent because two or more agents attack the cancer cell in concert, and may also enhance patient compliance if the chemotherapeutic agents are provided in a single composition.

Despite the advantages of combination therapies, the development of specific chemotherapy combinations that are effective against cancers is difficult because of the unpredictable effects of targeting different biological targets and the lack of information on the biochemical and molecular mechanisms of drug interaction at the cellular level. It is difficult to determine whether a specific drug combination will be synergistic (i.e., superior), simply additive (i.e., equal), or even antagonistic (i.e., inferior). Some chemotherapy combinations having a synergistic response at one ratio can be antagonistic when used in a different ratio.

3. SUMMARY

The present disclosure relates to methods of treating cancer by using a combination of a protein kinase C (PKC) activating compound, particularly a diterpenoid PKC activator, and a second therapeutic agent. In one aspect, a method of treating a cancer comprises administering to a subject in need thereof a therapeutically effective amount of a diterpenoid PKC activator and one or more of a therapeutic agent selected from a phosphoinositol-3 kinase (PI3K) inhibitor, AKT inhibitor, mammalian target of rapamycin (mTOR) inhibitor, poly ADP ribose polymerase (PARP) inhibitor, platinum-based anti-cancer compound (PBAC), CBP/β-catenin inhibitor, Tankyrase (TNKS) inhibitor, probable protein-cysteine N-palmitoyltransferase (PORCN) inhibitor, scr kinase/bcr-abl kinase inhibitor, Smoothened inhibitor, anti-cancer nucleoside analog or anti-metabolite (e.g., cytarabine), histone deacetylase (HDAC) inhibitor, Bromodomain and Extra-Terminal motif (BET) inhibitor, all-trans-retinoic acid (ATRA), Bruton's tyrosine kinase (BTK) inhibitor, and combinations thereof.

In another aspect, a method of treating cancer comprises administering to a subject in need thereof a therapeutically effective amount of a diterpenoid PKC activator and one or more of an inhibitor of PI3K/AKT/mTOR signaling pathway. In various embodiments, an inhibitor of the PI3K/AKT/mTOR signaling pathway is selected from a PI3K inhibitor, AKT inhibitor, mTOR inhibitor, dual mTORC1/2 inhibitor, dual PI3K/mTOR inhibitor, and combinations thereof. In some embodiments, the combination treatment with the diterpenoid PKC activator and an inhibitor of the PI3K/AKT/mTOR signaling pathway further comprises administering a therapeutically effective amount of a PARP inhibitor and/or PBAC.

In another aspect, a method of treating cancer comprises administering to a subject in need thereof a therapeutically effective amount of a diterpenoid PKC activator and one or more of an inhibitor of the Wnt/β-catenin signaling pathway. In some embodiments, the inhibitor of the Wnt/β-catenin signaling is selected from an inhibitor/antagonist of CBP/β-catenin, TNKS inhibitor, PORCN inhibitor, and combinations thereof. In some embodiments, the combination treatment with the diterpenoid PKC activator and an inhibitor of Wnt/β-catenin signaling pathway further comprises administering a therapeutically effective amount of a PARP inhibitor and/or PBAC.

In another aspect, a method of treating cancer comprises administering to a subject in need thereof a therapeutically effective amount of a diterpenoid PKC activator and a second therapeutic agent selected from an anti-cancer nucleoside analog, anti-metabolite, histone deacetylase (HDAC) inhibitor, Bromodomain and Extra-Terminal motif (BET) inhibitor, all-trans-retinoic acid (ATRA), microtubule inhibitor, Bruton's tyrosine kinase (BTK) inhibitor, epidermal growth factor (EGFR) inhibitor, proteasome inhibitor, and combinations thereof. In some embodiments, the foregoing therapeutic agents are used in combination with the PKC activating compound in treating hematologic cancer, such as leukemias or lymphomas.

In the combination treatments, the PKC activating compound comprises a diterpenoid compound capable of activating PKC activity. In some embodiments, the diterpenoid PKC activator compound includes PKC activating tigliane (e.g., phorbol, deoxyphorbol, etc.), ingenane (e.g., ingenol), daphnane and lathyrane diterpenoids. In some embodiments, the PKC activator for use in the methods herein include PKC activating phorbol, deoxyphorbol, ingenane, daphnane and lathyrane compounds, including enantiomers, derivatives, analogs, and prodrugs thereof, and salts, hydrates, and solvates thereof, as provided in the detailed description.

In some embodiments, various types of cancers can be treated with the combination therapy, including adrenocortical cancer, anal cancer, biliary cancer, bladder cancer, bone cancer (e.g., osteosarcoma), brain cancer (e.g., glioma, astrocytoma, neuroblastoma, etc.), breast cancer, cervical cancer, colon cancer, endometrial cancer, esophageal cancer, head and neck cancer, hematologic cancer (e.g., leukemias and lymphomas), intestinal cancer (small intestine), kidney cancer, liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma, squamous cell carcinoma, etc.), stomach cancer, testicular cancer, throat cancer, thyroid cancer, uterine cancer, and vaginal cancer.

In some embodiments, the combination therapy is used to treat a hematologic cancer, including, among others, acute lymphoblastic leukemia (ALL), acute myeloid leukemia (AML), lymphomas (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

In some embodiments, the cancer selected for treatment with the combination therapy is identified as having an activating or oncogenic RAS activity, particularly an activating or oncogenic mutation in K-RAS, N-RAS, or H-RAS. In some embodiments, the cancer selected for treatment with the combination therapy is identified as having an activating or oncogenic mutation at codon 12, codon 13 and/or codon 61 of K-RAS, N-RAS or H-RAS.

In some embodiments, the cancer identified as having an activating or oncogenic K-RAS mutation and selected for treatment with the combination therapy can be, among others, cancer of the pancreas, lung, colon, head and neck, stomach (gastric), biliary tract, endometrium, ovary, small intestine, urinary tract, liver, cervix, breast, kidney, renal, or hematologic (e.g., leukemia, lymphomas, etc.) tissues or cells.

In some embodiments, the cancer identified as having an activating or oncogenic N-RAS mutation and selected for treatment with the combination therapy is a hematologic cancer, such as, among others, acute myeloid leukemia, chronic myeloid leukemia, acute lymphoblastic leukemia, juvenile myelomonocytic leukemia, chronic myelomonocytic leukemia, myelodysplastic syndrome, myeloproliferative neoplasia, and multiple myeloma, or other types of leukemias.

In some embodiments, the cancer identified as having an activating or oncogenic H-RAS mutation and selected for treatment with the combination therapy is cancer of the cervix, prostate, salivary gland, skin, upper aerodigestive tract, or urinary tract.

In some embodiments, the cancer for treatment with the combination therapy is selected for or identified as having sensitivity to the PKC activator compound, also referred to herein as an effective PKC activation potential. In some embodiments, the sensitivity of the cancer for the PKC activator compound is determined by measuring the phosphorylation activity in the cancer cell, particularly following treatment of the cancer cells with the PKC activator. In some embodiments, the sensitivity of the cancer for the PKC activator compound is determined by measuring the phosphorylation level of one or more of PKC $\alpha$, $\beta$, $\gamma$, $\delta$, $\epsilon$, $\eta$, $\theta$, $\iota/\lambda$, $\mu$ and $\zeta$ enzymes, particularly PKCµ, e.g., at Ser910, or PKCδ, e.g., at Tyr311. In some embodiments, the sensitivity of the cancer for the PKC activator compound is assessed based on identification of loss-of-function mutations in one or more genes encoding PKC enzymes PKC $\alpha$, $\beta$, $\gamma$, $\delta$, $\epsilon$, $\eta$, $\theta$, $\iota/\lambda$, $\mu$ and $\zeta$.

In some embodiments, cancers for treatment with the combination therapy is selected for or identified as having an activating or oncogenic RAS activity, e.g., activating or oncogenic K-RAS, N-RAS, or H-RAS mutation, and an effective PKC activation potential. In some embodiments, such cancers can be, among others, a cancer of the pancreas, lung, colon, head and neck, stomach (gastric), biliary tract, endometrium, ovary, small intestine, urinary tract, liver, cervix, breast, kidney, renal, or hematologic (e.g., leukemia, lymphomas, etc.) tissues or cells identified as having an activating or oncogenic RAS activity and an effective PKC activation potential.

4. BRIEF DESCRIPTION OF THE FIGURES

FIG. 1 shows a summary of viability data (% Top inhibition) for PKC activator compounds K101A, K101E, K102, and K103 in different cancer cell lines along with the RAS mutation status of the cell lines.

FIGS. 2A-2H show effect of PKC activator compound K101A (prostratin) in combination with a second therapeutic agent on growth inhibition of lung cancer cell line A549: FIG. 2A—trametinib or idelalisib; FIG. 2B—dasatinib or everolimus; FIG. 2C—paclitaxel or olaparib; FIG. 2D—MK2206 or lapatinib; FIG. 2E—gemcitabine or cisplatin; FIG. 2F—BKM-120 or staurosporine, STS; FIG. 2G—(±)-JQ1 or XAV-939; and FIG. 2H—ICG-001.

FIGS. 3A-3F show effect of PKC activator compound K101E in combination with a second therapeutic agent on growth inhibition of lung cancer cell line A549: FIG. 3A—trametinib or idelalisib; FIG. 3B—dasatinib or everolimus; FIG. 3C—paclitaxel or olaparib; FIG. 3D—MK2206 or lapatinib; FIG. 3E—gemcitabine or cisplatin; and FIG. 3F—BKM-120 or staurosporine, STS.

FIGS. 4A-4H show effect of PKC activator K102 (ingenol-3-angelate) in combination with a second therapeutic agent on growth inhibition of lung cancer cell line A549: FIG. 4A—trametinib or idelalisib; FIG. 4B—dasatinib or everolimus; FIG. 4C—paclitaxel or olaparib; FIG. 4D—MK2206 or lapatinib; FIG. 4E—gemcitabine or cisplatin; and FIG. 4F—BKM-120 or staurosporine, STS; FIG. 4G—(±)-JQ1 or XAV-939; and FIG. 4H—ICG-001.

FIG. 12A—olaparib or cisplatin; and FIG. 12B—XAV-939 or ICG-001.

5. DETAILED DESCRIPTION

Figure 1:
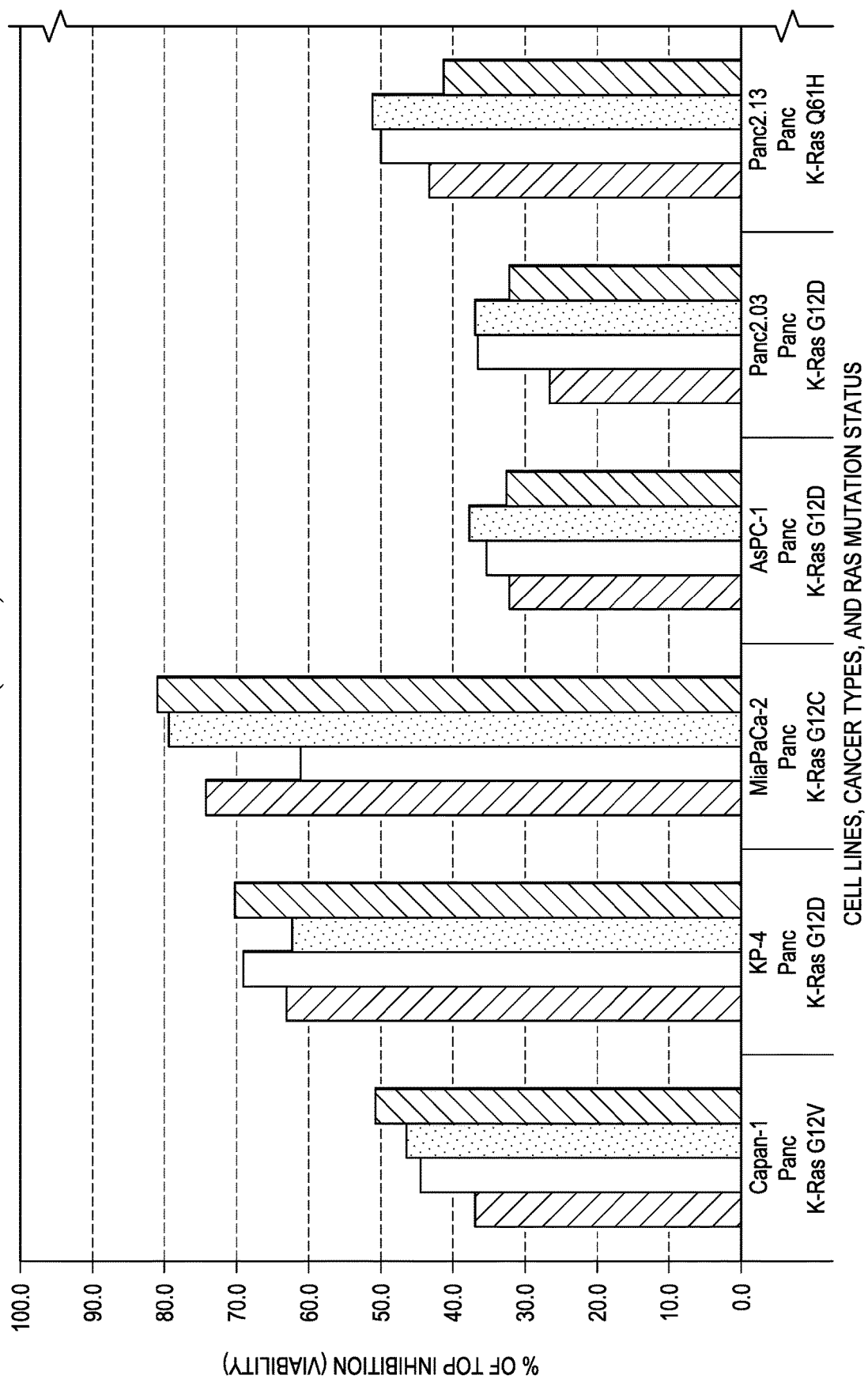
Figure 1:
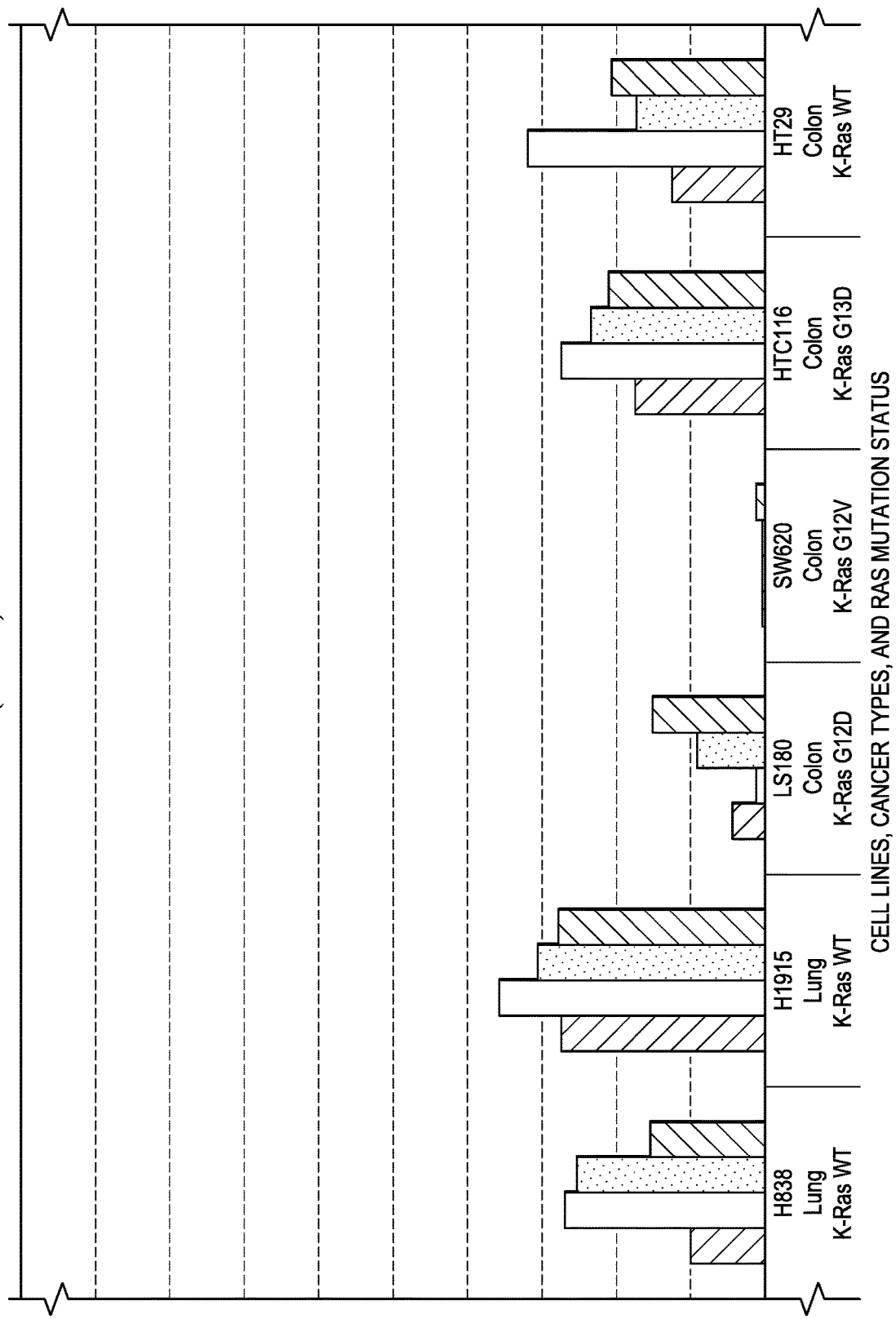

As used in this specification and the appended claims, the singular forms "a", "an" and "the" include plural referents unless the context clearly indicates otherwise. Thus, for example, reference to "a protein" includes more than one protein, and reference to "a compound" refers to more than one compound.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

It is to be understood that both the foregoing general description, including the drawings, and the following detailed description are exemplary and explanatory only and are not restrictive of this disclosure. The section headings used herein are for organizational purposes only and not to be construed as limiting the subject matter described.

5.1. Definitions

In reference to the present disclosure, the technical and scientific terms used in the descriptions herein will have the meanings commonly understood by one of ordinary skill in the art, unless specifically defined otherwise. Accordingly, the following terms are intended to have the meanings as described below.

"Polypeptide," "peptide" and "protein" are used interchangeably herein to denote a polymer of at least two amino acids covalently linked by an amide bond, regardless of length or modification, e.g., post-translational modification such as glycosylation, phosphorylation, lipidation, myristilation, ubiquitination, etc.

"Polynucleotide" or "nucleic acid" refers to two or more nucleosides that are covalently linked together. The polynucleotide may be wholly comprised ribonucleosides (i.e., an RNA), wholly comprised of 2' deoxyribonucleotides (i.e., a DNA) or mixtures of ribo- and 2' deoxyribonucleosides. While the nucleosides will typically be linked together via standard phosphodiester linkages, the polynucleotides may include one or more non-standard linkages. Non-limiting examples of such non-standard linkages include phosphoramidates, phosphorothioates, O-methylphosphodiesters, positively-charged linkages and non-ionic linkages. The polynucleotide may be single-stranded or double-stranded, or may include both single-stranded regions and double-stranded regions. Moreover, while a polynucleotide will typically be composed of the naturally occurring encoding nucleobases (i.e., adenine, guanine, uracil, thymine and cytosine), it may include one or more modified and/or synthetic nucleobases, such as, for example, inosine, xanthine, hypoxanthine, etc. Preferably, such modified or synthetic nucleobases will be encoding nucleobases.

"Domain" and "region" are used interchangeably herein and refer to a contiguous sequence of amino acids within a defined protein, such as a PKC protein, typically characterized by being either conserved or variable.

"Protein Kinase C" or "PKC" refers to a family of protein kinases involved in cellular signal transduction systems. Structurally, the typical PKC comprises a regulatory domain and a catalytic domain separated by a hinge region. PKC enzymes can be characterized by conserved domains, e.g., C1 to C4, each domain having different properties. In many PKC enzymes, the C1 domain interacts with diacylglycerol/phorbol esters; the C2 domain contains the recognition site for acidic lipids, and in some isozymes the $Ca^{+2}$ binding site; and the C3 and C4 domains form the ATP and substrate binding site. Some PKC enzymes differ in the C1 domain, and may not respond to phorbol esters. PKC proteins can be present as various isozymes and include, without limitation, α, βI, βII, γ, δ, ε, η, ι, ζ, θ, and μ.

"Protein kinase C activator" or "PKC activator" or "PKC activating compound" refers to a moiety that enhances the activity of one or more PKC enzymes. The moiety can be, without limitation, a small molecule, a peptide, lipid, or carbohydrate. While PKC activation can be direct or indirect, unless otherwise specified, a PKC activator as used herein refers to a moiety that interacts with the PKC enzyme.

"Protein kinase activation potential" or "PKC activation potential" refers to the degree in which PKC activity can be increased by treatment with a PKC activator and/or the total PKC activity that can be achieved by treatment with a PKC activator.

"Phosphoinositol-3 kinase" or "PI3K" refers to signal transducer enzyme capable of phosphorylating the 3 position hydroxyl group of the inositol ring of phosphatidylinositol (PtdIns). PI3K have been grouped into several classes, e.g., Class I, Class II, Class III, and Class IV, distinguished by various combinations of catalytic and regulator domains. The 3-phosphorylated phosphoinositides produced by PI3K (e.g., PtdIns3P, PtdIns(3,4)P2, PtdIns(3,5)P2, and PtdIns(3,4,5)P3) can interact with proteins having phosphoinositide binding domains, such as PX domain, pleckstrin homology domains (PH domains), and FYVE domains, and thereby affecting activity and/or cell localization. "PI3K" as used herein encompasses variants, including orthologs and interspecies homologs, of the human PI3K proteins. An inhibitor of PI3K or PI3K inhibitor refers to a compound which inhibits or attenuates the activity of PI3K and includes dual inhibitor of PI3K/mTOR.

"AKT" refers to a serine-threonine kinase that contain SH2 (Src homology 2-like) domains and is a downstream target of phosphoinositide 3-kinase (PI3-kinase). The enzyme belongs to the AGC kinase family, related to AMP/GMP kinases and protein kinase C. They typically consist of three conserved domains: an N-terminal PH domain, a central kinase CAT domain, and a C-terminal extension (EXT) containing a regulatory hydrophobic motif (HM). The pleckstrin homology domain of AKT binds to PtdIns (3,4,5)P3 and PtdIns(3,4)P2, which are produced by activated PI3K. "AKT" as used herein encompasses variants, including orthologs and interspecies homologs, of the human AKT protein, including isoforms AKT1, AKT2 and AKT2. An inhibitor of AKT or AKT inhibitor refers to a compound which inhibits or attenuates the activity of AKT, including pan- and isoform specific inhibitors of AKT1, AKT2 and AKT3.

"Mammalian target of rapamycin" or "mTOR" refers to a kinase within the family of phosphatidylinositol-3 kinase-related kinases (PIKKs), which is a family of serine/threonine protein kinases, with a sequence similarity to the family of lipid kinases, PI3Ks. PIKKs generally have four domains at the protein level, which distinguish them from other protein kinases. These domains include FRAP-ATM-TRAAP (FAT), the kinase domain (KD), the PIKK-regulatory domain (PRD), and the FAT-C-terminal (FATC). The FAT domain, consisting of four α-helices, is N-terminal to KD, but that part is referred to as the FKBP12-rapamycin-binding (FRB) domain, which binds the FKBP12-rapamycin complex. The FAT domain consists of repeats, referred to as HEAT (Huntingtin, Elongation factor 3, A subunit of protein phosphatase 2A and TOR1). mTOR can phosphorylate AKT, which leads to its activation. Two forms of mTOR have been identified: mTORC1 and mTORC2. "mTOR" as used herein encompasses variants, including orthologs and interspecies homologs, of the human mTOR proteins. An inhibitor of mTOR or mTOR inhibitor refers to a compound which inhibits or attenuates the activity of mTOR. A dual inhibitor of mTORC1/mTORC2 refers to a compound which inhibits or attenuates the activity of both mTORC1 and mTORC2. Also included as inhibitors in this group are dual inhibitor of PI3K/mTOR.

"Poly ADP ribose polymerase" or "PARP" refers to cell signaling enzymes that catalyze the transfer of ADP-ribose units from NAD+ to a number of acceptor proteins. PARP is typically composed of a DNA-binding domain, a caspase-cleaved domain, an auto-modification domain, and a catalytic domain. PARP binds to single-strand DNA breaks (SSDB) and initiates synthesis of poly (ADP-ribose) chain (PAR) as a signal for the other DNA-repairing enzymes such as DNA ligase III (LigIII), DNA polymerase beta (polβ), and scaffolding proteins such as X-ray cross-complementing gene 1 (XRCC1). "PARP" as used herein encompasses variants, including orthologs and interspecies homologs, of the human PARP protein. An inhibitor of PARP or PARP inhibitor refers to a compound which inhibits or attenuates the activity of PARP, including pan- and isoform specific inhibitors of PART isoforms, e.g., PARP1 to PARP14.

"TRF1-Interacting Ankyrin-Related ADP-Ribose Polymerase," "Tankyrase," or "TNKS" refers to a poly-ADP-ribosyltransferase which modifies various proteins, including Terf 1, Axin 1, Axin 2, Blzf 1, and Cas 3. It acts, in part, to regulate Wnt signaling and telomere length. Two forms of TNKS have been identified: TNKS-1 and TNKS-2. "TNKS" as used herein encompasses variants, including orthologs and interspecies homologs, of the human TNKS proteins. An inhibitor of TNKS or TNKS inhibitor refers to a compound which inhibits or attenuates the activity of a TNKS, including pan and isoform specific inhibitors of TNKS-1 and/or TNKS-2.

"Probable protein-cysteine N-palmitoyltransferase" or "porcupine protein" or "PORCN" refers to O-acyltransferase, in particular O-palmitoleoyltransferase, which acts as a regulator of the Wnt signaling pathway by mediating the attachment of palmitoleate to Wnt proteins. Palmitoleylation of WNT proteins mediates, among others, efficient binding to frizzled receptors. "PORCN" as used herein encompasses variants, including orthologs and interspecies homologs, of the human PORCN proteins. An inhibitor of PORCN or PORCN inhibitor refers to a compound which inhibits or attenuates the activity of PORCN.

"CBP/β-catenin" refers to a protein functioning in cell-cell interactions and gene transcription, and which in humans is encoded by the CTNNB1 gene. β-catenin is characterized by repeats of approximately 40 amino acids long, referred to as armadillo repeats, which together fold into a single, protein domain with an elongated shape, the armadillo (ARM) domain. It functions as a mediator in the Wnt signaling pathway. "CBP/β-catenin" as used herein encompasses variants, including orthologs and interspecies homologs, of the human CBP/β-catenin protein. An inhibitor of CBP/β-catenin or CBP/β-catenin inhibitor refers to a compound which inhibits or attenuates the activity of β-catenin.

"Src kinase" refers to a non-receptor tyrosine kinase protein that is encoded by the SRC gene. This protein phosphorylates specific tyrosine residues in other proteins. Generally, c-Src is made up of 6 functional regions: Src homology (SH) 4 domain (SH4 domain), unique region, SH3 domain, SH2 domain, catalytic domain and short regulatory tail. "Src kinase" as used herein encompasses variants, including orthologs and interspecies homologs, of the human Src kinase proteins. An inhibitor of src kinase or src kinase inhibitor refers to a compound which inhibits or attenuates the activity of src kinase, including pan- and isoform specific inhibitors of src-kinase.

"Brc-abl kinase" refers to a chimeric protein formed by fusion of the abl kinase gene and break point cluster (Bcr) gene, resulting in a fusion protein having a constitutively active tyrosine kinase activity. The bcr-abl kinase is associated with chronic myelogenous leukemia (CML). "Brc-abl kinase" as used herein encompasses variants, including orthologs and interspecies homologs, of the human brc-abl kinase protein. An inhibitor of bcr-abl kinase or bcr-abl kinase inhibitor refers to a compound which inhibits or attenuates the activity of bcr-abl kinase.

"Platinum-based anti-cancer compound" or "PBAC" refers to platinum containing compounds used as anti-cancer treatments. These compounds can crosslink DNA and induce DNA strand breaks. Exemplary PBACs include, cisplatin (cisplatinum), carboplatin, and oxaliplatin.

"PI3K/AKT/mTOR pathway" or "PI3K/AKT/mTOR signaling pathway" refers to a signaling pathway involving PI3K, AKT and mTOR. Generally, cell signaling in this pathway involves PI3K activation, which phosphorylates and activates AKT, a serine/threonine kinase. AKT enzyme can regulate several different downstream biological targets, such as CREB, p27, PtdIns-3ps, and mTOR. mTOR can be activated by AKT, and leads to increased synthesis of multiple proteins, such as Cyclin D1, which allows progression through the cell cycle. An inhibitor of the PI3K/AKT/mTOR pathway refers to a compound that inhibits or attenuates the activity of at least one member of the pathway, e.g., PI3K, AKT or mTOR. Included as inhibitors are pan- and isoform specific PI3K inhibitors, pan- and isoform specific AKT inhibitors, pan- and isoform specific mTOR inhibitors, dual IP3K/mTOR inhibitors, and dual mTORC1/mTORC2 inhibitors.

"Wnt/β-catenin pathway" or "Wnt/β-catenin signaling pathway" refers to a cellular signal transduction pathway involving β-catenin and downstream and upstream cellular elements, such as CBP-β-catenin, TNKS, and PORCN. Other cellular components in the Wnt/β-catenin signaling pathway include, among others, adenomatous polyposis coli (APC), glycogen synthase kinase (GSK)-3β, T-cell factor (TCF), and lymphoid enhancer factor (LEF).

"Smoothened" or "SMO" or "smoothened receptor" is a component of the hedgehog signaling pathway. It is classified as a class frizzled (class F) G-protein-coupled receptor (GPCR), and is encoded by the SMO gene. Generally, the protein is characterized by an N-terminal extracellular cysteine-rich domain (CRD) connected via a linker to 7 membrane-spanning helices (7TM) and an extended C-terminal tail. "SMO" as used herein encompasses variants, including orthologs and interspecies homologs, of the human SMO proteins. An inhibitor of the SMO or SMO inhibitor refers to a compound that inhibits or attenuates the activity SMO.

"Histone deacetylase" or "HDAC" refers to a class of enzymes that remove acetyl groups from histones. HDACs have been classified into four different groups based on function and sequence similarity. Class I, II and IV are considered "classical" HDACs and have a zinc dependent active site. These "classical" enzymes include HDAC1, HDAC2, HDAC3, HDAC4, HDAC5, HDAC6, HDAC7, HDAC8, HDAC9, and HDAC10. Class III enzymes are a family of NAD+-dependent proteins. HDACs regulate chromatin structure and gene expression by affecting the acetylation level of histones. "HDAC" as used herein encompasses variants, including orthologs and interspecies homologs, of the human HDAC proteins. An inhibitor of HDAC or HDAC inhibitor refers to a compound that inhibits or attenuates the activity of HDACs, particularly the classical HDACs.

"Bromodomain and Extra-Terminal Motif protein" or "BET" refers to a class of proteins that have a bromodomain and recognize acetylated proteins, particularly by interacting with acetylated lysine residues. The BET proteins are generally characterized by the presence of two tandem bromodomains and an extra-terminal domain. Mammalian BET family includes BRD2, BRD3, BRD4 and BRDT. These BET proteins may regulate gene expression by interactions with histones during cellular proliferation and differentiation processes. Human BRD2 is also characterized by the presence of serine/tyrosine kinase activity. See, e.g., Taniguchi et al., 2016, Int. J Mol Sci. 17:1849. "BET" as used herein encompasses variants, including orthologs and interspecies homologs, of the human BET proteins. An inhibitor of BET or BET inhibitor refers to a compound that inhibits or attenuates the activity of BET.

"Bruton's Tyrosine Kinase" or "tyrosine-protein kinase BTK" or "BTK" refers to a non-receptor tyrosine kinase encoded by the BTK gene, and is a prototypical member of the Tec family of protein kinases. Generally, BTK protein contains an N-terminal pleckstrin homology (PH) domain that binds phosphatidylinositol (3,4,5)-trisphosphate (PIP3), a proline-rich TEC homology domain, SRC homology domains SH2 and SH3, and a C-terminal kinase domain. BTK acts in regulating B-cell development, activation, signaling, and survival, and in a number of other hematopoietic cell signaling pathways, e.g., Toll like receptor (TLR) and cytokine receptor-mediated TNF-α production in macrophages, IgE receptor (FcepsilonRI) signaling in Mast cells, inhibition of Fas/APO-1 apoptotic signaling in B-lineage lymphoid cells, and collagen-stimulated platelet aggregation. "BTK" as used herein encompasses variants, including orthologs and interspecies homologs, of the human BTK protein. An inhibitor of BTK or BTK inhibitor refers to a compound that inhibits or attenuates the activity of BTK.

"Proteasome" as used herein refers to complexes of proteins, the proteasome or ubiquitin proteasome, involved in degradation of other proteins tagged with ubiquitin, a tagging process generally carried out by ubiquitin ligases. An inhibitor of ubiquitin proteasome or proteasome inhibitor refers to a compound which inhibits or attenuates the degradation of proteins via the ubiquitin mediated process, particularly by targeting proteasomes 26S or 20S proteasomes.

"K-RAS" refers to Kirsten rat sarcoma viral oncogene homolog, a small GTPase and a member of the RAS family of proteins involved in signal transduction. Human K-RAS gene and protein sequences are provided in GenBank Nos. M54968.1 and AAB414942.1, respectively. "K-RAS" as used herein encompasses variants, including orthologs and interspecies homologs, of the human K-RAS protein.

"Mutant K-RAS polypeptide", "mutant K-RAS protein" and "mutant K-RAS" are used interchangeably and refer to a K-RAS polypeptide comprising at least one K-RAS mutation as compared to the corresponding wild-type K-RAS sequence. Certain exemplary mutant K-RAS polypeptides include, but are not limited to, allelic variants, splice variants, derivative variants, substitution variants, deletion variants, insertion variants, and fusion polypeptides.

"N-RAS" refers to Neuroblastoma RAS Viral (V-RAS) oncogene homolog, a small GTPase and a member of the RAS family of proteins involved in signal transduction. Human N-RAS gene and protein sequences are provided in NCBI Accession No. NP_002515 and GenBank Accession No. X02751, respectively. "N-RAS" as used herein encompasses variants, including orthologs and interspecies homologs of the human N-RAS protein.

"Mutant N-RAS polypeptide", "mutant N-RAS protein" and "mutant N-RAS" are used interchangeably and refer to an N-RAS polypeptide comprising at least one N-RAS mutation as compared to the corresponding wild-type N-RAS sequence. Certain exemplary mutant N-RAS polypeptides include, but are not limited to, allelic variants, splice variants, derivative variants, substitution variants, deletion variants, insertion variants, and fusion polypeptides.

"H-RAS" refers to Harvey Rat Sarcoma viral oncogene homolog, a small GTPase and a member of the RAS family of proteins involved in signal transduction. Exemplary human H-RAS nucleic acid and protein sequences are provided in NCBI Accession No. P01112 and GenBank Accession No. NM_176795, respectively. "H-RAS" as used herein encompasses variants, including orthologs and interspecies homologs of the human H-RAS protein.

"Mutant H-RAS polypeptide", "mutant H-RAS protein" and "mutant H-RAS" are used interchangeably and refer to an H-RAS polypeptide comprising at least one H-RAS mutation as compared to the corresponding wild-type H-RAS sequence. Certain exemplary mutant H-RAS polypeptides include, but are not limited to, allelic variants, splice variants, derivative variants, substitution variants, deletion variants, insertion variants, and fusion polypeptides.

"Activating K-RAS" refers to a form of K-RAS that has increased activity compared to wild-type K-RAS. The activation of K-RAS activity can result from a mutation or in some embodiments, overexpression of the K-RAS protein.

"Activating N-RAS" refers to a form of N-RAS that has increased activity compared to wild-type N-RAS. The activation of N-RAS activity can result from a mutation, or in some embodiments, overexpression of the N-RAS protein.

"Activating H-RAS" refers to a form of H-RAS that has increased activity compared to wild-type H-RAS. The activation of H-RAS activity can result from a mutation, or in some embodiments, overexpression of the H-RAS protein.

"Mutation" or "mutant" refers to an amino acid or polynucleotide sequence which has been altered by substitution, insertion, and/or deletion. In some embodiments, a mutant or variant sequence can have increased, decreased, or substantially similar activities or properties in comparison to the parental sequence.

"Gain-of-function" refers to enhancement of activity or acquisition of a new or abnormal activity of a nucleic acid or protein. "Gain-of-function mutation" in the context of a protein refers to an altered form of the protein that has enhanced activity or acquires a new or abnormal protein activity.

"Loss-of-function" refers to reduced or abolished activity (e.g., partially or wholly inactivated) of a nucleic acid or protein. "Loss-of-function mutation" in the context of a protein generally refers to an altered form of the protein that has reduced or complete loss of the activity associated with the protein.

"Dominant negative" refers to the effect of an alteration in a gene that results in negation or attenuation of the effect of the normal or wild-type copy of the gene. The dominant negative effect may result from an expression product of the gene, such as an expressed RNA or expressed protein. By way of example and not limitation, a mutated, dominant negative PKC resulting in loss or attenuation of PKC activity can further lead to loss or attenuation of PKC activity of the normal or wild-type PKC, or in some instances, loss or attenuation of PKC activity of other PKC isoforms.

"Dominant negative mutation" refers to a change in an amino acid or polynucleotide sequence which has been altered by substitution, insertion, and/or deletion, and results in the "dominant negative" effect on a biological process, for example a signal transduction pathway.

"Identified" or "determined" refers to analyzing for, detection of, or carrying out a process for the presence or absence of one or more specified characteristics.

"Frizzled protein" or "Frizzled" or "Fzd" refers to members of the family of G-protein coupled receptor proteins involved in the Wnt signaling pathway. As such, frizzled belongs to the seven transmembrane class of receptors. Human frizzled proteins include, without limitation, Frizzled-1, Frizzled-2, Frizzled-3, Frizzled-4, Frizzled-5, Frizzled-6, Frizzled-7, and Frizzled-8.

"Ca2+/calmodulin-dependent protein kinase II" or "CaM kinase II" and "CaMKii" are used interchangeably herein and refer to serine/threonine-specific protein kinase that is regulated by the Ca2+/calmodulin complex. General structure of CaMKii includes a catalytic domain, an autoinhibitory domain, a variable segment, and a self-association domain. Phosphorylation at amino acid Thr286 in human CaMKii activates the kinase and regulates autoinhibition.

"Leukemia inhibitory factor" or "LIF" refers to an interleukin 6 class cytokine that affects cell growth by inhibiting differentiation. Of the several biological activities of LIF, it induces the terminal differentiation of myeloid leukemic cells. Exemplary human LIF protein sequence is provided as UniProtKB/Swiss-Prot. Accession No. P15018.1.

"Extracellular signal-regulated kinase 1/2," "Erk1/2," "Mitogen-activated protein kinase 1/2," and "MAPK1/2" refer to members of protein-serine/threonine kinases that participate in the Ras-Raf-MEK-ERK signal transduction cascade. Human ERK1 and ERK2 are 84% identical in sequence and share many biological functions. ERK1/2 are proline-directed kinases that preferentially catalyze the phosphorylation of substrates containing a Pro-Xxx-Ser/Thr-Pro sequence.

"Wild-type" or "naturally occurring" refers to the form found in nature. For example, a naturally occurring or wild-type polypeptide or polynucleotide sequence is a sequence present in an organism that can be isolated from a source in nature and which has not been intentionally modified by human manipulation.

"Control" or "control sample" or "control group" refers to a sample or group that is compared to another sample or group, where generally the control sample or group are the same as a comparison group except for one or more factors being compared.

"Selecting" refers to the process of determining that a subject will receive an agent to treat the occurrence of a condition. Selecting can be based on an individual susceptibility to a particular disease or condition due to, for example, presence of an identifying cellular, physiological or environment factor or factors. In some embodiments, selecting can be based on determining or identifying whether that subject will be responsive to an agent, for example as assessed by identifying the presence of a biomarker and/or drug target marker that makes the subject sensitive, insensitive, responsive, or unresponsive to an agent or treatment.

"Biological sample" refers to any sample including a biomolecule, such as a protein, a peptide, a nucleic acid, a lipid, a carbohydrate or a combination thereof, that is obtained from an organism, particularly a mammal. Examples of mammals include humans; veterinary animals like cats, dogs, horses, cattle, and swine; and laboratory animals like mice, rats and primates. In some embodiments, a human subject in the clinical setting is referred to as a patient. Biological samples include tissue samples (such as tissue sections and needle biopsies of tissue), cell samples (for example, cytological smears such as Pap or blood smears or samples of cells obtained by microdissection), or cell fractions, fragments or organelles (such as obtained by lysing cells and separating their components by centrifugation or otherwise). Other examples of biological samples include blood, serum, urine, semen, fecal matter, cerebrospinal fluid, interstitial fluid, mucous, tears, sweat, pus, biopsied tissue (for example, obtained by a surgical biopsy or a needle biopsy), nipple aspirates, milk, vaginal fluid, saliva, swabs (such as buccal swabs), or any material containing biomolecules that is derived from a first biological sample. In particular embodiments, the biological sample is a "cell free sample", such as cell free or extracellular polynucleotides, and cell free or extracellular proteins. In some embodiments, cell free DNA or cfDNA refers to extracellular DNA obtained from blood, particularly the serum.

"Subject" as used herein refers to a mammal, for example a dog, a cat, a horse, or a rabbit. In some embodiments, the subject is a non-human primate, for example a monkey, chimpanzee, or gorilla. In some embodiments, the subject is a human, sometimes referred to herein as a patient.

"Treating" or "treatment" of a disease, disorder, or syndrome, as used herein, includes (i) preventing the disease, disorder, or syndrome from occurring in a subject, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art, particularly in view of the guidance provided in the present disclosure.

"Therapeutically effective amount" refers to that amount which, when administered to an animal for treating a disease, is sufficient to effect such treatment for the disease, disorder, or condition.

"Alkyl" refers to straight or branched chain hydrocarbon groups of 1 to 20 carbon atoms, particularly 1 to 12 carbon atoms, and more particularly 1 to 8 carbon atoms. Exemplary "alkyl" includes, but are not limited to, methyl, ethyl, n-propyl, i-propyl, n-butyl, s-butyl, t-butyl, n-pentyl, and s-pentyl.

"Alkenyl" refers to straight or branched chain hydrocarbon group of 2 to 20 carbon atoms, particularly 2 to 12 carbon atoms, and most particularly 2 to 8 carbon atoms, having at least one double bond. Exemplary "alkenyl" includes, but are not limited to, vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

"Alkynyl" refers to a straight or branched chain hydrocarbon group of 2 to 12 carbon atoms, particularly 2 to 8 carbon atoms, containing at least one triple bond. Exemplary "alkynyl" includes ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

"Alkylene", "alkenylene" and "alkynylene" refers to a straight or branched chain divalent hydrocarbon radical of the corresponding alkyl, alkenyl, and alkynyl, respectively. The "alkylene", "alkenylene" and "alkynylene" may be optionally substituted, for example with alkyl, alkyloxy, hydroxyl, carbonyl, carboxyl, halo, nitro, and the like.

"Lower" in reference to substituents refers to a group having between one and six carbon atoms.

"Cycloalkyl" refers to any stable monocyclic or polycyclic system which consists of carbon atoms, any ring of which being saturated. "Cycloalkenyl" refers to any stable monocyclic or polycyclic system which consists of carbon atoms, with at least one ring thereof being partially unsaturated. Examples of cycloalkyls include, but are not limited to, cyclopropyl, cyclobutyl, cyclopentyl, cyclohexyl, cycloheptyl, adamantyl, cyclooctyl, and bicycloalkyls.

"Heterocycloalkyl" or "heterocyclyl" refers to a substituted or unsubstituted 5 to 8 membered, mono- or bicyclic, non-aromatic hydrocarbon, wherein 1 to 3 carbon atoms are replaced by a heteroatom. Heteroatoms and/or heteroatomic groups which can replace the carbon atoms include, but are not limited to, —O—, —S—, —S—O—, —NR'—, —PH—, —S(O)—, —S(O)$_2$—, —S(O) NR'—, —S(O)$_2$NR'—, and the like, including combinations thereof, where each R' is independently hydrogen or lower alkyl. Examples include pyrrolidin-2-yl; pyrrolidin-3-yl; piperidinyl; morpholin-4-yl and the like.

"Aryl" refers to a six- to fourteen-membered, mono- or bi-carbocyclic ring, wherein the monocyclic ring is aromatic and at least one of the rings in the bicyclic ring is aromatic. Unless stated otherwise, the valency of the group may be located on any atom of any ring within the radical, valency rules permitting. Examples of "aryl" include phenyl, naphthyl, indanyl, and the like.

"Heteroaryl" means an aromatic heterocyclic ring, including both monocyclic and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur.

"Carbonyl" refers to —C(O)—. The carbonyl group may be further substituted with a variety of substituents to form different carbonyl groups including acids, acid halides, aldehydes, amides, esters, and ketones. For example, an —C(O)R', wherein R' is an alkyl is referred to as an alkylcarbonyl. In some embodiments, R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Halogen" or "halo" refers to fluorine, chlorine, bromine and iodine.

"Hydroxy" refers to —OH.

"Oxy" refer to group —O—, which may have various substituents to form different oxy groups, including ethers and esters. In some embodiments, the oxy group is an —OR', wherein R' is selected from an optionally substituted: alkyl, cycloalkyl, cycloalkylalkyl, heterocycloalkyl, heterocycloalkylalkyl, aryl, arylalkyl, heteroaryl, and heteroarylalkyl.

"Alkyloxy" refers to —OR', wherein R' is an optionally substituted alkyl.

"Aryloxy" refers to —OR', wherein R' is an optionally substituted aryl.

"Carboxy" refers to —COO— or COOM, wherein M is H or a counterion.

"Carbamoyl" refers to —C(O)NR'R', wherein each R' is independently selected from H or an optionally substituted: alkyl, cycloalkyl, cycloalkylalkyl, heterocycloalkyl, heterocylcoalkylalkyl, aryl, arylalkyl, heteroaryl, or heteroarylalkyl.

"Cyano" refers to —CN.

"Ester" refers to a group such as —C(═O)OR', wherein R' is selected from an optionally substituted: alkyl, cycloalkyl, cycloalkylalkyl, heterocycloalkyl, heterocyclolalkylalkyl, aryl, arylalkyl, heteroaryl, and heteroarylalkyl.

"Thiol" refers to —SH.

"Sulfanyl" refers to —SR', wherein R' is selected from an optionally substituted: alkyl, cycloalkyl, cycloalkylalkyl, heterocyloalkyl, heterocycloalkylalkyl, aryl, arylalkyl, heteroaryl, and heteroarylalkyl. For example, —SR, wherein R is an alkyl is an alkylsulfanyl.

"Sulfonyl" refers to —S(O)$_2$—, which may have various substituents to form different sulfonyl groups including sulfonic acids, sulfonamides, sulfonate esters, and sulfones. For example, —S(O)$_2$R', wherein R' is an alkyl refers to an alkylsulfonyl. In some embodiments of —S(O)$_2$R', R' is selected from an optionally substituted: alkyl, cycloalkyl, cycloalkylalkyl, heterocyloalkyl, heterocycloalkylalkyl, aryl, arylalkyl, heteroaryl, and heteroarylalkyl.

"Sulfinyl" refers to —S(O)—, which may have various substituents to form different sulfinyl groups including sulfinic acids, sulfinamides, and sulfinyl esters. For example, —S(O)R', wherein R' is an alkyl refers to an alkylsulfinyl. In some embodiments of —S(O)R', R' is selected from an optionally substituted: alkyl, cycloalkyl, cycloalkylalkyl, heterocyloalkyl, heterocycloalkylalkyl, aryl, arylalkyl, heteroaryl, and heteroarylalkyl.

"Selenide" refers to Se, which may have various substituents, particularly alkyl groups. For example, —SeR', wherein R' is an alkyl group refers to an alkylselenide. In some embodiments, R' is selected from an optionally substituted: alkyl, cycloalkyl, cycloalkylalkyl, heterocyloalkyl, heterocycloalkylalkyl, aryl, arylalkyl, heteroaryl, and heteroarylalkyl.

"Phosphine" refers to —PR'R'R', wherein each R' is independently selected from H and an optionally substituted: alkyl, cycloalkyl, cycloalkylalkyl, heterocyloalkyl, heterocycloalkylalkyl, aryl, arylalkyl, and heteroarylalkyl.

"Phosphate" refers to a group of formula —OP(═O)(OR')$_2$, wherein each R' is independently selected from H and an optionally substituted: alkyl, cycloalkyl, cycloalkylalkyl, heterocyloalkyl, heterocycloalkylalkyl, aryl, arylalkyl, heteroaryl, and heteroarylalkyl.

"Phosphono" refers to a group of formula —P(═O)(OR')$_2$, wherein each R' is independently selected from H and an optionally substituted: alkyl, cycloalkyl, cycloalkylalkyl, heterocyloalkyl, heterocycloalkylalkyl, aryl, arylalkyl, heteroaryl, and heteroarylalkyl.

"Phosphoramide" refers to a group of formula —OP(═O)R'R', wherein at least one of R' is an —NR"R", wherein each R" is independently selected from H and an optionally substituted: alkyl, cycloalkyl, cycloalkylalkyl, heterocyloalkyl, heterocycloalkylalkyl, aryl, arylalkyl, heteroaryl, and heteroarylalkyl.

"Phosphoramidite" refers to a group of formula —OP(OR')NR'R', wherein each R' is independently selected from an optionally substituted: alkyl, cycloalkyl, cycloalkylalkyl, heterocyloalkyl, heterocycloalkylalkyl, aryl, arylalkyl, heteroaryl, and heteroarylalkyl.

"Phosphoramidate" refers to —OP(═O)(OR')NR'R, wherein each R' is independently selected from H and an optionally substituted: alkyl, cycloalkyl, cycloalkylalkyl, heterocyloalkyl, heterocycloalkylalkyl, aryl, arylalkyl, heteroaryl, and heteroarylalkyl.

"Phosphonate" refers to —P(═O)(OR')$_2$, wherein each R' is independently selected from H and an optionally substituted: alkyl, cycloalkyl, cycloalkylalkyl, heterocyloalkyl, heterocycloalkylalkyl, aryl, arylalkyl, heteroaryl and heteroarylalkyl.

"Ureide" refers to a cyclic or acyclic organic molecule of natural or synthetic origin that comprises one or more ureide moieties or derivatives thereof. Exemplary ureides include, among others, urea, uric acid, hydantoin, allantoin, imidazolidinyl urea (1,1'-methylenebis(3-[1-(hydroxymethyl)-2,5-dioxoimidazolidin-4-yl]urea), diazolydinyl urea (1,3-bis (hydroxymethyl)-1-(1,3,4-tris(hydroxymethyl)-2,5-dioxoimidazolidin-4-yl)urea), purines, and derivatives thereof.

"Urea" refers to a group such as —NHC(═O)NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Amino" or "amine" refers to the group —NR'R' or —NR'R'R', wherein each R' is independently selected from H and an optionally substituted: alkyl, cycloalkyl, heterocycloalkyl, alkoxy, aryl, heteroaryl, heteroarylalkyl, acyl, alkoxycarbonyl, sulfanyl, sulfinyl, sulfonyl, and the like. Exemplary amino groups include, but are not limited to, dimethylamino, diethylamino, trimethylammonium, triethylammonium, methylsulfonylamino, furanyl-oxy-sulfamino, and the like.

"Amide" refers to a group such as, —C(═O)NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Sulfonamide" refers to —S(O)$_2$NR'R', wherein each R' is independently selected from H and an optionally substituted: alkyl, heteroalkyl, heteroaryl, heterocycle, alkenyl, alkynyl, arylalkyl, heteroarylalkyl, heterocyclylalkyl, -alkylenecarbonyl-, or alkylene-O—C(O)—OR", where R" is selected from H, alkyl, heteroalkyl, cyclylalkyl, heterocyclyl, aryl, heteroaryl, alkenyl, alkynyl, arylalkyl, heterocycloalkyl, heteroarylalkyl, amino, and sulfinyl.

"Guanidine" refers to —NR'C(═NR')NR'R', wherein each R' is independently selected from H and an optionally substituted: alkyl, cycloalkyl, cycloalkylalkyl, heterocycloalkyl, heterocycloalkylalkyl, aryl, arylalkyl, heteroaryl, and heteroarylalkyl.

"Optional" or "optionally" refers to a described event or circumstance may or may not occur, and that the description includes instances where the event or circumstance occurs and instances where the event or circumstance does not. For example, "optionally substituted alkyl" refers to an alkyl group that may or may not be substituted and that the description encompasses both substituted alkyl group and unsubstituted alkyl group.

"Optionally substituted" as used herein means one or more hydrogen atoms of the group can each be replaced with a substituent atom or group commonly used in pharmaceutical chemistry. Each substituent can be the same or different. Examples of suitable substituents include, but are not limited to, alkyl, alkenyl, alkynyl, cycloalkyl, aryl, arylalkyl, cycloheteroalkyl, heteroaryl, OR (e.g., hydroxyl, alkoxy (e.g., methoxy, ethoxy, and propoxy), aryloxy, heteroaryloxy, arylalkyloxy, ether, ester, carbamate, etc.), hydroxyalkyl, alkoxycarbonyl, alkoxyalkoxy, perhaloalkyl, alkoxyalkyl, SR (e.g., thiol, alkylthio, arylthio, heteroarylthio, arylalkylthio, etc.), S$^+$R'$_2$, S(O)R', SO$_2$R', NR'R" (e.g., primary amine (i.e., NH$_2$), secondary amine, tertiary amine, amide, carbamate, urea, etc.), hydrazide, halo, nitrile, nitro, sulfide, sulfoxide, sulfone, sulfonamide, thiol, carboxy, aldehyde, keto, carboxylic acid, ester, amide, imine, and imide, including seleno and thio derivatives thereof, wherein each of the substituents can be optionally further substituted. In embodiments in which a functional group with an aromatic carbon ring is substituted, such substitutions will typically number less than about 10 substitutions, more preferably about 1 to 5, with about 1 or 2 substitutions being preferred.

"Prodrug" refers to a derivative of an active compound (e.g., drug) that requires a transformation under the conditions of use, such as within the body or appropriate in vitro conditions, to release the active drug. Prodrugs are frequently, but not necessarily, pharmacologically inactive until converted into the active drug. Prodrugs can be obtained by masking a functional group in the drug believed to be in part required for activity with a progroup to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

Various progroups, as well as the resultant promoieties, suitable for masking functional groups in the active drugs to yield prodrugs can be used. For example, a hydroxyl functional group may be masked as a sulfonate, ester or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed, e.g., in vivo or under appropriate in vitro conditions, to provide the amino group. A carboxyl group may be masked as an ester (including silyl esters and thioesters), amide or hydrazide promoiety, which may be hydrolyzed in vivo to provide the carboxyl group. Included within the scope of prodrugs are, among others, "biohydrolyzable carbonate", "biohydrolyzable ureide", "biohydrolyzable carbamate", "biohydrolyzable ester", "biohydrolyzable amide", and "biohydrolyzable phosphate" groups.

"Biohydrolyzable carbonate", "biohydrolyzable ureide" and "biohydrolyzable carbamate" refers to a carbonate, ureide, or carbamate form, respectively, of a drug substance, such as the PKC activating compound of the disclosure, which (a) does not interfere with the biological activity of the parent substance but confers on that substance advantageous properties in vivo such as duration of action, onset of action, and the like, or (b) is biologically inactive but is readily converted in vivo by the subject to the biologically active principle.

"Biohydrolyzable ester" is an ester of a drug substance, such as the PKC activating compounds of the disclosure, which either a) does not interfere with the biological activity of the parent substance but confers on that substance advantageous properties in vivo such as duration of action, onset of action, and the like, or b) is biologically inactive but is readily converted in vivo by the subject to the biologically active principle. Examples include, by way of example, lower alkyl esters, lower acyloxy-alkyl esters, lower alkoxyacyloxyalkyl esters, alkoxyacyloxy esters, alkyl acylamino alkyl esters, and choline esters.

"Biohydrolyzable amide" refers to an amide of a drug substance, such as the PKC activating compounds of the disclosure, which either a) does not interfere with the biological activity of the parent substance but confers on that substance advantageous properties in vivo such as duration of action, onset of action, and the like, or b) is biologically inactive but is readily converted in vivo by the subject to the biologically active principle.

"Solvate" refers to a complex of variable stoichiometry formed by a solute, such as a PKC activator compound, and a solvent. Such solvents are selected to minimally interfere with the biological activity of the solute. Solvents may be, by way of example and not limitation, water, ethanol, or acetic acid.

"Hydrate" refers to a combination of water with a solute, such as a PKC activator compound, wherein the water retains its molecular state as water and is either absorbed, adsorbed or contained within a crystal lattice of the solute (e.g., PKC activating compound).

"Pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure may contain both basic and acidic functionalities that allow the compounds to be converted into either base or acid addition salts. Lists of suitable salts are found in Remington's Pharmaceutical Sciences, 17th Ed., Mack Publishing Company, Easton, Pa., (1985) and Journal of Pharmaceutical Science, 66:2 (1977), each of which is incorporated herein by reference in its entirety.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

5.2. Combination Treatments with Diterpenoid PKC Modulators

Several classes of diterpenoid compounds, including phorbol and ingenol compounds, are known to modulate protein kinase C (PKC) activity. Evidence of overexpression or activation of PKC activity in association with tumor formation or progression in a variety of cancer types has led to development of PKC inhibitors as potential therapeutics for treating different types of cancers (see, e.g., Mullin et al., 2000, Ann. N. Y. Acad. Sci. 915:231-236). However, PKC inhibitors have not shown therapeutic efficacy in clinical trials for oncology indications (see, e.g., Mochly-Rosen et al., 2012, Nature Reviews Drug Discovery 11:937-957; Lam et al., 2010, Am J Clin Oncol. 33(2):121-124). While lack of specificity of the PKC inhibitors could explain their ineffectiveness in treatment of cancers, studies of PKC mutations in various cancers suggest that PKCs act in tumor suppression rather than in tumor formation or progression (Antal et al., 2015, Cell 160:489-502; D'Costa et al., 2006, Oncogene 25:378-386). Consistent with this suggestion is the observation that the phorbol compound prostratin, which is distinguished from some phorbol esters for its non-tumor promoting properties, can repress tumorigenesis in pancreatic cancer cells harboring K-RAS mutations (Wang et al., 2015, Cell 163(5):1237-51). Prostratin has also been shown to inhibit growth of acute myeloid leukemia cells by inducing their cellular differentiation and cell cycle arrest (see, e.g., Shen et al. 2015, Cancer Lett. 356:686-96; D'Costa et al., 2006, Oncogene 25:378-386).

The present disclosure provides combinations of compounds with PKC activating properties, particularly diterpenoid PKC activating compounds, such as prostratin and ingenol compounds, with other chemotherapeutic agents for use in the treatment of cancer. While prostratin in combination with one chemotherapeutic, Ara-C, potentiates cellular differentiation of acute myeloid leukemia cells in vitro (D'Costa et al., 2006, Oncogene 25: 378-386), the present disclosure shows that combinations with various chemotherapeutic compounds have antagonistic effects while other combinations show synergistic effects in inhibiting growth of cancer cells.

In particular, combination of diterpenoid PKC activating compound with an inhibitor targeting a biological component of the PI3K/AKT/mTOR cellular signaling pathway shows synergistic effects in inhibiting cancer cell growth. Moreover, unexpected synergistic effects are observed with an inhibitor of poly(ADP)-ribose polymerase (PARP), an enzyme involved in the cellular response to DNA breaks, and with a therapeutic agent known to induce DNA strand breaks. Without being bound by theory, inhibition of PARP and/or induction of DNA breaks may activate the PI3K/AKT/mTOR signaling pathway, which in part, appears to regulate various mechanisms of DNA repair and cell cycle progression (see, e.g., De et al., 2014, Neoplasia 16(1):43-72; Szanto et al., 2009, Biochemical Pharmacology 77(8): 1348-1357).

In addition, unexpected synergistic effects on inhibiting growth of cancer cells were also observed for diterpenoid PKC activating compounds in combination with Wnt/β-catenin signaling inhibitors, for example Tankyrase (TNKS) and probable protein-cysteine N-palmitoyltransferase (PORCN) inhibitors; smoothened (SMO) inhibitor; src/bcr-abl kinase inhibitor; anti-cancer nucleoside analogs or anti-metabolite (e.g., cytarabine/Ara-C); histone deacetylase (HDAC) inhibitor; Bromodomain and Extra-Terminal motif (BET) inhibitor; all-trans-retinoic acid (ATRA); and Bruton's tyrosine kinase (BTK) inhibitor.

Accordingly, in one aspect, a method of treating cancer comprises administering to a subject in need thereof a therapeutically effective amount of a diterpenoid PKC activator and a therapeutic agent (i.e., a second therapeutic agent) selected from a phosphoinositol-3 kinase (PI3K) inhibitor, AKT inhibitor, mammalian target of rapamycin (mTOR) inhibitor, poly ADP ribose polymerase (PARP) inhibitor, platinum-based anti-cancer compound (PBAC), CBP/β-catenin inhibitor, Tankyrase (TNKS) inhibitor, probable protein-cysteine N-palmitoyltransferase (PORCN) inhibitor, scr kinase/bcr-abl kinase inhibitor, Smoothened inhibitor, anti-cancer nucleoside analog or anti-metabolite, histone deacetylase (HDAC) inhibitor, Bromodomain and Extra-Terminal motif (BET) inhibitor, all-trans-retinoic acid (ATRA), Bruton's tyrosine kinase (BTK) inhibitor, and combinations thereof.

In some embodiments, the second therapeutic agent is a PI3K inhibitor. In some embodiments, the second therapeutic agent is an AKT inhibitor. In some embodiments, the second therapeutic agent is an mTOR inhibitor. In some embodiments, the second therapeutic agent is a PARP inhibitor. In some embodiments, the second therapeutic agent is a PBAC. In some embodiments, the second therapeutic agent is a CBP/β-catenin inhibitor. In some embodiments, the second therapeutic agent is a TNKS inhibitor. In some embodiments, the second therapeutic agent is a PORCN inhibitor. In some embodiments, the second therapeutic agent is a scr kinase or bcr-abl kinase inhibitor. In some embodiments, the second therapeutic agent is a SMO inhibitor. In some embodiments, the second therapeutic agent is an anti-cancer nucleoside analog or anti-metabolite. In some embodiments, the second therapeutic agent is a HDAC inhibitor. In some embodiments, the second therapeutic agent is a BET inhibitor. In some embodiments, the second therapeutic agent is ATRA. In some embodiments, the second therapeutic agent is a BTK inhibitor.

In some embodiments, a method of treating cancer comprises administering to a subject in need thereof a therapeutically effective amount of a PKC activator compound, particularly a diterpenoid PKC activator compound, and a second therapeutic agent, wherein the second therapeutic agent is an inhibitor of PI3K/AKT/mTOR signaling pathway. In some embodiments, a method of treating cancer comprises administering to a subject in need thereof a therapeutically effective amount of a diterpenoid PKC activator compound and one or more of an inhibitor of PI3K/AKT/mTOR signaling pathway. In some embodiments, the inhibitor of PI3K/AKT/mTOR signaling pathway is selected from a PI3K inhibitor, AKT inhibitor, mTOR inhibitor, and combinations thereof. In some embodiments, the inhibitor of PI3K/AKT/mTOR signaling pathway is a PI3K inhibitor. In some embodiments, the inhibitor of PI3K/AKT/mTOR signaling pathway is an AKT inhibitor. In some embodiments, the inhibitor of PI3K/AKT/mTOR signaling pathway is an mTOR inhibitor. In some embodiments, the inhibitor of PI3K/AKT/mTOR signaling pathway is a dual mTORC1/2 inhibitor or a dual PI3K/mTOR inhibitor. In some embodiments, the one or more of an inhibitor of PI3K/AKT/mTOR signaling pathway includes a PI3K inhibitor and mTOR inhibitor. In some embodiments, the one or more of an inhibitor of PI3K/AKT/mTOR signaling pathway includes an AKT inhibitor and mTOR inhibitor. In some embodiments, the one or more of an inhibitor of PI3K/AKT/mTOR signaling pathway includes a PI3K inhibitor and AKT inhibitor. In some embodiments, the one or more of an inhibitor of PI3K/AKT/mTOR signaling pathway includes a PI3K inhibitor, AKT inhibitor and mTOR inhibitor.

In some embodiments of the combination therapy using an inhibitor of the PI3K/AKT/mTOR signaling pathway, the method further comprises administering a therapeutically effective amount of a PARP inhibitor. In some embodiments of the combination therapy using an inhibitor of the PI3K/AKT/mTOR signaling pathway, the method further comprises administering a therapeutically effective amount of a PBAC. In some embodiments of the combination therapy using an inhibitor of the PI3K/AKT/mTOR signaling pathway, the method further comprises administering a therapeutically effective amount of a PARP inhibitor and PBAC.

In some embodiments, a method of treating cancer comprises administering to a subject in need thereof a therapeutically effective amount of a diterpenoid PKC activator and a second therapeutic agent, wherein the second therapeutic agent is an inhibitor of Wnt/β-catenin signaling pathway. In some embodiments, a method of treating cancer comprises administering to a subject in need thereof a therapeutically effective amount of a diterpenoid PKC activator and one or more of an inhibitor of Wnt/β-catenin signaling pathway. In some embodiments, the inhibitor of Wnt/β-catenin signaling pathway is selected from a CBP/β-catenin inhibitor, TNKS inhibitor, PORCN inhibitor, and combinations thereof. In some embodiments, the one or more inhibitor of Wnt/β-catenin signaling pathway includes a CBP/β-catenin inhibitor. In some embodiments, the one or more inhibitor of Wnt/β-catenin pathway includes a TNKS inhibitor. In some embodiments, the one or more inhibitor of Wnt/β-catenin signaling pathway includes a PORCN inhibitor. In some embodiments, the one or more inhibitor of Wnt/β-catenin signaling pathway includes a CBP/β-catenin inhibitor and PORCN inhibitor. In some embodiments, the one or more inhibitor of Wnt/β-catenin signaling pathway includes a CBP/β-catenin inhibitor and TNKS inhibitor. In some embodiments, the one or more inhibitor of Wnt/β-catenin signaling pathway includes a TNKS inhibitor and PORCN inhibitor. In some embodiments, the one or more inhibitor of Wnt/β-catenin signaling pathway includes a CBP/β-catenin inhibitor, TNKS inhibitor and PORCN inhibitor.

In some embodiments, the method of treating cancer using an inhibitor of Wnt/β-catenin signaling pathway further comprises administering a therapeutically effective amount of a PBAC, i.e., combination of diterpenoid PKC activator, inhibitor of Wnt/β-catenin signaling pathway, and a PBAC. In some embodiments, the combination treatment comprises a diterpenoid PKC activator, TNKS inhibitor, and PBAC. In some embodiments, the combination treatment comprises a diterpenoid PKC activator, PORCN inhibitor, and PBAC.

In some embodiments, the method of treating cancer using an inhibitor of Wnt/β-catenin signaling pathway further comprises administering a therapeutically effective amount of a PARP inhibitor, i.e., combination of diterpenoid PKC activator, inhibitor of Wnt/β-catenin signaling pathway, and PARP inhibitor. In some embodiments, the combination treatment comprises a diterpenoid PKC activator, TNKS inhibitor, and PARP inhibitor. In some embodiments, the combination treatment comprises a diterpenoid PKC activator, PORCN inhibitor, and PARP inhibitor.

In some embodiments, the method of treating cancer using an inhibitor of Wnt/β-catenin signaling pathway further comprises administering a therapeutically effective amount of a PARP inhibitor and PBAC, i.e., combination of diterpenoid PKC activator, inhibitor of Wnt/β-catenin signaling pathway, PARP inhibitor, and PBAC. In some embodiments, the combination treatment comprises a diterpenoid PKC activator, TNKS inhibitor, PARP inhibitor, and PBAC. In some embodiments, the combination treatment comprises a diterpenoid PKC activator, PORCN inhibitor, PARP inhibitor, and PBAC.

In some embodiments, the method of treating cancer comprises administering to a subject in need thereof a therapeutically effective amount of a diterpenoid PKC activator and a PARP inhibitor or PBAC. In some embodiments, the method of treating cancer comprises administering to a subject in need thereof a therapeutically effective amount of a diterpenoid PKC activator and a PARP inhibitor. In some embodiments, the method of treating cancer comprises administering to a subject in need thereof a therapeutically effective amount of a diterpenoid PKC activator and a PBAC, such as cisplatin or oxaliplatin. As noted above, PARP inhibitor and PBAC have in common the formation of DNA strand breaks. Thus, in some embodiments, a method of treating cancer comprises administering to a subject in need thereof a therapeutically effective amount of a diterpenoid PKC activator, PARP inhibitor and PBAC.

In some embodiments, a method of treating cancer comprises administering to a subject in need thereof a therapeutically effective amount of a diterpenoid PKC activator and a src kinase or bcr-abl kinase inhibitor. In some embodiments, a method of treating cancer comprises administering to a subject in need thereof a therapeutically effective amount of a diterpenoid PKC activator and a src kinase inhibitor. In some embodiments, a method of treating cancer comprises administering to a subject in need thereof a therapeutically effective amount of a diterpenoid PKC activator and a bcr-abl kinase inhibitor.

In some embodiments, a method of treating cancer comprises administering to a subject in need thereof a therapeutically effective amount of a diterpenoid PKC activator and a SMO inhibitor. SMO inhibition can attenuate or inhibit the downstream activation of GLI transcription factors, leading to suppression of those genes associated with cancer growth and progression, and may work in concert with PKC activation.

For the foregoing methods, various therapeutic agents that act on the specified biological target can be used in the combination treatment. In some embodiments, the PI3K inhibitor is selected from 5-[2,6-Di(4-morpholinyl)-4-pyrimidinyl]-4-(trifluoromethyl)-2-pyridinamine (i.e., BKM-120), idelalisib, pictilisib, duvelisib, pilaralisib, alpelisib, copanlisib, 2-amino-8-[4-(2-hydroxyethoxy)cyclohexyl]-6-(6-methoxypyridin-3-yl)-4-methylpyrido[2,3-d]pyrimidin-7-one (PF-04691502), N-{(s)-1-[7-Fluoro-2-(Pyridin-2-Y1)quinolin-3-Y1]ethyl}-9h-Purin-6-Amine (i.e., VCAMG319), 8-[(1R)-1-(3,5-difluoroanilino)ethyl]-N,N-dimethyl-2-morpholin-4-yl-4-oxochromene-6-carboxamide (i.e., AZD8186), 2-methyl-1-[[2-methyl-3-(trifluoromethyl)phenyl]methyl]-6-morpholin-4-ylbenzimidazole-4-carboxylic acid (i.e., GSK2636771), quercetin, and combinations thereof. In some embodiments, the PI3K inhibitor is a pan PI3K inhibitor. In some embodiments, the PI3K inhibitor is an isoform-specific PI3K inhibitor, such as a PI3K delta inhibitor. Other PI3K inhibitors are described in, among others, patent publications U.S. Pat. Nos. 6,608,053, 7,691,888, 7,888,344, 8,053,574, 8,242,116, 8,802,866, 8,895,559, 8,940,752, 9,150,579, US20130090323, US20140080810, and WO2015083008, all of which are incorporated herein by reference.

In some embodiments herein, the PI3K inhibitor or mTOR inhibitor is a dual PI3K/mTOR inhibitor, which refers to a compound inhibiting or attenuating activity of both PI3K and mTOR. In some embodiments, the dual PI3K/mTOR inhibitor is selected from voxtalisib, dactolisib, gedatolisib, apitolisib, 5-(9-Isopropyl-8-methyl-2-morpholino-9H-purin-6-yl)pyrimidin-2-amine (i.e., VS-5584), 2-methyl-2-(4-(3-methyl-2-oxo-8-(quinolin-3-yl)-2,3-dihydro-1H-imidazo[4,5-c]quinolin-1-yl)phenyl)propanenitrile (i.e., NVP-BEZ235); and combinations thereof. Other dual PI3K/mTOR inhibitors are described in, among others, patent publicatons US2010068204, US2011178070, US20140066431, US2014080810, US2014066431, US2014107100, U.S. Pat. Nos. 8,097,622, 8,101,622, 8,440,829, 8,450,329, 8,791,131, 8,921,361, 9,315,491, 9,284,334, 9,475,812, and 9,556,203, as well as in publications such as Welker et al., 2013, Bioorg Med Chem. 21(14): 4063-4091; and Raynaud, et al., (2007), Cancer Res. 67: 5840-5850; all of which are incorporated herein by reference.

In some embodiments herein, the AKT inhibitor is selected from perifosine, miltefosine, ipatasertib, 8-[4-(1-aminocyclobutyl)phenyl]-9-phenyl-2H-[1,2,4]triazolo[3,4-f][1,6]naphthyridin-3-one (i.e., MK2206), 4-amino-N-[(1S)-1-(4-chlorophenyl)-3-hydroxypropyl]-1-(7H-pyrrolo[2,3-d]pyrimidin-4-yl)piperidine-4-carboxamide (i.e., AZD5363), afuresertib, N-[(2S)-1-amino-3-(3,4-difluorophenyl)propan-2-yl]-5-chloro-4-(4-chloro-2-methylpyrazol-3-yl)furan-2-carboxamide (i.e., GSK2141795), S)-4-(2-(4-Amino-1,2,5-oxadiazol-3-yl)-1-ethyl-7-(piperidin-3-ylmethoxy)-1H-imidazo[4,5-c]pyridin-4-yl)-2-methylbut-3-yn-2-ol (i.e., GSK690693), 7-benzyl-4-(2-methylbenzyl)-1,2,6,7,8,9-hexahydroimidazo[1,2-A]pyrido[3,4-E]pyrimidin-5(4H)-one (i.e., TIC10), and combinations thereof. Other AKT inhibitors are described in, among others, patent publicatons US20120309739, US2013065908, US2015051217, U.S. Pat. Nos. 7,576,209, 7,998,977, 8,003,651, 8,273,782, 8,329,701, 8,377,937, 8,618,097, 8,822,524, 8,853,216, 9,156,853, 9,303,040, WO07076704, and WO15144021, all of which are incorporated herein by reference.

In some embodiments herein, the mTOR inhibitor is selected from sirolimus, everolimus, temsirolimus, tacrolimus, ridaforolimus, ridaforolimus, dactolisib and other rapamycin analogs. In some embodiments, the mTOR inhibitor is a dual mTORC1/mTORC2 inhibitor, which refers to a compound which inhibits or attenuates the activity of mTORC1 and mTORC2. In some embodiments, the dual mTORC1/mTORC2 inhibitor is selected from [5-[2-[(2R,6S)-2,6-dimethylmorpholin-4-yl]-4-morpholin-4-ylpyrido[2,3-d]pyrimidin-7-yl]-2-methoxyphenyl]methanol (i.e., Ku-0063794), [5-[2,4-bis[(3 S)-3-methylmorpholin-4-yl]pyrido[2,3-d]pyrimidin-7-yl]-2-methoxyphenyl]methanol (i.e., AZD8055), and 9-(6-aminopyridin-3-yl)-1-[3-(trifluoromethyl)phenyl]benzo[h][1,6]naphthyridin-2-one (Torin 2). In some embodiments, the mTOR inhibitor is a dual PI3K/mTOR inhibitor described above. Other mTOR inhibitors are described in, among others, patent publications US20160244424, US2015368274, US2015051242, U.S. Pat. Nos. 7,700,594, 8,557,814, 8,110,578, and 9,242,993, all of which are incorporated herein by reference.

In some embodiments herein, the PARP inhibitor is selected from olaparib, veliparib, rucaparib, iniparib, talazoparib, niraparib, E7016, BGB-290 and combinations thereof. Other PARP inhibitors are described in, among others, patent publications U.S. Pat. Nos. 5,756,510, 6,495,541, 7,781,596, 6,509,365, 6,903,098, 7,122,679, 7,268,138, 7,351,701, 7,449,464, 7,652,014, 7,692,006, 7,803,795, 7,875,621, 7,879,857, 7,928,104, 8,071,623, 8,080,557, 8,299,090, 9,273,052, 9,290,460, 9,062,061, 9,255,106, and WO15154630, all of which are incorporated herein by reference.

In some embodiments herein, the PBAC is selected from cisplatin, carboplatin, oxaliplatin, dicycloplatin, nedaplatin, lobaplatin, heptaplatin, phenathriplatin, phosphaplatin, LA-12, and combinations thereof.

In some embodiments herein, the CBP/β-catenin inhibitor is selected from (6S,9aS)-Hexahydro-6-[(4-hydroxyphenyl)methyl]-8-(1-naphthalenylmethyl)-4,7-dioxo-N-(phenylmethyl)-2H-pyrazino[1,2-a]pyrimidine-1(6H)-carboxamide (i.e., ICG-001); (6S,9aS)—N-benzyl-6-(4-hydroxybenzyl)-8-(naphthalen-1-ylmethyl)-4,7-dioxooctahydro-1H-pyrazino[1,2-a]pyrimidine-1-carboxamide (i.e., PRI-724); and combinations thereof. Other CBP/β-catenin inhibitor are described in, among others, patent publications US2015274751, WO2013052162, and WO16141312, all of which are incorporated herein by reference.

In some embodiments herein, the TNKS inhibitor is selected from 2-[4-(trifluoromethyl)phenyl]-1,5,7,8-tetrahydrothiopyrano[4,3-d]pyrimidin-4-one (i.e., XAV-939); 4-yl]methylcarbamoyl]phenyl]furan-2-carboxamide (i.e., JW55); 4-(5-((E)-2-(4-(2-Chlorophenyl)-5-(5-(methylsulfonyl)pyridin-2-yl)-4H-1,2,4-triazol-3-yl)ethenyl)-1,3,4-oxadiazol-2-yl)benzonitrile (i.e., G007-LK), and combinations thereof. Other TNKS inhibitors are described in, among others, patent publications GB201615282, US2013345215, US20140121231, US2014121231, U.S. Pat. Nos. 8,722,661, 8,841,299, 9,120,805, 9,163,003, 9,174,995, 9,181,266, 9,227,982, 9,339,503, 9,340,549, 9,376,433, 9,388,142, 9,416,133, 9,505,749, WO2013177349, WO2013182546 WO2014045101, WO2014206524, WO2014087165, WO2015014442, WO2015018475, WO2015069512, WO2015096884, WO2015169421, and WO2016179066, as well as publications Lau et al., Cancer Res. 73(10):3132-3144; Scarborough et al., 2016, Clin Cancer Res. CCR-16-1179; and Okada-Iwasaki et al., 2016, Mol Cancer Ther. 15(7): 1525-34; all of which are incorporated herein by reference.

In some embodiments herein, the PORCN inhibitor is selected from 2-[5-methyl-6-(2-methylpyridin-4-yl)pyridin-3-yl]-N-(5-pyrazin-2-ylpyridin-2-yl)acetamide (i.e., LGK-974); 2-(1,3-dimethyl-2,6-dioxopurin-7-yl)-N-(6-phenylpyridazin-3-yl)acetamide (i.e., ETC-159), and combinations thereof. Other PORCN inhibitors are described in, among others, patent publications US2016115177, US2016090386, WO/2010/101849, WO2016055786, and WO2016055790, as well as in publications such as Duraiswamy et al., 2015, J. Med. Chem. 58 (15):5889-5899; You et al., 2016, Bioorg Med Chem Lett. 26(24):5891-5895; and Boone et al., 2016, Lab Invest. 96(2):249-59; all of which are incorporated herein by reference.

In some embodiments herein, the src inhibitor/bcr-abl inhibitor is selected from staurosporine, nilotinib, imatinib, ponatinib, saracatinib, dasatinib, bosutinib, saracatinib, N-benzyl-2-[5-[4-(2-morpholin-4-ylethoxy)phenyl]pyridin-2-yl]acetamide (i.e., KX2-391), and combinations thereof. Other src/bcr-abl inhibitors are described in, among others, patent publications US2003207873, US2010099710, US2011112110, U.S. Pat. Nos. 5,869,485, 6,337,335, 6,054,470, 6,596,746, 7,153,856, 6,506,769, 6,689,778, 7,163,941, 7,285,556, 7,381,730, 7,494,997, 7,091,345, 7,417,148, 7,462,623, 7,491,725, 7,528,142, 7,534,797, 7,728,131, 7,910,598, 8,119,649, 8,114,874, 8,546,399, 8,580,815, 8,658,659, 8,895,744, 8,921,336, 9,255,107, 9,522,881, WO2015074135, and WO2016165205, all of which are incorporated herein by reference.

In some embodiments, the SMO inhibitor is selected from cyclopamine, vismodegib, glasdegib, SANT-1, sonidegib, saridegib, taladegib, N-[2-methyl-5-(methylaminomethyl)phenyl]-4-[(4-phenylquinazolin-2-yl)amino]benzamide (i.e., BMS-833923), and 2-[5-[(2R)-4-(6-benzyl-4,5-dimethylpyridazin-3-yl)-2-methylpiperazin-1-yl]pyrazin-2-yl]propan-2-ol (i.e., LEQ506). Other SMO inhibitors are described in, among others, patent publications US2013274233, U.S. Pat. Nos. 7,812,164, 8,778,927, 8,486,936, 9,174,949, 9,579,319, WO2011014888, and WO13110358, all of which are incorporated herein by reference.

In some embodiments, a method of treating cancer comprises administering to a subject in need thereof a therapeutically effective amount of a diterpenoid PKC activator and a second therapeutic agent selected from an anti-cancer nucleoside analog, anti-metabolite, histone deacetylase (HDAC) inhibitor, Bromodomain and Extra-Terminal motif (BET) inhibitor, all-trans-retinoic acid (ATRA), microtubule inhibitor, Bruton's tyrosine kinase (BTK) inhibitor, epidermal growth factor (EGFR) inhibitor, proteasome inhibitor, and combinations thereof. Some of the foregoing therapeutic compounds display synergism in combination with PKC activating compound in certain cancer cell lines, particularly hematologic cancer cell lines, such as leukemia and lymphoma cells.

In some embodiments, a method of treating cancer comprises administering to a subject in need thereof a therapeutically effective amount of a diterpenoid PKC activator and an anti-cancer nucleoside analog and/or anti-metabolite. In some embodiments, the combination of a diterpenoid PKC activator and an anti-cancer nucleoside analog and/or anti-metabolite is used to treat a hematologic cancer, such as a leukemia or lymphoma. In some embodiments, the anti-cancer nucleoside analog or anti-metabolite is selected from gemcitabine, capecitabine, cytarabine, azacitidine, azathioprine, hydroxyurea, methotrexate, thioguanine, 5-fluorouracil (5-FU), and combinations thereof. In some embodiments, the nucleoside analog and/or anti-metabolite is not cytarabine.

In some embodiments, a method of treating cancer comprises administering to a subject in need thereof a therapeutically effective amount of a diterpenoid PKC activator and a Bromodomain and Extra-Terminal motif (BET) inhibitor. In some embodiments, the combination of a diterpenoid PKC activator and a BET inhibitor is used to treat a hematologic cancer, such as a leukemia or lymphoma. In some embodiments, the BET inhibitor is an inhibitor of one or more of BET proteins BRD2, BRD3, BRD4, and BRDT. In some embodiments, the BET inhibitor is selected from tert-butyl 2-(4-(4-chlorophenyl)-2,3,9-triMethyl-6H-thieno[3,2-f][1,2,4]triazolo[4,3-a][1,4]diazepin-6-yl)acetate (i.e., (±) JQ1); 7-(3,5-dimethyl-1,2-oxazol-4-yl)-8-methoxy-1-[(1R)-1-pyridin-2-ylethyl]-3H-imidazo[4,5-c]quinolin-2-one (i.e., GSK1210151A; I-BET151); 2-[(4S)-6-(4-chlorophenyl)-8-methoxy-1-methyl-4H-[1,2,4]triazolo[4,3-a][1,4]benzodiazepin-4-yl]-N-ethylacetamide (i.e., GSK525762; I-BET 762); (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide (i.e., birabresib; OTX-015); TEN-010; 2-(4-(4-chlorophenyl)-2,3,9-trimethyl-6h-thieno[3,2-f][1,2,4]triazolo[4,3-a][1,4]diazepin-6-yl)acetamide (i.e., CPI-203); 2-[(4S)-6-(4-chlorophenyl)-1-methyl-4H-[1,2]oxazolo[5,4-d][2]benzazepin-4-yl]acetamide (i.e., CPI-0610); olinone; 2-(4-(2-Hydroxyethoxy)-3,5-dimethylphenyl)-5,7-dimethoxyquinazolin-4(3H)-one (i.e., RVX-208); 2-(4-Morpholinyl)-8-phenyl-4H-1-benzopyran-4-one; 2-morpholino-8-phenyl-4H-chromen-4-one (i.e., LY294002) and combinations thereof.

In some embodiments, a method of treating cancer comprises administering to a subject in need thereof a therapeutically effective amount of a diterpenoid PKC activator and a HDAC inhibitor. In some embodiments, the combination of a diterpenoid PKC activator and a HDAC inhibitor is used to treat a hematologic cancer, such as a leukemia or lymphoma. In some embodiments, the HDAC inhibitor is selected from vorinostat (SAHA), entinostat, panobinostat, mocetinostat, belinostat, romidepsin, rocilinostat, abexinostat, resminostat, givinostat, quisinostat, pracinostat, kevetrin, 7-[4-(3-ethynylanilino)-7-methoxyquinazolin-6-yl]oxy-N-hydroxyheptanamide (i.e., CUDC-101), (E)-N-(2-aminophenyl)-3-[1-[4-(1-methylpyrazol-4-yl)phenyl]sulfonylpyrrol-3-yl]prop-2-enamide; 4-methylbenzenesulfonic acid (i.e., 4SC-202), valproic acid, and combinations thereof.

In some embodiments, a method of treating cancer comprises administering to a subject in need thereof a therapeutically effective amount of a diterpenoid PKC activator and ATRA. In some embodiments, the combination of a diterpenoid PKC activator and ATRA is used to treat a hematologic cancer, such as a leukemia or lymphoma.

In some embodiments, a method of treating cancer comprises administering to a subject in need thereof a therapeutically effective amount of a diterpenoid PKC activator and a BTK inhibitor. In some embodiments, the combination of a diterpenoid PKC activator and a BTK inhibitor is used to treat a hematologic cancer, such as a leukemia or lymphoma. In some embodiments, the BTK inhibitor is selected from ibrutinib; spebrutinib (CC-292; AVL-292); 4-[4-[[5-fluoro-4-[3-(prop-2-enoylamino)anilino]pyrimidin-2-yl]amino]phenoxy]-N-methylpyridine-2-carboxamide (i.e., CNX-774); 6-cyclopropyl-8-fluoro-2-[2-(hydroxymethyl)-3-[1-methyl-5-[[5-(4-methylpiperazin-1-yl)pyridin-2-yl]amino]-6-oxopyridin-3-yl]phenyl]isoquinolin-1-one (i.e., RN486); (Z)-2-cyano-N-(2,5-dibromophenyl)-3-hydroxybut-2-enamide (i.e., LFM-A13); acalabrutinib (i.e., ACP-196); 4-tert-butyl-N-[2-methyl-3-[4-methyl-6-[4-(morpholine-4-carbonyl)anilino]-5-oxopyrazin-2-yl]phenyl]benzamide (i.e., CGI1746); and combinations thereof.

In some embodiments, a method of treating cancer comprises administering to a subject in need thereof a therapeutically effective amount of a diterpenoid PKC activator and a microtubule inhibitor. Microtubule inhibitors can be selected from taxanes, vinca alkyloids, colchicines, podophyllotoxins, and griseofulvins. In some embodiments, the microtubule inhibitor is selected from paclitaxel, docetaxel, vinblastine, vincristine, vindesine, vinorelbine, colchicine, griseofulvin, and combinations thereof.

In some embodiments, a method of treating cancer comprises administering to a subject in need thereof a therapeutically effective amount of a diterpenoid PKC activator and an epidermal growth factor (EGFR) receptor inhibitor, including inhibitor of EGFR, HER2, HER3, and/or HER4. In some embodiments, the EGFR receptor inhibitor is selected from trastuzumab, pertuzumab, ado-trastuzumab emtansine, cetuximab, panitumumab, nimotuzuma, mAb806, rrindopepimut, lapatinib, erlotinib, gefitinib, afatinib, neratinib, osimertinib, rociletinib, canertinib, dacomitinib, 2-[4-[4-(3-chloro-2-fluoroanilino)-7-methoxyquinazolin-6-yl]oxypiperidin-1-yl]-N-methylacetamide (i.e., AZD8931), and combinations thereof.

In some embodiments, a method of treating cancer comprises administering to a subject in need thereof a therapeutically effective amount of a diterpenoid PKC activator and proteasome inhibitor. In some embodiments, the proteasome inhibitor is selected from carfilzomib, bortezomib, ixazomib, oprozomib, and combinations thereof.

In the combination treatments herein, compounds with PKC activating properties can be used. Preferably, the PKC activating compound is a diterpenoid PKC activating compound. In some embodiments, the diterpenoid PKC activating compound or diterpenoid PKC activator is capable of activating the activity of one or more of the PKC isoforms, including isoforms selected from PKC $\alpha$, $\beta$, $\gamma$, $\delta$, $\epsilon$, $\eta$, $\theta$, $\iota/\lambda$, $\mu$, and $\zeta$. In some embodiments, the PKC activating compound is capable of activating PKC$\alpha$. In some embodiments, the PKC activating compound is capable of activating PKC$\zeta$. In some embodiments, the PKC activating compound is capable of activating PKC$\gamma$. In some embodiments, the PKC activating compound is capable of activating PKC$\delta$. In some embodiments, the PKC activating compound is capable of activating PKC$\epsilon$. In some embodiments, the PKC activating compound is capable of activating PKC$\eta$. In some embodiments, the PKC activating compound is capable of activating PKC$\theta$. In some embodiments, the PKC activating compound is capable of activating PKC$\iota/\lambda$. In some embodiments, the PKC activating compound is capable of activating PKC$\mu$. In some embodiments, the PKC activating compound is capable of activating PKC$\zeta$.

Classes of diterpenoid compounds capable of modulating PKC activity include tigliane (e.g., phorbol, deoxyphorbol, etc.), ingenane (e.g., ingenol), daphnane, and lathyrane diterpenoids. In some embodiments, the PKC activator for use in the methods herein include PKC activating phorbol, deoxyphorbol, ingenol, daphnane, and lathyrane compounds, including enantiomers, derivatives, analogs, and prodrugs thereof, and salts, hydrates, and solvates thereof. See, e.g., Duran-Pena et al., 2014, The Royal Society of Chemistry, Electronic Supplementary Material (ESI) for Natural Product Reports S1-2-38; incorporated herein by reference).

The phorbol class of PKC activating compounds comprise a partial structure of formula A:

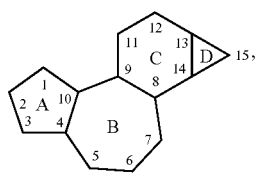

A

In some embodiments, the bond between carbon atoms 5 and 6, carbon atoms 6 and 7, and carbon atoms 1 and 2, are each independently a double bond, as illustrated in formula A1 and A2, below. In some embodiments, carbon atoms 5 and 6 or carbon atoms 6 and 7 are bonded to a common oxygen atom to form an epoxide, as illustrated in formula A3 and A4.

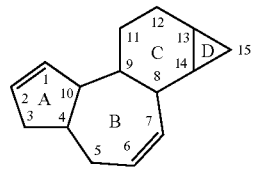

A1

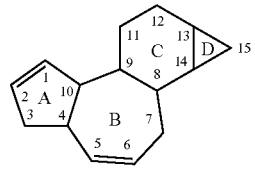

A2

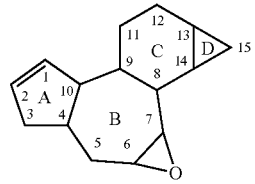

A3

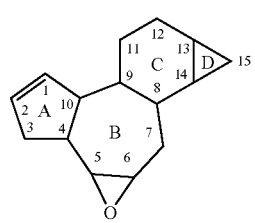

A4

In various embodiments, substituents can be present on one or more of carbon atoms 2, 3, 4, 5, 6, 7, 9, 11, 12, 13, 14, and 15 of formula A, particularly of formula A1, A2, A3 or A4. PKC activating phorbol compounds and derivatives, analogs, and prodrugs thereof, and methods of their synthesis are described in, among others, U.S. Pat. Nos. 4,716,179; 5,145,842; 6,268,395; Kawamura et al., 2016, "Nineteen-step total synthesis of (+)-phorbol," Nature 532:90; Duran-Pena et al., 2014, Natural Product Reports 31:940-952; Shi et al., 2008, Chem. Rev. 108:4295-4327; all of which are incorporated herein by reference.

Deoxyphorbols comprise a partial structure of formula A, particularly the partial structures of formula A1, A2, A3 or A4, except that the carbon atom at position 12 of the structural formula is unsubstituted (i.e., H). In some embodiments, substituents can be present on one or more of carbon atoms 2, 3, 4, 5, 6, 7, 9, 11, 13, 14, and 15 of formula A, particularly of formula A1, A2, A3 or A4 where the PKC activating compound is deoxy at carbon atom 12. PKC activating deoxyphorbol compounds and derivatives, analogs, and prodrugs thereof, and methods of their synthesis are described in among others, U.S. Pat. Nos. 6,432,452; 8,022,103, 8,067,632; 8,431,612; 8,536,378; 8,816,122; US 20090187046; US 20110014699; US 20120101283; US2011/0224297; Wender, et al., 2008, "Practical Synthesis of Prostratin, DPP, and Their Analogs, Adjuvant Leads Against Latent HIV," Science. 320(5876):649-652; Beans et al., 2013, "Highly potent, synthetically accessible prostratin analogs induce latent HIV expression in vitro and ex vivo," Proc Natl Acad Sci USA 110(29):11698-11703; Tsai et al., 2016, "Isolation of Phorbol Esters from Euphorbia grandicornis and Evaluation of Protein Kinase C- and Human Platelet-Activating Effects of Euphorbiaceae Diterpenes," J Nat Prod. 79(10):2658-2666; Duran-Pena et al., 2014, Natural Product Reports 31:940-952; Shi et al., 2008, Chem. Rev. 108:4295-4327; all publications incorporated herein by reference.

In some embodiments, the tigliane class of PKC activating compounds (e.g., phorbol and deoxyphorbol) have an alkyl (e.g., methyl) at carbon atoms 2, 11, and 15, and an optionally substituted alkyl, e.g., methyl or methylene at carbon atom 6. As will be understood by the skilled artisan, the numbering of the carbon atoms for such structures can use the following:

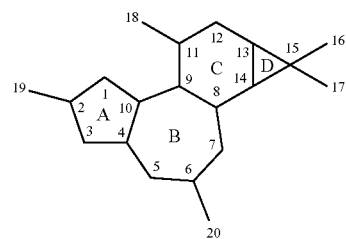

In some embodiments, the diterpenoid PKC activating compound is an ingenane or ingenol class of PKC modulating compounds. These compounds comprise a partial structure of formula B:

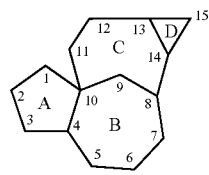

B

In some embodiments, the bond between carbon atoms 6 and 7 and carbon atoms 1 and 2 are each independently a double bond, as illustrated in formula B1 below. In some embodiments, carbon atom 9 is bonded to an oxygen atom to form a carbonyl, as illustrated in formula B2. In some embodiments, carbon atoms 6 and 7 are bonded to a common oxygen atom to form an epoxide, as illustrated in formula B3. In some embodiments, substituents can be present on one or more carbon atoms 2, 3, 4, 5, 6, 7, 9, 11, 12, 13, 14 and 15 of formula B, particularly of formula B1, B2 and B3.

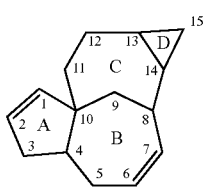

B1

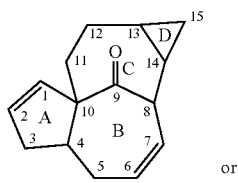

B2 or

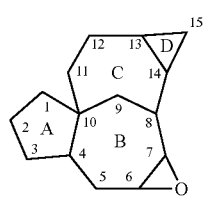

B3

Ingenol compounds and derivatives, analogs, and prodrugs thereof, and methods of their synthesis are described in among others, U.S. Pat. Nos. 6,432,452; 8,022,103; 8,106,092; 8,431,612; 8,901,356; 9,102,687; US 20080069809; US 2010204318; US 20130324600; US 20130331446; US 20140371311; US 20150175622; WO20130182688; WO2014066967; Jorgensen et al., 2013, "14-Step Synthesis of (+)-Ingenol from (+)-3-Carene," Science 341(6148):878-882; McKerral et al., 2014, "Development of a Concise Synthesis of (+)-Ingenol," J. Am Chem Soc. 136 (15):5799-5810; Liang et al., 2013, Bioorg Med Chem Lett. 23:5624-5629; Grue-Sorensen et al., 2014, "Synthesis, biological evaluation and SAR of 3-benzoates of ingenol for treatment of actinic keratosis and non-melanoma skin cancer," Bioorg Med Chem Lett. 24:54-60; Duran-Pena et al., 2014, Natural Product Reports 31:940-952; Shi et al., 2008, Chem. Rev. 108:4295-4327; and Yang et al., 2014, Fitoterapia 97:211-218; all of which are incorporated herein by reference.

In some embodiments, the ingenane class of PKC activating compounds (e.g., ingenols) have an alkyl (e.g., methyl) at carbon atoms 2, 11, and 15, and an optionally substituted alkyl, e.g., methyl or methylene at carbon atom 6. As will be understood by the skilled artisan, the numbering of the carbon atoms for such structures can use the following:

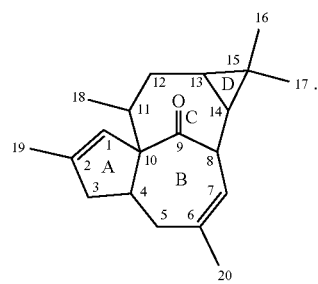

In some embodiments, the diterpenoid PKC activating compound is a daphnane class of PKC modulating compounds. These compounds comprise a partial structure of formula C:

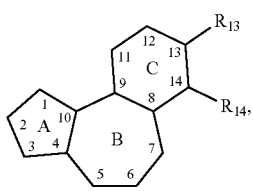

wherein one of $R_{13}$ and $R_{14}$ is an optionally substituted lower alkenyl of structure:

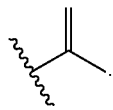

The daphnane class of diterpenoid PKC modulators constitutes a diverse group of compounds. In some embodiments, the bond between carbon atoms 6 and 7 and the bond between carbon atoms 1 and 2 are each independently a double bond, as illustrated in formula C1 and C3 below. In some embodiments, the carbon atoms 6 and 7 are bonded to a common oxygen atom to form an epoxide, as illustrated in formula C2 and C4.

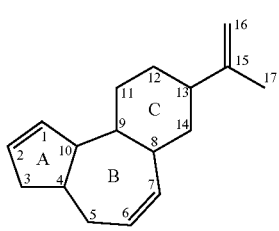

C1

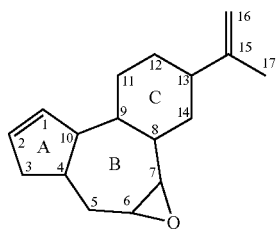

C2

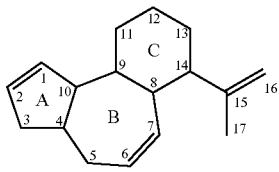

C3

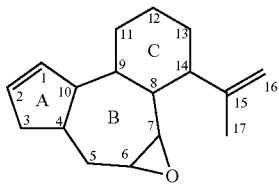

C4

In some embodiments, substituents can be present on one or more carbon atoms 1, 2, 3, 4, 5, 6, 7, 9, 12, 13, and 14 of formula C, and additionally at carbon atom 17 for compounds of formula C1, C2, C3 and C4. Exemplary daphnane diterpenoid PKC activators include, among others, GD-1, yuanhuacine, mezerein, sapintoxin D, thymeleatoxin A, simplexin, gnidimacrin, pimelea factor S7, geniididin, geniditrin and gnidilatin. Daphnane PKC activating compounds, and derivatives and analogs thereof, are described in among others, U.S. Pat. No. 5,145,842; Wender et al., 2011, Nat Chem. 3(8):615-619; Yoshida et al., 1996, Int J Cancer 66(2):268-73; and Brooks et al., 1989, Carcinogenesis 10(2):283-8; all publications incorporated herein by reference.

In some embodiments, the diterpenoid PKC activating compound is a lathyrane class of PKC modulating compounds. These compounds comprise a partial structure of formula D:

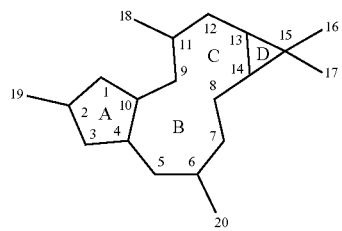

The lathyrane class of diterpenoid PKC modulators constitutes a diverse group of compounds. Some embodiments are shown in Formula D1-D5. Exemplary lathyrane diterpenoid PKC activators include Latilagascenes, jolkinol B, Euphorbia factors, japodagrol, and euphohelioscopin A (Duran-Pena et al., 2014, Natural Product Reports 31:940-952; Shi et al., 2008, Chem. Rev. 108:4295-4327; de Lichtervelde et al., 2012, Chemistry & Biology 19:994-1000; all publications incorporated herein by reference).

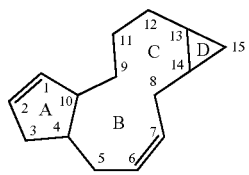

D1

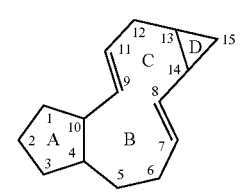

D2

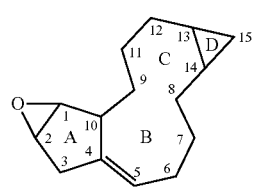

D3

D4

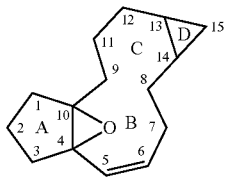

D5

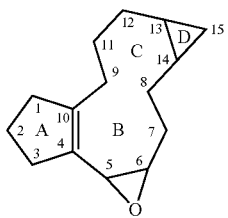

In some embodiments, the PKC activating tigliane, ingenane, daphnane or lathyrane compound for use in the methods herein is a non-tumor promoting tigliane, ingenane, daphnane or lathyrane diterpenoid compound. "Tumor promoting" refers to the ability of a compound to promote tumorigenesis, while a "non-tumor promoting" characteristic refers to the absence or insignificant activity in promoting tumorigenesis.

In some embodiments, the PKC activating tigliane, ingenane, daphnane or lathyrane compound for use in the methods does not significantly down-regulate expression of PKC protein. While many tigliane, ingenane, daphnane and lathyrane diterpenoids have PKC activating activity, some of the compounds also down-regulate expression of PKC protein. In some instances, this down-regulation could reduce or negate the advantageous effects of PKC activation. For example, PKC activating compounds that have tumor-promoting properties, such as 12-O-Tetradecanoylphorbol-13-acetate (TPA), also known as phorbol 12-myristate 13-acetate (PMA), have been shown to down-regulate PKC expression following extended exposure of cells to the compound (see, e.g., Lu et al., Mol Cell Biol., 17(6):3418-3428). In some embodiments, PKC activating tigliane, ingenane, daphnane or lathyrane compound can be selected for low or minimal PKC down-regulating characteristics. In some embodiments, PKC activating compounds are selected which does not downregulate PKC activity by more than 20%, 30%, 40%, 50%, 60%, or 70% of activity present in the absence of the PKC activating compound. In some embodiments, the down-regulation (or absence of down-regulation) is for global PKC expression. In some embodiments, the down-regulation is with respect to one or more of PKC isoforms selected from PKC α, β, γ, δ, ε, η, θ, ι/λ, μ, and ζ. Exemplary non-tumor promoting diterpenoid PKC activating compounds are based on 12-deoxyphorbol compounds, such as prostratin.

In some embodiments, the PKC activator is a compound of structural formula (PI):

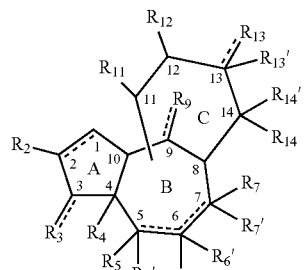

(PI)

or an enantiomer, hydrate, solvate, or pharmaceutically acceptable salt thereof
wherein
Ring C is attached to Ring B at carbon atom 9 or 10;
$R_2$ is selected from H or lower alkyl;
$R_3$ is H, or O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl, —$S(O)_2R_b$, —$S(O)_2OR_b$, or —$P(O)(OR_b)_2$;
$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —$S(O)_2R_b$, —$S(O)_2OR_b$, and —$P(O)(OR_b)_2$;
$R_5'$ and $R_6'$ are H, or $R_5'$ and $R_6'$ together form a bond or are bonded to a common oxygen atom to form an epoxide;
$R_6$ is —$NR_bR_b$, —$NHC(O)R_b$, —$SR_b$, $SOR_b$, —$S(O)_2R_b$, —$S(O)_2OR_b$, —$P(O)(OR_b)_2$, —$SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$C_{1-4}$alkyl-O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, —S(O)$_2$R$_b$, —S(O)$_2$OR$_b$, —P(O) (OR$_b$), or R$_d$ is a promoiety which is hydrolyzable under biological conditions to yield an -alkyl-OH.

R$_6$' and R$_7$' are H, or R$_6$' and R$_7$' together form a bond or are bonded to a common oxygen atom to form an epoxide;

R$_7$ is H or OH;

R$_9$ is H, oxo, or —OR$_f$, wherein R$_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl, or R$_9$', is an O atom which is bonded to an optionally substituted common C atom bonded to R$_{13}$' and R$_{14}$', wherein R$_{13}$' and R$_{14}$' each is an O atom;

R$_{11}$ is lower alkyl;

R$_{12}$ is H, halo, —NR$_b$R$_b$, —NHC(O)R$_b$, —SR$_b$, SOR$_b$, —S(O)$_2$R$_b$, —S(O)$_2$OR$_b$, —P(O) (OR$_b$)$_2$, —SeR$_b$, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or R$_{12}$ is —OR$_g$, wherein R$_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —S(O)$_2$R$_b$, —S(O)$_2$OR$_b$, and —P(O) (OR$_b$)$_2$;

R$_{13}$ is H, halo, oxo, —NR$_b$R$_b$, —NHC(O)R$_b$, —SR$_b$, SOR$_b$, —S(O)$_2$R$_b$, —S(O)$_2$OR$_b$, —P(O) (OR$_b$)$_2$, —SeR$_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —OR$_h$, wherein R$_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —S(O)$_2$R$_b$, —S(O)$_2$OR$_b$, and —P(O) (OR$_b$)$_2$;

R$_{13}$' and R$_{14}$' are independently H, OH, or are bonded to a common carbon atom to form a cyclopropyl ring, wherein the cyclopropyl ring is optionally mono- or disubstituted with OH, halo, —NR$_b$R$_b$, —NHC(O)R$_b$, —SR$_b$, SOR$_b$, —S(O)$_2$R$_b$, —S(O)$_2$OR$_b$, and —OP(O) (OR$_b$)$_2$, —SeR$_b$, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, carbamate, phosphine, phosphoramide, phosphoramidite, phosphoramidate, phosphonate, sulfonamide, amide, guanidine, urea; or a progroup which is hydrolysable under biological conditions to yield an -alkyl-OH group, or R$_{13}$' and R$_{14}$' are each an O atom which is bonded to an optionally substituted common C atom bonded to R$_9$, wherein R$_9$ is an O atom;

R$_{14}$ is H, OH or optionally substituted alkenyl; wherein each R$_b$ is independently H, optionally substituted alkyl, optionally substituted alkenyl, alkynyl, optionally substituted aryl, optionally substituted heteroaryl, optionally substituted arylalkyl, or optionally substituted heteroarylalkyl; and the dashed line (- - - - -) represents an optional bond.

In some embodiments of structural formula (PI), R$_6$ is CH$_2$R$_h$, wherein R$_h$ is —O—C(O)—R$_i$, wherein R$_i$ is a moiety which bears a permanent charge or which is ionizable at a pH in the range of about 2 to 8, and wherein the —O—C(O)—R$_1$ is hydrolyzable under biological conditions to yield an —OH group. In some embodiments, R$_i$ is an optionally substituted carboxyalkyl, wherein the carboxy is COOM, and wherein M is an H or a counterion. In some embodiments, the alkyl of R$_i$ is a C$_{1-6}$ alkyl. In some embodiments, R$_j$ is an amino acid of structure —(CH$_2$)$_n$—CH(CH$_2$)$_n$—NH$_2$)—(CH$_2$)$_n$—C(O)OM or —(CH$_2$)$_n$—CHNH$_2$—(CH$_2$)$_n$—C(O)OM, wherein n is 0, 1, 2, 3 or 4. In some embodiments, R$_i$ is an aminoalkyl, wherein the amino group is —NR$_j$R$_j$ or —NR$_k$R$_k$R$_k$, wherein each R$_j$ and R$_k$ is independently H, lower alkyl, lower alkyloxyalkyl, heteroalkyl, or two R$_j$ taken together with the nitrogen atom to which they are bonded form a 5-7 membered heteroatomic ring. In some embodiments, the alkyl of the aminoalkyl is a C$_{1-6}$ alkyl. In some embodiments, —NR$_j$R$_j$ is N-morpholinyl, piperazinyl, 1-piperazinyl, 1-methyl-piperazinyl, or 1-methyl-4-piperazinyl. Other progroup and promoieties are described in, for example, patent publication US2011/0224297, paragraphs [0036] to [0045], incorporated herein by reference.

In some embodiments, the PKC activator is a compound of structural formula (PII):

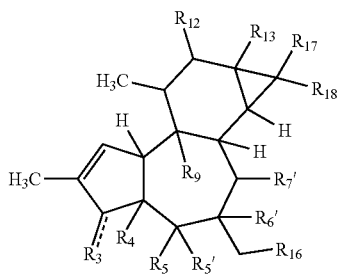
(PII)

or an enantiomer, hydrate, solvate, or pharmaceutically acceptable salt thereof,
wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5'$ and $R_6'$ are H, or $R_5'$ and $R_6'$ together form a bond or are bonded to a common oxygen atom to form an epoxide;

$R_6'$ and $R_7'$ are H, or $R_6'$ and $R_7'$ together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{12}$ is H, halo, or —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted aryloxy, optionally substituted arylalkyloxy, optionally substituted alkylcarbonyloxy, optionally substituted alkenylcarbonyloxy, optionally substituted arylcarbonyloxy, optionally substituted arylalkylcarbonyloxy, phosphine, phosphate, phosphoramide, phosphoramidite, phosphoramidate, phosphonate, sulfate, sulfonate, sulfonamide, sulfone, sulfite, amide, guanidine, or urea.

In some embodiments of structural formula (PII), $R_{16}$ is —O—C(O)—$R_i$, wherein $R_i$ is a moiety which bears a permanent charge or which is ionizable at a pH in the range of about 2 to 8, and wherein the —O—C(O)—$R_i$ is hydrolyzable under biological conditions to yield an —OH group. In some embodiments, $R_i$ is an optionally substituted carboxyalkyl, wherein the carboxy is COOM, and wherein M is an H or a counterion. In some embodiments, the alkyl of $R_i$ is a $C_{1-6}$ alkyl. In some embodiments, $R_i$ is an amino acid of structure —$(CH_2)_n$—$CH(CH_2)_n$—$NH_2)$—$(CH_2)_n$—$C(O)$OM or —$(CH_2)_n$—$CHNH_2$—$(CH_2)_n$—$C(O)OM$, wherein n is 0, 1, 2, 3 or 4. In some embodiments, $R_i$ is an aminoalkyl, wherein the amino group is —$NR_jR_j$ or —$NR_kR_kR_k$, wherein each $R_j$ and $R_k$ is independently H, lower alkyl, lower alkyloxyalkyl, heteroalkyl, or two $R_j$ taken together with the nitrogen atom to which they are bonded form a 5-7 membered heteroatomic ring. In some embodiments, the alkyl of the aminoalkyl is a $C_{1-6}$ alkyl. In some embodiments, —$NR_jR_j$ is N-morpholinyl, piperazinyl, 1-piperazinyl, 1-methyl-piperazinyl, or 1-methyl-4-piperazinyl. Other progroup and promoieties are described in, for example, patent publication US2011/0224297, paragraphs [0036] to [0045], incorporated herein by reference.

In some embodiments, the PKC activator comprises the compound of formula (PIIa):

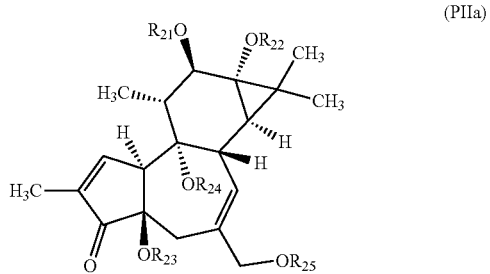

(PIIa)

or an enantiomer, hydrate, solvate, or pharmaceutically acceptable salt thereof,
wherein
$R_{21}$, $R_{22}$, $R_{23}$, and $R_{24}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and
$R_{25}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{25}$ is a promoiety which is hydrolyzable under biological conditions to yield an —OH group at the C20 carbon atom.

In some embodiments, the PKC activator comprises a compound of formula (PIIb):

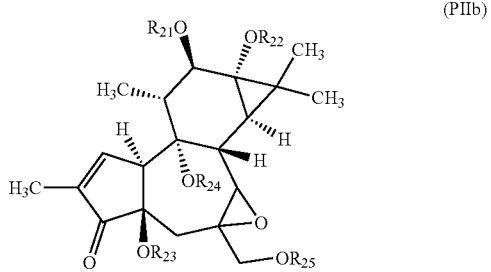

(PIIb)

or an enantiomer, hydrate, solvate, or pharmaceutically acceptable salt thereof,
wherein,
$R_{21}$, $R_{22}$, $R_{23}$, $R_{24}$ and $R_{25}$ are as defined for formula (IIa).

In some embodiments, the PKC activator comprises a compound of formula (PIIc):

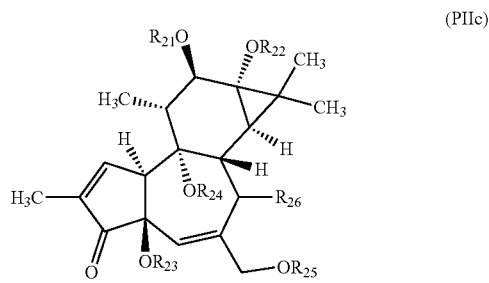

(PIIc)

or an enantiomer hydrate, solvate, or pharmaceutically acceptable salt thereof,
wherein,
$R_{21}$, $R_{22}$, $R_{23}$, $R_{24}$ and $R_{25}$ are as defined for formula (IIa), and $R_{26}$ is H or OH.

In some embodiments, the PKC activator comprises a compound of formula (PIId):

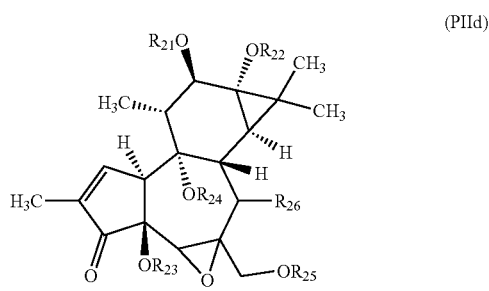

(PIId)

or an enantiomer, hydrate, solvate, or pharmaceutically acceptable salt thereof,
wherein,
$R_{21}$, $R_{22}$, $R_{23}$, $R_{24}$ and $R_{25}$ are as defined for formula (PIIa), and
$R_{26}$ is H or OH.

In some embodiments of structural formula (PIIa), (PIIb), (PIIc) or (PIId), the aryl is an optionally substituted phenyl.

In some embodiments of structural formula (PIIa), (PIIb), (PIIc) and (PIId), $R_{25}$ forms a promoiety as described in formula (II) above. In some embodiments of structural formula (PIIa), (PIIb), (PIIc) and (PIId), $R_{25}$ is an optionally substituted carboxyalkylcarbonyl, wherein the carboxy is COOM, wherein M is an H or a counterion. In some embodiments, the alkyl is a $C_{1-6}$ alkyl. In some embodiments, $R_{25}$ is an amino acid carbonyl, where the amino acid portion has the structure —$(CH_2)_n$—CH$(CH_2)_n$—NH$_2$)—$(CH_2)_n$—C(O)OM or —$(CH_2)_n$—CHNH$_2$—$(CH_2)_n$—C(O)OM, wherein n is 0, 1, 2, 3, or 4. In some embodiments, $R_{25}$ is an aminoalkylcarbonyl, wherein the alkyl is a $C_{1-6}$ alkyl and the amino group is —NR$_j$R$_j$, or —NR$_k$R$_k$R$_k$, wherein each R$_j$ and R$_k$ is independently H, lower alkyl, lower alkyloxyalkyl, heteroalkyl, or two R$_j$ taken together with the nitrogen atom to which they are bonded form a 5-7 membered heteroatomic ring. In some embodiments, —NR$_j$R$_j$ is N-morpholinyl, piperazinyl, 1-piperazinyl, 1-methyl-piperazinyl, or 1-methyl-4-piperazinyl.

In some embodiments, the PKC activator is selected from the exemplary phorbol compounds presented below, including, among others, phorbol 13-butyrate; phorbol 12-decanoate; phorbol 13-decanoate; phorbol 12,13-diacetate, phorbol 13,20-diacetate, phorbol 12,13-dibenzoate, phorbol 12,13 dibutyrate, phorbol 12,13 didecanoate; phorbol 12,13-dihexanoate; phorbol 12,13 dipropionate, phorbol 12-myristate; phorbol 13-myristate, phorbol 12-myristate-13-acetate (TPA), phorbol 12,13,20-triacetate; phorbol 12-acetate, phorbol 13-acetate, phorbol-12-tigliate 13-decanoate, or salts, hydrates, solvates, or prodrugs thereof. In some embodiments, the prodrugs for the specified phorbol compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified compound contains a biohydrolyzable ester, more particularly at the C20 carbon.

Phorbol Compounds

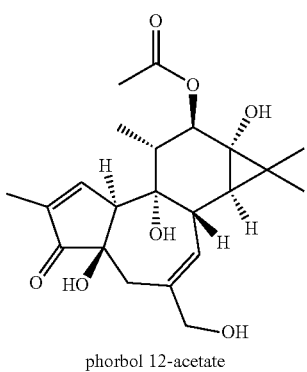

phorbol 12-acetate

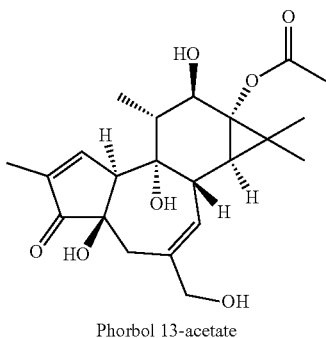

Phorbol 13-acetate

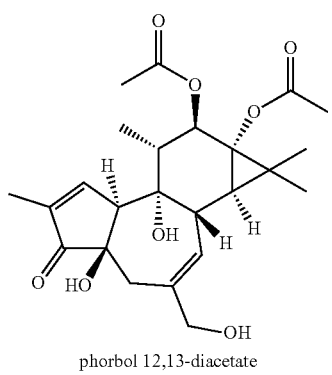

phorbol 12,13-diacetate

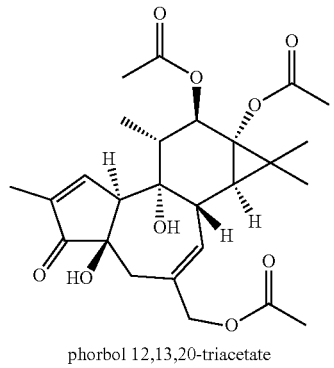

phorbol 12,13,20-triacetate

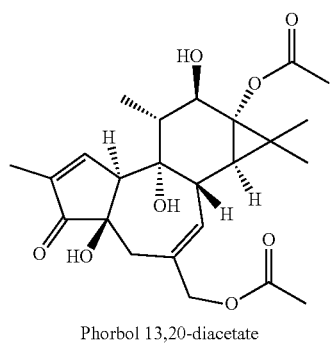

Phorbol 13,20-diacetate

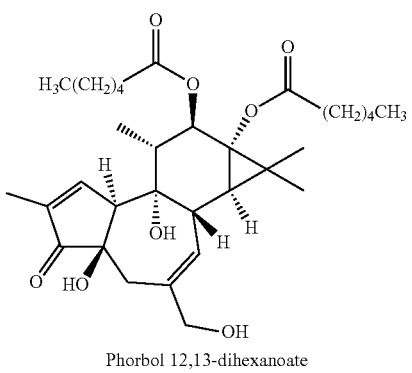

Phorbol 12,13-dihexanoate

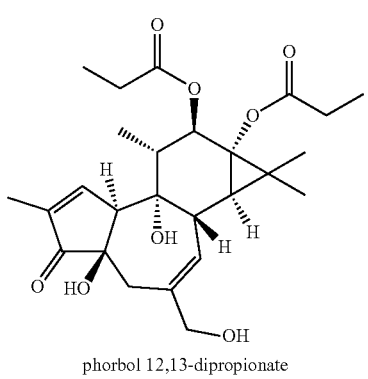

phorbol 12,13-dipropionate

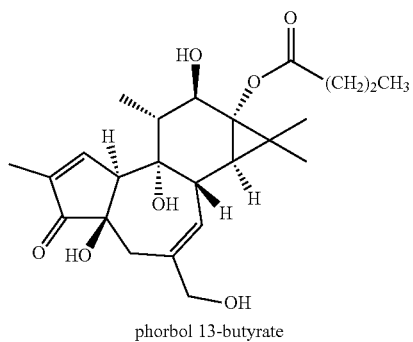
phorbol 13-butyrate
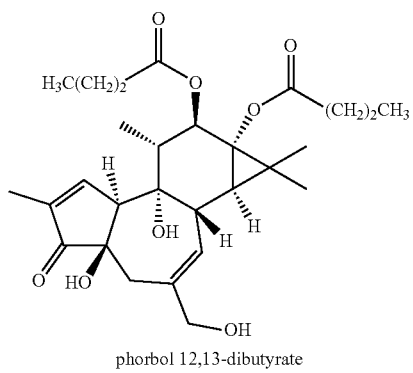
phorbol 12,13-dibutyrate
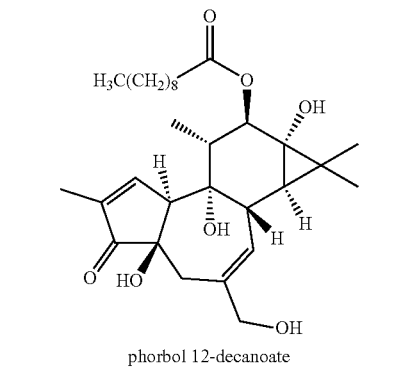
phorbol 12-decanoate
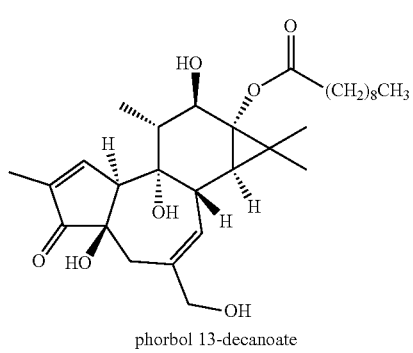
phorbol 13-decanoate
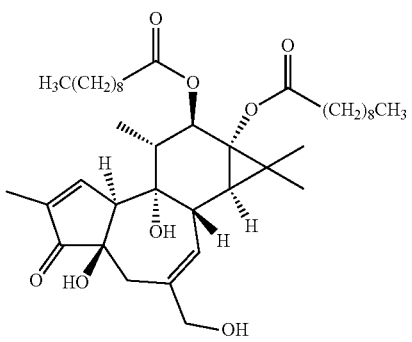
phorbol 12,13-decanoate
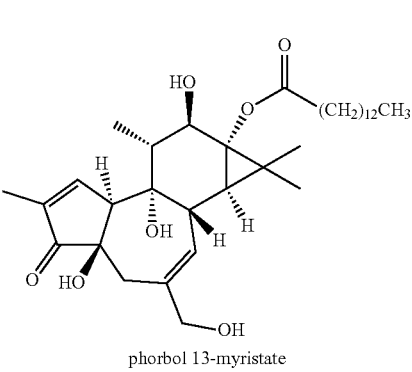
phorbol 13-myristate
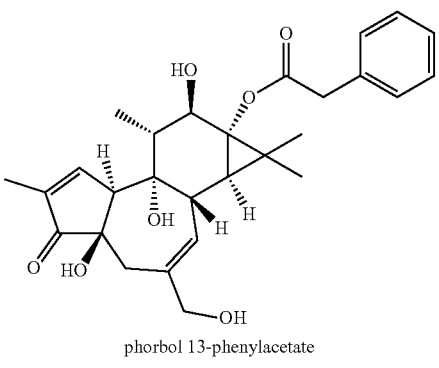
phorbol 13-phenylacetate
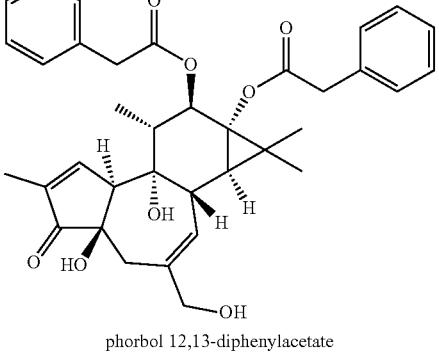
phorbol 12,13-diphenylacetate

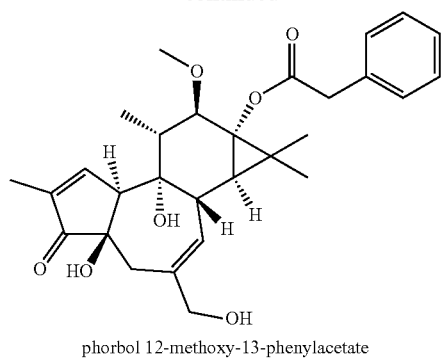
phorbol 12-methoxy-13-phenylacetate
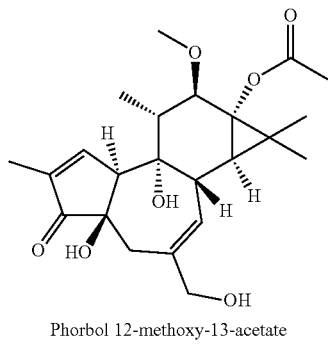
Phorbol 12-methoxy-13-acetate
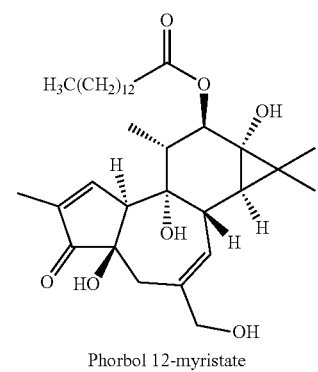
Phorbol 12-myristate
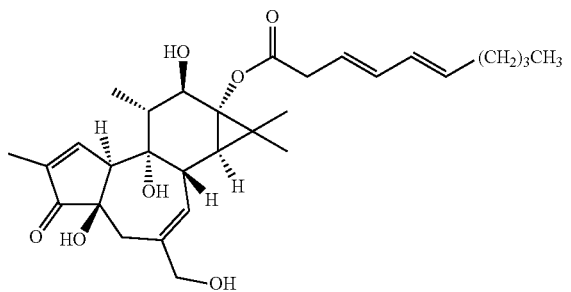
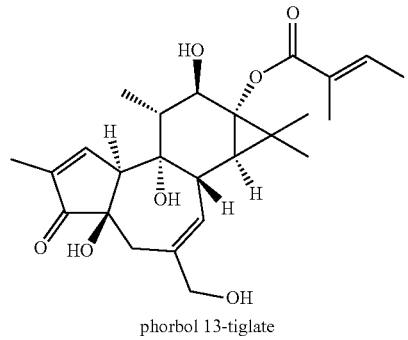
phorbol 13-tiglate
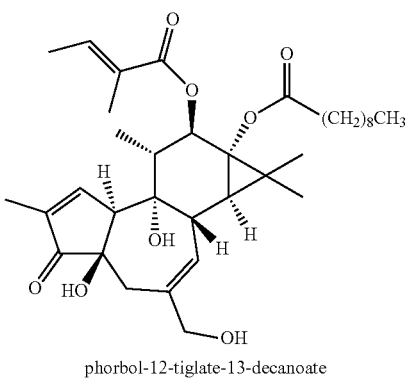
phorbol-12-tiglate-13-decanoate
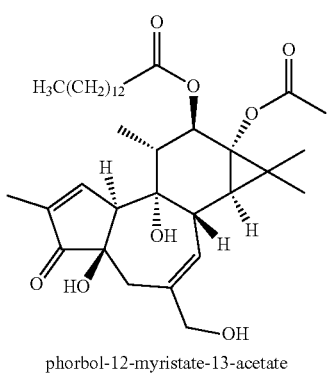
phorbol-12-myristate-13-acetate
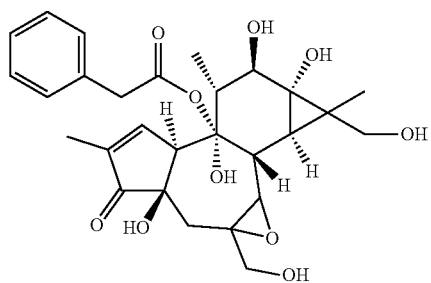
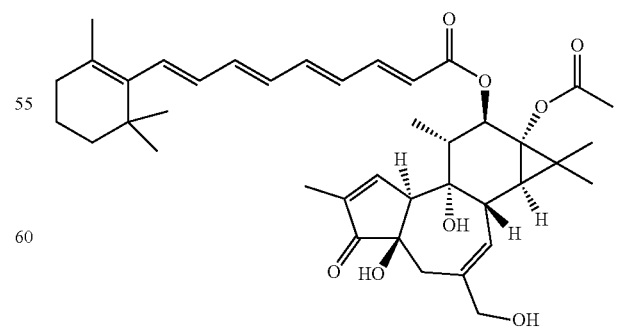
In some embodiments, the PKC activator is compound of structural formula (PIII):

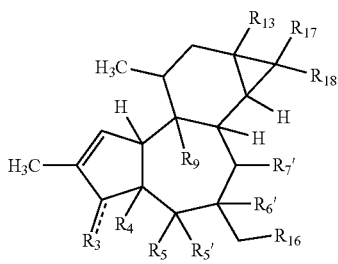

(PIII)

or an enantiomer, hydrate, solvate, or pharmaceutically acceptable salt thereof,
wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5'$ and $R_6'$ are H, or $R_5'$ and $R_6'$ together form a bond or are bonded to a common oxygen atom to form an epoxide;

$R_6'$ and $R_7'$ are H, or $R_6'$ and $R_7'$ together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at the C20 carbon atom; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, phosphine, phosphate, phosphoramide, phosphoramidite, phosphoramidate, phosphonate, sulfate, sulfonate, sulfonamide, sulfone, sulfite, amide, guanidine, urea, or a progroup which is hydrolyzable under biological conditions to yield an -alkyl-OH group.

In some embodiments of structural formula (PIII), $R_{16}$ is —O—C(O)—$R_i$, wherein $R_i$ is a moiety which bears a permanent charge or which is ionizable at a pH in the range of about 2 to 8, and wherein the —O—C(O)—$R_i$ is hydrolyzable under biological conditions to yield an —OH group. In some embodiments, $R_i$ is an optionally substituted carboxyalkyl, wherein the carboxy is COOM, and wherein M is an H or a counterion. In some embodiments, the alkyl of $R_i$ is a lower alkylene. In some embodiments, $R_i$ is an amino acid of structure —$(CH_2)_n$—$CH(CH_2)_n$—$NH_2)$—$(CH_2)_n$—C(O)OM or —$(CH_2)_n$—$CHNH_2$—$(CH_2)_n$—C(O)OM, wherein n is 0, 1, 2, 3 or 4. In some embodiments, $R_i$ is an aminoalkyl, wherein the amino group is —$NR_jR_j$ or —$NR_kR_kR_k$, wherein each $R_j$ and $R_k$ is independently H, lower alkyl, lower alkyloxyalkyl, heteroalkyl, or two RR taken together with the nitrogen atom to which they are bonded form a 5-7 membered heteroatomic ring. In some embodiments, the alkylene of the aminoalkyl is a lower alkyl. In some embodiments, —NR$_j$R$_j$ is N-morpholinyl, piperazinyl, 1-piperazinyl, 1-methyl-piperazinyl, or 1-methyl-4-piperazinyl. Other progroup and promoieties are described in, for example, patent publication US2011/0224297, paragraphs [0036] to [0045], incorporated herein by reference.

In some embodiments, the PKC activator comprises a compound of formula (PIIIa) or (PIIIb):

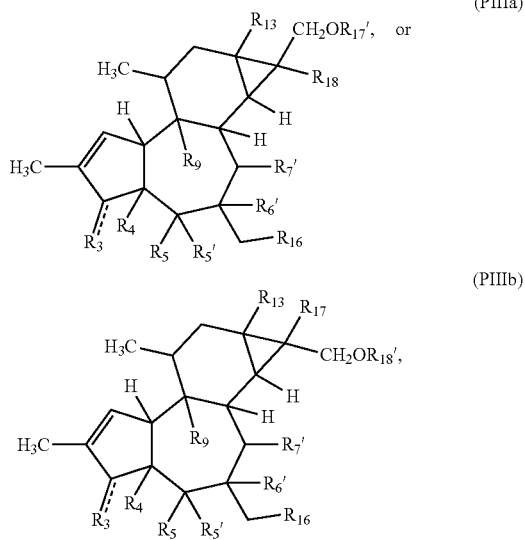

or an enantiomer, hydrate, solvate, or pharmaceutically acceptable salt thereof,
wherein
R$_3$, R$_4$, R$_5$, R$_5'$ R$_6'$, R$_7'$, R$_9$, R$_{13}$, and R$_{16}$ are as defined for formula (III);

R$_{17}$ or R$_{18}$ is H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted aryloxy, optionally substituted arylalkyloxy, phosphine, phosphate, phosphoramide, phosphoramidite, phosphoramidate, phosphonate, sulfate, sulfonate, sulfonamide, sulfone, sulfite, amide, guanidine, or urea; and R$_{17}'$ or R$_{18}'$ is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a progroup which is hydrolyzable under biological conditions to yield an —OH group.

In some embodiments, the PKC activator comprises a compound of formula (PIIIc):

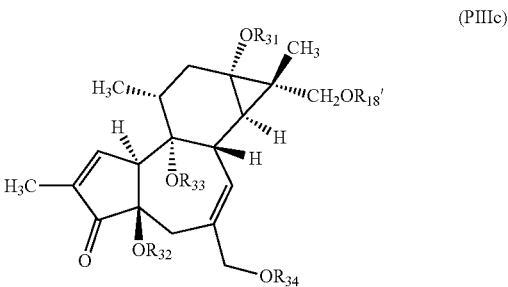

or an enantiomer, hydrate, solvate, or pharmaceutically acceptable salt thereof,
wherein,
R$_{18}'$ is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group;

R$_{31}$, R$_{32}$, and R$_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and R$_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a promoiety which is hydrolyzable under biological conditions to yield an —OH group at the C20 carbon atom.

In some embodiments, the PKC activator comprises a compound of formula (PIIId):

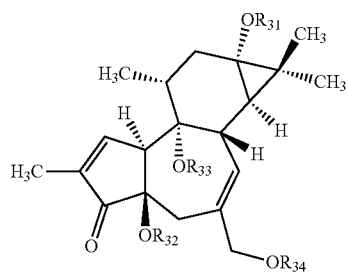
(PIIId)

or an enantiomer, hydrate, solvate, or pharmaceutically acceptable salt thereof,
wherein $R_{31}$, $R_{32}$, and $R_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a promoiety which is hydrolyzable under biological conditions to yield an —OH group at the C20 carbon atom.

In some embodiments, the PKC activator comprises a compound of formula (PIIIe):

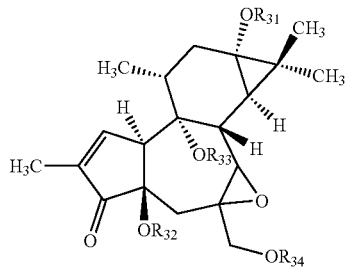
(PIIIe)

or an enantiomer, hydrate, solvate, or pharmaceutically acceptable salt thereof,
wherein, $R_{31}$, $R_{32}$, $R_{33}$, and $R_{34}$ are as defined for formula (PIIIc).

In some embodiments of the compound of formula (PIIIc), (PIIId) and (PIIIe), $R_{34}$ is an optionally substituted carboxyalkylcarbonyl, wherein the carboxy is —COOM, wherein M is an H or a counterion. In some embodiments, the alkyl is a $C_{1-6}$ alkyl. In some embodiments, $R_{34}$ is an amino acid carbonyl of structure —C(O)—$(CH_2)_n$—CH$(CH_2)_n$—NH$_2$)—$(CH_2)_n$—C(O)OM or —C(O)—$CH_2)_n$—CHNH$_2$—$(CH_2)_n$—C(O)OM, wherein n is 0, 1, 2, 3, or 4. In some embodiments, $R_{34}$ is an aminoalkyl, wherein the amino group is —$NR_jR_j$ or —$NR_kR_kR_k$, wherein each $R_j$ and $R_k$ are independently H, lower alkyl, lower alkyl, alkyloxyalkyl, heteroalkyl, or two $R_j$ taken together with the nitrogen atom to which they are bonded form a 5-7 membered heteroatomic ring. In some embodiments, the alkyl of $R_{34}$ is a $C_{1-6}$ alkyl. In some embodiments, the —$NR_jR_j$ is N-morpholinyl, piperazinyl, 1-piperazinyl, 1-methyl-piperazinyl, or 1-methyl-4-piperazinyl.

In some embodiments, the PKC activator is selected from the exemplary deoxyphorbol compounds presented below, including, among others, 12-deoxyphorbol 13-angelate, 12-deoxyphorbol 13-angelate 20-acetate, 12-deoxyphorbol 13-isobutyrate, 12-deoxyphorbol 13-isobutyrate 20-acetate, 12-deoxyphorbol 13-phenylacetate, 12-deoxyphorbol 13-phenylacetate 20-acetate, 12-deoxyphorbol 13-tetradecanoate, 12-deoxyphorbol 13-acetate (prostratin), or salts, hydrates, solvates, or prodrugs thereof. In some embodiments, the prodrugs for the specified deoxyphorbol compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified deoxyphorbol compound contains a biohydrolyzable ester, more particularly at the C20 carbon.

Deoxyphorbol Compounds

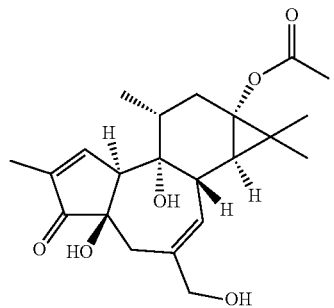

12-deoxyphorbol-13-acetate

-continued
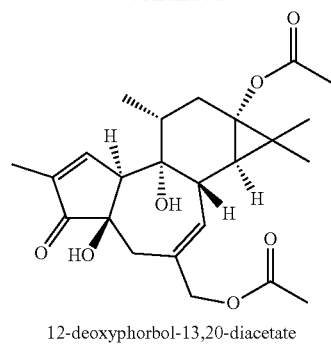
12-deoxyphorbol-13,20-diacetate
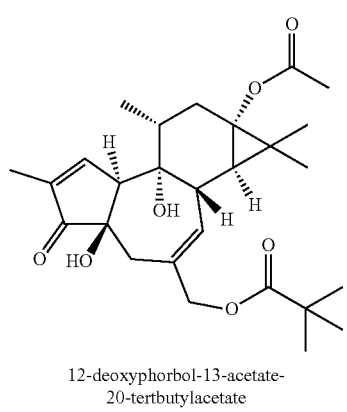
12-deoxyphorbol-13-acetate-
20-tertbutylacetate
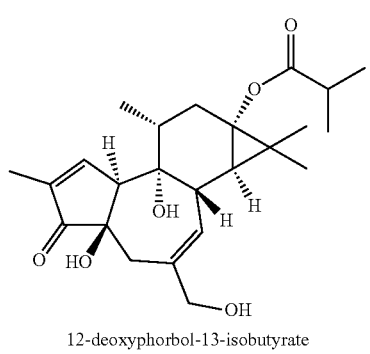
12-deoxyphorbol-13-isobutyrate
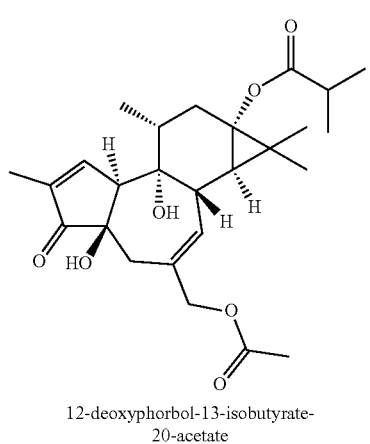
12-deoxyphorbol-13-isobutyrate-
20-acetate
-continued
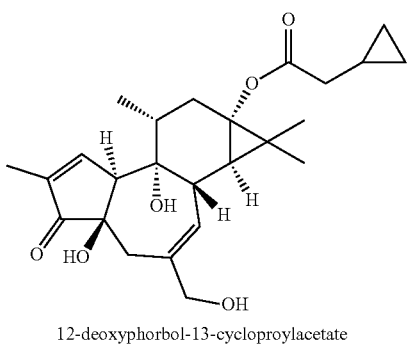
12-deoxyphorbol-13-cyploroylacetate
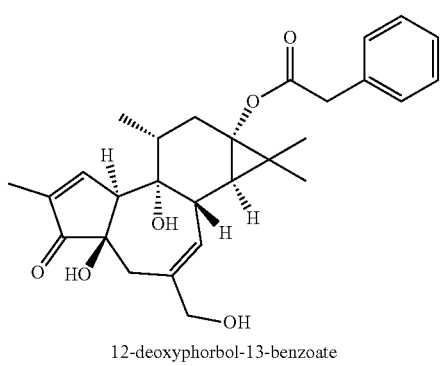
12-deoxyphorbol-13-benzoate
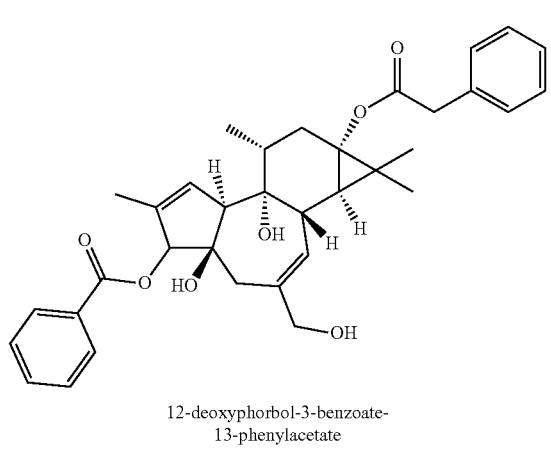
12-deoxyphorbol-3-benzoate-
13-phenylacetate
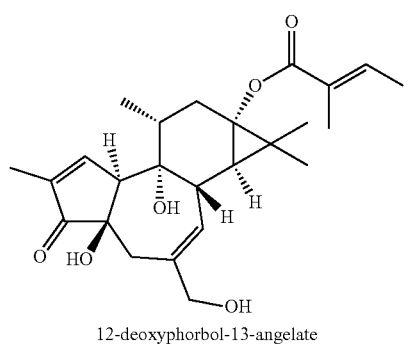
12-deoxyphorbol-13-angelate

55
-continued
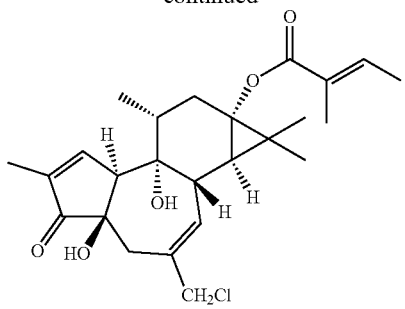
12-deoxyphorbol-6-chloromethyl-
13-angelate
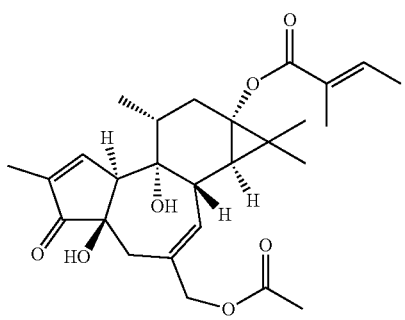
12-deoxyphorbol 13-angelate
20-acetate
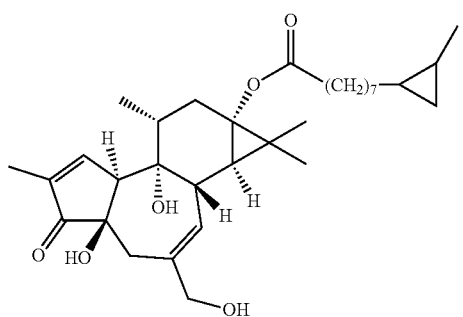
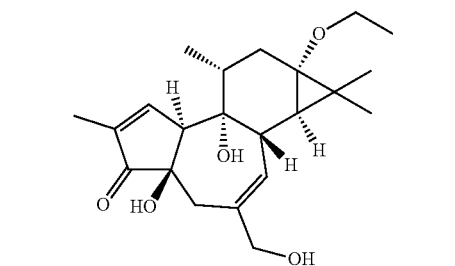
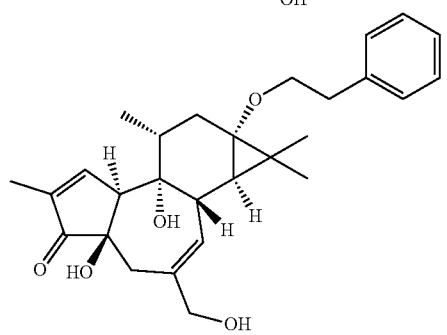
56
-continued
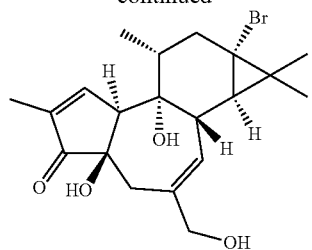
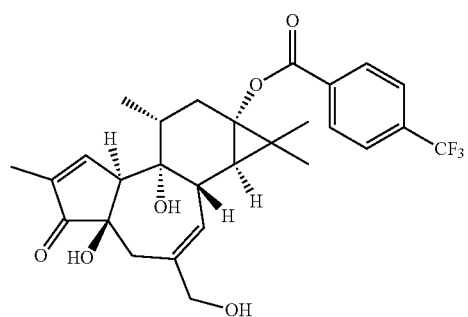
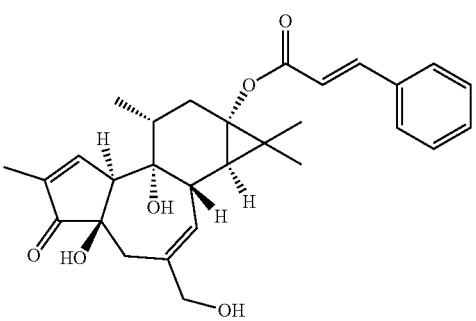
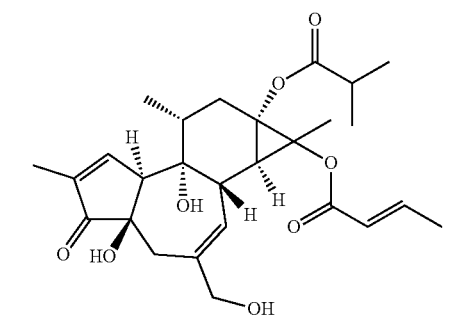
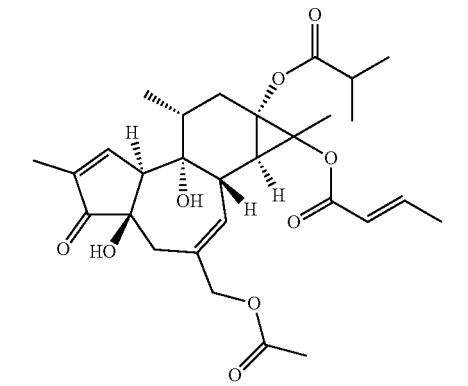

-continued

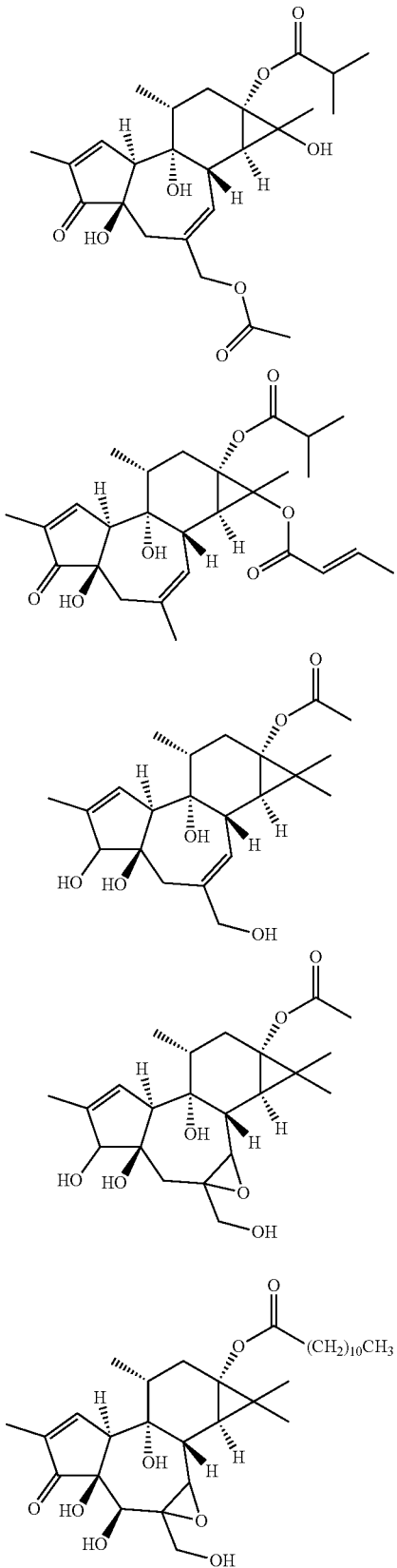

In some embodiments, the PKC activator comprises a compound of formula (PIV):

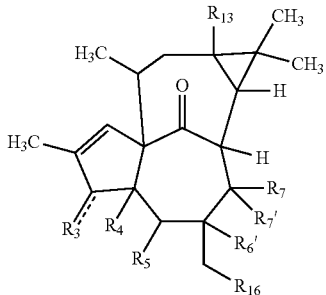

(PIV)

or an enantiomer, hydrate, solvate, or pharmaceutically acceptable salt thereof,
wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_6'$ and $R_7'$ are H, or $R_6'$ and $R_7'$ together form a bond or are bonded to a common oxygen atom to form an epoxide;

$R_7$ is H or OH;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$.

In some embodiments, the PKC activator comprises a compound of formula (PIVa):

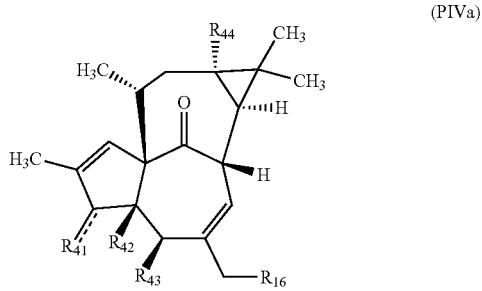

(PIVa)

or an enantiomer, hydrate, solvate, or pharmaceutically acceptable salt thereof,
wherein $R_{41}$ is O double bonded to the ring carbon, or $R_{41}$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_{42}$ and $R_{43}$ are independently H, halo, or —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{44}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a biohydrolyzable promoiety which is hydrolyzable under biological conditions to yield an —OH group at $R_{16}$.

In some embodiments, the PKC activator comprises a compound of formula (PIVb):

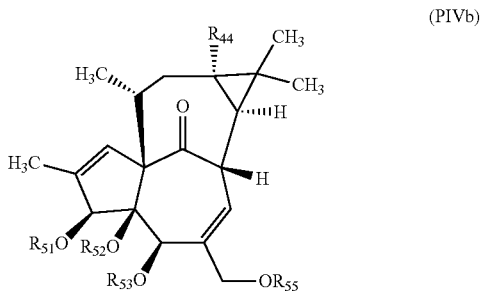

(PIVb)

or an enantiomer, hydrate, solvate, or pharmaceutically acceptable salt thereof,
wherein $R_{44}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{51}$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl; and $R_{52}$ and $R_{53}$ are independently H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{55}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group at the C20 carbon atom. Other progroup and promoieties for $R_{55}$ are described in, for example, patent publication US2011/0224297, paragraphs [0036] to [0045], incorporated herein by reference.

In some embodiments, the PKC activator comprises a compound of formula (PIVc):

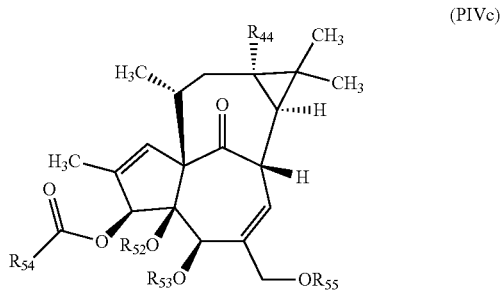

(PIVc)

or an enantiomer, hydrate, solvate, or pharmaceutically acceptable salt thereof, wherein $R_{44}$ is H or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{52}$ and $R_{53}$ are independently H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{54}$ is H, an optionally substituted alkyl, optionally substituted alkenyl, optionally substituted cycloalkyl, optionally substituted aryl, optionally substituted heteroaryl, optionally substituted arylalkyl, optionally substituted arylalkenyl, optionally substituted heteroarylalkyl, optionally substituted heteroarylalkenyl; and $R_{55}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group at the C20 carbon atom.

In some embodiments of the compound of formula (PIVb) and (PIVc), $R_{55}$ is an optionally substituted carboxyalkylcarbonyl, wherein the carboxy is —COOM, wherein M is an H or a counterion. In some embodiments, the alkyl is a lower alkyl. In some embodiments, $R_{55}$ is an amino acid carbonyl of structure —C(O)—$(CH_2)_n$—CH($(CH_2)_n$—$NH_2$)—$(CH_2)_n$—C(O)OM or —C(O)—$CH_2)_n$—$CHNH_2$—$(CH_2)_n$—C(O)OM, wherein n is 0, 1, 2, 3, or 4. In some embodiments, $R_{55}$ is an aminoalkyl, wherein the amino group is —$NR_jR_j$ or —$NR_kR_kR_k$, wherein each $R_j$ and $R_k$ are independently H, lower alkyl, lower alkyloxyalkyl, heteroalkyl, or two RR taken together with the nitrogen atom to which they are bonded form a 5-7 membered heteroatomic ring. In some embodiments, the alkyl of $R_{55}$ is a lower alkyl. In some embodiments, the —$NR_jR_j$ is N-morpholinyl, piperazinyl, 1-piperazinyl, 1-methyl-piperazinyl, or 1-methyl-4-piperazinyl.

In some embodiments, the PKC activator comprises a compound of formula (PIVd):

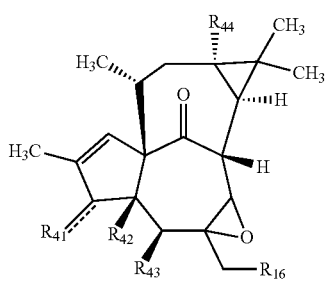

(PIVd)

or an enantiomer, hydrate, solvate, or pharmaceutically acceptable salt thereof, wherein $R_{41}$, $R_{42}$, $R_{43}$, $R_{44}$ and $R_{16}$ are as defined for formula (PIVa).

In some embodiments, the PKC activator is selected from the exemplary ingenane compounds presented below, including, among others, ingenol-3-angelate, ingenol-5-angelate, ingenol-3,20-dibenzoate, 20-O-acetyl-ingenol-3-angelate, ingenol-30-(3,5-diethyl-4-isoxazolecarboxylate), or 20-deoxy-ingenol-3-angelate, ingenol-20-benzoate, or solvates, hydrates, and prodrugs thereof. In some embodiments, the prodrugs for the specified ingenol compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified ingenane compounds contains a biohydrolyzable ester, more particularly at the C20 carbon atom.

Ingenane Compounds.

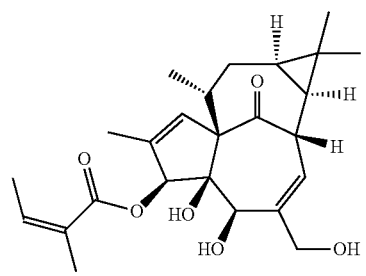

Ingenol 3-angelate

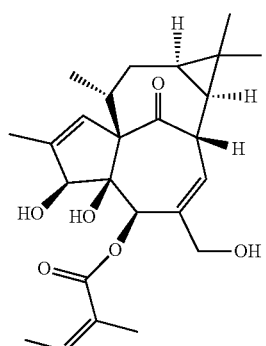

Ingenol 5-angelate

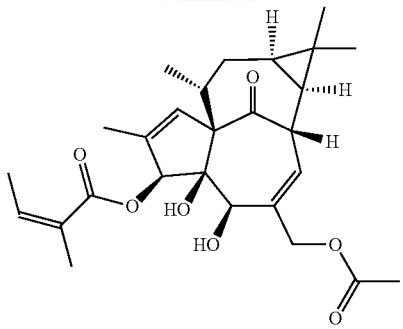

20-O-acetyl-ingenol-3-angelate

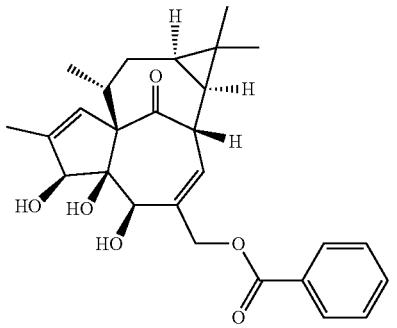

Ingenol 20-benzoate

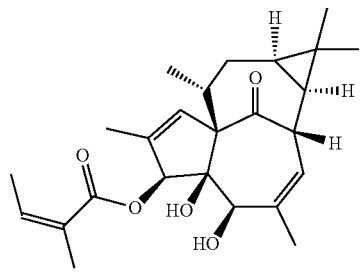

20 deoxy-ingenol-3-angelate

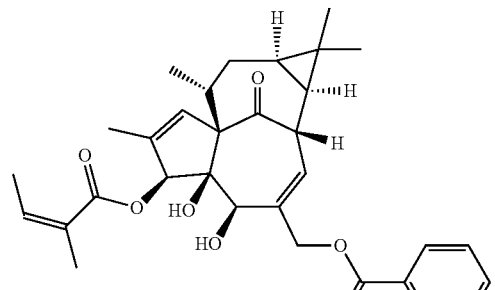

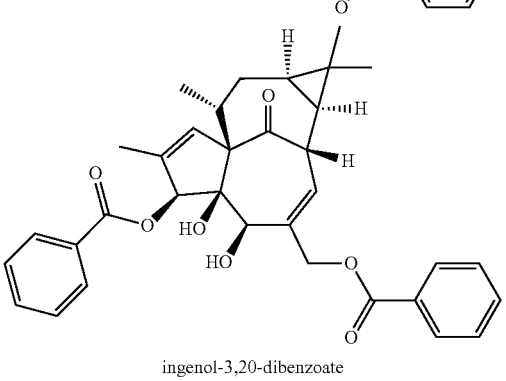

ingenol-3,20-dibenzoate

-continued
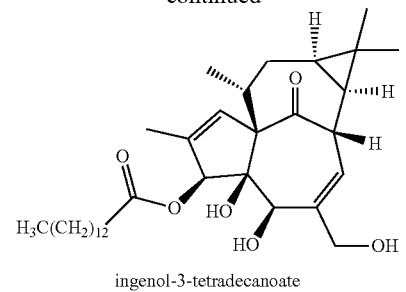
ingenol-3-tetradecanoate
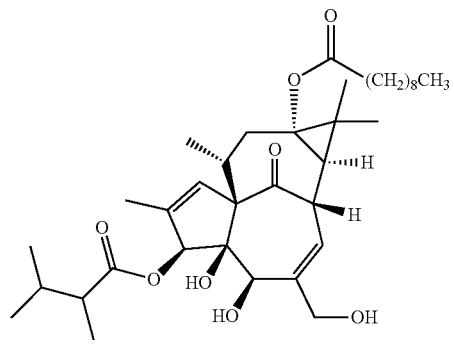
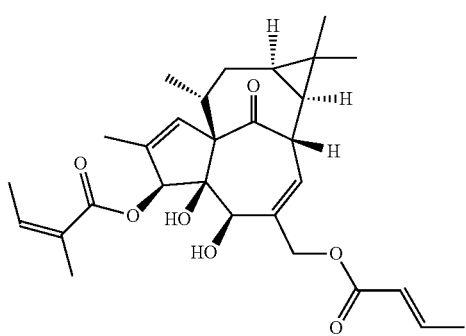
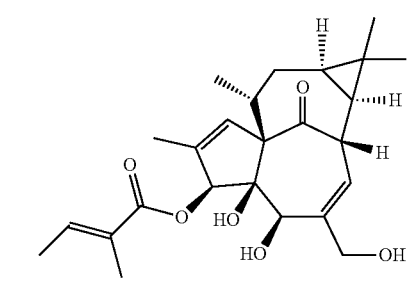
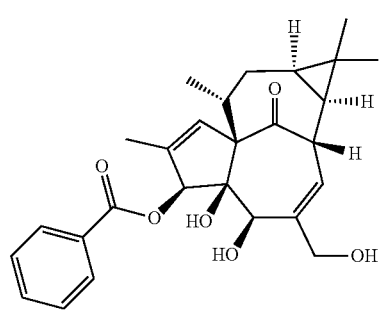
-continued
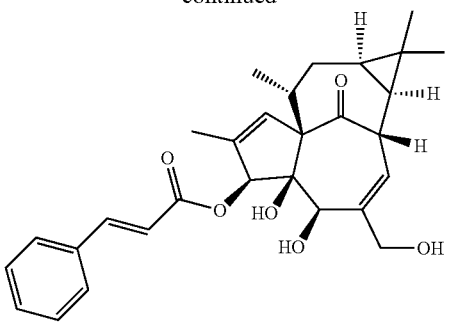
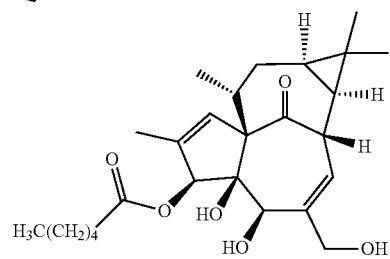
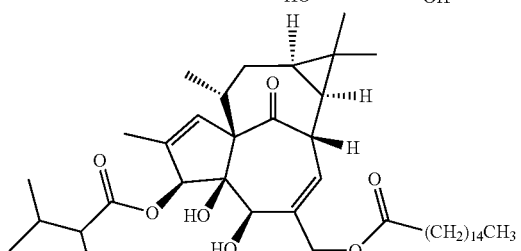
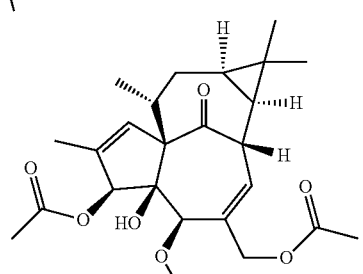
ingenol 3,5,20-triacetate
In some embodiments, the PKC activator comprises a compound of formula (V):
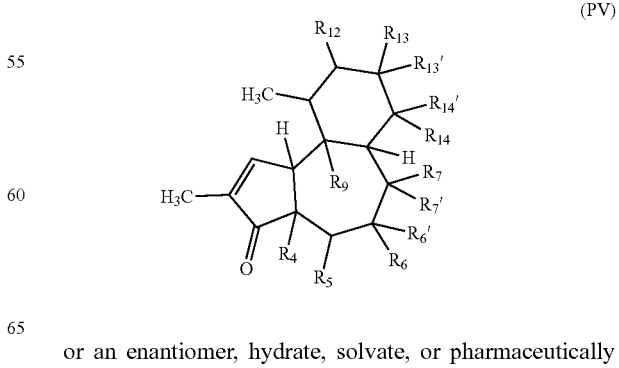
(PV)
or an enantiomer, hydrate, solvate, or pharmaceutically acceptable salt thereof, wherein, R$_4$ and R$_5$ are independently H, halo, cyano, or R$_4$ is —OR$_c$, wherein R$_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, or R$_9$' is an O atom which is bonded to an optionally substituted common C atom bonded to R$_{13}$' and R$_{14}$', wherein R$_{13}$' and R$_{14}$' each is an O atom;

R$_6$ is —NR$_b$R$_b$, —NHC(O)R$_b$, —SR$_b$, —SOR$_b$, —S(O)$_2$R$_b$, —S(O)$_2$OR$_b$, —P(O) (OR$_b$)$_2$, —SeR$_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or -alkyl-O—R$_d$, wherein R$_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, —S(O)$_2$R$_b$, —S(O)$_2$OR$_b$, —P(O) (OR$_b$), or R$_d$ is a promoiety which is hydrolyzable under biological conditions to yield an -alkyl OH;

R$_6$' and R$_7$' are H, or R$_6$' and R$_7$' together form a bond or are bonded to a common oxygen atom to form an epoxide;

R$_7$ is H or OH;

R$_9$ is H or —OR$_f$, wherein R$_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

R$_{12}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or R$_{12}$ is —OR$_g$, wherein R$_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

R$_{13}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —OR$_h$, wherein R$_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, or optionally substituted heteroarylalkenylcarbonyl;

R$_{13}$' and R$_{14}$' are independently H or OH, or R$_{13}$ and R$_{14}$ are each an O atom which is bonded to an optionally substituted common C atom which is bonded to R$_9$, wherein R$_9$ is an O atom; and R$_{14}$ is H, OH or optionally substituted alkenyl; wherein one of R$_{13}$ and R$_{14}$ is an alkenyl of structure

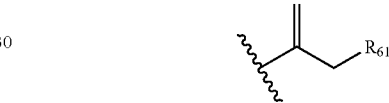

wherein R$_{61}$ is H or OH.

In some embodiments, the PKC activator comprises a compound of formula (PVa):

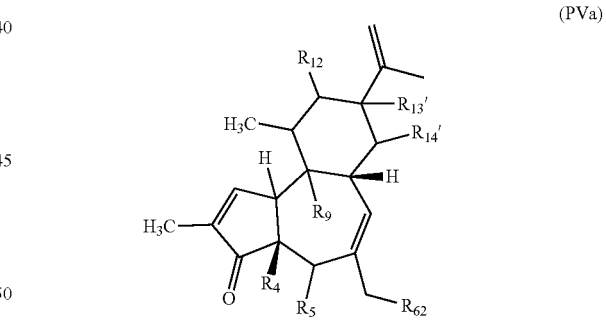

(PVa)

or an enantiomer, hydrate, solvate, or pharmaceutically acceptable salt thereof, wherein, R$_4$ and R$_5$ are independently H, halo, cyano, or R$_4$ is —OR$_c$, wherein R$_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, or R$_9$' is an O atom which is bonded to an optionally substituted common C atom bonded to R$_{13}$' and R$_{14}$', wherein R$_{13}$' and R$_{14}$' each is an O atom;

R$_9$ is H or —OR$_f$, wherein R$_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, optionally substituted arylalkyloxycarbonyl, or R$_9$ is an O atom which is bonded to an optionally substituted common C atom bonded to R$_{13}$' and R$_{14}$', wherein R$_{13}$' and R$_{14}$' each is an O atom;

R$_{12}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or R$_{12}$ is —OR$_g$, wherein R$_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

R$_{13}$' and R$_{14}$' are independently H or OH, or R$_{13}$' and R$_{14}$' are each an O atom which is bonded to an optionally substituted common C atom which is bonded to R$_9$, wherein R$_9$ is an O atom; and R$_{62}$ is H, halo, or —OR$_d$, wherein R$_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or R$_d$ is a promoiety which is hydrolyzable under biological conditions to yield an —OH group at R$_{62}$.

In some embodiments, the PKC activator comprises a compound of formula (PVb):

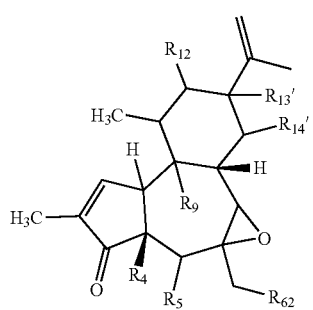

(PVb)

or an enantiomer, hydrate, solvate, or pharmaceutically acceptable salt thereof,
wherein
R$_4$, R$_5$, R$_9$, R$_{12}$, R$_{13}$', R$_{14}$', and R$_{62}$ are as defined for the compound of formula (PVa).

In some embodiments, the PKC activator comprises a compound of formula (PVc):

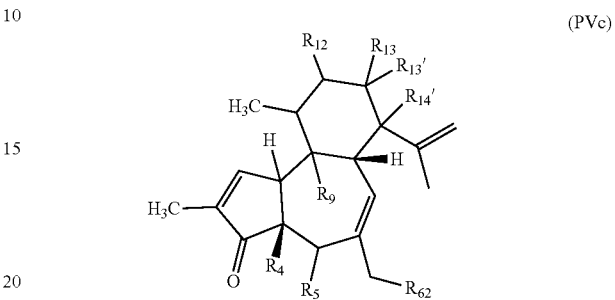

(PVc)

or an enantiomer, hydrate, solvate, or pharmaceutically acceptable salt thereof
wherein, R$_4$ and R$_5$ are independently H, halo, cyano, or R$_4$ is —OR$_c$, wherein R$_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, or R$_9$ is an O atom which is bonded to an optionally substituted common C atom bonded to R$_{13}$' and R$_{14}$', wherein R$_{13}$' and R$_{14}$' each is an O atom;

R$_9$ is H or —OR$_f$, wherein R$_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, optionally substituted arylalkyloxycarbonyl, or R$_9$ is an O atom which is bonded to an optionally substituted common C atom bonded to R$_{13}$' and R$_{14}$', wherein R$_{13}$' and R$_{14}$' each is an O atom;

R$_{12}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or R$_{12}$ is —OR$_g$, wherein R$_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, or optionally substituted heteroarylalkenylcarbonyl;

$R_{13}$' and $R_{14}$' are independently H or OH, or $R_{13}$' and $R_{14}$' are each an O atom which is bonded to an optionally substituted common C atom which is bonded to $R_9$, wherein $R_9$ is an O atom; and $R_{62}$ is H, halo, or —O— $R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{62}$.

In some embodiments, the PKC activator comprises a compound of formula (PVd):

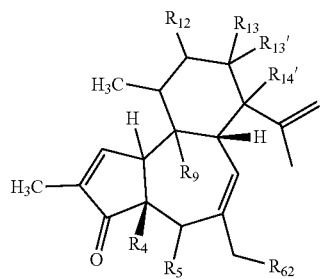

(PVd)

or an enantiomer, hydrate, solvate, or pharmaceutically acceptable salt thereof,
wherein
$R_4$, $R_5$, $R_9$, $R_{12}$, $R_{13}$, $R_{13}$', $R_{14}$' and $R_{62}$ are as defined for formula (PVc).

In some embodiments, the PKC activator comprises a compound of formula (PVe):

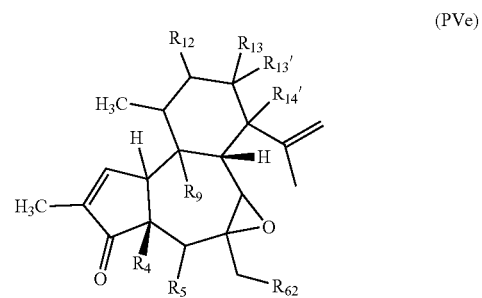

(PVe)

or an enantiomer, hydrate, solvate, or pharmaceutically acceptable salt thereof,
wherein
$R_4$, $R_5$, $R_9$, $R_{12}$, $R_{13}$, $R_{13}$', $R_{14}$' and $R_{62}$ are as defined for formula (PVc).

In some embodiments, the daphnane PKC activator is a compound selected from GD-1, yuanhuacine, sapintoxin D, thymeleatoxin A, simplexin, gnidimacrin, pimelea factor S7, genididin, geniditrin and gnidilatin. In some embodiments, the prodrugs for the specified daphnane compounds contain a biohydrolyzable carbonate, biohydrolyzable ureide, biohydrolyzable carbamate, biohydrolyzable ester, biohydrolyzable amide, or biohydrolyzable phosphate group. In particular, the prodrug for the specified daphnane compounds contains a biohydrolyzable ester, more particularly at the C20 carbon of formula (PV).

In some embodiments, the PKC activator compound is a PKC activating lathyrane compound. Exemplary lathyrane compounds with PKC activating properties include, by way of example and not limitation, Latilagascenes, jolkinol B, Euphorbia factors, japodagrol, and Euphohelioscopin A (see, e.g., Pusztai et al., 2007, Anticancer Res. 27:201-206; de Lichterveide et al., 2012, Chem Biol. 19(8): 994-1000; Tian et al., 2011, J. Nat. Prod. 74 (5):1221-1229; all publications incorporated herein by reference). Exemplary lathyrane compounds include, among others, the compounds of structural formula:

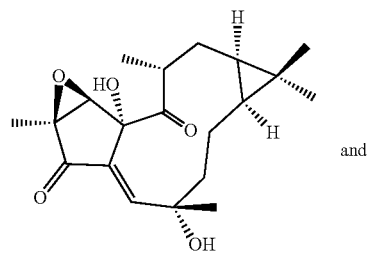

Japodargrin and

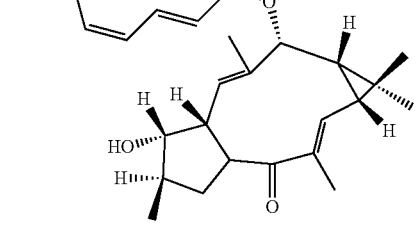

Euphohelioscopin A

5.3. Treatments Based on RAS Activity Status and/or PKC Activation Potential In some embodiments of the combination treatments, the cancer to be treated, and thus the subject, can be selected based on RAS activity status (e.g., K-RAS activity, N-RAS activity, or H-RAS activity), and/or PKC activation potential of the cancer, as further described in detail below. In some embodiments, a method of treating a subject with a cancer comprises administering to a subject in need thereof a therapeutically effective amount of a combination of diterpenoid PKC activator and a second therapeutic agent as described herein, wherein the cancer is identified as having an activating or oncogenic RAS activity.

In some embodiments, a method of treating a subject with a cancer comprises administering to a subject in need thereof a therapeutically effective amount of a combination of diterpenoid PKC activator and a second therapeutic agent, wherein the cancer is identified as having an effective PKC activation potential. In some embodiments, the identified K-RAS, N-RAS or H-RAS activity status can be used in combination with the determined PKC activation potential as the basis for selecting a cancer to be treated with the combination therapeutic.

5.3.1. Cancer Selection Based on Activating or Oncogenic RAS Activity

In some embodiments, a method of treating a subject with a cancer comprises administering to a subject in need thereof a therapeutically effective amount of a combination of diterpenoid PKC activator and a second therapeutic agent, wherein the cancer selected for treatment is identified as having or determined to have an activating or oncogenic RAS activity. In some embodiments, the activating RAS activity is K-RAS, H-RAS or N-RAS. In some embodiments, the activating or oncogenic RAS is an activating or oncogenic RAS mutation.

In some embodiments, the cancer to be treated with the combination therapy is selected based K-RAS activity status. In some embodiments, the activating form of K-RAS can be normally occurring K-RAS which has elevated expression in the cancer or an activating or oncogenic K-RAS mutation.

In some embodiments, the activating K-RAS mutation comprises an activating mutation in human K-RAS at one or more of codon 5, codon 9, codon 12, codon 13, codon 14, codon 18, codon 19, codon 22, codon 23, codon 24, codon 26, codon 33, codon 36, codon 57, codon 59, codon 61, codon 62, codon 63, codon 64, codon 68, codon 74, codon 84, codon 92, codon 35, codon 97, codon 110, codon 115, codon 117, codon 118, codon 119, codon 135, codon 138, codon 140, codon 146, codon 147, codon 153, codon 156, codon 160, codon 164, codon 171, codon 176, codon 185, and codon 188.

Various mutations for the above referenced codons can include activating mutations in which: codon 5 is K5E; codon 9 is V9I; codon 12 is G12A, G12C, G12D, G12F, G12R, G12S, G12V, or G12Y; codon 13 is G13C, G13D, or G13V; codon 14 is V14I or V14L; codon 18 is A18D; codon 19 is L19F; codon 22 is Q22K; codon 23 is L23R; codon 24 is I24N; codon 26 is N26K; codon 33 is D33E; codon 36 is I36L or I36M; codon 57 is D57N; codon 59 is A59E, A59G, or A59T; codon 61 is Q61H, Q61K, Q61L, or Q61R; codon 62 is E62G or E62K; codon 63 is E63K; codon 64 is Y64D, Y64H, or Y64N; codon 68 is R68S; codon 74 is T74P; codon 84 is I84T; codon 92 is D92Y; codon 97 is R97I; codon 110 is P110H or P110S; codon 115 is G115E; codon 117 is K117N; codon 118 is C118S; codon 119 is D119N; codon 135 is R135T; codon 138 is G138V; codon 140 is P140H; codon 146 is A146T or A146V; codon 147 is K147N; codon 153 is D153N; codon 156 is F156L; codon 160 is V160A; codon 164 is R164Q; codon 171 is I117M; codon 176 is K176Q; codon 185 is C185R or C185S; and codon 188 is M188V.

In particular, the cancer for treatment with the combination therapy is identified as having or determined to have an oncogenic or activating K-RAS mutation at codon 12, codon 13 and/or codon 61. In some embodiments, the oncogenic or activating K-RAS mutation at codon 12 is G12A, G12C, G12D, G12F, G12R, G12S, G12V, or G12Y; at codon 13 is G13C, G13D, or G13V; and at codon 61 is Q61H, Q61K, Q61L, or Q61R. In some embodiments, the oncogenic or activating K-RAS mutation is a combination of oncogenic or activating K-RAS mutations at codon 12 and codon 13; codon 12 and codon 61; codon 13 and 61; or codon 12, codon 13 and codon 61.

In some embodiments, a cancer with an activating mutation at codon 12, codon 13 and/or codon 61 is selected for treatment with the combination therapy, as the majority of activating K-RAS mutations observed in various cancers, such as pancreatic, colon, and lung cancer, occur in the three specified codons. In some embodiments, the cancer identified as having an activating K-RAS mutation and selected for treatment with the combination therapy can be a cancer of the pancreas, lung, colon, head and neck, stomach (gastric), biliary tract, endometrium, ovary, small intestine, urinary tract, liver, cervix, breast, kidney, renal, or hematopoietic (e.g., leukemia) tissues or cells.

In some embodiments, the cancer is pancreatic cancer identified as having an activating K-RAS mutation. Pancreatic cancers are known to have high rates (about 95%) of activating or oncogenic K-RAS mutations. Thus, a pancreatic cancer having an identified activating or oncogenic K-RAS mutation, in particular those described above, can be selected for treatment with the combination therapy. In some embodiments, the pancreatic cancer has an identified activating K-RAS mutation in codon 12, codon 13, and/or codon 61.

In some embodiments, the pancreatic cancer is pancreatic adenocarcinoma or metastatic pancreatic cancer having an identified activating or oncogenic K-RAS mutation. In some embodiments, the pancreatic cancer is pancreatic adenocarcinoma diagnosed as stage I, stage II, stage III, or stage IV, where the pancreatic adenocarcinoma has an identified activating or oncogenic K-RAS mutation.

In some embodiments, the cancer is lung cancer identified as having an activating or oncogenic K-RAS mutation. In particular, lung cancer having an identified activating or oncogenic K-RAS mutation, such as those specified above, can be selected for treatment with the combination therapy. In some embodiments, the lung cancer has an identified activating or oncogenic K-RAS mutation at codon 12, codon 13, and/or codon 61.

In some embodiments, the lung cancer selected for treatment is small cell lung cancer identified as having an activating or oncogenic K-RAS mutation. In some embodiments, the lung cancer selected for treatment is non-small cell lung cancer identified as having an activating or oncogenic K-RAS mutation. In some embodiments, the non-small cell lung cancer selected for treatment is an adenocarcinoma, squamous cell carcinoma, or large cell carcinoma identified as having an activating or oncogenic K-RAS mutation. In some embodiments, the lung cancer selected for treatment is metastatic lung cancer identified as having an activating or oncogenic K-RAS mutation.

In some embodiments, the cancer selected for treatment with the combination therapy is colon cancer identified as having an activating or oncogenic K-RAS mutation. In particular, colon cancer having an identified activating or oncogenic K-RAS mutation, such as those specified above, can be selected for treatment with the combination therapy. In some embodiments, the colon cancer has an identified activating or oncogenic K-RAS mutation at codon 12, codon 13, and/or codon 61.

In some embodiments, the colon cancer is colon adenocarcinoma or a metastatic colon cancer identified as having an activating or oncogenic K-RAS mutation.

In some embodiments, the cancer selected for treatment is a hematologic cancer, preferably a leukemia or lymphoma having an activating K-RAS mutation. In some embodiments, the leukemia or lymphoma is selected for treatment can be acute myeloid leukemia, chronic myeloid leukemia, acute lymphoblastic leukemia, juvenile myelomonocytic leukemia, chronic myelomonocytic leukemia, myelodysplastic syndrome, myeloproliferative neoplasia, multiple myeloma, Hodgkin's lymphoma, Non-Hodgkin's lymphoma, Burkitt's lymphoma, or other types of leukemias or lymphomas.

In some embodiments, where the cancer to be treated with the combination therapy is selected based on N-RAS activity status, the activating form of N-RAS can be normally occurring N-RAS which has elevated expression in the cancer or an activating or oncogenic N-RAS mutation.

In some embodiments, the cancer selected for treatment with the combination therapy has an activating or oncogenic N-RAS mutation in human N-RAS at codon 12, codon 13, and/or codon 61. In some embodiments, the activating or oncogenic N-RAS mutation at codon 12 is G12A, G12C, G12D, G12R, G12S, or G12V. In some embodiments, the activating or oncogenic N-RAS mutation at codon 13 is G13A G13C, G13D, G13R, G13S, or G13V. In some embodiments, the activating or oncogenic N-RAS mutation at codon 61 is Q61E, Q61H, Q61K, Q61L, Q61P, or Q61R. In some embodiments, the activating or oncogenic N-RAS mutation is a combination of activating or oncogenic N-RAS mutations at codon 12 and codon 13; codon 12 and codon 61; codon 13 and 61; or codon 12, codon 13 and codon 61.

In some embodiments, the cancer selected for treatment based on N-RAS status is a melanoma or hematologic cancer, preferably a leukemia. In some embodiments, the leukemia having an activating or oncogenic N-RAS activity can be acute myeloid leukemia, chronic myeloid leukemia, acute lymphoblastic leukemia, juvenile myelomonocytic leukemia, chronic myelomonocytic leukemia, myelodysplastic syndrome, myeloproliferative neoplasia, and multiple myeloma, or other types of leukemia.

In some embodiments, where the cancer to be treated with the combination therapy is selected based on H-RAS activity status, the activating form of N-RAS can be normally occurring N-RAS which has elevated expression in the cancer or an activating or oncogenic N-RAS mutation.

In some embodiments, the cancer selected for treatment with the combination therapy is identified as having or determined to have an activating or oncogenic H-RAS mutation. In some embodiments, the cancer selected for treatment is identified as having an activating or oncogenic mutation in human H-RAS at one or more of codon 12, codon 13 and codon 61. In some embodiments, the activating or oncogenic H-RAS mutation at codon 12 is G12A, G12C, G12D, G12R, G12S, or G12V. In some embodiments, the activating or oncogenic H-RAS mutation at codon 13 is G13A, G13C, G13D, G13R, G13S, or G13V. In some embodiments, the activating or oncogenic H-RAS mutation at codon 61 is Q61E, Q61H, Q61K, Q61L, Q61P, or Q61R. In some embodiments, the activating or oncogenic H-RAS mutation is a combination of activating or oncogenic H-RAS mutations at codon 12 and codon 13; codon 12 and codon 61; codon 13 and 61; or codon 12, codon 13 and codon 61.

In some embodiments, the cancer selected for treatment with the combination therapy based on H-RAS status can be a cancer of the cervix, prostate, salivary gland, skin, upper aerodigestive tract, and urinary tract.

In some embodiments, the cancer for treatment with the combination therapy can be a cancer having prevalence (e.g., at least about 5% or more, at least about 10% or more, or about 15% or more of the cancers), of an activating or oncogenic RAS mutation (e.g., K-RAS, N-RAS, or H-RAS), such as cancer of the biliary tract, cervix, endometrium, pancreas, lung, colon, head and neck, stomach (gastric), biliary tract, endometrium, hematologic (e.g., leukemia, lymphomas, etc.) cells, large intestine, lung, ovary, pancreas, prostate, salivary gland, skin, small intestine, stomach thyroid, aerodigestive tract, urinary tract, ovary, small intestine, or urinary tract (see, e.g., Prior et al., 2012, Cancer Res. 72(10): 2457-2467, incorporated herein by reference).

5.3.2. Cancer Selection Based on PKC Activating Potential

In some embodiments, the cancer to be treated with the combination therapy can be selected for sensitivity to the diterpenoid PKC activator, particularly by assessing the PKC activation potential of the cancer (see, e.g., International application PCT/US2016/61711, incorporated herein by reference). In some embodiments, a method of treating a subject with cancer comprises determining or identifying a PKC activation potential of the cancer for a PKC activator, and administering to the subject having a cancer determined to have an effective PKC activation potential a therapeutically effective amount of a diterpenoid PKC activator and a second therapeutic agent, as described herein.

In some embodiments, a method of treating a subject with cancer comprises administering to a subject in need thereof a therapeutically effective amount of a diterpenoid PKC activator and a second therapeutic agent, wherein the cancer has been determined or identified as having an effective PKC activation potential for the diterpenoid PKC activator.

In some embodiments, the PKC activation potential can take into account (a) the basal level of PKC activity present in the cancer cell, and/or (b) the increase in PKC activity upon contacting the cancer cell or upon treatment of the cancer with the PKC activator. In some embodiments, the level of PKC activity can be assessed for total PKC activity or activity of one or more specific PKC isoforms.

The presence of an effective PKC activation potential for a PKC activator can be determined by various methods. In some embodiments, the effective PKC activation potential can be determined by measuring the level of PKC activation in cancer cells sensitive to the PKC activator, e.g., based on inhibition of cell proliferation. For example, the level of PKC activation associated with 50% inhibition of cell proliferation ($IC_{50}$) by a PKC activator can be used as an effective PKC activation potential for the PKC activator. In some embodiments, a cancer cell insensitive or resistant to the PKC activator, e.g., insignificant effect on cell proliferation at concentration of PKC activator sufficient to inhibit proliferation of PKC-activator sensitive cells (e.g., IC50), can be used to identify the PKC enzyme activated by the PKC activator in sensitive cancer cells. In some embodiments, the basal level of PKC activity in PKC activator sensitive cells as compared to level of PKC activity in PKC activator insensitive cells can be used to determine a basal level of PKC activity, either as total PKC activity or activity of one or more specific PKC isoforms, associated with sensitivity to the PKC activator.

In some embodiments, the effective PKC activation potential for a PKC activator can be determined by the use of a PKC inhibitor. The PKC inhibitor can be a broad spectrum inhibitor or a specific inhibitor targeting one or a limited set of the PKC isoforms. In some embodiments, a cancer cell sensitive to a PKC activator can be treated with different concentrations of a PKC inhibitor and then treated with the PKC activator. The reduction in PKC activator-mediated inhibition of cell proliferation by treatment with the PKC inhibitor and the associated level of PKC activation can provide a measure of the level of effective PKC activation sufficient for inhibiting cell proliferation. In some embodiments, the PKC inhibitor used is an inhibitor specific to a PKC isoform or specific to a limited set of PKC isoforms.

In some embodiments, a cancer with a basal level of total PKC activity of at least 20%, 30%, 40%, 50%, 60%, 70%, 80%, 90% or more of the basal PKC activity present in a suitable control, for example non-cancerous cells or tissues or normal cells or tissues, can provide an indication of sensitivity to a PKC activator, and thus a basis for selection of the cancer for treatment with a combination of the PKC activator and second therapeutic agent.

In some embodiments, a cancer which displays an increase in total PKC activity of at least 30%, 40% 50%, 60%, 70%, 80%, 90%, 100%, 150%, 200% or more above the PKC activity of untreated cancer cells, in presence of or following treatment with the PKC activator indicates sensitivity to the PKC activator and thus a basis for selection of the cancer for treatment with a combination of the PKC activator and second therapeutic agent.

In some embodiments, a cancer which has increased total PKC activity upon treatment with the PKC activator, such as in the foregoing, and in which the total PKC activity following treatment is at least 30%, 40%, 50%, 60%, 70%, 80%, 90%, 100%, 150%, 200% or more of the PKC activity of control non-cancerous cells or tissue indicates sensitivity to the PKC activator and thus a basis for selection of the cancer for treatment with a combination of the PKC activator and second therapeutic agent.

In some embodiments, the selection of a cancer for treatment with a combination therapy is based on the PKC activation potential for one or more of PKC isoforms. In some embodiments, the PKC activation potential is determined or measured for one or more of PKC isoforms selected from PKC α, β, γ, δ, ε, η, θ, ι/λ, μ and ζ. In some embodiments, the PKC activation potential is determined or measured for one or more classical PKCs. Exemplary classical PKCs include PKC α, β (e.g., βI, βII), and γ. In some embodiments, the PKC activation potential is determined or measured for one or more novel PKCs. Exemplary novel PKCs include δ, ε, η, and θ. In some embodiments, the PKC activation potential is determined or measured for one or more atypical PKCs. Exemplary atypical PKCs include ι/λ and ζ. In some embodiments, the PKC activation potential is determined or measured for PKCμ, which is a member of the protein kinase D (PKD) family.

In some embodiments, a cancer with a basal level of PKC activity of at least 20%, 30%, 40%, 50%, 60%, 70%, 80%, 90% or more of the basal PKC activity for one or more of PKC isoforms selected from PKC α, β, γ, δ, ε, η, θ, ι/λ, μ and ζ as compared to a suitable control level, for example the basal level in non-cancerous cells or tissues (e.g., normal cells or tissues), can provide an indication of sensitivity to a PKC activator, and thus a basis for selection of the cancer for treatment with a combination of the PKC activator and second therapeutic agent. In some embodiments, the determination of a basal level of PKC activity can be useful where the PKC activity is known to be expressed in the control cells or tissues in the absence of treatment with the PKC activator.

In some embodiments, a cancer which displays or is capable of an increase in one or more of PKC α, β, γ, δ, ε, η, θ, ι/λ, μ and ζ activity of at least 30%, 40%, 50%, 60%, 70%, 80%, 90%, 100%, 150%, 200% or more above the PKC α, β, γ, δ, ε, η, θ, ι/λ, μ and ζ activity, respectively, of a control level, e.g., untreated cancer cells, in presence of or following treatment with the PKC activator is selected for treatment with a combination of the PKC activator and second therapeutic agent.

In some embodiments, the PKC activation potential is measured for one or more of PKC α, β, and γ. In some embodiments, a cancer with a basal level of PKC α, β, or γ activity of at least 20%, 30%, 40%, 50%, 60%, 70%, 80%, 90% or more of the basal PKC α, β, or γ activity, respectively, of a control level, e.g., normal cells or normal tissue, is indicated for treatment with a combination of the PKC activator and second therapeutic agent. In some embodiments, a cancer which displays or is capable of an increase in one or more of PKC α, β, and γ activity of at least 30%, 40%, 50%, 60%, 70%, 80%, 90%, 100%, 150%, 200% or more above the PKC α, β, or γ activity, respectively, of a control level, e.g., untreated cancer cells, in presence of or following treatment with the PKC activator is selected for treatment with a combination of the PKC activator and second therapeutic agent. In some embodiments, a cancer which displays or is capable of an increase in PKC α, β, or γ activity upon treatment with the PKC activator, such as in the foregoing, and in which the total PKC α, β, or γ activity is at least 30%, 40%, 50%, 60%, 70%, 80%, 90%, 100%, 150%, 200% or more of the PKC activity of a control level, e.g., untreated cells, in presence of or following treatment with the PKC activator is selected for treatment with a combination of the PKC activator and second therapeutic agent.

In some embodiments, the PKC activation potential is measured for one or more of PKC δ, ε, η, or θ. In some embodiments, a cancer with a basal level of PKC δ, ε, η, or θ activity of at least 20%, 30%, 40%, 50%, 60%, 70%, 80%, 90% or more of the basal PKC δ, ε, η, or θ activity, respectively, of a control level, e.g., normal cells or normal tissue, is indicated for treatment with a combination of the PKC activator and second therapeutic agent. In some embodiments, a cancer which displays or is capable of an increase in one or more of PKC δ, ε, η, or θ activity of at least 30%, 40%, 50%, 60%, 70%, 80%, 90%, 100%, 150%, 200% or more above the PKC δ, ε, η, or θ activity, respectively, of a control level, e.g., untreated cancer cells, in presence of or following treatment with the PKC activator is selected for treatment with a combination of the PKC activator and second therapeutic agent. In some embodiments, a cancer which displays or is capable of an increase in PKC δ, ε, η, or θ activity upon treatment with the PKC activator, such as in the foregoing, and in which the total PKC δ, ε, η, or θ activity is at least 30%, 40%, 50%, 60%, 70%, 80%, 90%, 100%, 150%, 200% or more of the PKC activity of a control level, e.g., untreated cells, in presence of or following treatment with the PKC activator is selected for treatment with a combination of the PKC activator and second therapeutic agent.

In some embodiments, the PKC activation potential is measured for one or more of PKC ι/λ, μ or ζ. In some embodiments, a cancer with a basal level of PKC ι/λ, μ or ζ activity of at least 20%, 30%, 40%, 50%, 60%, 70%, 80%, 90% or more of the basal PKC ι/λ, μ or ζ activity, respectively, of a control level, e.g., normal cells or normal tissue, is indicated for treatment with a combination therapy. In some embodiments, a cancer which displays or is capable of an increase in one or more of PKC ι/λ, μ or ζ activity of at least 30%, 40%, 50%, 60%, 70%, 80%, 90%, 100%, 150%, 200% or more above the PKC ι/λ, μ or ζ activity, respectively, of a control level, e.g., untreated cancer cells, in presence of or following treatment with the PKC activator is selected for treatment with a combination of the PKC activator and second therapeutic agent. In some embodiments, a cancer which displays or is capable of an increase in PKC ι/λ, μ or ζ activity upon treatment with the PKC activator, such as in the foregoing, and in which the total PKC ι/λ, μ or ζ activity is at least 30%, 40%, 50%, 60%, 70%, 80%, 90%, 100%, 150%, 200% or more of the PKC activity of a control level, e.g., untreated cells, in presence of or following treatment with the PKC activator is selected for treatment with a combination of the PKC activator and second therapeutic agent.

In some embodiments, the PKC activation potential can be assessed by detecting or measuring one or more phosphorylated amino acid sequences in the PKC enzyme, particularly phosphorylation associated with activation or activity of the PKC enzyme. In some embodiments, the phosphorylated amino acid sequence detected has (i) increased phosphorylation induced by the PKC activator in a control, e.g., normal cells, and/or (ii) increased phosphorylation in control PKC activator-sensitive cancer cells but not in control PKC activator insensitive cancer cells. Determining the PKC activation potential can be based on identified phosphorylated amino acid sequences in one or more of PKC α, β (e.g., βI or βII), γ, δ, ε, η, θ, ι/λ, μ, and ζ, particularly phosphorylated amino acid sequences localized in the protein kinase domain and carboxy terminal tail of the PKC, also referred to as the C3 and C4 domains (see, e.g., Newton, A. C., 2010, Am J Physiol Endocrinol Metab. 298:E395-E402; Steinberg, S. F., 2008, Physiol Rev. 88(4): 1341-1378; incorporated herein by reference). Compilation of phosphorylated sites in each of the PKC enzymes is available at PhosphoSitePlus® at world wide web (www) at phosphosite.org.

In some embodiments, determining PKC activation potential for human PKCα can measure phosphorylation at one or more of S226, T228, T497, T638, S657 and Y658, particularly T497, T638, S657 and Y658.

In some embodiments, determining PKC activation potential for human PKCβ (βI/βII) can measure phosphorylation at one or more of Y368, T500, T504, Y507, Y515, Y518, T635, T642(641), and S661(660), particularly T500, T642(641), and S661(660).

In some embodiments, determining PKC activation potential for human PKCγ can measure phosphorylation at one or more of T514, T518, Y521, Y529, Y532, T655, T674 and S687, particularly T514 and T674.

In some embodiments, determining PKC activation potential for human PKCδ can measure phosphorylation at one or more of Y64, T141, Y187, T295, S299, Y313, Y374, S503, T505, S506, T507, T511, Y514, Y567, S630, S643, S645, Y646, S647, S658, and S664, particularly Y64, Y187, Y313, T505, T507, T511, Y514, Y567, S630, S643, S645, Y646, S647, S658, and S664.

In some embodiments, determining PKC activation potential for human PKCε can measure phosphorylation at one or more of Y250, T309, S329, S337, S346, S350, S368, S388, T566, T710, and S729, particularly T566, T710, and S729.

In some embodiments, determining PKC activation potential for human PKC can measure phosphorylation at one or more of S28, S32, Y94, S317, S327, Y381, T656, S676, S685, S695, and S675, particularly S327, Y381, T656, and S675.

In some embodiments, determining PKC activation potential for human PKCθ can measure phosphorylation at one or more of Y90, T219, T307, T536, T538, Y545, S676, S685, and S695, particularly Y90, T538, S676, S685 and S695.

In some embodiments, determining PKC activation potential for human PKCι/λ can measure phosphorylation at one or more of Y136, T403, T409, T410, S411, T412, S459, T555, T557, T564, Y584, and S591, particularly T403, T409, T410, S411, T412, S459, T555, T557, T564, Y584, and S591.

In some embodiments, determining PKC activation potential for human PKC ι can measure phosphorylation at one or more of Y95, S205, S208, S219, S223, Y463, S738, S742, T746, S748, and S910, particularly Y95, Y463, S738, S742, S744, T746, S748, and S910, more particularly S910. The S910, Ser738, and Ser742 in human PKCμ are equivalent to Ser916, Ser744, and Ser748, respectively, in mouse PKCμ.

In some embodiments, determining PKC activation potential for human PKCζ can measure phosphorylation at one or more of S262, Y263, R375, T410, Y417, Y428, S520, T560, and S591, particularly T410, Y417, Y428, S520, T560, and S591.

In some embodiments, the PKC activation potential is determined by measuring phosphorylation at the kinase domain activation loop, the turn motif, and/or the hydrophobic motif of the PKC. In some embodiments, the PKC activation potential is determined by detecting phosphorylation at the kinase domain activation loop. Exemplary phosphorylations occurring at the activation loop of human PKCs include T497 for PKCα, T500 for PKCβ, T514 for PKCγ, T505 for PKCδ, T538 for PKCθ, T566 for PKCε, T512 for PKC η, T410 for PKCζ, T403 for PKCι/λ, and S738/S742 for PKCμ.

In some embodiments, the PKC activation potential is determined by measuring phosphorylation at the kinase domain turn motif. Exemplary phosphorylations occurring at the turn motif of PKCs include S638 for PKCα, T641 for PKCβ (βII and βII), T655 for PKCγ, T643 for PKCδ, S676 for PKCθ, T710 for PKCs, T645 for PKC η, and T560 for PKCζ.

In some embodiments, the PKC activation potential is determined by measuring phosphorylation at the kinase domain hydrophobic motif and/or carboxy terminal domain. Exemplary phosphorylations occurring at the hydrophobic motif and/or carboxy terminal domain include S657 for PKCα, S660 for PKCβ (βII and βII), S674 for PKCγ, S662 for PKCδ, S695 for PKCθ, S729 for PKCs, S664 for PKC η, and S910 for PKCμ.

In some embodiments, the PKC activation potential is determined by measuring phosphorylation at one or more autophosphorylation sites in the PKC enzyme. Exemplary autophosphorylation sites include: S638 for PKCα, T641 for PKCβ, T141/T295/T514 for PKCγ, T295/T505 for PKCδ, T219/T538/S676/S695 for PKCθ, S729 for PKCε, T655 for PKCη, T560 for PKCζ, and S738/S742/S910 for PKCμ.

In some embodiments, the PKC activation potential is determined for phosphorylation of PKCμ at Ser910, which is equivalent to Ser916 in mouse. In some embodiments, a method of determining the sensitivity of a cancer or selecting a cancer for treatment with a combination of the PKC activator and second therapeutic agent includes determining the level of phosphorylated PKCμ at Ser910 in the cancer, wherein an elevated level of phosphorylated PKCμ at Ser910 upon treatment with the PKC activator indicates sensitivity of the cancer to the PKC activator. In some embodiments, a cancer or a subject with cancer is selected for treatment with a combination of the PKC activator and second therapeutic agent if the cancer is determined to have (i) an elevated level of phosphorylated PKCμ at Ser910 upon treatment of the cancer with the PKC activator, or (ii) an elevated level of phosphorylated PKCμ at Ser910 upon treatment of the cancer with the PKC activator as compared to a control level, e.g., basal level in untreated cancer or normal cells or tissues. In some embodiments, a method of treating a subject with cancer comprises administering to a subject in need thereof a therapeutically effective amount of a diterpenoid PKC activator and a second therapeutic agent as described herein, wherein the cancer is determined to have an elevated level of phosphorylated PKCμ at Ser910 upon treatment of the cancer with the PKC activator.

It is to be understood that in some embodiments, phosphorylation of a PKC can be correlated with insensitivity of a cancer to a PKC activator, in contrast to phosphorylation of a PKC that is correlated with sensitivity to the PKC activator. In some embodiments, the phosphorylated PKC can be present endogenously in the absence of treatment with a PKC activator, where presence of the phosphorylated PKC correlates with insensitivity to the PKC activator. In some embodiments, the phosphorylation of the PKC correlated with insensitivity to the PKC activator occurs in response to treatment of the cancer with a PKC activator. In some embodiments, the phosphorylation correlated with insensitivity to a PKC activator is phosphorylation of PKCδ, particularly phosphorylation of PKCδ at Tyr311. In some embodiments, a method of determining the sensitivity of a cancer or selecting a cancer for treatment with a combination of the PKC activator and second therapeutic agent includes determining the level of phosphorylated PKCδ at Tyr311 in the cancer, wherein (i) an absence of phosphorylated PKCδ at Tyr311, or (ii) a basal level of phosphorylated PKCδ at Tyr311 as compared to a control level, e.g., basal level in control PKC activator sensitive cancer, indicates sensitivity of the cancer to the PKC activator. A basal level as used in this context refers to the level of phosphorylated PKCδ at Tyr311 in control PKC activator sensitive cancer cells, with or without treatment with the PKC activator. In some embodiments, a cancer or a subject with a cancer is selected for treatment with a combination of the diterpenoid PKC activator and a second therapeutic agent if the cancer has: (i) an absence of phosphorylated PKCδ at Tyr311, or (ii) a basal level of phosphorylated PKCδ at Tyr311 as compared to a control level. In some embodiments, a method of treating a subject with cancer comprises administering to the subject in need thereof a therapeutically effective amount of a diterpenoid PKC activator and a second therapeutic agent, as described herein, wherein the cancer is determined to have: (i) an absence of phosphorylated PKCδ at Tyr311, and/or (ii) a basal level of phosphorylated PKCδ at Tyr311 as compared to a control level, e.g., basal level in control PKC activator sensitive cancer cells or tissues.

In some embodiments, a cancer or a subject with cancer is not selected for treatment with a the PKC activator and second therapeutic agent if the cancer is determined to have (i) phosphorylated PKCδ at Tyr311, and/or (ii) an elevated level of phosphorylated PKCδ at Tyr311 as compared to a basal control level, e.g., level in control PKC activator sensitive cancer cells or tissues, or normal cells or tissue. In some embodiments, a cancer or a subject with cancer is not selected for treatment with the combination therapy when the level of phosphorylated PKCδ at Tyr311 is elevated compared to a control basal level, e.g., basal level in PKC activator sensitive cancer cells or tissues, or normal cells or tissues. In some embodiments, the sensitivity or insensitivity of a cancer to a PKC activator can be based on assessment of the level of phosphorylated PKC at Ser910 (Ser916), and the level of phosphorylated PKCδ at Tyr311.

In some embodiments, a cancer or a subject with a cancer is selected for treatment with the combination therapy if the cancer is determined to have (i) an elevated level of phosphorylated PKC at Ser910 upon treatment with the PKC inhibitor, and (ii) an absence or a basal level of phosphorylated PKCδ at Tyr311 as compared to a control level. In some embodiments, a method of treating a subject with cancer comprises administering to the subject in need thereof a therapeutically effective amount of a diterpenoid PKC activator and a second therapeutic agent, wherein the cancer is determined to have: (i) an elevated level of phosphorylated PKC at Ser910 upon treatment with the PKC inhibitor, and (ii) an absence or a basal level of phosphorylated PKCδ at Tyr311 as compared to a control level.

In some embodiments, the PKC activation potential can be assessed by determining the presence or absence of mutations in the gene encoding a PKC enzyme, where the mutations result in inactivation or attenuation of PKC activity, such as gene deletions and other loss-of-function mutations. The presence of such mutations in the PKC gene may result in low or no basal level of PKC activity and also display ineffective PKC activation upon treatment with the PKC activator. Accordingly, in some embodiments, the PKC activation potential is assessed by identifying or determining in the cancer the presence or absence of one or more loss-of-function mutations (e.g., inactivating or activity-attenuating) in the gene encoding the PKC enzyme. In various embodiments, a cancer determined or identified as being negative for loss-of-function mutations in one or more of PKC enzymes is selected for treatment with the combination therapy. In some embodiments, cancer determined or identified as being negative for two or more, three or more, four or more, or five or more loss-of-function mutations is selected for treatment with the combination therapy. In some embodiments, a cancer is not selected for treatment if it is determined or identified as having loss-of-function mutations in one or more PKC enzymes. In some embodiments, a cancer is not selected for treatment if it is determined or identified as having two or more, three or more, four or more, or five or more loss-of-function mutations. In view of the presence of various PKC isoforms, in some embodiments, the cancer is not selected for treatment with the combination if two or more, three or more, four or more, or five or more PKC isoforms are determined or identified as having a loss-of-function mutation. In some embodiments, a cancer assessed for presence of a loss-of-function PKC mutation and measured for activation potential identifies the basis for selecting the cancer for treatment with the combination therapy. In some embodiments, assessment based on identification of or absence of a loss-of-function mutation alone is used as the basis for selecting or not selecting the cancer for treatment with the combination therapy.

In some embodiments, the loss-of-function mutation is assessed for one or more PKC isoforms selected from PKC α, β, γ, δ, ε, η, θ, ι/λ, µ and ζ. In some embodiments, the loss-of-function mutation is assessed for one or more classical PKCs, including PKC α, β (e.g., βI, βII), and γ. In some embodiments, the loss-of-function mutation is assessed for one or more novel PKCs, including PKC δ, ε, η, and θ. In some embodiments, the loss-of-function mutation is assessed for one or more atypical PKCs, including PKC ι/λ and ζ. In some embodiments, the loss-of-function mutation is assessed for PKCµ.

In some embodiments, the loss-of-function mutation is assessed for one or more PKC isoforms selected from PKC α, β, and γ.

In some embodiments, the PKC is PKCα, and the loss-of-function mutation is an inactivating or activity-attenuating deletion or partial deletion of the gene encoding PKCα, or a loss-of-function mutation at one or more of codon 58, codon 61, codon 63, codon 75, codon 257, codon 435, codon 444, codon 481, codon 506, and codon 508. In some embodiments, the loss-of-function mutation in PKCα is one or more of αW58L, αG61W, αQ63H, αH75Q, αG257V, αF435C, αA444V, αD481E, αA506V, αA506T, and αE508K.

In some embodiments, the PKC is PKCβ, and the loss-of-function mutation is an inactivating or activity-attenuating deletion or partial deletion of the gene encoding PKCβ, or a loss-of-function mutation at one or more of codon 61, codon 353, codon 417, codon 484, codon 509, codon 523, codon 561, codon 585, and codon 619. In some embodiments, the loss-of-function mutation in PKCβ is one or more of βG61W, βF353L, βY417H, βD484N, βA509V, βA509T, βD523N, βP561H, βG585S, and βP619Q.

In some embodiments, the PKC is PKCγ, and the loss-of-function mutation is an inactivating or activity-attenuating deletion or partial deletion of the gene encoding PKCγ, or a loss-of-function mutation at one or more of codon 23, codon 57, codon 193, codon 218, codon 254, codon 362, codon 431, codon 450, codon 461, codon 498, codon 524, codon 537, and codon 575. In some embodiments, the loss-of-function mutation in PKCγ is one or more of γG23E, γG23W, γW57splice, γD193N, γT218M, γT218R, γD254N, γF362fs, γF362L, γG450C, γY431F, γA461T, γA461V, γD498N, γP524L, γP524R, γD537G, γD537Y, and γP575H.

In some embodiments, the loss-of-function mutation is assessed for one or more PKC isoforms selected from PKC δ, ε, η, or θ.

In some embodiments, the PKC is PKCδ, and the loss-of-function mutation is an inactivating or activity-attenuating deletion or partial deletion of the gene encoding PKCδ, or a loss-of-function mutation at one or more of codon 146, codon 454, codon 517, codon 530, and codon 568. In some embodiments, the loss-of-function mutation in PKCδ is one or more of δG146R, δA454V, δP517S, δD530G, δP568A, and δP568S.

In some embodiments, the PKC is PKCε, and the loss-of-function mutation is an inactivating or activity-attenuating deletion or partial deletion of the gene encoding PKCε, or a loss-of-function mutation at one or more of codon 162, codon 197, codon 502, and codon 576. In some embodiments, the loss-of-function mutation in PKCε is one or more of εR162H, εQ197P, εR502X, and εP576S.

In some embodiments, the PKC is PKCη, and the loss-of-function mutation is an inactivating or activity-attenuating deletion or partial deletion of the gene encoding PKCη, or a loss-of-function mutation at one or more of codon 284, codon 591, codon 596, and codon 598. In some embodiments, the loss-of-function mutation in PKCη is one or more of ηH284Y, ηK591E, ηK591N, ηR596H, and ηG598V.

In some embodiments, the PKC is PKCθ, and the loss-of-function mutation is an inactivating or activity-attenuating deletion or partial deletion of the gene encoding PKC θ, or a loss-of-function mutation at one or more of codon 171, codon 485, codon 548, and codon 616. In some embodiments, the loss-of-function mutation in PKCθ is one or more of θW171X, θA485T, θP548S, and θR616Q.

In some embodiments, the loss-of-function mutation is assessed for one or more PKC isoforms selected from PKCι/λ, µ and ζ.

In some embodiments, the PKC is PKCι/λ, and the loss-of-function mutation is an inactivating or activity-attenuating deletion or partial deletion of the gene encoding PKCι/λ, or a loss-of-function mutation at one or more of codon 179, codon 359, codon 396, and codon 423. In some embodiments, the loss-of-function mutation in PKCι/λ is one or more of ιH179Y, ιS359, ιD396E, and ιE423D.

In some embodiments, the PKC is PKCµ, and the loss-of-function mutation is an inactivating or activity-attenuating deletion or partial deletion of the gene encoding PKCµ, or a loss-of-function mutation at one or more of the mutations found in breast and colon cancer (see, e.g., Kan et al., 2010, Nature 466:869-873).

In some embodiments, the PKC is PKCζ, and the loss-of-function mutation is an inactivating or activity-attenuating deletion or partial deletion of the gene encoding PKCζ, or a loss-of-function mutation at codon 421. In some embodiments, the loss-of-function mutation in PKCζ is ζE421K.

In some embodiments, the PKC loss-of-function mutation is in the kinase domain of PKC, which sequence is conserved in eukaryotic PKCs (see, e.g., Kornev et al., 2006, Proc Natl Acad Sci. USA 103:17783-17788, incorporated herein by reference). In some embodiments, the PKC loss-of-function mutation is a loss-of-function mutation in the activation loop, the turn motif, and/or the hydrophobic motif of the PKC kinase domain.

In some embodiments, the PKC mutations are dominant negative mutations, particularly dominant negative mutations which result in attenuated global PKC activity in the cancer cell and which can attenuate activation by PKC activators. In some embodiments, the dominant negative mutation is one or more of PKCα (e.g., H75Q), PKCγ (e.g., P524R), and PKCβ (e.g., A509V). In some embodiments, a subject with a cancer which is determined or identified as having one or more dominant negative PKC mutations is not selected for treatment with the combination. In some embodiments, a subject with a cancer which is determined or identified as being negative for at least one, at least two or more, at least three or more, or at least for or more dominant negative mutations in PKC are selected for treatment with the combination.

In some embodiments, the PKC activation potential can be assessed by determining or identifying in the cancer the presence or absence of mutations affecting interaction of the PKC enzyme with the PKC activator, particularly a diterpenoid PKC activator. In some embodiments, a cancer with identified mutations occurring in the C1 domain of PKC and affecting interaction with a diterpenoid PKC activator with the PKC is not selected for treatment with the combination therapy. For example, exemplary mutations affecting the interaction of PKC with phorbol PKC activator are described in, for example, Wang et al., 2001, J Biol Chem.

276:19580-19587; and Kazanietz et al, 1995, J Biol Chem. 270:21852-21859; incorporated herein by reference. In some embodiments, a cancer determined or identified as negative for mutations affecting interaction of a PKC activator with the PKC protein is indicated for treatment with the combination therapy.

In some embodiments, the assessment of the PKC activation potential of the cancer can also include determining or identifying the expression level of the PKC enzyme during or following treatment with the PKC activator. In some embodiments, the determining or identifying the expression level of the PKC enzyme is carried out as an adjunct to assessment of the PKC activation potential based on PKC activity, e.g., PKC phosphorylation. In some embodiments, the expression level of the PKC enzyme is determined for one or more PKC isoforms α, β (e.g., βI or βII), γ, δ, ε, η, θ, τ/λ, μ, and ζ. In some embodiments, an assessment of the PKC activation potential includes determining or identifying the expression level of one or more of PKC isoforms α, β (e.g., βI or βII), and γ. In some embodiments, an assessment of the PKC activation potential includes determining or identifying the expression level of one or more of PKC isoforms δ, ε, η, and θ. In some embodiments, an assessment of the PKC activation potential includes determining or identifying the expression level of one or more of PKC isoforms ι/λ, μ, and ζ. In various embodiments, the measured expression level of the PKC enzyme is compared to a control or reference level, such as the level of PKC in the cancer prior to treatment with the PKC activator and/or the level of PKC in non-cancerous cell or tissue, e.g., normal cell or tissue. In some embodiments, the measured expression level of PKC enzyme is compared to the level in the cancer prior to treatment with the PKC activator. In some embodiments, the expression level of the PKC enzyme is determined at the protein level or at the level of mRNA. In some embodiments, a cancer having an effective PKC activation potential and elevated expression of PKC enzymes is selected for treatment with the PKC activator.

In some embodiments, cancers for selection and treatment with the combination therapy based on its PKC activation potential includes, among others, adrenocortical cancer, anal cancer, biliary cancer, bladder cancer, bone cancer (e.g., osteosarcoma), brain cancer (e.g., glioma, astrocytoma, neuroblastoma, etc.), breast cancer, cervical cancer, colon cancer, endometrial cancer, esophageal cancer, head and neck cancer, hematologic cancer (e.g., leukemias and lymphomas), intestinal cancer (small intestine), kidney cancer, liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma, squamous cell carcinoma, etc.), stomach cancer, testicular cancer, throat cancer, thyroid cancer, uterine cancer, and vaginal cancer. In some embodiments, the PKC activation potential in the cancer is determined for one or more of PKC isoforms selected from PKC α, β, γ, δ, ε, η, θ, ι/λ, μ and ζ.

In some embodiments, the cancer selected based on PKC activation potential is pancreatic cancer. In some embodiments, the pancreatic cancer is pancreatic adenocarcinoma or metastatic pancreatic cancer. In some embodiments, the PKC activation potential in the pancreatic cancer is determined for one or more of PKC isoforms selected from PKC α, β, γ, δ, ε, η, θ, ι/λ, μ and ζ. In some embodiments, the pancreatic cancer is selected for treatment with the combination therapy if the cancer is identified as being negative for loss-of-function mutations in one or more of PKC γ, δ, ε, μ, and θ. In some embodiments, the pancreatic cancer is not selected for treatment with the combination if the cancer is determined or identified as having a loss-of-function mutations in one or more of PKC γ, δ, ε, μ and θ.

In some embodiments, the cancer selected based on PKC activation potential is colon cancer. In some embodiments, the colon cancer is a colon adenocarcinoma or a metastatic colon cancer. In some embodiments, the PKC activation potential in the colon cancer is determined for one or more of PKC isoforms selected from PKC α, β, γ, δ, ε, η, θ, ι/λ, μ and ζ. In some embodiments, the colon cancer is selected for treatment with the combination therapy if the cancer is determined or identified as being negative for loss-of-function mutations in one or more of PKC α, β, γ, δ, η, and ι/λ. In some embodiments, the colon cancer is not selected for treatment with the combination therapy if the cancer is determined or identified as having loss-of-function mutations in one or more of PKC α, β, γ, δ, η, μ and ι/λ.

In some embodiments, the cancer selected based on PKC activation potential is lung cancer. In some embodiments, the lung cancer is small cell lung cancer. In some embodiments, the lung cancer is non-small cell lung cancer. In some embodiments, the non-small cell lung cancer is an adenocarcinoma, squamous cell carcinoma, or large cell carcinoma. In some embodiments, the lung cancer is metastatic lung cancer. In some embodiments, the PKC activation potential in the lung cancer is determined for one or more of PKC isoforms selected from PKC α, β, γ, δ, ε, η, θ, ι/λ, μ and ζ. In some embodiments, the lung cancer is selected for treatment with the combination therapy if the cancer is determined or identified as being negative for loss-of-function mutations in one or more of PKC γ, β, α, δ, ε, μ and η. In some embodiments, the lung cancer is not selected for treatment with the combination therapy if the cancer is determined or identified as having loss-of-function mutations in one or more of PKC γ, β, α, δ, ε, μ and η.

In some embodiments, the cancer selected based on PKC activation potential is stomach or gastric cancer. In some embodiments, the PKC activation potential in the stomach or gastric cancer is determined for one or more of PKC isoforms selected from PKC α, β, γ, δ, ε, η, θ, ι/λ, μ and ζ. In some embodiments, the stomach or gastric cancer is selected for treatment with the combination therapy if the cancer is determined or identified as being negative for loss-of-function mutations in one or more of PKC γ, δ and μ. In some embodiments, the stomach or gastric cancer is not selected for treatment with the combination therapy if the cancer is determined or identified as having loss-of-function mutations in one or more of PKC γ, δ and μ.

In some embodiments, the cancer selected based on PKC activation potential is endometrial or ovarian cancer. In some embodiments, the PKC activation potential in the endometrial or ovarian cancer is determined for one or more of PKC isoforms selected from PKC α, β, γ, δ, ε, η, θ, ι/λ, μ and ζ. In some embodiments, the endometrial or ovarian cancer is selected for treatment with the combination therapy if the cancer is determined or identified as being negative for loss-of-function mutations in one or more of PKC α, β, γ, δ, ε, η, ι/λ, μ and θ. In some embodiments, the endometrial or ovarian cancer is not selected for treatment with the combination therapy if the cancer is determined or identified as having loss-of-function mutations in one or more of PKC α, β, γ, δ, ε, η, ι/λ, μ and θ.

In some embodiments, the cancer selected based on PKC activation potential is breast cancer. In some embodiments, the breast cancer is metastatic breast cancer. In some embodiments, the breast cancer is estrogen receptor negative breast cancer. In some embodiments, the breast cancer is Her2 negative breast cancer. In some embodiments, the breast cancer is estrogen receptor positive breast cancer. In some embodiments, the breast cancer is Her2 positive breast cancer. In some embodiments, the breast cancer is selected for treatment with the combination therapy if the cancer is determined or identified as being negative for loss-of-function mutations in one or more of PKC $\alpha$, $\beta$, $\gamma$ $\delta$, $\epsilon$, $\eta$, $\iota/\lambda$, $\mu$ and $\theta$. In some embodiments, the breast cancer is not selected for treatment with the combination therapy if the cancer is determined or identified as having loss-of-function mutations in one or more of PKC $\alpha$, $\beta$, $\gamma$ $\delta$, $\epsilon$, $\eta$, $\iota/\lambda$, $\mu$ and $\theta$.

In some embodiments, the cancer selected based on PKC activation potential is head and neck cancer. In some embodiments, the head and neck cancer is selected for treatment with the combination therapy if the cancer is determined or identified as being negative for loss-of-function mutations in one or more of PKC $\alpha$, $\beta$, $\gamma$ $\delta$, $\eta$, $\mu$ and $\iota/\lambda$. In some embodiments, the head and neck cancer is not selected for treatment with the combination therapy if the cancer is determined or identified as having loss-of-function mutations in one or more of PKC $\alpha$, $\beta$, $\gamma$ $\delta$, $\eta$, $\mu$ and $\iota/\lambda$.

5.3.3. Cancer Selection Based on Other Diagnostic Indicators

In some embodiments, targets of PKC and/or downstream elements of the RAS, particularly K-RAS, signaling pathway can be analyzed to assess the sensitivity of the cancer to the PKC activator and/or effectiveness of the PKC activator in the combination therapy.

As such, in some embodiments, the cancer selected for treatment with the combination therapy is identified as capable of or having elevated expression of frizzled (Fzd) protein when treated with the PKC activator. Expression of some Fzd proteins is increased in response to attenuation of K-RAS activity, and decreases in response to activated K-RAS activity. A PKC activator compound, inhibiting or attenuating the activity of K-RAS, should result in increased expression of certain Fzd proteins. In some embodiments, the increased expression of Fzd protein is Frizzled-8 (Fzd8). Thus, in some embodiments, the cancer selected for treatment with the combination therapy is identified as capable of or having increased or elevated expression of Fzd8 when treated with the PKC activator. In some embodiments, the expression of Frizzled protein in the cancer cell can be measured before, during and/or following treatment with the PKC activator in the combination therapy.

Another component of the K-RAS signaling pathway is CaMKii, which is a downstream effector of calmodulin and whose interaction with K-RAS is affected by PKC activity. In some embodiments, the cancer selected for treatment with the combination therapy is identified as capable of or having increased or elevated level of phosphorylation of CaMKii when the cancer is treated with the PKC activator. In some embodiments, the level of phosphorylated CaMKii is measured before, during and/or following treatment with the PKC activator in the combination therapy.

In some embodiments, the cancer selected for treatment with the combination therapy is identified as being capable of or having elevated or increased phosphorylation of K-RAS by treatment with the PKC activator. In some embodiments, the phosphorylation is at amino acid residue 181 of human K-RAS. In some embodiments, the phosphorylation of K-RAS in the cancer can be measured before, during and/or following treatment with the PKC activator in the combination therapy.

In some embodiments, the cancer selected for treatment with the combination therapy is identified as capable of or having lower levels of leukemia inhibitory factor (LIF) by treatment with the PKC activator compound. LIF is known for its ability to induce differentiation of myeloid leukemic cells. LIF is upregulated, at the mRNA and protein level, in cancers with activating K-RAS mutations, and thus attenuating K-RAS activity through activation of PKC by a PKC activator should result in a decrease or reduction in levels of LIF. In some embodiments, the levels of LIF can be measured at the mRNA and/or protein level. In some embodiments, the level of LIF is measured before, during and/or following treatment with the PKC activator in the combination therapy.

In some embodiments, the cancer is assessed for levels of phosphorylated Erk1/2, which phosphorylation is mediated by PKC. An elevated level of phosphorylated Erk1/2 as compared to a control level, e.g., untreated cancer cells or tissues, or normal cells or tissues, indicates sensitivity of the cancer to the PKC activator. In some embodiments, the cancer selected for treatment with the combination therapy is determined or identified as being capable of or having increased or elevated levels of phosphorylated Erk1/2 when the cancer is treated with the PKC activator. In some embodiments, the levels of phosphorylated Erk1/2 in the cancer can be measured before, during and/or following treatment with the PKC activator.

In some embodiments, a cancer capable of or having at least one, or a combination of, or all of: (i) increased expression of Fzd protein, particularly Fzd8, (ii) elevated phosphorylation of CaMKii, (iii) increased phosphorylation levels of K-RAS, particularly at amino acid residue 181, (iv) reduction in expression of LIF, and (iv) elevated level of phosphorylated Erk1/2 can be used to assess the sensitivity of the cancer to treatment with the combination therapy. In some embodiments, the forgoing factors can be measured before, during and/or following treatment with the PKC activator in the combination therapy.

5.3.4. Expression and Mutation Status Detection

In some embodiments, the expression levels and mutations, for example in K-RAS, N-RAS, H-RAS, PKC enzymes, FzD and LIF, can be identified using various techniques available to the skilled artisan. In various embodiments, the presence or absence of a mutation can be determined by DNA or RNA detection methods, for example, DNA sequencing, oligonucleotide hybridization, polymerase chain reaction (PCR) amplification with primers specific to the mutation, or protein detection methods, for example, immunoassays or biochemical assays to identify a mutated protein, such as mutated K-RAS, N-RAS or PKC. In some embodiments, the nucleic acid or RNA in a sample can be detected by any suitable method or technique of detecting gene sequence. Such methods include, but are not limited to, PCR, reverse transcriptase-PCR (RT-PCR), in situ PCR, in situ hybridization, Southern blot, Northern blot, sequence analysis, microarray analysis, or other DNA/RNA hybridization platforms (see, e.g., Taso et al., 2010, Lung Cancer 68(1):51-7). In particular, detection of mutations using samples obtained non-invasively, such as cell free nucleic acid (e.g., cfDNA) from blood, can be used.

In some embodiments, mutations can be detected using various Next-Gen sequencing (NGS) techniques, particularly high-throughput NGS techniques. Exemplary NGS techniques include, among others, Polony sequencing (see, e.g., Shendure et al., 2005, Science 309(5741): 1728-32), IonTorrent sequencing (see, e.g., Rusk, N., 2011, Nat Meth 8(1):44-44), pyrosequencing (see, e.g., Marguiles et al., 2005, Nature 437(7057):376-380), reversible dye sequencing with colony sequencing (Bentley et al., 2008, Nature 456(7218):53-59; Illumina, CA, USA), sequencing by ligation (e.g., SOLid systems of Applied Biosystems; Valouev et al., 2008, Genome Res. 18(7):1051-1063), high throughput rolling circle "nanoball" sequencing (see, e.g., Drmanac et al., 2010, Science 327 (5961):78-81; Porreca, G. J., 2010, Nature Biotech. 28 (1):43-44), and zero-mode wave guide based sequencing (see, e.g., Chin et al., 2013, Nat Methods 10(6):563-569); all publications incorporated herein by reference. In some embodiments, massively parallel sequencing of target genes, such as genes encoding K-RAS, N-RAS, and PKC can be carried out to detect or identify presence or absence of mutations in the cancer being assessed for treatment with the PKC activator and second therapeutic agent.

In some embodiments, detection of point mutations in target nucleic acids can be accomplished by molecular cloning of the target nucleic acid molecules and sequencing the nucleic acid molecules using available techniques. Alternatively, amplification techniques such as PCR can be used to amplify target nucleic acid sequences directly from a genomic DNA preparation from a tumor tissue, cell sample, or cell free sample (e.g., cell free plasma from blood). The nucleic acid sequence of the amplified molecules can then be determined to identify mutations. Design and selection of appropriate primers are well within the abilities of one of ordinary skill in the art.

In some embodiments, ligase chain reaction (Wu et al., 1989, Genomics 4:560-569) and allele-specific PCR (Ruano and Kidd, 1989, Nucleic Acids Res. 17:8392) can also be used to amplify target nucleic acid sequences. Amplification by allele-specific PCR uses primers that hybridize at their 3' ends to a particular target nucleic acid mutation. If the particular mutation is not present, an amplification product is not observed. Insertions and deletions of genes can also be detected by cloning, sequencing and amplification. In addition, restriction fragment length polymorphism probes for the gene or surrounding marker genes can be used to score alteration of an allele or an insertion in a polymorphic fragment. Single stranded conformation polymorphism analysis can also be used to detect base change variants of an allele (Orita et al., 1989, Proc. Natl. Acad. Sci. USA 86:2766-2770). Other known techniques for detecting insertions and deletions can also be used with the claimed methods.

In some embodiments, mismatch detection can be used to detect point mutations in a target nucleic acid molecule, such as GRIN2A or TRRAP. Mismatches are hybridized nucleic acid duplexes which are not 100% complementary. The lack of total complementarity can be due to deletions, insertions, inversions, substitutions or frameshift mutations. An example of a mismatch cleavage technique is the RNase protection method, which is described in detail in Winter et al., 1985, Proc. Natl. Acad. Sci. USA 82:7575-7579, and Myers et al., 1985, Science 230:1242-1246. For example, detection of mutations in K-RAS can involve the use of a labeled riboprobe that is complementary to wild-type K-RAS. The riboprobe and nucleic acid molecule to be tested (for example, obtained from a tumor sample) are annealed (hybridized) together and subsequently digested with the enzyme RNase A, which is able to detect mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the target nucleic acid mRNA or gene, but can be a portion of the target nucleic acid, provided it encompasses the position suspected of being mutated. If the riboprobe comprises only a segment of the target nucleic acid mRNA or gene, it may be desirable to use a number of these probes to screen the whole target nucleic acid sequence for mismatches if desired.

In a similar manner, DNA probes can be used to detect mismatches, for example through enzymatic or chemical cleavage (Cotton et al., 1988, Proc. Natl. Acad. Sci. USA 85: 4397; Shenk et al., 1975, Proc. Natl. Acad. Sci. USA 72:989). Alternatively, mismatches can be detected by shifts in the electrophoretic mobility of mismatched duplexes relative to matched duplexes (see, e.g., Cariello et al., 1988, Human Genetics 42:726). With riboprobes or DNA probes, the target nucleic acid mRNA or DNA which may contain a mutation can be amplified before hybridization. Changes in target nucleic acid DNA can also be detected using Southern hybridization, especially if the changes are gross rearrangements, such as deletions and insertions.

In some embodiments, amplified nucleic acid sequences can also be screened using allele-specific probes. These probes are nucleic acid oligomers, each of which contains a region of the target nucleic acid gene harboring a known mutation. For example, one oligomer may be about 30 nucleotides in length, corresponding to a portion of the target gene sequence. By use of a battery of such allele-specific probes, target nucleic acid amplification products can be screened to identify the presence of a previously identified mutation in the target gene. Hybridization of allele-specific probes with amplified target nucleic acid sequences can be performed, for example, on a nylon filter. Hybridization to a particular probe under stringent hybridization conditions indicates the presence of the same mutation in the tumor tissue as in the allele-specific probe.

In some embodiments, gene-specific primers are useful for determination of the nucleotide sequence of a target nucleic acid molecule using nucleic acid amplification techniques such as the polymerase chain reaction. Pairs of single stranded DNA primers can be annealed to sequences within or surrounding the target nucleic acid sequence in order to prime amplification of the target sequence. Allele-specific primers can also be used. Such primers anneal only to particular mutant target sequence, and thus will only amplify a product in the presence of the mutant target sequence as a template. In order to facilitate subsequent cloning of amplified sequences, primers may have restriction enzyme site sequences appended to their ends. Such enzymes and sites are well known in the art. The primers themselves can be synthesized using techniques which are available in the art.

In some embodiments, mutations in nucleic acid molecules can also be detected by screening for alterations of the corresponding protein. For example, monoclonal antibodies immunoreactive with a target gene product, for example an antibody that is known to bind to a particular mutated position of the gene product (protein), can be used to screen a tissue. For example, a suitable antibody may be one that binds to a deleted exon or that binds to a conformational epitope comprising a deleted portion of the target protein. Lack of cognate antigen would indicate a mutation. Such immunological assays can be accomplished using any convenient format known in the art, such as Western blot, immunohistochemical assay and ELISA. For example, antibody-based detection of K-RAS mutations is described in Elisabah et al., 2013, J Egypt Natl Canc Inst. 25(1):51-6.

The expression of mRNA or proteins, such as expression of PKC or downstream elements, such as frizzled, can use standard methods available to the skilled artisan, including some of the methods described above. For example, the mRNA encoding a protein of interest can be detected by hybridization with nucleic acid probes, reverse transcription, polymerase chain reaction, and combinations thereof (e.g., RT-qPCR). In some embodiments, chip-based or bead-based microarrays containing nucleic acid probes hybridizing to the target sequence can be used. In some embodiments, mRNA expression can be detected directly in the target cells, such as by in-situ hybridization.

In some embodiments, the protein products can be detected directly. Direct detection can use a binding agent that binds specifically to the protein, such as antibodies or target-interacting proteins or small molecule reagents that bind specifically with the protein target of interest. For example antibodies to PKC enzymes are available commercially or can be produced, such as by polyclonal production methods or by generation of monoclonal antibodies (see, e.g., Current Protocols in Immunology, Coligan et al., eds., John Wiley & Sons (updates to 2015); Immunoassays: A Practical Approach, Gosling, ed., Oxford University Press (2000)). In some embodiments, the protein product can be detected by immunological methods. Various immunoassays include, by way of example, enzyme immunoassays, enzyme-linked immunoassays, fluorescence polarization immunoassay, and chemiluminescence assay. For example, "Western" based immunological detection of PKC enzymes are described in Chen et al., 2013, Anal Biochem. 442(1): 97-103. Other references describing detection of PKC enzymes include, among others, Garaczarczyk et al., 2010, Chem Biol Interact. 181(1):25-32; Ali et al., 2009, Life Sci. 84(21-22):766-71; Stross et al., 2009, J Biol Chem. 390(3): 235-44; Clark et al., 2003, Cancer Res. 63(4):780-786; Han et al., 2002, World J Gastroenterol 8(3):44-445; and Manzow et al., 2000, Int J Cancer 85(4):503-507; all publications incorporated herein by reference. Exemplary descriptions of antibodies to frizzled protein, such as FZD8 are provided in, among others, Yin et al., 2013, Mol Cancer Ther. 12:491-498 and Wang et al., 2012, Biochem Biophys Res Commun. 417(1):62-6.

For determining PKC activation potential, general methods for detecting PKC activity can be used, such as described in Protein Kinase C Protocols, Newton, A. C. ed., Humana Press, Totowa, N.J. USA (2003), incorporated herein by reference. In some embodiments, the assays for detecting kinase activity can use synthetic substrates or natural substrates that are the target of the PKC enzymes and detecting the phosphorylated substrate, for example by transfer of detectable phospho group (e.g., $^{32}$P-labeled or ligand labeled ATP) or detection of the phosphorylated product, such as with an antibody that binds the phosphorylated product (PegTag®, Promega, USA). In some embodiments, PKC activity can be detected in situ (see, e.g., Iori et al., 2003, Diabetologia. 46(4):524-30). Samples for examining PKC activity includes cells and tissues obtained from a patient, and/or circulating cancer cells obtained from the peripheral blood or lymph of patients (see, e.g., Karabacak et al., 2014, Nat Protoc. 9(3):694-710; van de Stolpe et al., 2011, Cancer Res. 71:5955-5960; Yu et al., 2011, J Cell Biol. 192(3):373-382; and Stott et al., 2010, Proc Natl Acad Sci. USA 107(43):18392-18397; all publications incorporated herein by reference). In some embodiments, the PKC activity can be measured by use of synthetic peptide substrates. These synthetic peptide substrates can be based on amino acid sequences known to be phosphorylated naturally by a PKC enzyme. Substrates for PKCα, β and γ are described in Toomik et al., 1997, Biochem J. 322:455-460; substrates for PKCα, βI, δ, ζ, and μ are described in Nishikawa et al., J Biol Chem. 272(2):952-960; Chen et al., 1993, Biochem. 32(4):1032-1039; and Wang et al., 2012, Structure 20(6):791-801; incorporated herein by reference. PKC substrates are also available commercially (see, e.g., Abcam, MA, USA; Perkin Elmer, USA; ImmuneChem, BC, Canada; and Promega, USA).

Detection of phosphorylated proteins, such as phosphorylated PKC enzymes, K-RAS, Fzd8, CaMKii, Erk can use standard techniques, such as antibodies that distinguish phosphorylated protein from non-phosphorylated protein or by detection of a labeled phosphate group (e.g., $^{32}$P) (see, e.g., Barcelo et al., 2014, Cancer Res. 74:1190-1190; Vila Petroff et al., 2010, J Mol Cell Cardiol. 9(1):106-112; Zhang et al., 2002, J Biol Chem. 277(42):39379-39387; Dissanayake et al., 2008, Methods Mol Biol. 468:187; all publications incorporated herein by reference). In some embodiments, antibodies that detect phosphorylated target proteins can be obtained commercially (see, e.g., Abcam, USA; Cell Signaling Technology, USA). In some embodiments, detecting or measuring phosphorylated proteins by use of anti-phospho antibodies can comprise: affinity isolating the PKC protein; and detecting phosphorylated protein with an anti-phospo antibody. In some embodiments, the affinity isolated PKC protein can be separated, such as by gel electrophoresis, the separated proteins bound onto a membrane substrate; and the membrane probed with an anti-phospho antibody. The binding of the anti-phospho antibody to phosphorylated protein can be detected with anti-phospho antibodies containing a detectable label, or by use of a secondary antibody directed against the primary anti-phospho antibody, where the secondary antibody contains a detectable label. The detectable label can be, by way of example and not limitation, a radioactive label, detectable enzyme (e.g., horseradish peroxidase); or fluorescent molecule. Exemplary antibodies for detecting phosphorylated sequences in PKC enzymes are provided below on Table A.

TABLE A

| Antibody Name | Vendor | Cat No. | Species |
| --- | --- | --- | --- |
| GAPDH (loading control) | Millipore | MAB374 | Mouse |
| β-Actin (loading control) | Sigma | A5441 | Mouse |
| Vinculin (loading control) | Sigma | V9131 | Mouse |
| Phospho-CaMKii (Thr286) | Abcam | ab32678 | Rabbit |
| Phospho-PKC substrate Motif [(R/KXpSX(R/K)] MultiMab ™ | Cell Signaling | 6967 | Rabbit |
| Phospho(Ser)-PKC substrate | Cell Signaling | 2261 | Rabbit |
| Phospho-PKC(pan)(βII Ser660) | Cell Signaling | 9371 | Rabbit |
| Phospho-PKCα/β (Thr638/641) | Cell Signaling | 9375 | Rabbit |
| Phospho-PKCδ/θ (Ser643/676) | Cell Signaling | 9376 | Rabbit |
| Phospho-PKD/PKCμ (Ser744/748) | Cell Signaling | 2054 | Rabbit |
| Phospho-PKD/PKCμ (Ser916) | Cell Signaling | 2051 | Rabbit |
| Phospho-PKCδ (Thr505) | Cell Signaling | 9374 | Rabbit |
| Phospho-PKCδ (Tyr311) | Cell Signaling | 2055 | Rabbit |
| Phospho-PKCζ/λ (Thr410/403) | Cell Signaling | 9378 | Rabbit |
| PKD/PKCμ | Cell Signaling | 2052 | Rabbit |
| P44/42 Erk1/2 | Cell Signaling | 9102 | Rabbit |
| Phospho-p44/42 Erk1/2 (Thr202/Tyr204) | Cell Signaling | 9106 | Mouse |
| Phospho-c-Raf (Ser338) | Cell Signaling | 9427 | Rabbit |

In some embodiments, phosphorylation can be detected in situ in a cell, for example, using an antibody directed against the phosphorylated protein. In some embodiments, the technique of in situ proximity ligation assay can be used to detect phosphorylated proteins in situ (see, e.g., Soderberg et al., 2006, Nat Methods 3:995-1000; Jarvious et al., 2007, Method Mol Cell Proteomics 6:1500-1509). Other methods of in situ detection of phosphorylated proteins are described in, for example, Roche et al., "Detection of Protein Phosphorylation in Tissues and Cells," in Current Protocols in Neuroscience, John Wiley & Sons (2001); incorporated herein by reference.

Biological sample for the methods herein include any samples that are amenable to analysis, such as tissue or biopsy samples containing cancer cells, or any biological fluids that contain the material of interests (e.g., DNA), such as blood, plasma, saliva, tissue swabs, and intestinal fluids. In some embodiments, exosomes extruded by cancer cells and obtained from blood or other body fluids can be used to detect nucleic acids and proteins produced by the cancer cells.

General biological, biochemical, immunological and molecular biological methods applicable to the present disclosure are described in Sambrook et al., Molecular Cloning: A Laboratory Manual $2^{nd}$ Ed. (1989) Cold Spring Harbor Laboratory Press, Cold Spring Harbor, N.Y.; Current Protocols in Molecular Biology, Ausubel et al., ed., John Wiley & Sons (2015); Current Protocols in Immunology, Coligan, J E ed., John Wiley & Sons (2015); and Methods in Enzymology, Vol. 200, Abelson et al., ed., Academic Press (1991). All publications are incorporated herein by reference.

5.4. Formulations and Administration

The PKC activating compounds, such as the phorbol, deoxyphorbol, ingenane, daphnane and lathyrane compounds, and the second therapeutic agent, particularly PI3K inhibitor, AKT inhibitor, mTOR inhibitor, PARP inhibitor, PBAC, CBP/β-catenin inhibitor, TNKS inhibitor, PORCN inhibitor, scr kinase/bcr-abl kinase inhibitor, SMO inhibitor, anti-cancer nucleoside analog or anti-metabolite, HDAC inhibitor, BET inhibitor, ATRA, BTK) inhibitor, can be prepared as a pharmaceutical composition or a medicament with excipients or carriers suitable for administration, either together or independently.

In some embodiments, the pharmaceutical compositions of the therapeutic agents can be formulated by standard techniques using one or more physiologically acceptable carriers or excipients. Suitable pharmaceutical carriers are described herein and in Remington: The Science and Practice of Pharmacy, $21^{st}$ Ed. (2005). The therapeutic compounds and their physiologically acceptable salts, hydrates and solvates can be formulated for administration by any suitable route, including, among others, topically, nasally, orally, parenterally, rectally or by inhalation. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablet or a capsule prepared by conventional means with a pharmaceutically acceptable excipient. Tablets and capsules comprising the active ingredient can be prepared together with excipients such as: (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate; (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; (c) binders, e.g., magnesium aluminum silicate, starch paste, gelatin, tragacanth, methylcellulose, sodium carboxymethylcellulose, polyvinylpyrrolidone and/or hydroxypropyl methylcellulose; (d) disintegrants, e.g., starches (including potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners. The compositions are prepared according to conventional mixing, granulating or coating methods, respectively, and in some embodiments, contain about 0.1 to 75%, preferably about 1 to 50%, of the active ingredient.

Tablets may be either film coated or enteric coated according to methods known in the art. Liquid preparations for oral administration can take the form of, for example, solutions, syrups, or suspensions, or they can be presented as a dry product for reconstitution with water or other suitable vehicle before use. Such liquid preparations can be prepared by conventional means with pharmaceutically acceptable additives, for example, suspending agents, e.g., sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

The therapeutic compounds can be formulated for parenteral administration by injection, for example by bolus injection or continuous infusion. Formulations for injection can be presented in unit dosage form, for example, in ampoules or in multi-dose containers, with or without an added preservative. Injectable compositions can be aqueous isotonic solutions or suspensions. In some embodiments for parenteral administration, the compounds can be prepared with a surfactant, such as Cremaphor, or lipophilic solvents, such as triglycerides or liposomes. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for reconstitution with a suitable vehicle, for example, sterile pyrogen-free water, before use. In addition, they may also contain other therapeutically effective substances.

For administration by inhalation, the therapeutic compounds may be conveniently delivered in the form of an aerosol spray presented from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

Suitable formulations for transdermal application include an effective amount of a therapeutic compound of the present disclosure with carrier. Preferred carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such formulations may contain solubilizers, stabilizers, tonicity enhancing agents, buffers and preservatives.

The compounds can also be formulated in rectal compositions, for example, as suppositories or retention enemas, which may contain conventional suppository bases, for example, cocoa butter or other glycerides, or gel forming agents, such as carbomers.

Furthermore, the compounds can be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

5.5. Therapeutically Effective Amount and Dosing

In some embodiments, a pharmaceutical composition of the therapeutic agent is administered to a subject, preferably a human, at a therapeutically effective dose to prevent, treat, or control a condition or disease as described herein. The pharmaceutical composition or medicament is administered to a subject in an amount sufficient to elicit an effective therapeutic response in the subject. An effective therapeutic response is a response that at least partially arrests or slows the symptoms or complications of the condition or disease. An amount adequate to accomplish this is defined as "therapeutically effective dose."

The dosage of therapeutic compounds of the combination therapy can take into consideration, among others, the species of mammal, the body weight, age, condition being treated, the severity of the condition being treated, the form of administration, route of administration. The size of the dose also will be determined by the existence, nature, and extent of any adverse effects that accompany the administration of a particular therapeutic compound in a particular subject.

In some embodiments, the diterpenoid PKC activator can be administered with one or more of the second therapeutic agent sequentially or concurrently, either by the same route or by different routes of administration. When administered sequentially, the time between administrations is selected to benefit, among others, the therapeutic efficacy and/or safety of the combination treatment. In some embodiments, the diterpenoid PKC activator can be administered first followed by a second therapeutic agent, or alternatively, the second therapeutic agent administered first followed by the diterpenoid PKC activator. By way of example and not limitation, the time between administrations is about 1 hr, about 2 hr, about 4 hr, about 6 hr, about 12 hr, about 16 hr or about 20 hr. In some embodiments, the time between administrations is about 1, about 2, about 3, about 4, about 5, about 6, or about 7 more days. In some embodiments, the time between administrations is about 1 week, 2 weeks, 3 weeks, or 4 weeks or more. In some embodiments, the time between administrations is about 1 month or 2 months or more.

When administered concurrently, the diterpenoid PKC modulator can be administered separately at the same time as the second therapeutic agent, by the same or different routes, or administered in a single composition by the same route.

In some embodiments, the amount and frequency of administration of the second therapeutic agent can used standard dosages and standard administration frequencies used for the particular therapeutic agent. See, e.g., Physicians' Desk Reference, 70$^{th}$ Ed., PDR Network, 2015; incorporated herein by reference.

In some embodiments, a pharmaceutical composition of the diterpenoid PKC activating compound, either in a composition with the second therapeutic agent, or separately from the second therapeutic agent, is administered in a daily dose in the range from about 0.01 mg per kg of subject weight (0.1 mg/kg) to about 1 g/kg. In some embodiments, the daily dose is a dose in the range of about 0.1 mg/kg to about 500 mg/kg. In some embodiments, the daily dose is a dose in the range of about 1 mg/kg to about 500 mg/kg. In some embodiments, the daily dose is about 2 mg/kg to about 250 mg/kg. In another embodiment, the daily dose is about 5 mg/kg to about 100 mg/kg. In another embodiment, the daily dose is about 5 mg/kg to about 100 mg/kg. In some embodiments, the daily dose is about 0.01 mg/kg, 0.05 mg/kg, 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/kg, 10 mg/kg, 20 mg/kg, 40 mg/kg, 50 mg/kg, 100 mg/kg, 200 mg/kg or 500 mg/kg. The daily dose can be administered once per day or divided into subdoses and administered in multiple doses, e.g., twice, three times, or four times per day.

In some embodiments, a pharmaceutical composition of the second therapeutic agent, either in a composition with the diterpenoid PKC modulating compound, or separately from the PKC modulating compound, is administered in a daily dose that corresponds to the therapeutically effective dose for the particular compound. In some embodiments, the second therapeutic agent is administered in a daily dose in the range from about 0.001 mg per kg of subject weight (0.001 mg/kg) to about 1 g/kg. In some embodiments, the daily dose is a dose in the range of about 0.01 mg/kg to about 1 g/kg. In some embodiments, the daily dose is a dose in the range of about 0.1 mg/kg to about 500 mg/kg. In some embodiments, the daily dose is a dose in the range of about 1 mg/kg to about 500 mg/kg. In some embodiments, the daily dose is about 2 mg/kg to about 250 mg/kg. In some embodiments, the daily dose is about 0.01 mg/kg, 0.05 mg/kg, 0.1 mg/kg, 0.2 mg/kg, 0.3 mg/kg, 0.4 mg/kg, 0.5 mg/kg, 1 mg/kg, 2 mg/kg, 3 mg/kg, 4 mg/kg, 5 mg/kg, 10 mg/kg, 20 mg/kg, 40 mg/kg, 50 mg/kg, 100 mg/kg, 200 mg/kg or 500 mg/kg. The daily dose can be administered once per day or divided into subdoses and administered in multiple doses, e.g., twice, three times, or four times per day. In some embodiments, the doses for approved drugs are available in the Physicians Desk Reference, 70$^{th}$ Ed. 2016, incorporated herein by reference.

In some embodiments, the dose of the second therapeutic agent is less than the standard dose used for the specified indication, particularly where the combination of the PKC activator compound and the second therapeutic agent indicates similar efficacy but at lower doses of the second therapeutic agent than the standard dose, for example, PBAC (e.g., cisplatin), or anti-cancer nucleoside analogs or anti-metabolites (e.g., cytarabine). In some embodiments, the dose of the second therapeutic agent is lower than the standard dose by about 5%, 10%, 15%, 20%, 25%, or 30% or more. In some embodiments, the dose of the second therapeutic agent is lower than the standard dose by about 5% to about 30%, about 10% to about 30%, about 10% to about 25%, about 15% to about 25%, or about 10% to about 20%.

To achieve the desired therapeutic effect, the therapeutic compounds, either individually or in a composition, may be administered for multiple days at the therapeutically effective daily dose. Thus, therapeutically effective administration of compounds to treat a condition or disease described herein in a subject may require periodic (e.g., daily) administration that continues for a period ranging from three days to two weeks or longer. Typically, the therapeutic compounds can be administered for at least three consecutive days, often for at least five consecutive days, more often for at least ten, and sometimes for 20, 30, 40 or more consecutive days. While consecutive daily doses may be used to achieve a therapeutically effective dose, a therapeutically beneficial effect can be achieved even if the compounds are not administered daily, so long as the administration is repeated frequently enough to maintain a therapeutically effective concentration of the compounds in the subject. For example, the compounds can be administer every other day, every third day, or, if higher dose ranges are employed and tolerated by the subject, once a week. A dosing schedule can be, for example, administering daily for a week, one week off and repeating this cycle dosing schedule for 3-4 cycles.

Optimum dosages, toxicity, and therapeutic efficacy of such therapeutic compounds may vary depending on the relative potency of individual compounds and can be determined by standard pharmaceutical procedures in cell cultures or experimental animals, for example, by determining the LD50 (the dose lethal to 50% of the population) and the ED50 (the dose therapeutically effective in 50% of the population). The dose ratio between toxic and therapeutic effects is the therapeutic index and can be expressed as the ratio, $LD_{50}/ED_{50}$. Combinations of compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, cell culture assays and animal studies can be used to formulate a dosage range for use in humans. The dosage of small molecule compounds can be preferably within a range of circulating concentrations that include the ED50 with little or no toxicity. The dosage can vary within this range depending upon the dosage form employed and the route of administration. For any compounds used in the methods herein, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

5.6. Disease Indications

As described herein, various cancers can be treated with the combination of the PKC activator and second therapeutic agent. Cancers for treatment with the combination therapy include among others, adrenocortical cancer, anal cancer, biliary cancer, bladder cancer, bone cancer (e.g., osteosarcoma), brain cancer (e.g., gliomas, astrocytoma, neuroblastoma, etc.), breast cancer, cervical cancer, colon cancer, endometrial cancer, esophageal cancer, head and neck cancer, hematologic cancer (e.g., leukemias and lymphomas), intestinal cancer (small intestine), liver cancer, lung cancer (e.g., bronchial cancer, small cell lung cancer, non-small cell lung cancer, etc.), oral cancer, ovarian cancer, pancreatic cancer, renal cancer, prostate cancer, salivary gland cancer, skin cancer (e.g., basal cell carcinoma, melanoma), stomach cancer, testicular cancer, throat cancer, thyroid cancer, uterine cancer, and vaginal cancer.

In some embodiments, the cancer is a hematologic cancer, including, among others, acute lymphoblastic leukemia (ALL), acute myeloid leukemia (AML), lymphoma (e.g., Hodgkin's lymphoma, Non-Hodgkin's lymphoma, Burkitt's lymphoma), chronic lymphocytic leukemia (CLL), chronic myelogenous leukemia (CML), Hairy Cell chronic myelogenous leukemia (CML), and multiple myeloma.

In some embodiments, cancers having an identified activating or oncogenic RAS activity can be selected for treatment with the combination therapy. In some embodiments, the cancer identified as having an activating or oncogenic K-RAS activity, e.g., activating K-RAS mutation, can be selected for treatment with the combination therapy, such as described herein. In some embodiments, the cancer identified as having an activating K-RAS mutation and selected for treatment with the combination therapy can be a cancer of the pancreas, lung, colon, head and neck, stomach (gastric), biliary tract, endometrium, ovary, small intestine, urinary tract, liver, cervix, breast, or hematologic (e.g., leukemia, lymphomas, etc.) tissues or cells.

In some embodiments, cancers having an identified activating or oncogenic N-RAS activity, e.g., activating N-RAS mutation, can be selected for treatment with the combination therapy, such as described herein. In some embodiments, the cancer having an N-RAS mutation selected for treatment is a melanoma or a hematologic cancer, such as acute myeloid leukemia, chronic myeloid leukemia, acute lymphoblastic leukemia, juvenile myelomonocytic leukemia, chronic myelomonocytic leukemia, myelodysplastic syndrome, myeloproliferative neoplasia, and multiple myeloma, or other types of leukemias.

In some embodiments, cancers having an identified activating or oncogenic H-RAS activity, e.g., activating H-RAS mutation, can be selected for treatment with the combination therapy, such as described herein. In some embodiments, the cancer having an H-RAS mutation selected for treatment is a cancer of the cervix, prostate, salivary gland, skin, upper aerodigestive tract, or urinary tract.

In some embodiments, cancers having an identified effective PKC activation potential can be selected for treatment with the combination therapy, such as described herein. In some embodiments, the cancer identified as having an effective activation potential and selected for treatment with the combination therapy can be any of the cancers described above.

In some embodiments, cancers having an activating K-RAS activity, e.g., activating K-RAS mutation, or activating N-RAS activity, e.g., activating N-RAS mutation, and an identified effective PKC activation potential can be selected for treatment with the combination therapy, such as described herein. In some embodiments, such cancers selected for treatment with the combination therapy can be a cancer of the pancreas, lung, colon, head and neck, stomach (gastric), biliary tract, endometrium, ovary, small intestine, urinary tract, liver, cervix, breast, or hematologic (e.g., leukemia, lymphomas, etc.) tissues or cells.

6. EXAMPLES

Example 1: Proliferation Assays

PKC activator compounds were tested in a panel of K-RAS mutant pancreatic, lung, and colon cancer cell lines, as well as a number of leukemia cell lines having either mutant K-RAS or N-RAS. The cell lines, tumor types, and their K- and N-RAS mutation status are listed in Table 1A.

TABLE 1A

Cancer Cell Lines and RAS Status

| Cell Line Name | Tumor Type | RAS Mutation |
|---|---|---|
| CaPan-1 | Pancreatic, adenocarcinoma, liver metastasis | K-RAS: G12V |
| MiaPaCa-2 | Pancreatic, carcinoma | K-RAS: G12C |
| KP-4 | Pancreatic carcinoma | K-RAS: G12C |
| Panc2.03 | Pancreatic, adenocarcinoma | K-RAS: G12D |
| Panc2.13 | Pancreatic, adenocarcinoma | K-RAS: Q61H |
| AsPC1 | Pancreatic, ascites | K-RAS: G12D |
| A549 | Lung, adenocarcinoma | K-RAS: G12S |
| H358 | Lung, carcinoma | K-RAS: G12C |
| H441 | Lung, papillary adenocarcinoma | K-RAS: G12V |

TABLE 1A-continued

Cancer Cell Lines and RAS Status

| Cell Line Name | Tumor Type | RAS Mutation |
|---|---|---|
| H727 | Lung, bronchial carcinoids | K-RAS: G12V |
| AGS | Gastric, adenocarcinoma | K-RAS: G12D |
| HCT116 | Colon, carcinoma | K-RAS: G13D |
| LS180 | Colon, adenocarcinoma | K-RAS: G12D |
| SW620 | Colon, adenocarcinoma, lymph node mets | K-RAS: G12V |
| CCRF-CEM | Leukemia, acute lymphoblastic leukemia | K-RAS: G12D |
| HL-60 | Leukemia, acute promyelocytic leukemia | N-RAS: Q61L |
| THP-1 | Leukemia, acute monocytic leukemia | N-RAS: G12D |

Other cancer cell lines with either wild-type or mutant K-RAS were also examined with various PKC activators. These cell lines, tumor types, and their K-RAS mutation status are listed in Table 1B.

TABLE 1B

| Cell Line Name | Tumor Type | RAS Status |
|---|---|---|
| BxPC-3 | Pancreatic, adenocarcinoma | WT |
| SW900 | Lung, squamous cell carcinoma | K-RAS: G12V |
| H838 | Lung, adenocarcinoma | WT |
| H1915 | Lung, carcinoma | WT |
| HT29 | Colon, adenocarcinoma | WT |
| Colo205 | Colon, adenocarcinoma, ascites | WT |
| RPMI8226 | Blood, plasmacytoma, myeloma | K-RAS: G12A |

The PKC activator compounds, including prostratin, prostratin analogs and prodrugs, ingenol, TPA, and Bryostatin 1, tested on the cell lines are listed in Table 2.

TABLE 2

| Compound | Structure |
|---|---|
| K101A, or K101 Prostratin | 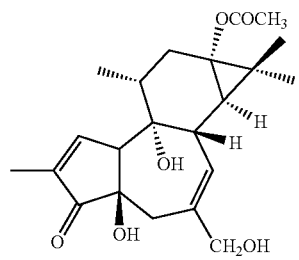 |
| K101B (succinate prodrug) R = prodrug moiety, sodium salt | 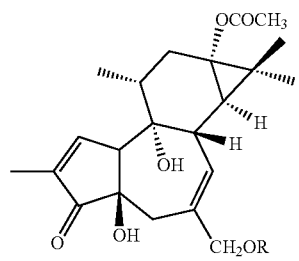 |

TABLE 2-continued

| Compound | Structure |
|---|---|
| K101C<br>R = substituent | (structure shown)<br>R = OH |
| K101D<br>R1, R2 = substituents<br>SA-101D2 (one epimer of two configurations of SA-101D) | (structure shown)<br>R₁ = OH<br>R₂ = O |
| K101E, F<br>R1, R2 = substituents | (structure shown)<br>E: R₁ = Ac, R₂ = Ac<br>F: R₁ = H, R₂ = H |
| K101I (amino acid prodrug)<br>R = prodrug moiety, sodium salt | (structure shown)<br>R = OCOCH₂CH(NH₂)COO⁻Na⁺ |

TABLE 2-continued

| Compound | Structure |
|---|---|
| K102 Ingenol-3-angelate | 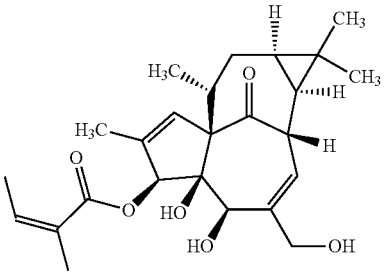 [SMILES: C/C=C(/C)C(=O)O[C@H]1C(C)=C[C@]23C(=O)[C@@H](C=C(CO)[C@@H](O)[C@]12O)[C@H]1[C@@H](C[C@H]3C)C1(C)C] |
| K103 12-O-Tetradecanoyl-phorbol-13-acetate (TPA) | 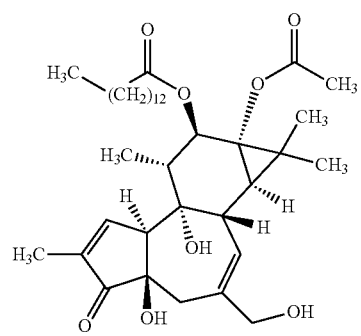 |
| K104 Bryostatin 1 | 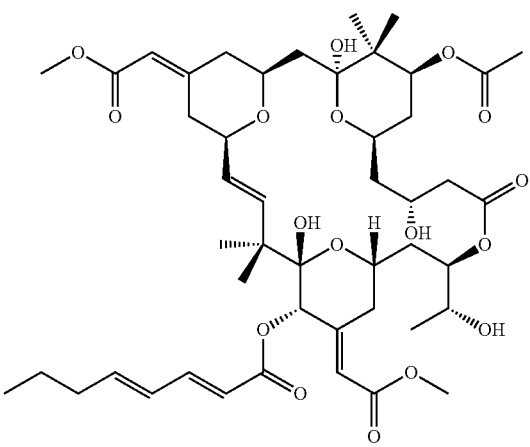 |

Briefly, cells at a density of 1,000-10,000 cells/well were seeded in 96-well plates and incubated at 37° C. for 24 hours. A series of 9 different concentrations of compound stocks (500×) were prepared by 3-fold serial dilution in DMSO. These compounds were further diluted in culture media and then added to cells so that the final DMSO concentration was 0.2%. After 96 hours of incubation, 50 µL of CellTiter Glo reagent (Promega) was added to each well and luminescence was measured after 10 minutes using EnVision (PerkinElmer). Paclitaxel was used as the reference compound and the dose range was 0.08 nM-0.5 µM. The dose range for most compounds was 4.6 nM-30 µM. The dose ranges for some compounds were adjusted downward to 0.46 nM-3 µM or 0.08 nM-0.5 µM or 0.03 nM-0.2 µM. Luminescence from cells treated with 0.02% DMSO alone was set as Max and % of inhibition was calculated as follows: Inhibition %=(Max-Sample value)/Max*100. Data was analyzed using XL-fit software (ID Business Solutions Ltd.) and EC50, relative EC50, and % of top inhibition were calculated. The results are shown in Tables 3-6 for pancreatic cancer, lung cancer, colon/gastric cancer, and leukemia. Table 5 shows absolute EC50, relative EC50, and % of top inhibition of testing agents in blocking cell proliferation in colon and gastric cancer cell lines harboring various K-RAS mutations.

The screening results from 17 cell lines of 5 different cancer types indicated that prostratin and prostratin analogs showed good inhibitory activities in pancreatic and lung cancer cell lines harboring K-RAS mutations. Cell lines with different types of K-RAS mutations, including G12V, G12D, G12C, G12S, and Q61H, were sensitive to prostratin and analogs. Unexpectedly, these compounds did not inhibit proliferation of the colon cancer cell lines harboring K-RAS mutations at the highest concentration tested. The types of K-RAS mutations in a given cell line did not seem to be the factors determining the sensitivity. Interestingly, all three leukemia cell lines tested were sensitive to prostratin and analogs, regardless of their K-RAS mutation status. Nevertheless, two of the sensitive leukemia cell lines have N-RAS mutations. Such sensitivity can be verified by the methods described in this application.

In addition, some PKC activator compounds, such as ingenol and PMA showed similar activity patterns as the prostratin and analogs whereas other PKC activator compounds such as bryostatin 1 showed different activity patterns. In general, the potency of these compounds to inhibit proliferation correlated with the known potency of PKC activation. For example, PMA and ingenol are more potent PKC activators than prostratin and they are also more potent in proliferation inhibition than prostratin. However, there are exceptions to this. For example, bryostatin 1 is more potent PKC activator but it is less potent in proliferation inhibition than prostratin. Furthermore, a prostratin prodrug was active in this assay even though it was less potent than its parent compound prostratin. Since the prodrug is not expected to bind PKC, it is possible that tumor cells have the ability to convert the prostratin prodrug to the parent compound.

Other cancer cell lines having wild-type K-RAS status and K-RAS mutation at G12 were also screened using the PKC activator compounds. As in the studies with the 17 cancer cell lines discussed above, paclitaxel was used as the reference compound, and its dose range was 0.08 nM-0.5 µM. K104 was tested in a range of 0.03 nM-0.2 µM. The dose range selected for most compounds (e.g., K101A, K101C, K101D, K101E, K101I, K102, and K103) was 4.6 nM-30 µM. The dose ranges were adjusted downward to 0.46 nM-3 µM for K102 and 0.08 nM-0.5 µM for K103 for some cell lines. The results of the screening of cancer cells lines with wild-type K-RAS status and K-RAS mutations at the G12 positions are presented in Table 7. Consistent with the observation made in the other cells lines above, prostratin, prostratin analogs, ingenol, and PMA showed similar activity patterns, which in general correlated with their known PKC activation potencies. However, bryostatin 1 showed different activity patterns and had much lower activity in cancer cell lines.

In Table 7, the % of top inhibition appears to be a very good indication whether a cell line is sensitive or refractory to inhibition by these compounds. Data from all 24 cell lines against four different compounds (e.g., K101A, K101E, K102 and K103) were graphed together and the data is shown on FIG. 1.

The data indicate that a number of pancreatic, lung, and leukemia cell lines tested are sensitive to diterpenoid family of PKC activators (e.g., prostratin and analogs, prostratin prodrugs, ingenol, and PMA, etc.). In general, it appears that the cancer cell lines harboring mutant K-RAS are more sensitive than those harboring wild-type K-RAS. However, some cell lines with wild-type K-RAS are sensitive to inhibition by the PKC activator compounds to some extent (e.g., BxPC-3 and Colo205). In addition, as noted above, colon cancer cell lines (4 out of 5 tested) appear to be somewhat resistant to these compounds regardless of K-RAS mutation status. The exception was colon cancer cell line Colo205, which has wild-type K-RAS and was very sensitive to inhibition by these compounds. Interestingly, Colo205 cells changed their morphology dramatically, from round to more extended and flat morphology, upon treatment with these compounds.

Results from these experiments allow identification of the most sensitive cell lines to inhibition by the prostratin analogs and other selected PKC activators. In addition, such screens also identify potent analogs from different classes of PKC activators for potential treatment of cancers with K-RAS mutations and leukemias.

Tables 3A and Table 3B: Absolute EC50, relative EC50, and % of top inhibition of testing agents in blocking cell proliferation in pancreatic cancer cell lines harboring various K-RAS mutations.

TABLE 3A

| | Capan-1 | | | KP-4 | | | MiaPaCa-2 | | |
|---|---|---|---|---|---|---|---|---|---|
| Compound ID | Ab EC50 (µM) | Re EC50 (µM) | Top Inhibition % | Ab EC50 (µM) | Re EC50 (µM) | Top Inhibition % | Ab EC50 (µM) | Re EC50 (µM) | Top Inhibition % |
| Paclitaxel | 0.011 | 0.0072 | 73.5 | 0.0019 | 0.0018 | 96.2 | 0.0034 | 0.0033 | 94.6 |
| K101A | >30 | 0.31 | 37.1 | 0.40 | 0.19 | 63.3 | 0.30 | 0.18 | 74.4 |
| K101C | >30 | 5.40 | 35.7 | 11 | 6.77 | 70.4 | >30 | 4.37 | 40.1 |
| K101D | >30 | 8.66 | 22.3 | >30 | 5.47 | 47.9 | >30 | — | 18.6 |
| K101E | >30 | 0.83 | 44.6 | 1.28 | 0.68 | 69.1 | 1.88 | 0.86 | 61.4 |
| K102 | >30 | 0.013 | 46.9 | 0.015 | 0.015 | 62.2 | 0.013 | 0.0090 | 79.3 |
| K103 | 0.014 | — | 51.0 | <0.0046 | — | 70.3 | 0.00028 | 0.00024 | 81.1 |

TABLE 3B

| | AsPC-1 | | | Pan2.03 | | | Pan2.13 | | |
|---|---|---|---|---|---|---|---|---|---|
| Compound ID | Ab EC50 (µM) | Re EC50 (µM) | Top Inhibition % | Ab EC50 (µM) | Re EC50 (µM) | Top Inhibition % | Ab EC50 (µM) | Re EC50 (µM) | Top Inhibition % |
| Paclitaxel | 0.010 | 0.0038 | 60.9 | 0.0033 | 0.0018 | 64.7 | 0.065 | 0.0027 | 53.2 |
| K101A | >30 | 0.27 | 32.4 | >30 | 0.12 | 27.0 | >30 | 0.017 | 43.4 |
| K101I | >30 | 6.64 | 25.0 | >30 | 6.04 | 26.3 | >30 | 0.16 | 48.3 |
| K104 | >0.2 | — | 4.2 | >0.2 | — | 0.0 | >0.2 | — | 32.2 |
| K101E | >30 | 2.78 | 35.2 | >30 | 1.92 | 36.5 | >0.2 | 0.044 | 49.8 |
| K102 | >3 | 0.014 | 37.8 | >3 | 0.0033 | 36.9 | 0.0039 | 0.0012 | 51.7 |
| K103 | >0.5 | 0.0013 | 32.7 | >0.5 | 0.00090 | 32.2 | >0.5 | 0.00066 | 41.9 |

TABLE 4

Absolute EC50, relative EC50, and % of top inhibition of testing agents in blocking cell proliferation in lung cancer cell lines harboring various K-RAS mutations.

| | A549 | | | HE58 | | |
|---|---|---|---|---|---|---|
| Compound ID | Ab EC50 (µM) | Re EC50 (µM) | Top Inhibition % | Ab EC50 (µM) | Re EC50 (µM) | Top Inhibition % |
| Paclitaxel | 0.0026 | 0.0023 | 86.0 | 0.0024 | 0.0018 | 89.2 |
| K101A | 0.49 | 0.27 | 76.0 | 4.9 | 0.16 | 56.4 |
| K101C | 13 | 6.68 | 70.3 | >30 | 4.98 | 44.0 |
| K101D | >30 | 7.72 | 44.4 | >30 | 11 | 23.0 |
| K101E | 2.64 | 1.56 | 78.7 | >30 | 1.25 | 47.9 |
| K102 | 0.017 | 0.017 | 80.8 | 0.097 | 0.0045 | 57.5 |
| K103 | <0.0046 | — | 80.6 | 0.0022 | 0.0004 | 59.6 |

| | H441 | | | H727 | | |
|---|---|---|---|---|---|---|
| Compound ID | Ab EC50 (µM) | Re EC50 (µM) | Top Inhibition % | Ab EC50 (µM) | Re EC50 (µM) | Top Inhibition % |
| Paclitaxel | 0.0358 | 0.0035 | 51.9 | >0.5 | 0.0023 | 49.0 |
| K101A | >30 | 0.32 | 42.1 | >30 | 0.19 | 48.3 |
| K101C | >30 | 7.44 | 37.0 | >30 | 3.61 | 42.8 |
| K101D | >30 | — | 11.6 | >30 | 8.37 | 31.8 |
| K101E | >30 | 2.61 | 49.1 | >30 | 0.62 | 49.1 |
| K102 | 1.01 | 0.0024 | 50.6 | 0.022 | 0.0043 | 61.0 |
| K103 | >0.5 | 0.00075 | 46.7 | 0.0022 | 0.00037 | 57.4 |

TABLE 5

Absolute EC50, relative EC50, and % of top inhibition of testing agents in blocking cell proliferation in colon (a) and gastric (b) cancer cell lines harboring various K-RAS mutations.

| | LS180 | | | SW620 | | |
|---|---|---|---|---|---|---|
| Compound ID | Ab EC50 (µM) | Re EC50 (µM) | Top Inhibition % | Ab EC50 (µM) | Re EC50 (µM) | Top Inhibition % |
| Paclitaxel | 0.014 | 0.0088 | 67.1 | 0.012 | 0.0094 | 92.1 |
| K101A | >30 | — | 4.4 | >30 | — | 0.0 |
| K101C | >30 | — | 6.8 | >30 | — | 0.0 |
| K101D | >30 | — | 8.2 | >30 | — | 0.0 |
| K101E | >30 | — | 1.3 | >30 | — | 0.0 |
| K102 | >30 | — | 9.3 | >30 | — | 0.0 |
| K103 | >10 | — | 14.7 | >10 | — | 1.2 |

| | HCT116 | | | AGS | | |
|---|---|---|---|---|---|---|
| Compound ID | Ab EC50 (µM) | Re EC50 (µM) | Top Inhibition % | Ab EC50 (µM) | Re EC50 (µM) | Top Inhibition % |
| Paclitaxel | 0.0022 | 0.0021 | 94.8 | 0.0047 | 0.0039 | 87.7 |
| K101A | >30 | — | 17.4 | >30 | 0.49 | 21.7 |
| K101C | >30 | — | 12.2 | >30 | 11 | 25.3 |
| K101D | >30 | — | 3.0 | >30 | — | 13.5 |
| K101E | >30 | 6.64 | 27.4 | >30 | 4.38 | 25.9 |
| K102 | >3 | 0.021 | 23.2 | >3 | 0.012 | 42.9 |
| K103 | >0.5 | 0.0012 | 21.4 | >0.5 | 0.0011 | 47.2 |

TABLE 6A

| | HL60 | | | THP1 | | |
|---|---|---|---|---|---|---|
| Compound ID | Ab EC50 (µM) | Re EC50 (µM) | Top Inhibition % | Ab EC50 (µM) | Re EC50 (µM) | Top Inhibition % |
| Paclitaxel | 0.0052 | 0.0052 | 98.7 | 0.0083 | 0.0076 | 91.2 |
| K101A | 0.47 | 0.40 | 61.3 | 0.87 | 0.30 | 51.8 |
| K101C | 17 | 13 | 63.9 | 16 | 8.11 | 51.4 |
| K101D | >30 | — | 14.4 | >30 | 14 | 33.6 |
| K101E | 3.05 | 1.92 | 63.4 | 3.60 | 1.02 | 51.6 |
| K102 | 0.015 | 0.014 | 60.1 | 0.015 | 0.012 | 52.4 |
| K103 | <0.0046 | — | 60.0 | <0.0046 | — | 52.9 |

TABLE 6B

| Compound ID | CCRF-CEM | | |
|---|---|---|---|
| | Ab EC50 (μM) | Re EC50 (μM) | Top Inhibition % |
| Paclitaxel | 0.0040 | 0.0039 | 97.8 |
| K101A | >30 | 0.051 | 35.9 |
| K101I | >30 | 1.51 | 37.4 |
| K104 | >0.2 | — | 6.0 |
| K101E | >30 | 0.27 | 34.3 |
| K102 | >3 | 0.0009 | 30.3 |
| K103 | >0.5 | 0.00024 | 37.7 |

TABLE 7

% or top inhibition of testing agents in blocking cell proliferation in cancer cell lines with wild-type K-RAS status and K-RAS mutations at G12.

| Compound ID | Top Inhibition % | | | | | | |
|---|---|---|---|---|---|---|---|
| | BxPC-3 | SW900 | H838 | H1915 | HT29 | Colo205 | RPMI8226 |
| Paclitaxel | 91.93% | 81.0% | 96.5% | 80.6% | 93.8% | 97.4% | 98.98% |
| K101A | 40.11% | 7.1% | 10.1% | 27.7% | 12.8% | 83.6% | 32.39% |
| K101C | 36.67% | 10.9% | 20.2% | 28.9% | 4.8% | 73.2% | 22.72% |
| K101D | 37.49% | not converged | 27.7% | 28.6% | 10.0% | 42.3% | not converged |
| K101E | 38.87% | 25.4% | 26.8% | 35.6% | 31.7% | 85.8% | 32.25% |
| K102 | 44.13% | 20.1% | 25.5% | 30.8% | 17.3% | 86.0% | 27.06% |
| K103 | 44.46% | 18.7% | 15.5% | 27.9% | 20.9% | 86.8% | 32.75% |
| K104 | 3.99% | not converged | 20.0% | 25.1% | 4.3% | 49.4% | not converged |
| K101I | 38.12% | 10.8% | 29.3% | 16.4% | 11.8% | 82.2% | 17.60% |

Example 2: Analysis of Expression of PKC Signaling Pathway Elements

Cancer cells (2-8 million cells) were seeded in 10 cm dishes and grown overnight. For A549 lung cancer cell line, about 3 million cells were seeded. Cells were then treated with different drugs at concentrations described in Table 8 for a period of time up to 48 hours. Cells were lysed in 0.3-0.5 mL of RIPA buffer (Sigma) supplemented with protease inhibitors (Roche) and phosphatase inhibitors (Sigma). Lysates were assayed for protein concentration using BCA kit (Pierce). Normalized amount of lysates (20-30 μg protein/lane) were run on 4-12% NuPage gel (Life Technologies) and the proteins were transferred to the PVDF or nitrocellulose membrane using iBlot® Transfer Stack (Life Technologies). The membranes were probed with primary antibodies shown in Table 9 at 4° C. overnight after blocking with 1×TBST containing 5% non-fat milk. Antibodies from other vendors could also be used in Western blot analysis. After washing 5 times with 1×TBS containing 0.1% Tween20, the membranes were probed with $2^{nd}$ antibodies Anti-mouse IgG Dylight 800 conjugate or Anti-rabbit IgG DyLight 680 conjugate (1:10000; Cell signaling or similar IR $2^{nd}$ antibodies from different vendors) at room temperature for one hour. After washing 5 times, the membranes were scanned using Odyssey® Imaging System (Licor Biosciences).

Treatment of A549 cells with K101A resulted in dose-dependent reduction in the protein levels of the leukemia inhibitory factor (LIF), a member of the IL-6 family. As expected, negative control compounds (Ref1 and Ref2) did not affect the levels of LIF. Interestingly, K103, K102, and K101E did not affect the levels of LIF at the concentrations tested. Since LIF has a well-established role in preventing stem-cell differentiation and maintaining stem cells in a pluripotent state, and LIF is one of the major cytokines that activates STAT3 and other stem cell factors such as SOX2, NANOG, OCT3/4, the reduction in LIF by selected PKC activators can cause loss of stemness of treated cancer cells.

Treatment of A549 cells with PKC activators (K103, K102 at 0.5 μM, and K101A at 2.5 μM) for 48 hours resulted in reduction of the phospho-PKC (pan) levels. This is consistent with the notion that chronic treatment of cells with TPA results in downregulation of PKC. However, it is worth noting that treatment with 0.5 μM of K101A lowered the LIF protein level without affecting the phospho-PKC (pan) level.

TABLE 8

Compounds and their concentrations used in WB analysis

| No. | Compound ID | Concentration | DMSO final conc. |
|---|---|---|---|
| 1 | DMSO | 0.2% | 0.2% |
| 2 | K101A | 0.1 μM | 0.2% |
| 3 | K101A | 0.5 μM | 0.2% |
| 4 | K101A | 2.5 μM | 0.2% |
| 5 | K101E | 2.5 μM | 0.2% |
| 6 | K102 | 0.1 μM | 0.2% |
| 7 | K102 | 0.5 μM | 0.2% |
| 8 | K103 | 0.01 μM | 0.2% |
| 9 | Ref1* | 1 μM | 0.2% |
| 10 | Ref2* | 0.01 μM | 0.2% |

*Ref1 and Ref2 are natural products unrelated to the PKC activators used in the present disclosure and do not display PKC activation activity. Ref1 and Ref2 are negative controls for PKC pathway activities.

Primary antibodies used for Western blot analysis to detect various PKC signaling elements are described in Table 9.

TABLE 9

| Antibody Name | Vendor | Cat No. | Species | MW | Dilution |
|---|---|---|---|---|---|
| GAPDH (loading control) | Millipore | MAB374 | Mouse | 37 kd | 1:10000 |
| β-Actin (loading control) | Sigma | A5441 | Mouse | 43 kd | 1:10000 |

TABLE 9-continued

| Antibody Name | Vendor | Cat No. | Species | MW | Dilution |
|---|---|---|---|---|---|
| FZD8 | Abcam | ab75235 | Rabbit | ~73 kd | 1:500 |
| Phosph-CaMKii (Thr286) | Abcam | ab32678 | Rabbit | ~50 & 60 kd | 1:1000 |
| CaMKii | Abcam | ab52476 | Rabbit | ~50 & 60 kd | 1:1000 |
| Phospho-PKC (pan) | Cell signaling | 9371 | Rabbit | 78-85 kd | 1:1000 |
| LIF | Abcam | ab34427 | Mouse | 20 kD (~34 kd) | 1:500 |

Example 3: Soft Agar Assays

Soft agar colony formation is one of the hallmarks (anchorage-independent growth) of cancer cells. Three-dimensional (3D) assay models have been shown to have advantages over conventional two-dimensional (2D) monolayer assay models. Many drugs active in 2D model do not show efficacy in preclinical models or in clinical trials. Accordingly, 3D assay models may represent a more biologically relevant system, bridging the gaps between the 2D assays with in vivo models.

To prepare a base agar layer (0.6%), melted 1.2% agar solution was mixed 1:1 (v/v) with 2×DMEM/20% FBS medium in a tube by inverting several times, and 50 µL of the mixture was immediately transferred to a well in a 96-well flat-bottom microplate. The plate was placed at 4° C. for 30 minutes to allow the base agar layer to solidify. Then, the cell agar layer (agar 0.4%) was prepared by transferring 75 µL of the cell and agar mixture containing 1:1:1 (v/v/v) of 1.2% agar solution, 2×DMEM/20% FBS and cell suspension (0.4-4×10E5/mL) to each well of the plates so that each well contained 1000-10000 cells per well. The plates were placed at 4° C. for 15 minutes and then 75 µL of media was added to each well. After incubating the plates overnight in a $CO_2$ incubator, 50 µL of media with or without 5× final concentrations of compounds were added to each well. Each compound was tested in 9-point 3-fold dilution series. The plates were incubated for 7-10 days at 37° C. At the end of incubation period, 28 µL of Calcein AM solution (5 µM) was added to the center of each well. The plates were incubated at 37° C. for 45 minutes before scanning on Acumen (TTP Labtech). Each compound was tested in triplicates. Data was analyzed and compound EC50s were calculated using GraphPad Prism 5.

The results indicated that selected PKC activators (K101A, K101E, K102, and K103) reduced the number of colonies formed by A549 cells in a dose-dependent manner. Most potent compound in this assay was K103, followed by K102, K101A, and K101E. Reduction in colony formation in soft agar reflected loss of anchorage-independent growth.

Example 4: Analysis of Diterpenoid PKC Activators in Combination with Other Chemotherapeutic Agents: Studies with A549 Cells The purpose of these experiments was to assess if PKC activating agents (e.g., K101A, K101E, and K102) could synergize with other chemotherapeutic agents, including standard chemotherapies and certain chemotherapeutic agents targeting certain cell signaling pathways, to reduce viability of cancer cells.

Single agent IC50 was determined using similar procedures as the standard viability assay in either 96-well or 384-well plates. Briefly, cells at density of 1,000-10,000 cells/well in 96-well plates or 200-1600 cells/well in 384-well plates were seeded and incubated at 37° C. for 24 hours before addition of compounds. A series of 9 different concentrations of compound stocks (500×) were prepared by 3-fold serial dilutions in DMSO. These compounds were further diluted in culture media and then added to cells so that the final DMSO concentration is 0.2%-0.25%. After 96 hours of incubation, 35 µL or 50 µL of CellTiter Glo reagent (Promega) was added to each well and luminescence was measured after 10 minutes using EnVision (PerkinElmer). Luminescence from cells treated with DMSO alone was set as Max and % of inhibition was calculated as follows: Inhibition %=(Max-Sample value)/Max*100. Data were analyzed using XLfit software (ID Business Solutions Ltd.) or GraphPad software and IC50, relative IC50, and % of top inhibition were calculated.

Various drugs or compounds (Table 10) were screened and assayed in 384-well plates as 9-point 3-fold dilution series alone and in combination with 2-3 doses of the specified PKC activator compounds (e.g., K101A, K101E, and K102). The top concentration for the tested PKC activator compound was set at roughly the IC50 when the same testing compound was used as a single agent assayed in the same cell line. The next dose was either 3-fold or 10-fold dilution from the top concentration. Results were analyzed by IC50 ratio, which is defined as the IC50 generated as a single agent (IC50 alone) divided by IC50 generated in combination with different doses of testing compounds (IC50 combination) (the effect of the testing compound on proliferation at each dose was corrected). If IC50 ratio is >2, synergistic effect is observed when two compounds are combined. If IC50 ratio is <0.5, antagonistic effect is observed when two compounds are combined.

A 96-well MacSynergy II format for combination test was also used. Some compounds that showed either synergism or antagonism in combination with the PKC activators were tested further for full dose range titrations of both agents. Data were analyzed according to the general methods described in Prichard et al., 1990, Antiviral Res. 14:181-206, incorporated herein by reference. The analysis was done with the SQRT(Data) scale and the four parameter Hill curve was fitted using XLfit5.1 (the MacSynergy II Excel Spreadsheet) for the inhibition data. Synergy (positive number) or Antagonism (negative number) volumes were calculated. Absolute values of <25 at 95% confidence indicated insignificant synergism/antagonism; 25-50 at 95% confidence indicated minor but significant synergism/antagonism; 50-100 at 95% confidence indicated moderate synergism/antagonism which might be important in vivo; and >100 at 95% confidence indicated strong synergism/antagonism which would probably be important in vivo; the values should not exceed 1000. The curve fitting was done for compound 1 at each level of compound 2, and vice versa. Three-dimensional MacSynergy II graphs were generated where positive values indicated synergism and negative values indicated antagonism.

Results. Three PKC activator compounds K101A, K101E, or K102 were assayed alone or in combination with a second therapeutic agent (summarized in Table 10) in 384-well viability/proliferation assays or in 96-well MacSynergy II format described above in cell lines such as A549. The results from testing on A549 lung cancer cell line are shown in Table 11A and Table 11B and FIG. 2A to FIG. 2H for compound K101A (prostratin); Table 12 and FIG. 3A to FIG. 3F for compound K101E; and Table 13A and Table 13B and FIG. 4A to FIG. 4H for compound K102 (ingenol-3-angelate).

TABLE 10

Summary of agents assayed in combination with the PKC activator compounds in A549 Cells

| Compound Name | Class | Combination n A549 | | |
|---|---|---|---|---|
| | | K101A | K101E | K102 |
| Trametinib*# | MEK inhibitor | Antagonism (strong) | None | Antagonism (strong) |
| Idelalisib* | PI3K inhibitor (delta) | Synergism | Synergism | Synergism |
| Dasatinib*# | SRC family kinase inhibitor | Synergism (moderate) | Synergism | Synergism (moderate) |
| Everolimus* | mTOR inhibitor | Synergism | Synergism. | Synergism |
| Paclitaxel* | Microtubule inhibitor | None | None | None |
| Olaparib* | PARP inhibitor | Synergism | None | Synergism |
| MK2206*# | AKT inhibitor | Synergism (strong) | Synergism | Synergism (strong) |
| Lapatinib* | EGFR and ErbB2 dual inhibitor | None | None | None |
| Gemcitabine* | Nucleoside metabolic inhibitor | None | None | None |
| Cisplatin*# | DNA cross linking agent | Synergism (strong) | None | Synergism (strong) |
| Oxaliplatin# | DNA cross linking agent | Synergism (borderline) | ND | Synergism (minor) |
| BKM-120*# | PK13 Inhibitor (Pan class II) | Synergism (strong) | None | Synergism (moderate) |
| STS (staurosporine)* | Multiple kinase inhibitor | Synergism | Synergism | Synergism |
| Carfilzomib# | Proteasome inhibitor | None | ND | None |
| Erlotinib* | EGFR inhibitor | Antagonism (moderate) | ND | Antagonism (moderate) |
| SAHA# | HDAC inhibitor | Antagonism (minor) | ND | Antagonism (minor) |
| (±)-JQ1* | BET bromodomain inhibitor | Antagonism | ND | Antagonism |
| XAV-939* | Tankyrase 1/2 inhibitor | Synergism | ND | Synergism |
| ICG-001* | CBP inhibitor | None | ND | None |
| LGK-974. | PORCN inhibitor | Synergism (minor) | ND | Synergism (minor) |
| Vismodegib* | Smoothened inhibitor | Synergism | ND | Synergism |

*Combination studies with 2-3 concentrations of K101A, K101E, or K102
Combination studies with full concentration ranges of K101A, K101E, or K102

TABLE 11A

IC50 ratios in combination with K101A.

| | Ratio (0.25% DMSO IC50/ combination IC50) | | |
|---|---|---|---|
| Compound ID | 0.5 μM K101A | 0.05 μM K101A | 0.005 μM K101A |
| Trametinib | 0.50 | 1.10 | 1.36 |
| Idelalisib | 5.05 | 1.89 | 1.04 |
| Dasatinib | 6.13 | 2.07 | 0.75 |
| Everolimus | >2 | >2 | NC |
| Paclitaxel | 1.15 | 0.95 | 0.85 |
| Olaparib | 2.76 | 1.38 | 0.91 |
| MK2206 | 6.03 | 2.13 | 0.68 |
| Lapatinib | 0.99 | 1.05 | 0.91 |
| Gemcitabine | 0.97 | 0.91 | 0.80 |
| Cisplatin | 2.68 | 0.86 | 0.53 |
| BKM-120 | 2.43 | 1.21 | 0.94 |
| STS | 12.87 | 2.02 | 0.77 |

NC: no change

TABLE 11B

IC50 ratios in combination with K101A.

| | Ratio (0.25% DMSO IC50/ combination IC50) | |
|---|---|---|
| Compound ID | 1 uM K101A | 0.33 uM K101A |
| (±) JQ1 | 0.09 | 0.27 |
| XAV-939 | 4.23 | 2.55 |
| ICG-001 | 1.10 | 1.05 |
| LGK-974# | n.d | n.d. |

IC50 ratio was not determined (n.d.) but the top inhibition % was increased about 2-fold.

TABLE 12

IC50 ratios in combination with K101E.

| | Ratio (0.25% DMSO IC50/ combination IC50) | | |
|---|---|---|---|
| Compound ID | 2.5 μM K101E | 0.25 μM K101E | 0.025 μM K101E |
| Trametinib | 0.71 | 1.34 | 1.37 |
| Idelalisib | 3.50 | 1.55 | 0.89 |
| Dasatinib | 3.50 | 1.45 | 0.90 |
| Everolimus | >2 | >2 | NC |
| Paclitaxel | 1.00 | 0.99 | 0.90 |
| Olaparib# | 1.97 | 1.30 | 1.15 |
| MK2206 | 3.95 | 1.61 | 0.84 |
| Lapatinib | 0.87 | 0.98 | 1.07 |
| Gemcitabine | 0.78 | 0.81 | 0.76 |
| Cisplatin** | 1.75 | 1.37 | — |
| BKM-120 | 1.76 | 1.09 | 0.91 |
| STS | 4.56 | 1.25 | 0.76 |

NC: no change
K101E concentrations used in combination with Olaparib were 3 μM, 0.3 μM and 0.03 μM
**K101E concentrations used in combination with Cisplatin were 3 μM and 1 μM

TABLE 13A

IC50 ratios in combination with K102.

| | Ratio (0.25% DMSO IC50/ combination IC50) | | |
|---|---|---|---|
| Compound ID | 0.02 μM K102 | 0.002 μM K102 | 0.0002 μM K102 |
| Trametinib | 0.44 | 0.80 | 0.72 |
| Idelalisib | 3.55 | 1.76 | 0.81 |
| Dasatinib | 7.12 | 3.95 | 0.68 |
| Everolimus | >2 | >2 | NC |
| Paclitaxel | 1.15 | 0.91 | 0.77 |
| Olaparib | 2.74 | 1.43 | 0.78 |
| MK2206 | 5.57 | 3.13 | 0.81 |
| Lapatinib | 0.81 | 0.63 | 0.58 |
| Gemcitabine | 0.69 | 0.76 | 0.72 |

TABLE 13A-continued

IC50 ratios in combination with K102.

| Compound ID | Ratio (0.25% DMSO IC50/combination IC50) | | |
| --- | --- | --- | --- |
| | 0.02 µM K102 | 0.002 µM K102 | 0.0002 µM K102 |
| Cisplatin** | 2.61 | 2.52 | — |
| BKM-120 | 2.36 | 1.24 | 0.86 |
| STS | 9.76 | 2.67 | 1.22 |

NC: no change
**K102 concentrations used in combination with Cisplatin were 0.04 µM and 0.13 µM

TABLE 13B

IC50 ratios in combination with K102

| Compound ID | Ratio (0.25% DMSO IC50/combination IC50) | |
| --- | --- | --- |
| | 0.04 µM K102 | 0.013 µM K102 |
| (±) JQ1 | 0.57 | 0.55 |
| XAV-939 | >2 | >2 |
| ICG-001 | 1.10 | 0.96 |
| LGK-974# | n.d | n.d. |

IC50 ratio was not determined (n.d.) but the top inhibition % was increased about 2-fold.

Figure 6A:
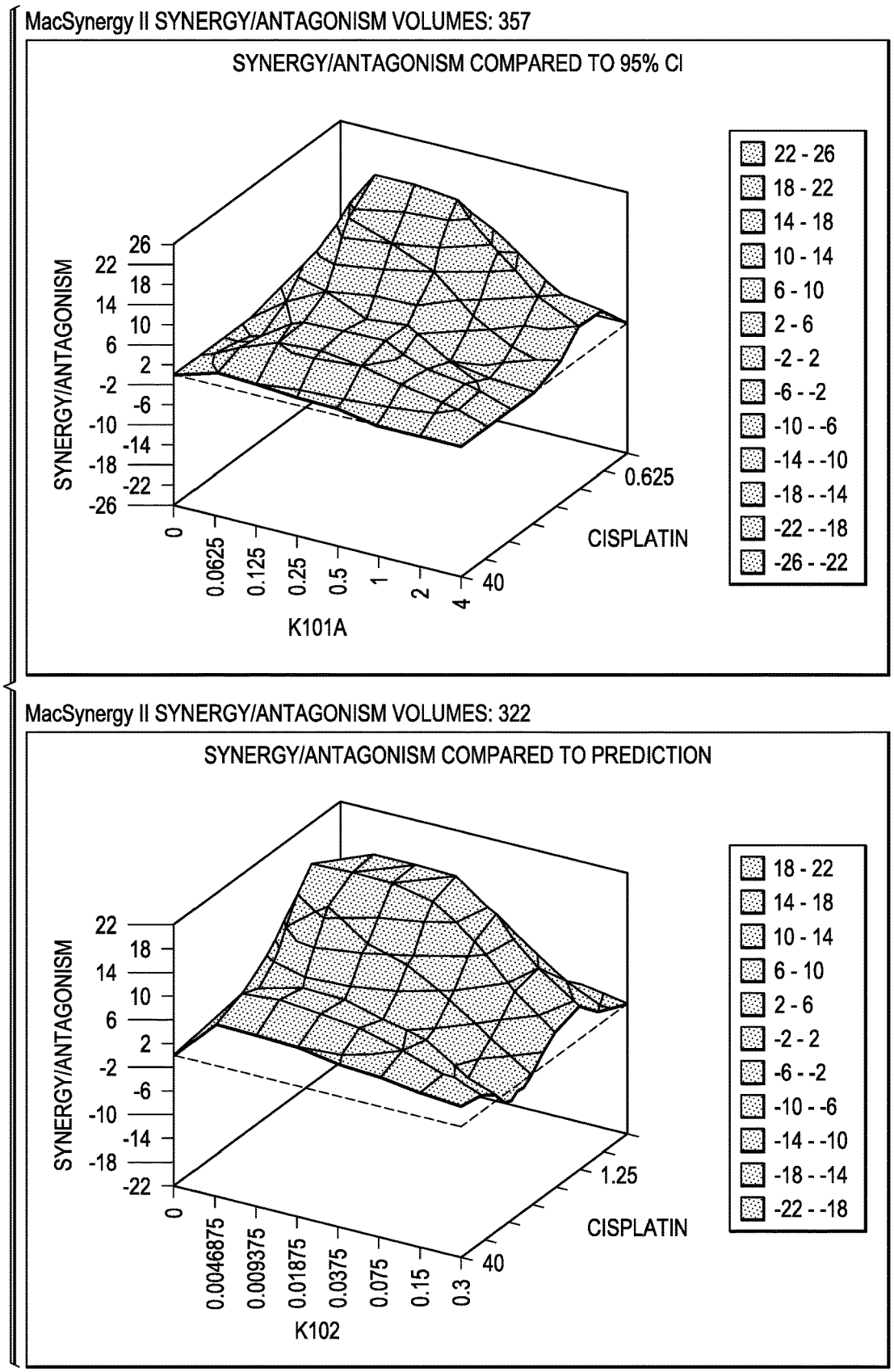
FIG. 6A shows synergism/antagonism plot of PKC activator K101A or K102 in combination with cisplatin on growth of inhibition of lung cancer cell line A549.

The results indicated that K101A, K101E, and K102 showed synergistic effect in combination with a number of therapeutic agents (shaded) in inhibiting the growth of A549 lung cancer cells. These included chemotherapeutic agents targeting DNA and DNA repair processes such as cisplatin as well as PARP inhibitors (e.g., olaparib) (Table 11A, Table 12, and Table 13A and FIG. 2A to FIG. 2G). The PKC activator compounds showed strong synergistic effect in combination with cisplatin, especially at lower doses of cisplatin. As shown in FIG. 6A, the dose range for the strongest synergy was between 0.625-2.5 µM for cisplatin. At cisplatin dose levels higher than 2.5 µM, minimal synergy was observed. It is known that A549 is a cisplatin-resistant lung cancer cell line, and cisplatin at concentrations between 0.625-2.5 µM had minimal effect on cell proliferation as a single agent. Therefore, the effective dose of cisplatin can be reduced significantly by combining it with the PKC activator compounds (e.g., K101A, K101E, or K102). It is significant that the PKC activator compounds can overcome the cisplatin resistance of A549 cells.

Figure 6B:
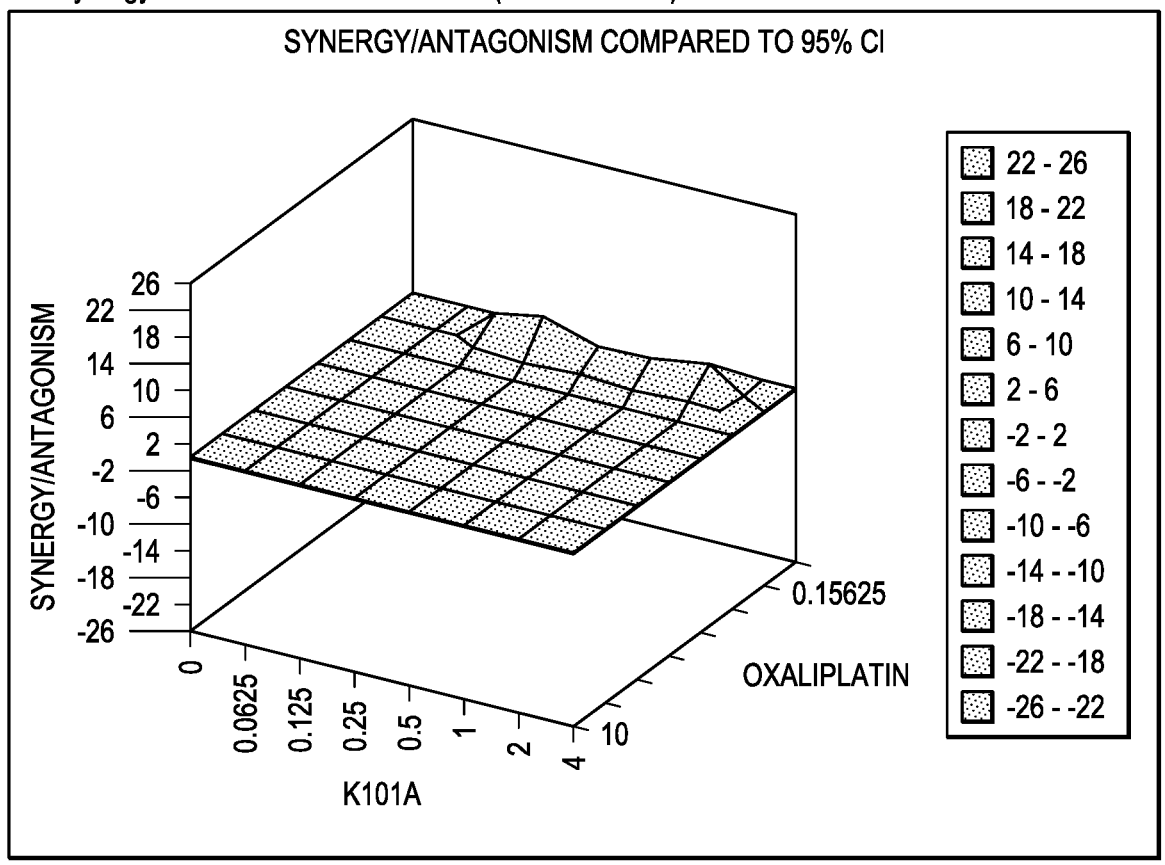
FIG. 6B shows synergism/antagonism plot of PKC activator K101A in combination with oxaliplatin on growth of inhibition of lung cancer cell line A549.

To examine if PKC activators could synergize with another of the platinum class of chemotherapeutic agents, PKC activator compounds in combination with oxaliplatin was tested. As shown in Table 10 and FIG. 6B, PKC activating compounds K101A and K102 demonstrated synergy with oxaliplatin, although the magnitude of synergy was smaller than that observed for cisplatin.

Figure 7A:
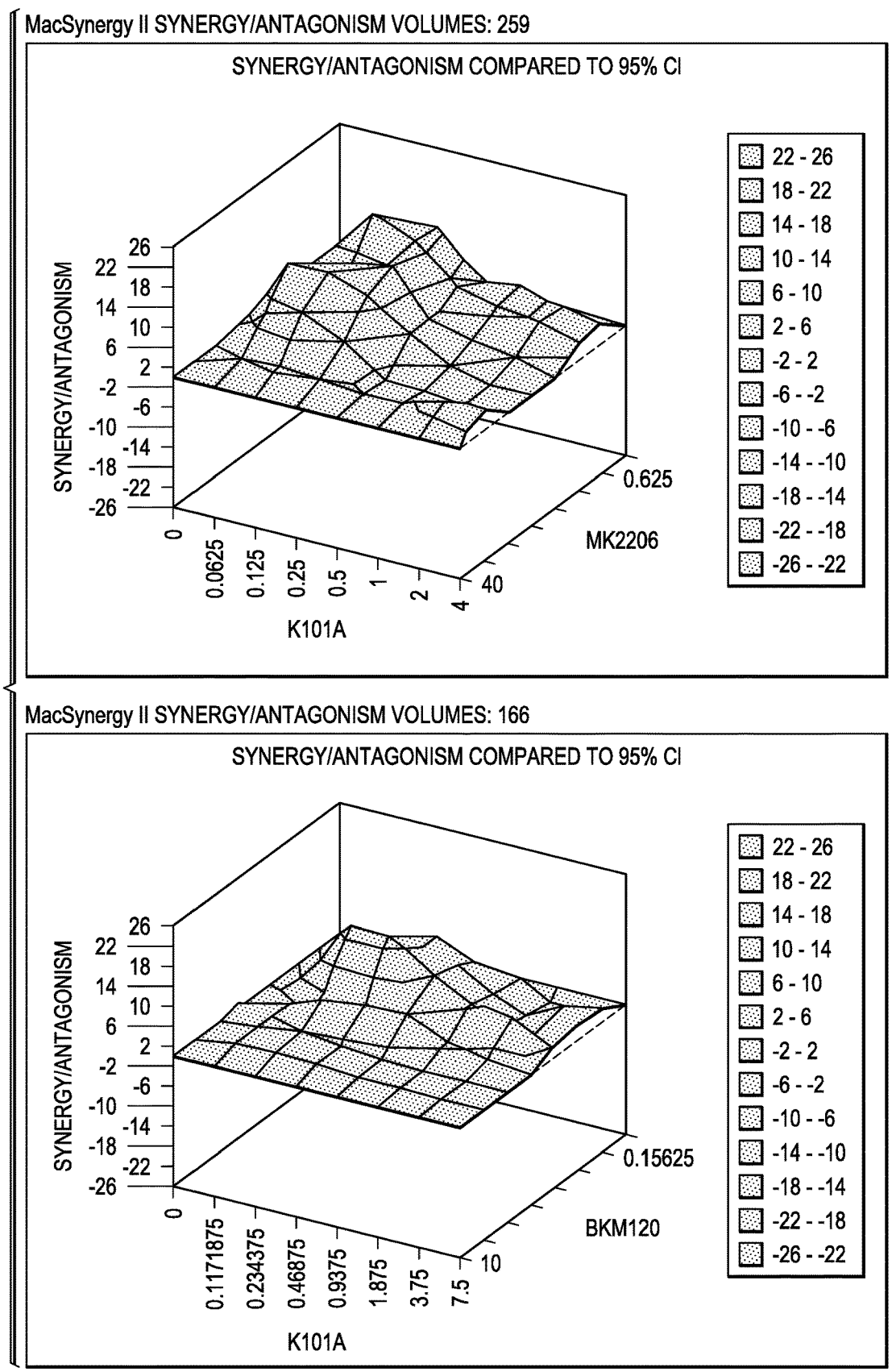
FIGS. 7A and 7B show synergism/antagonism plot of PKC activator K101A or K102 in combination with PI3K/AKT/mTOR pathway inhibitor MK2206 or BSM120 on growth of inhibition of lung cancer cell line A549.
Figure 7B:
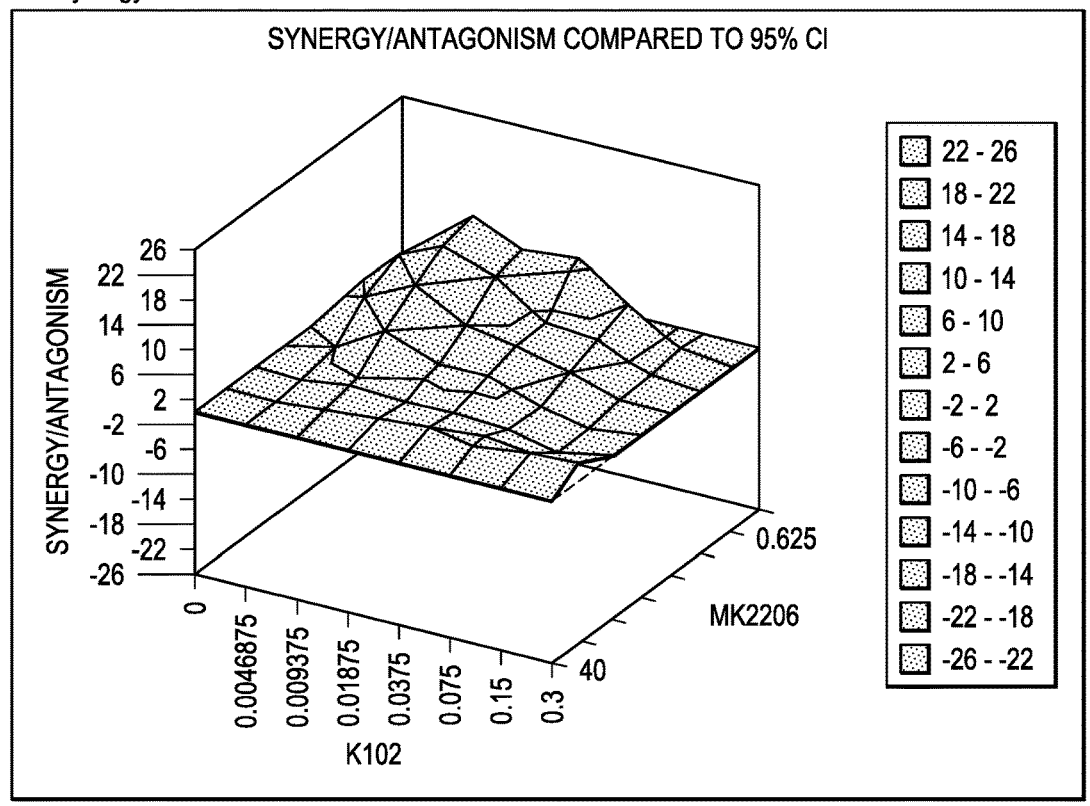
Figure 7B:
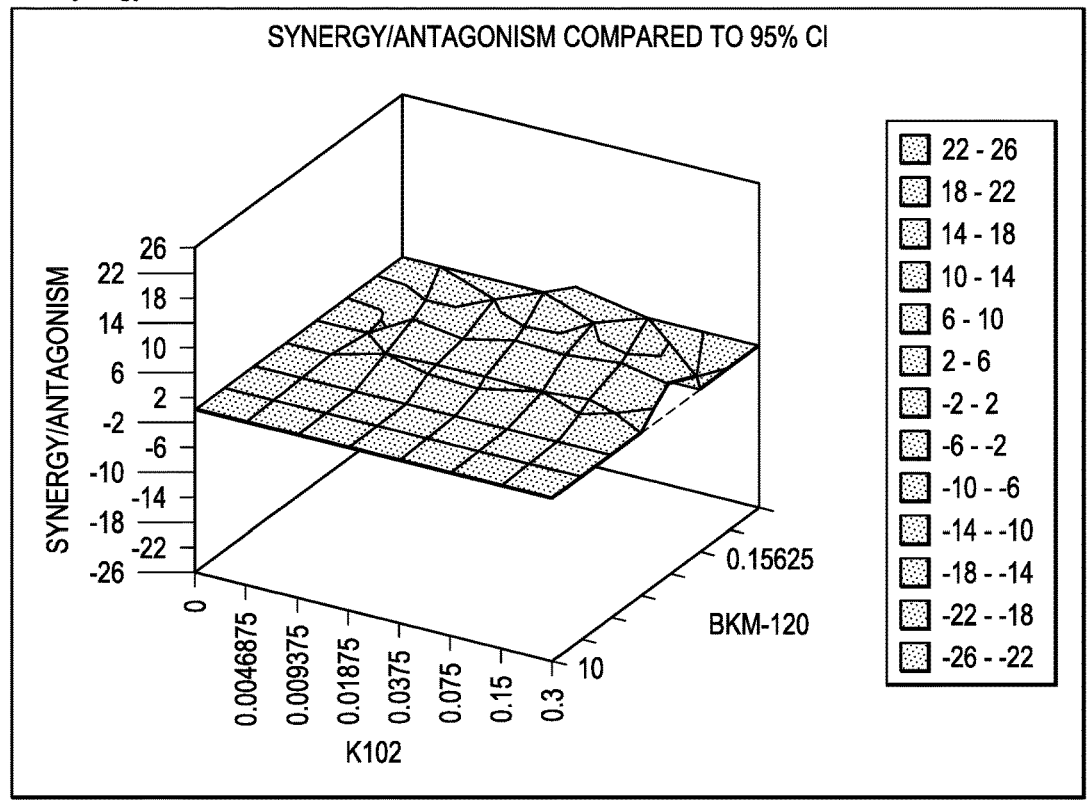

The PKC activator compounds also showed strong synergistic effect when combined with PI3K/AKT/mTOR pathway inhibitors (Table 11A, Table 12, and Table 13A; FIG. 2A, FIG. 2B, FIG. 2D, and FIG. 2F for compound K101A; FIG. 3A, FIG. 3B, FIG. 3D, and FIG. 3F for compound K101E; FIG. 4A, FIG. 4B, FIG. 4D, and FIG. 4F for compound K102). Interestingly, inhibitors targeting multiple components in this pathway such as PI3K inhibitors (pan, isoform-specific, and PI3K/mTOR dual inhibitors, e.g., idelalisib and BKM-120), AKT inhibitors (e.g., MK2206), and mTOR inhibitors (e.g., everolimus), all demonstrated strong synergy. As shown in FIG. 7A and FIG. 7B, synergism was observed in broad concentration ranges of AKT inhibitors and PI3K inhibitors.

Figure 2A:
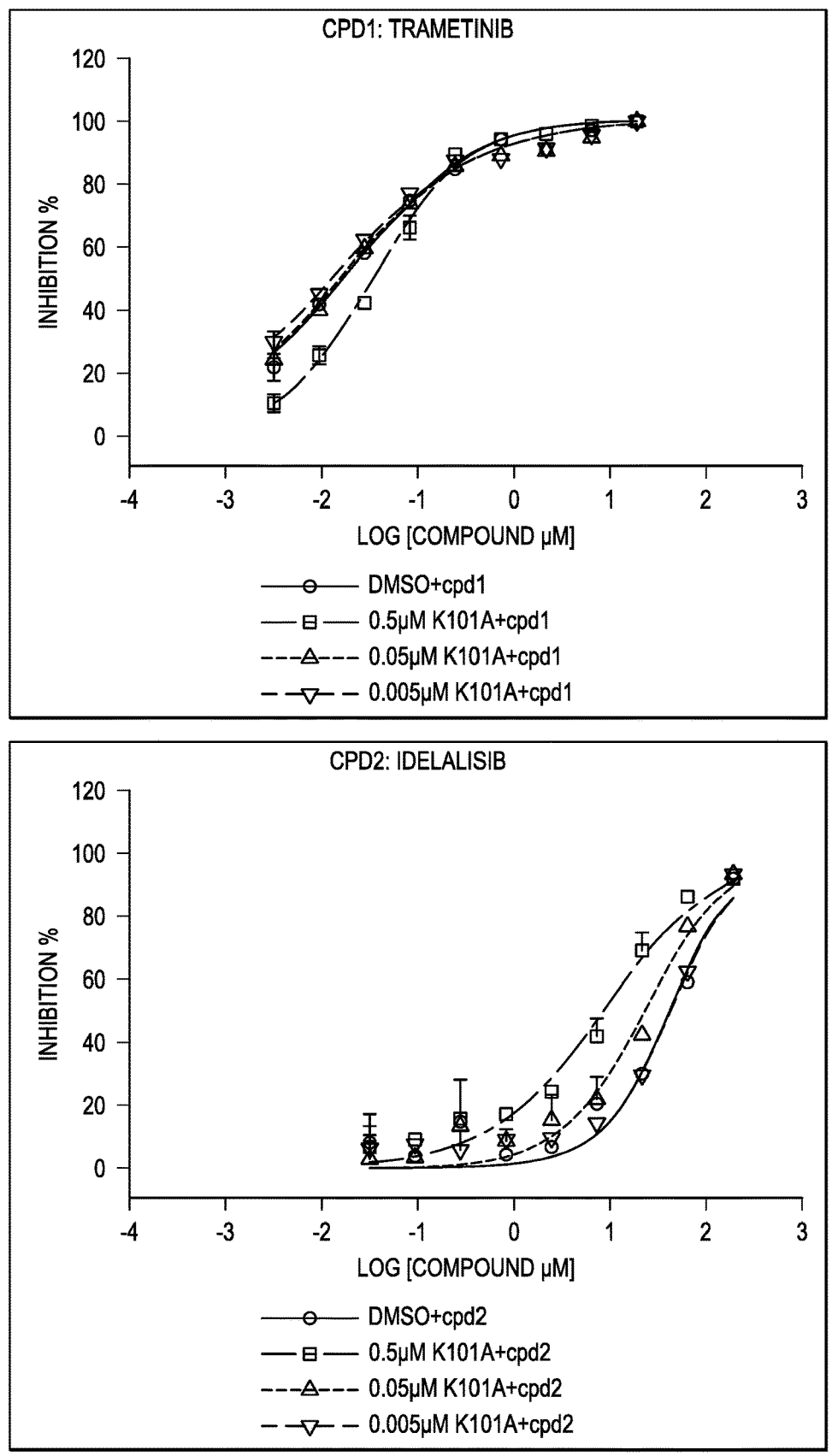
Figure 2B:
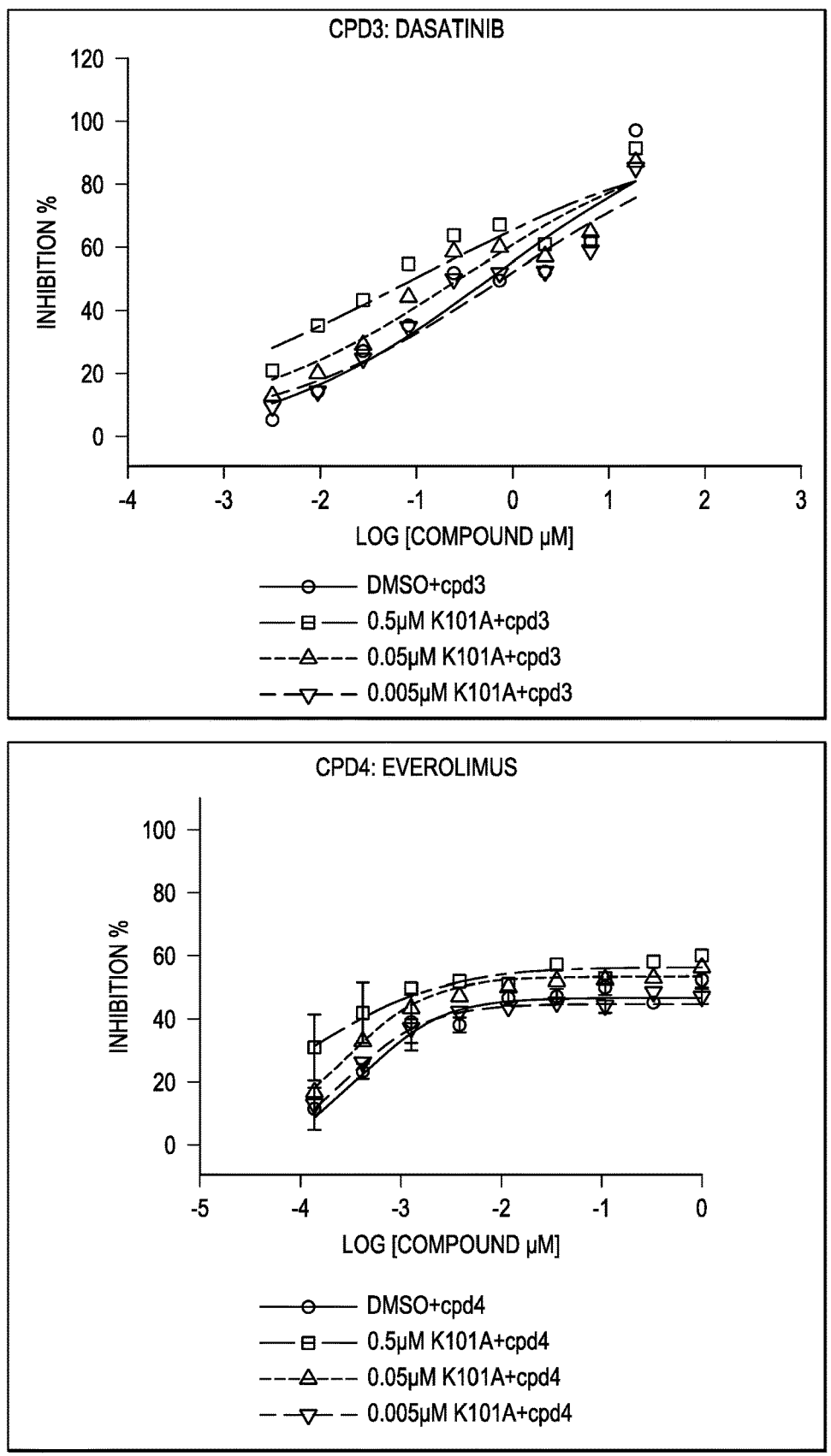
Figure 2C:
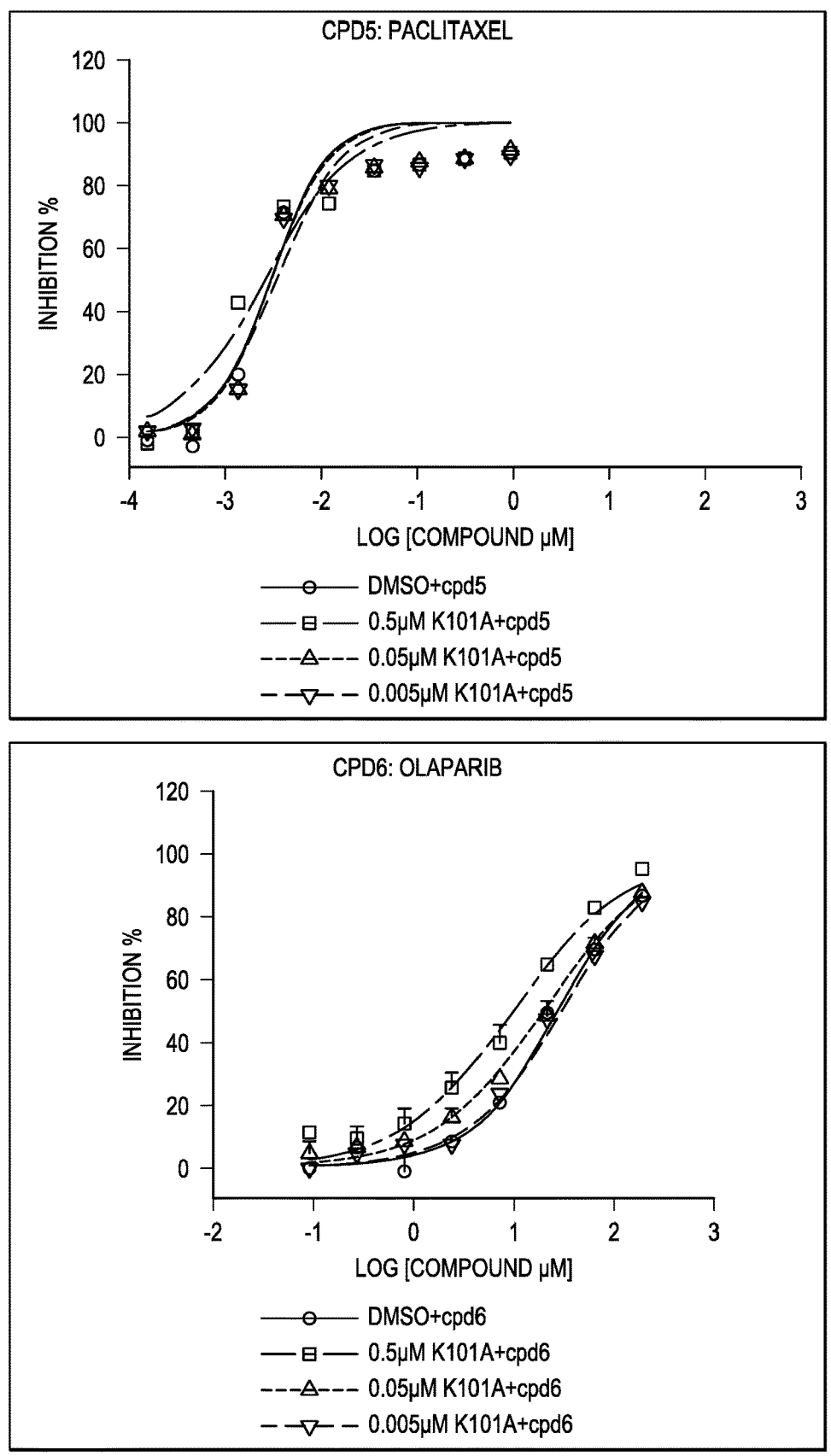
Figure 2D:
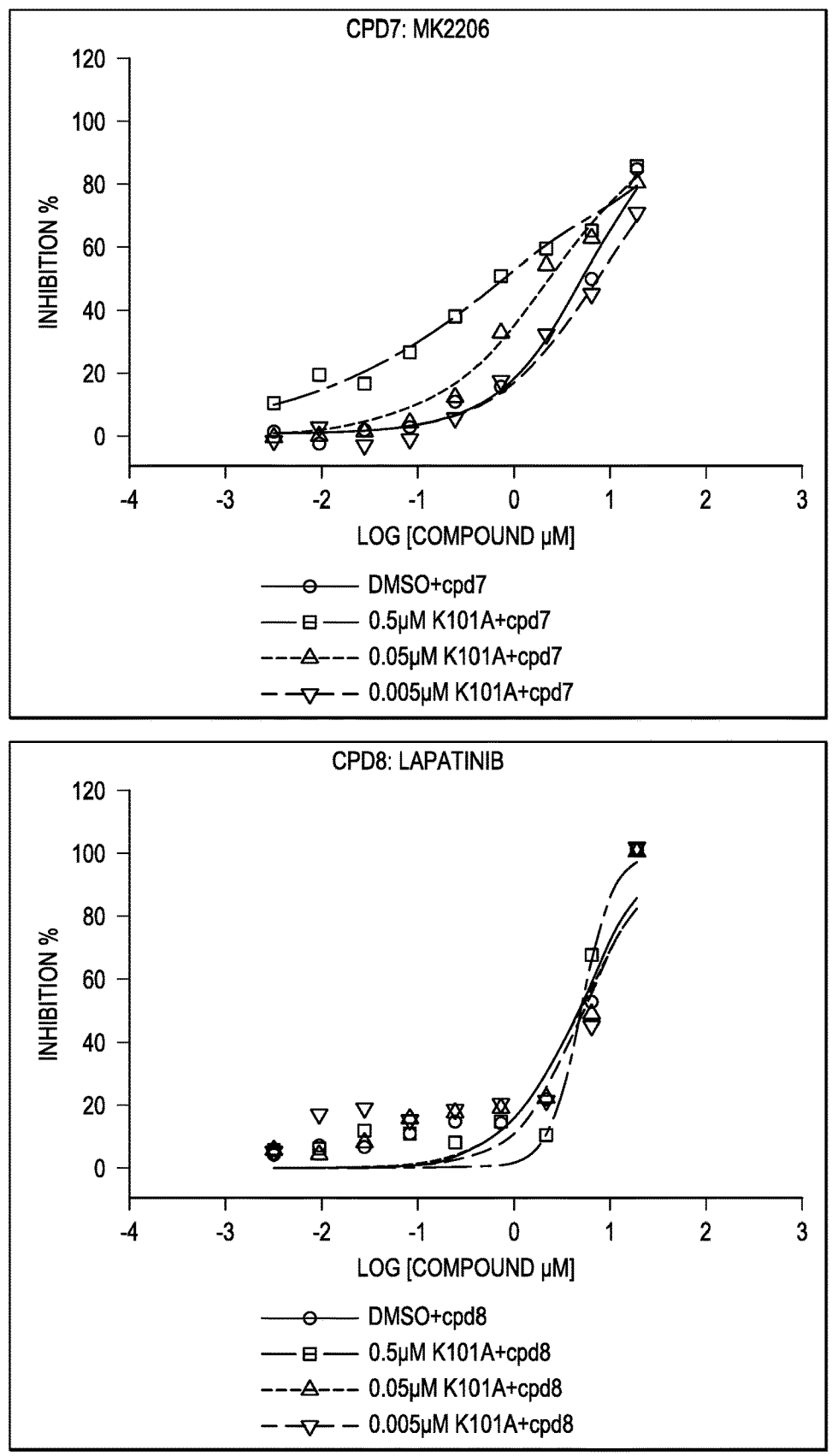
Figure 2E:
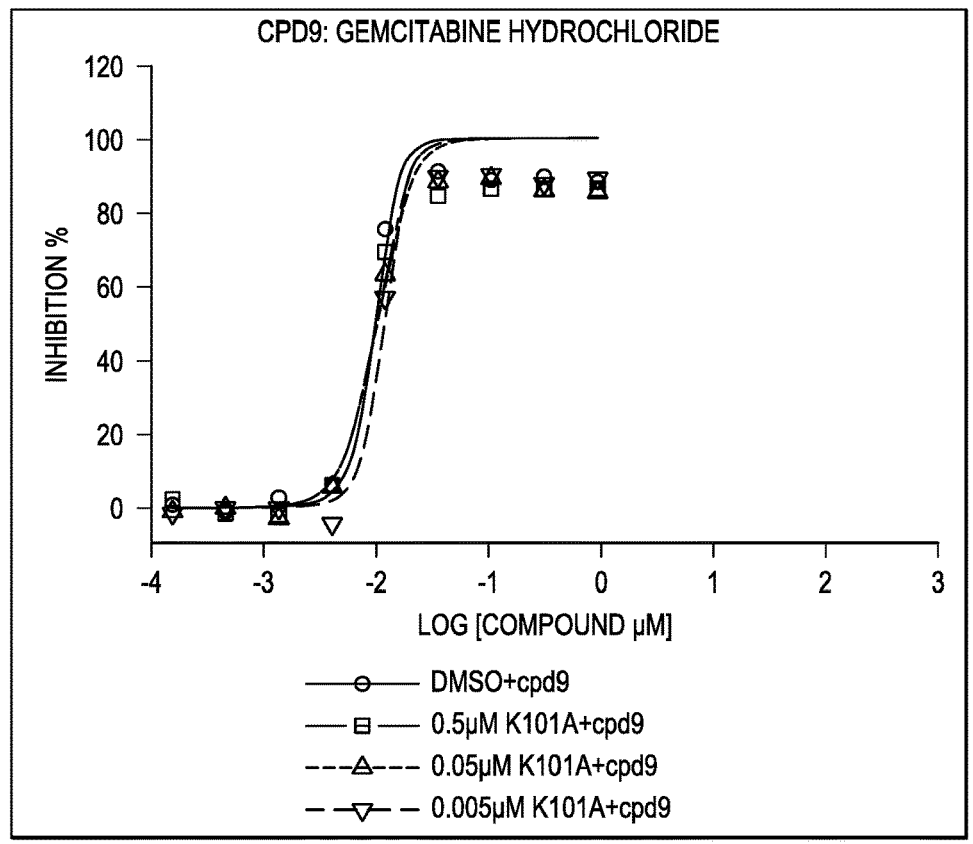
Figure 2E:
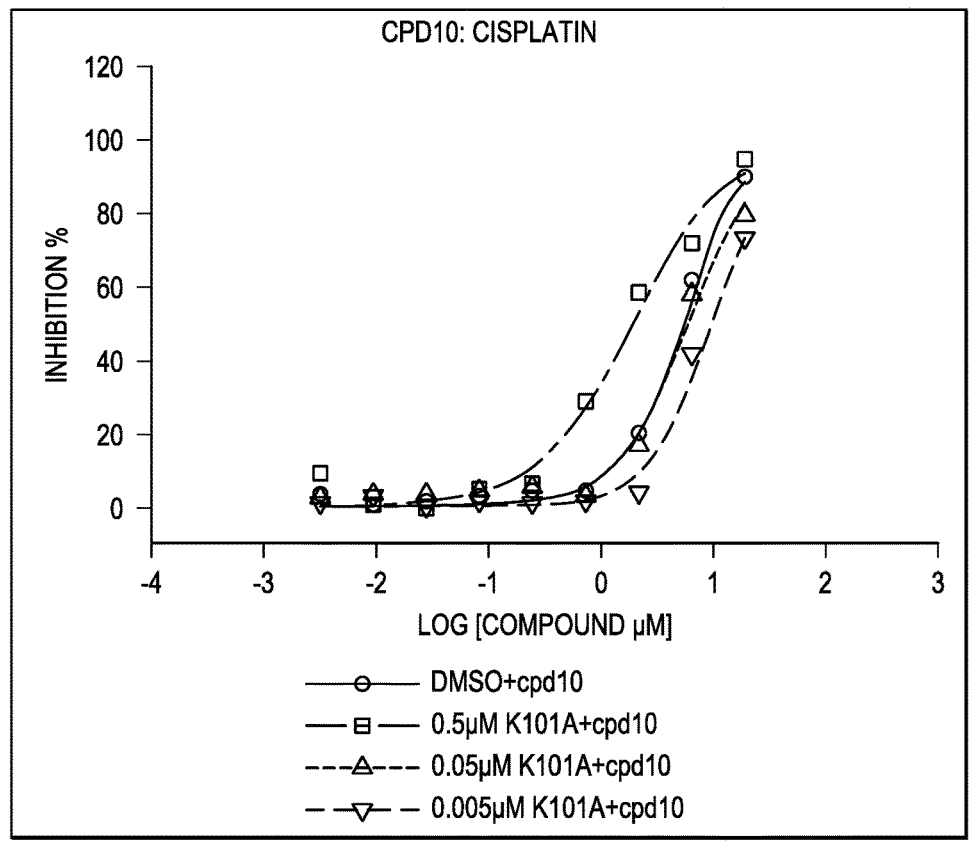
Figure 2F:
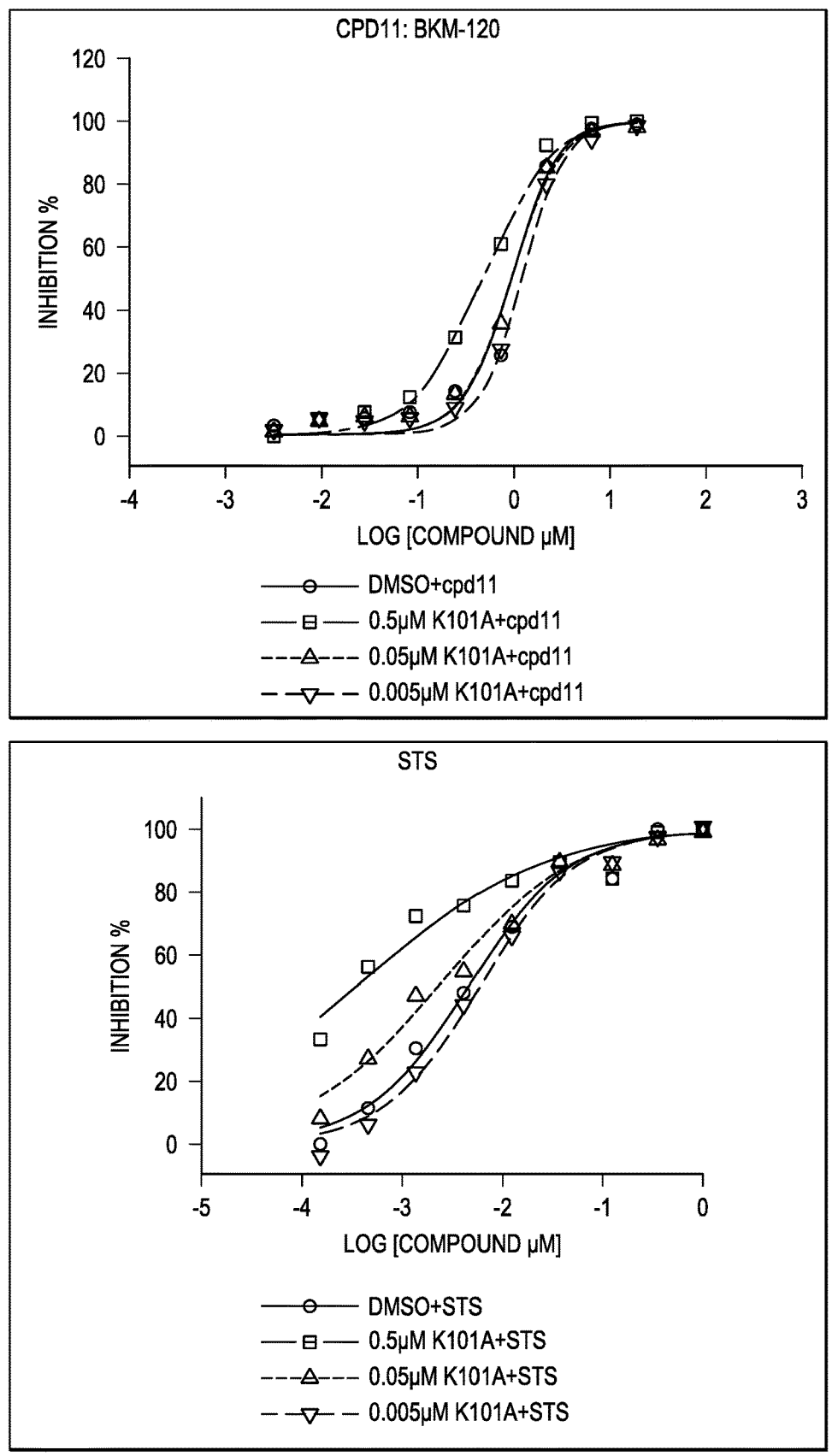
Figure 3A:
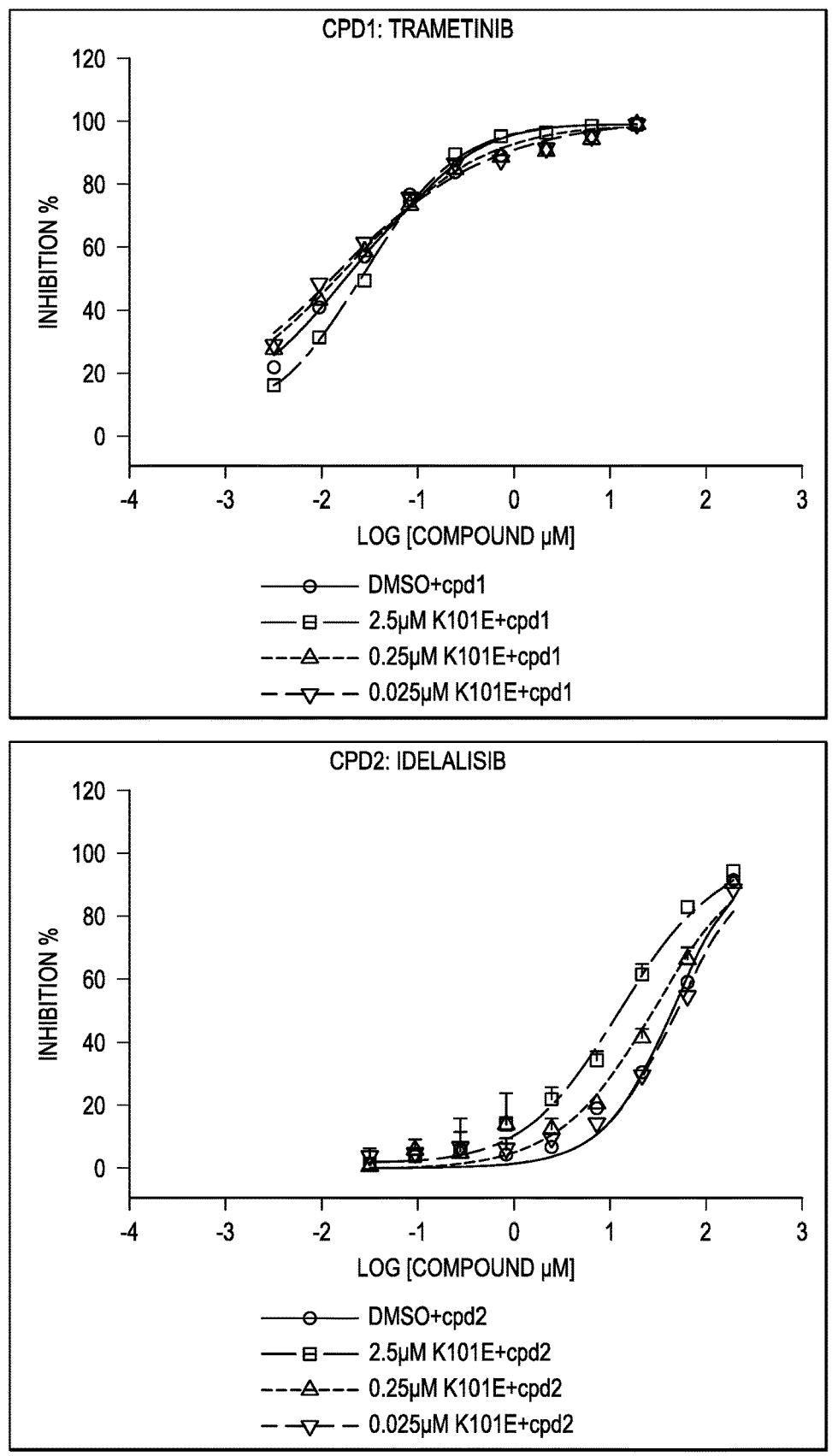
Figure 3B:
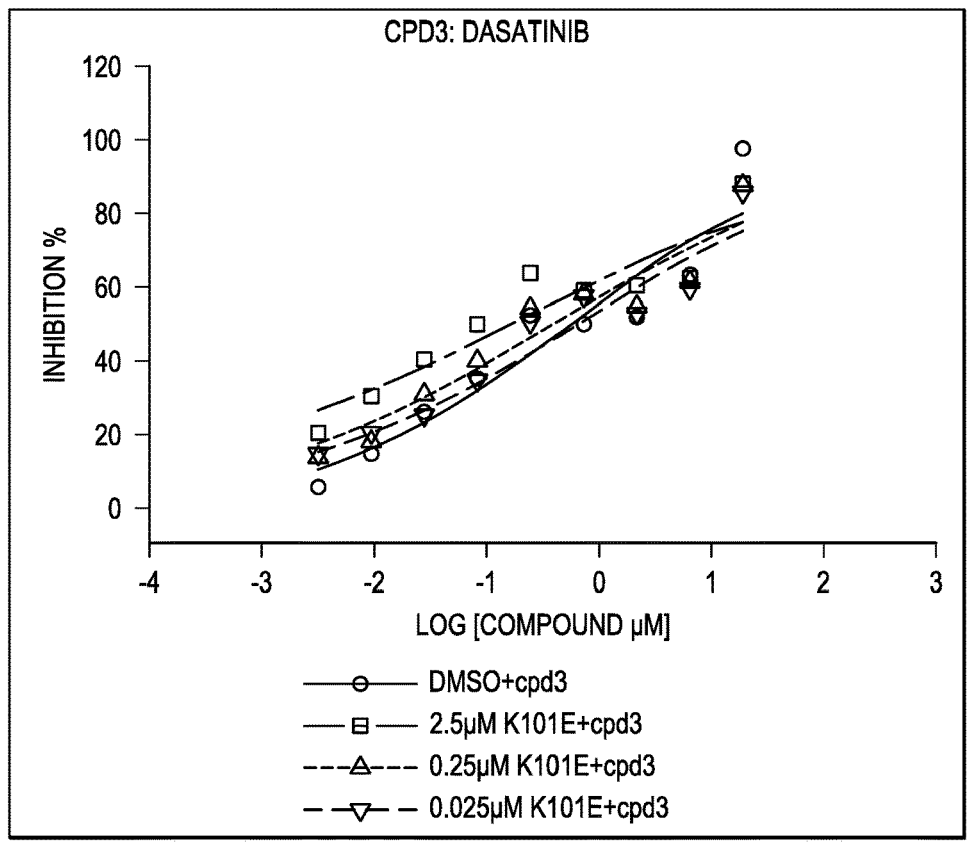
Figure 3B:
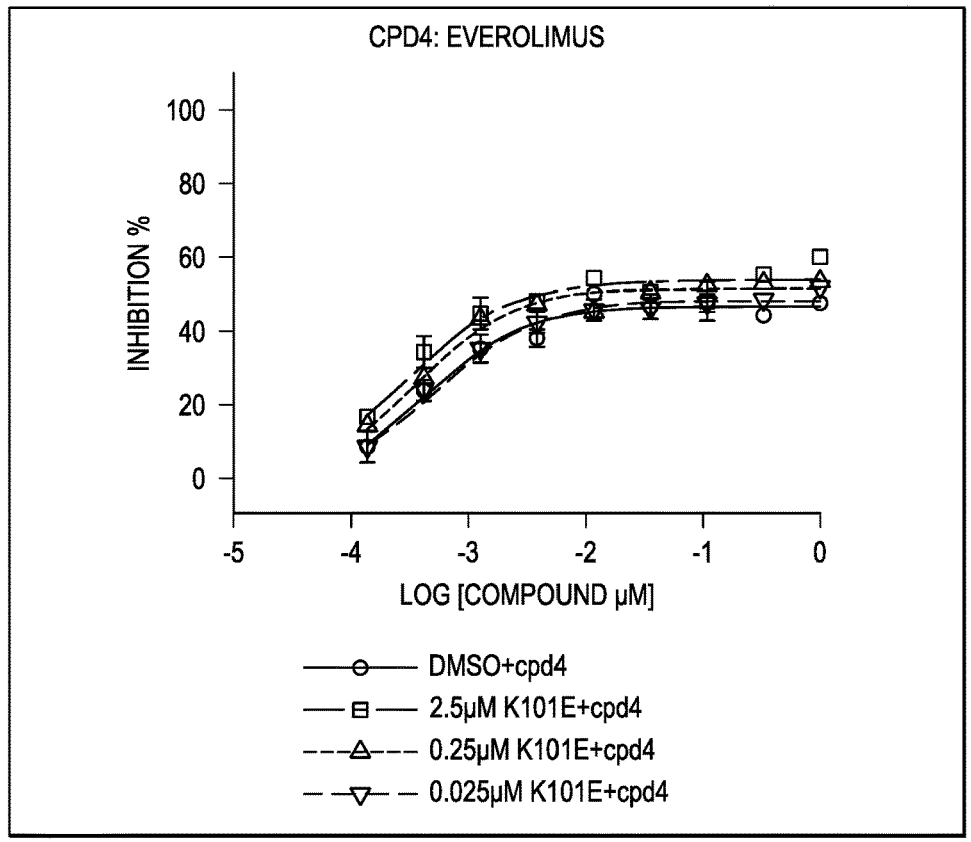
Figure 3C:
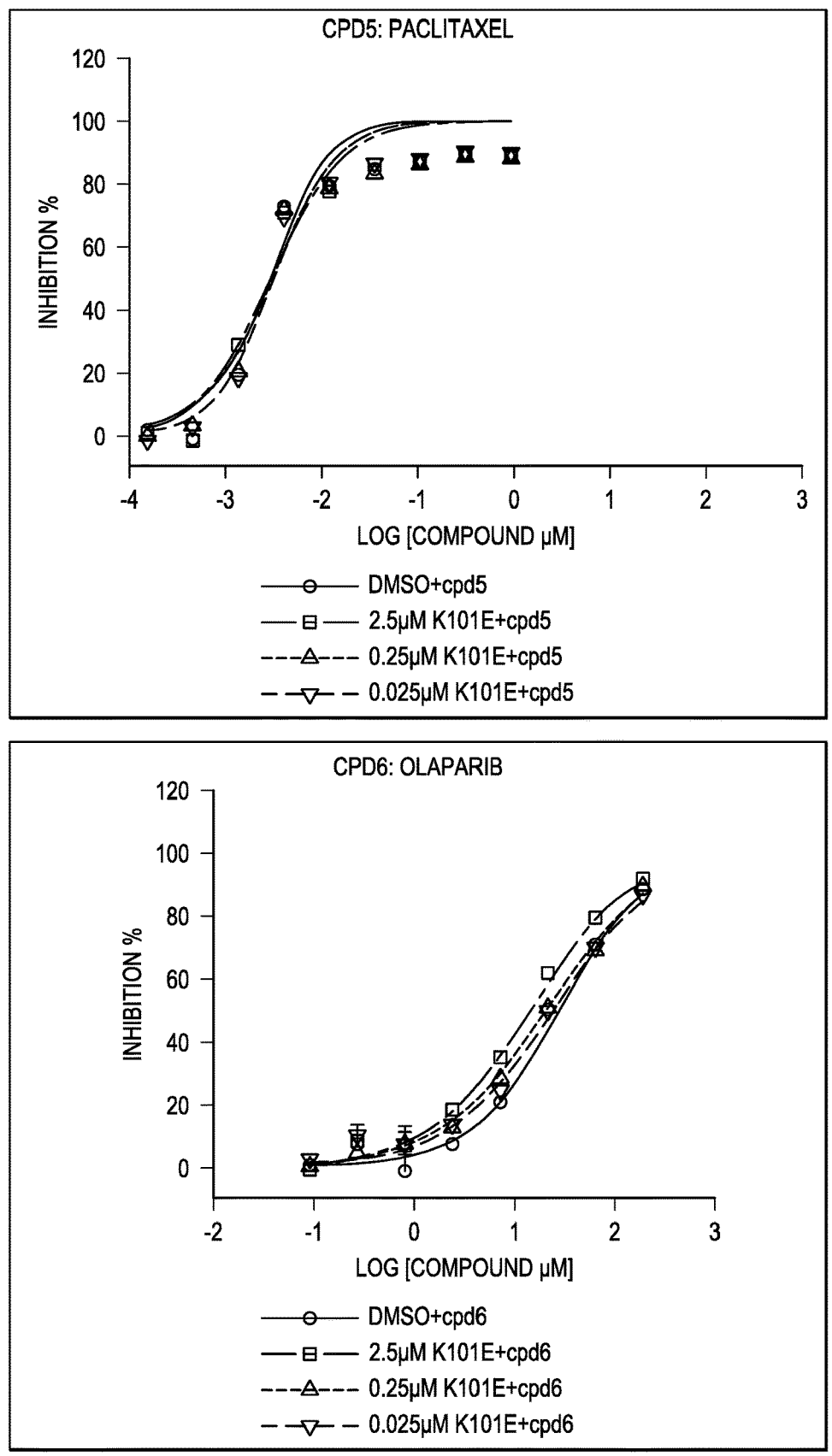
Figure 3D:
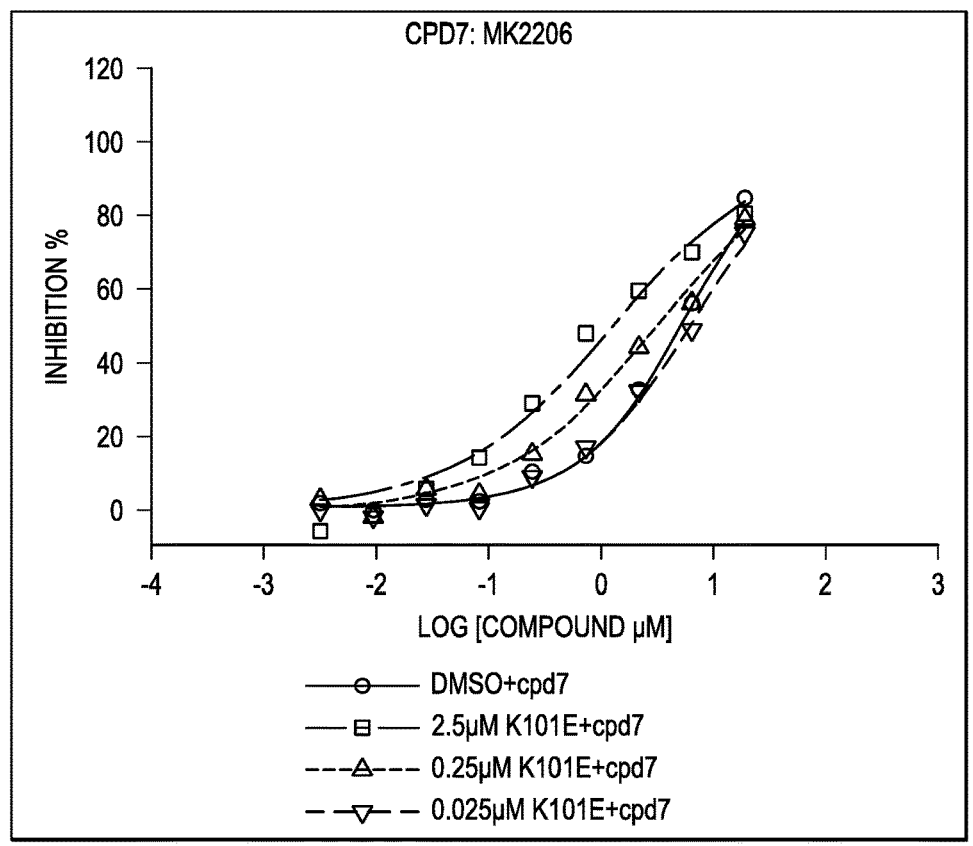
Figure 3D:
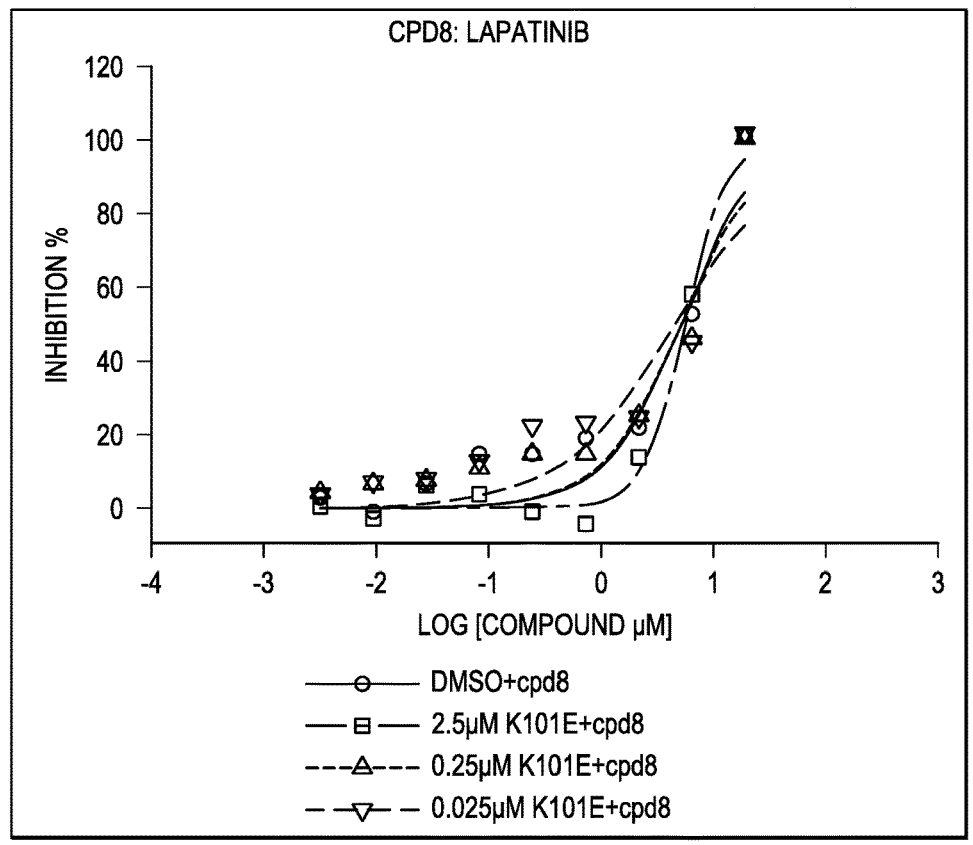
Figure 3E:
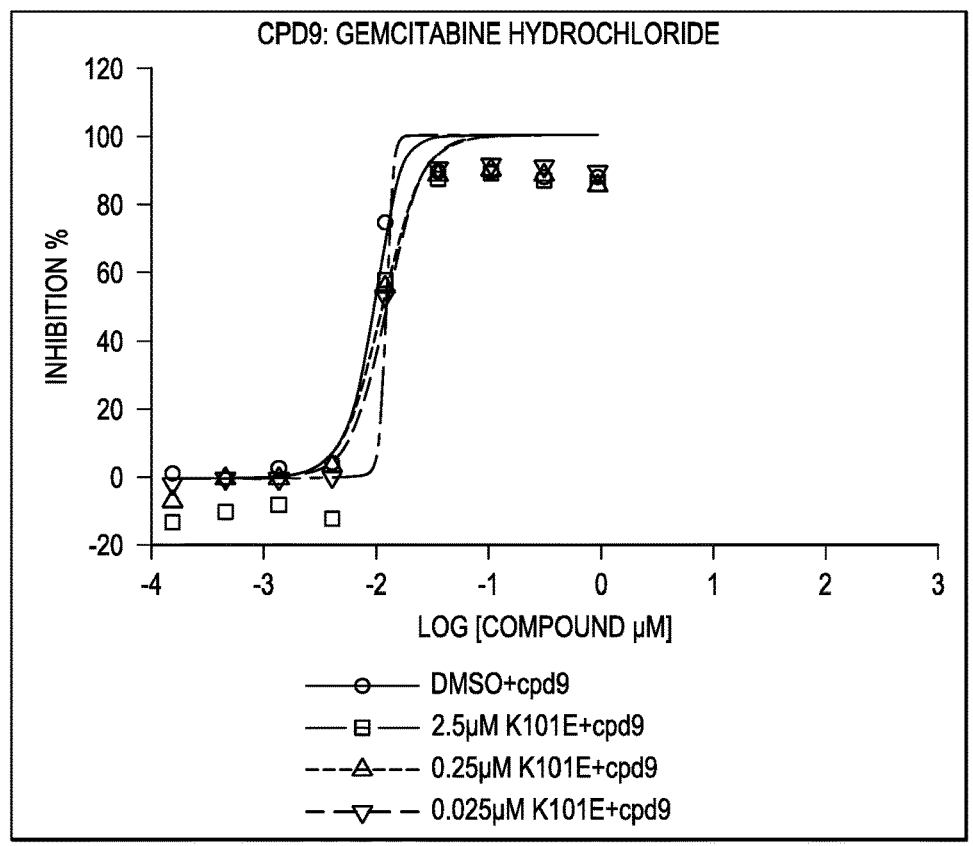
Figure 3E:
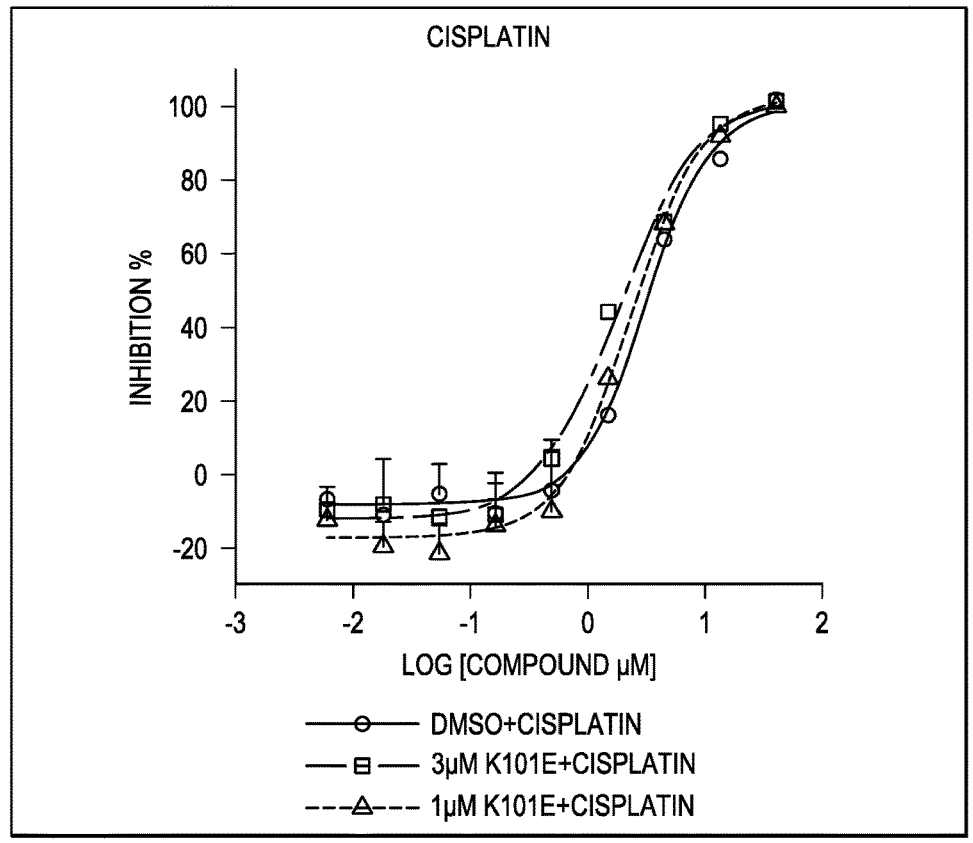
Figure 3F:
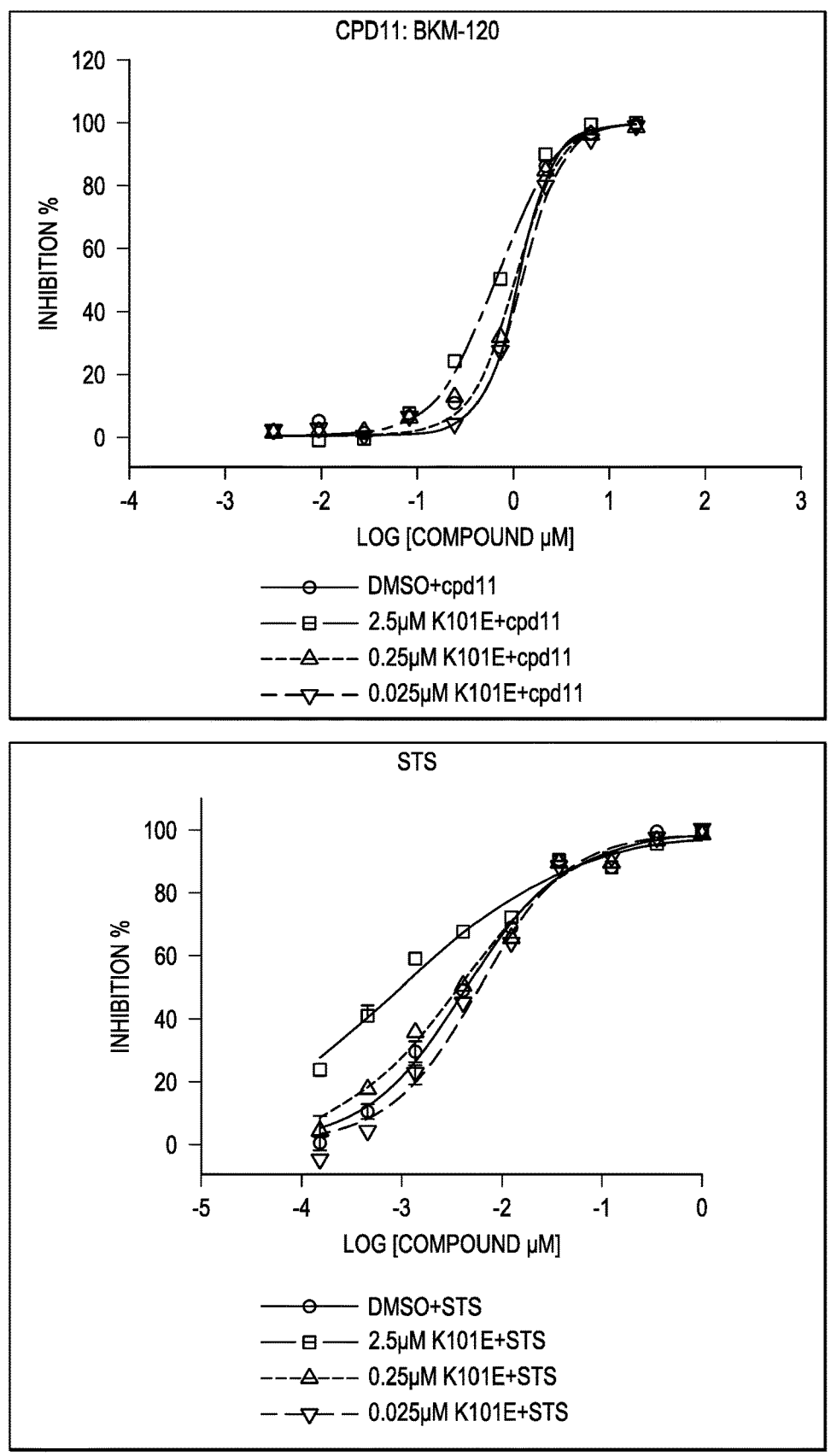
Figure 4A:
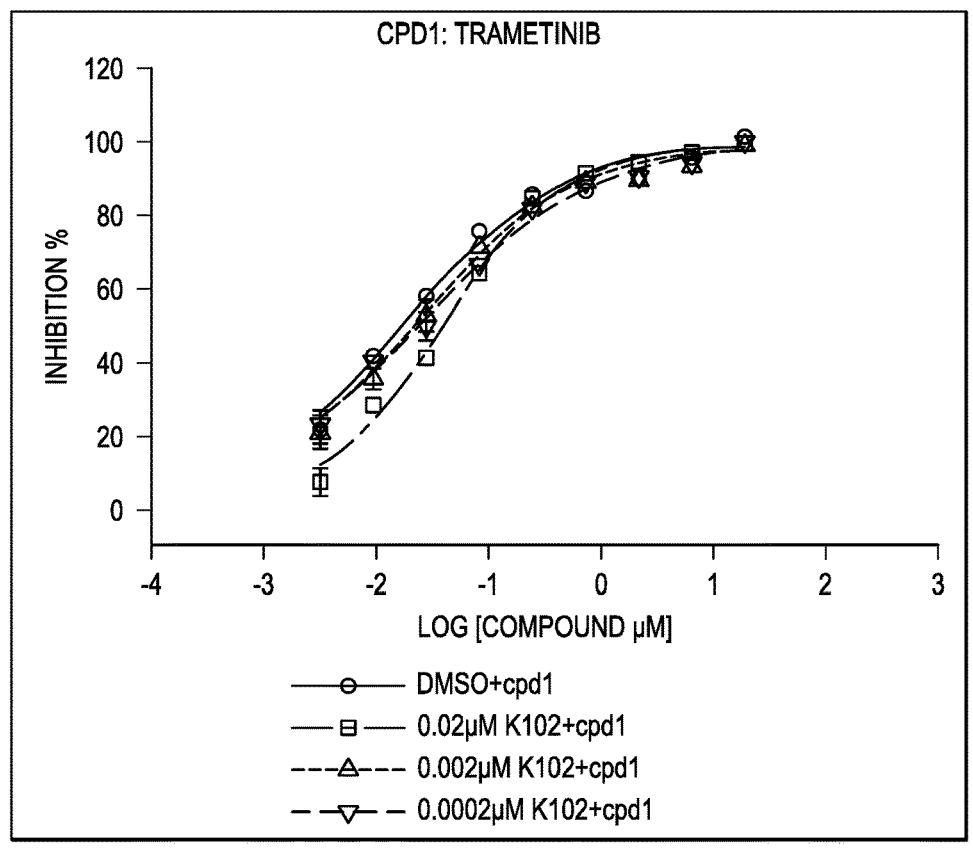
Figure 4A:
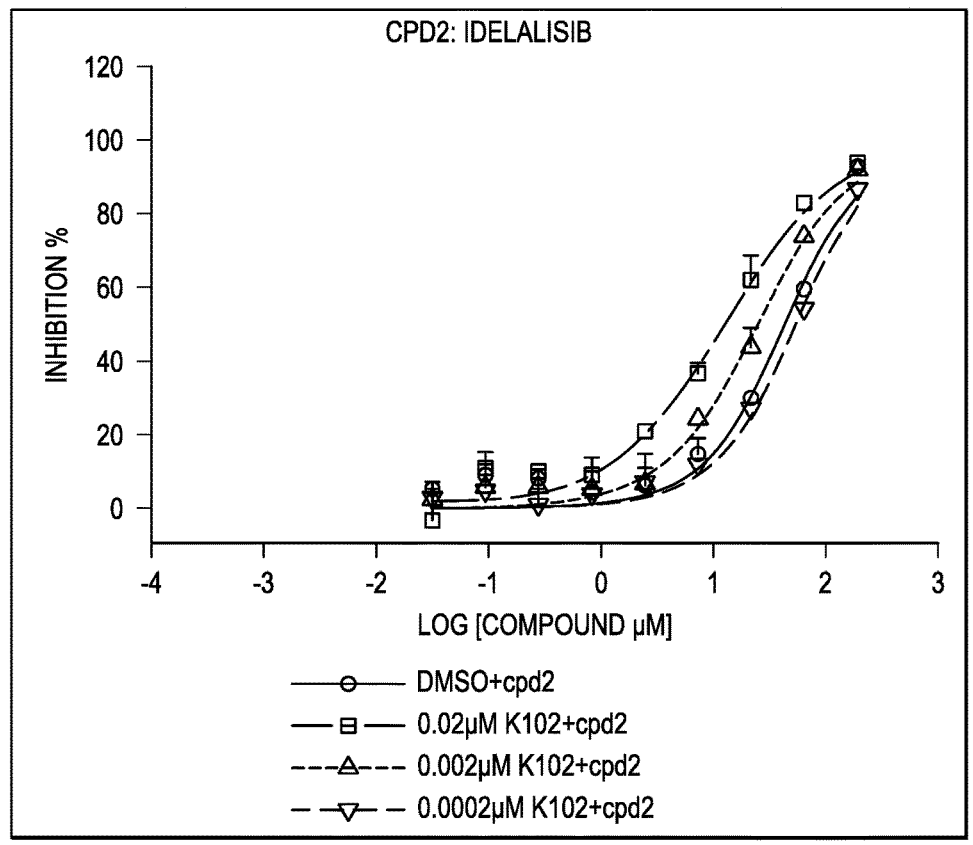
Figure 4B:
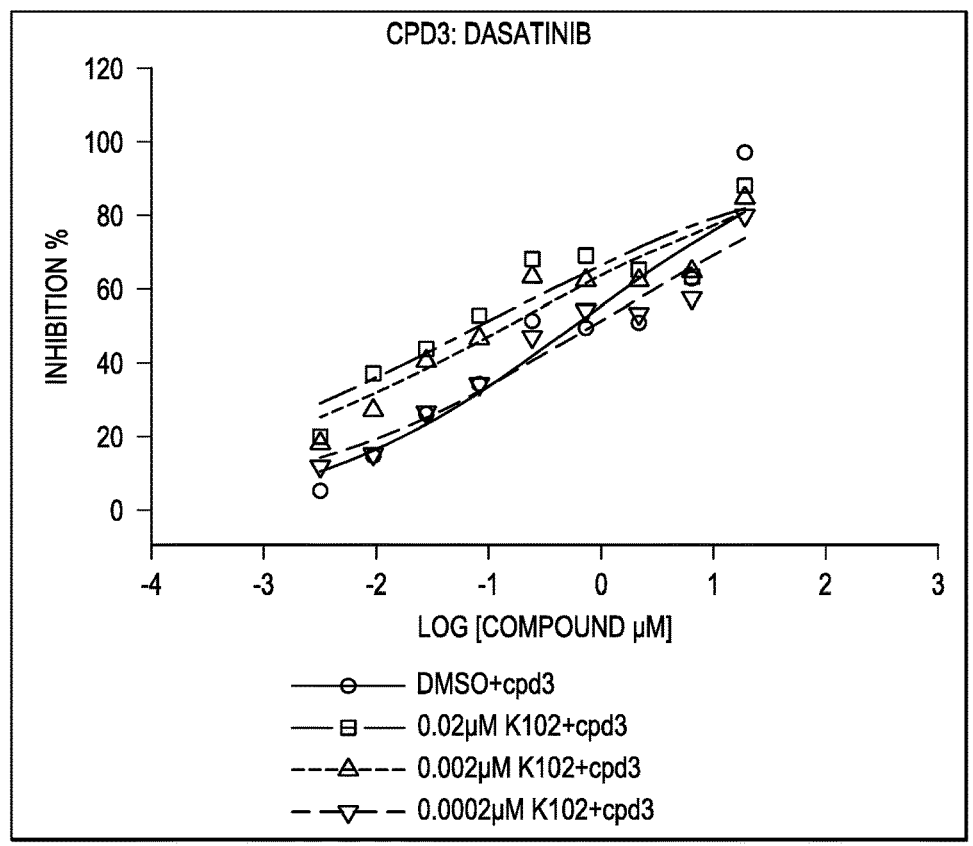
Figure 4B:
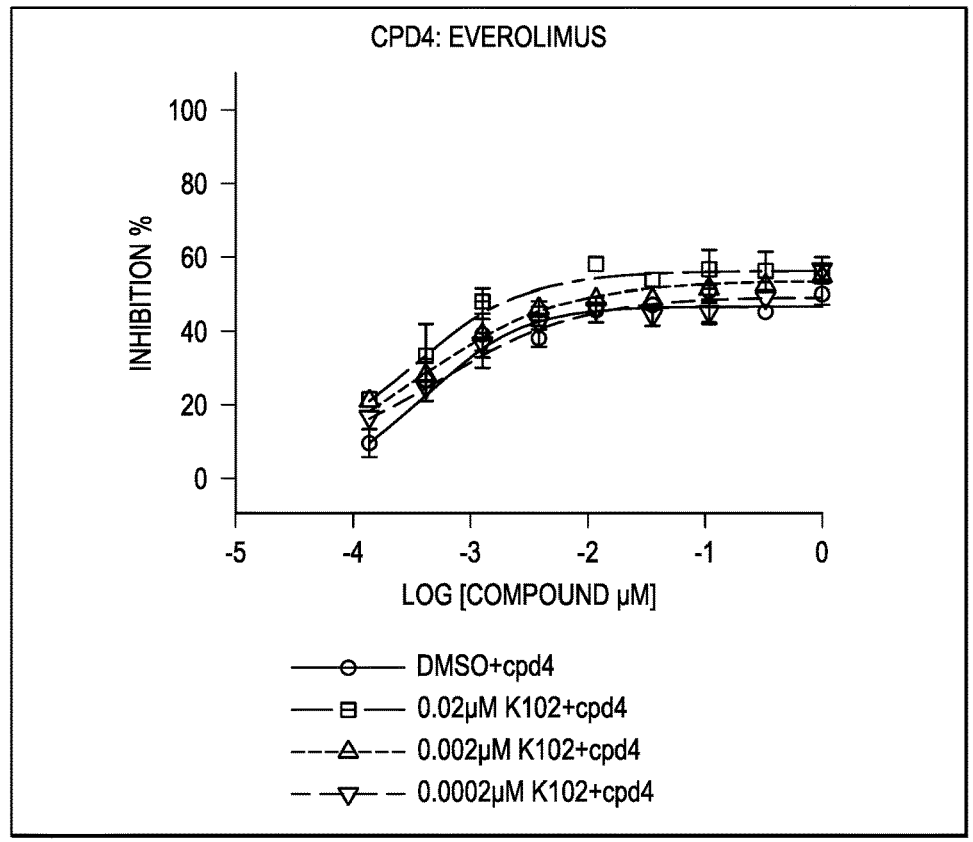
Figure 4C:
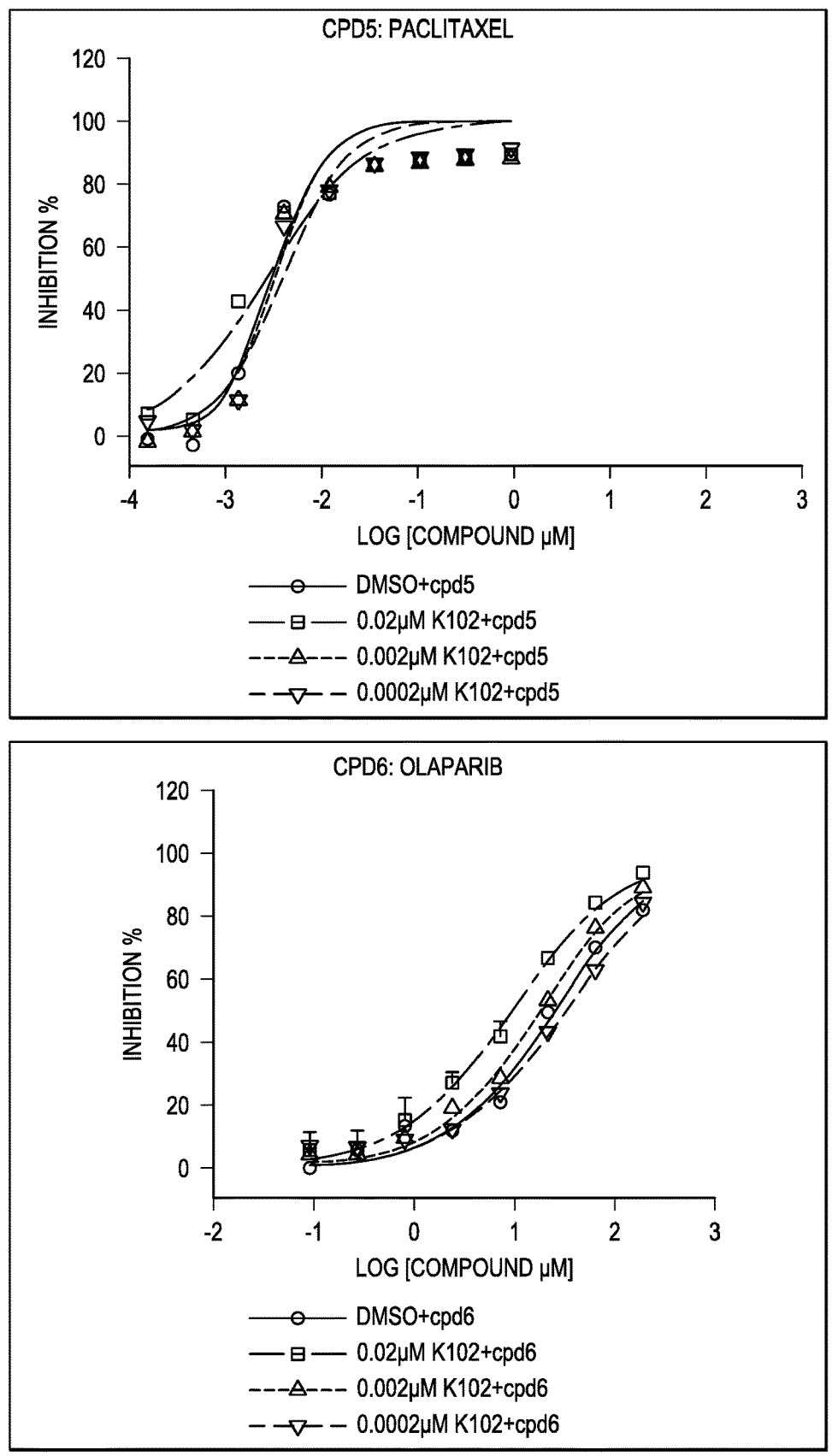
Figure 4D:
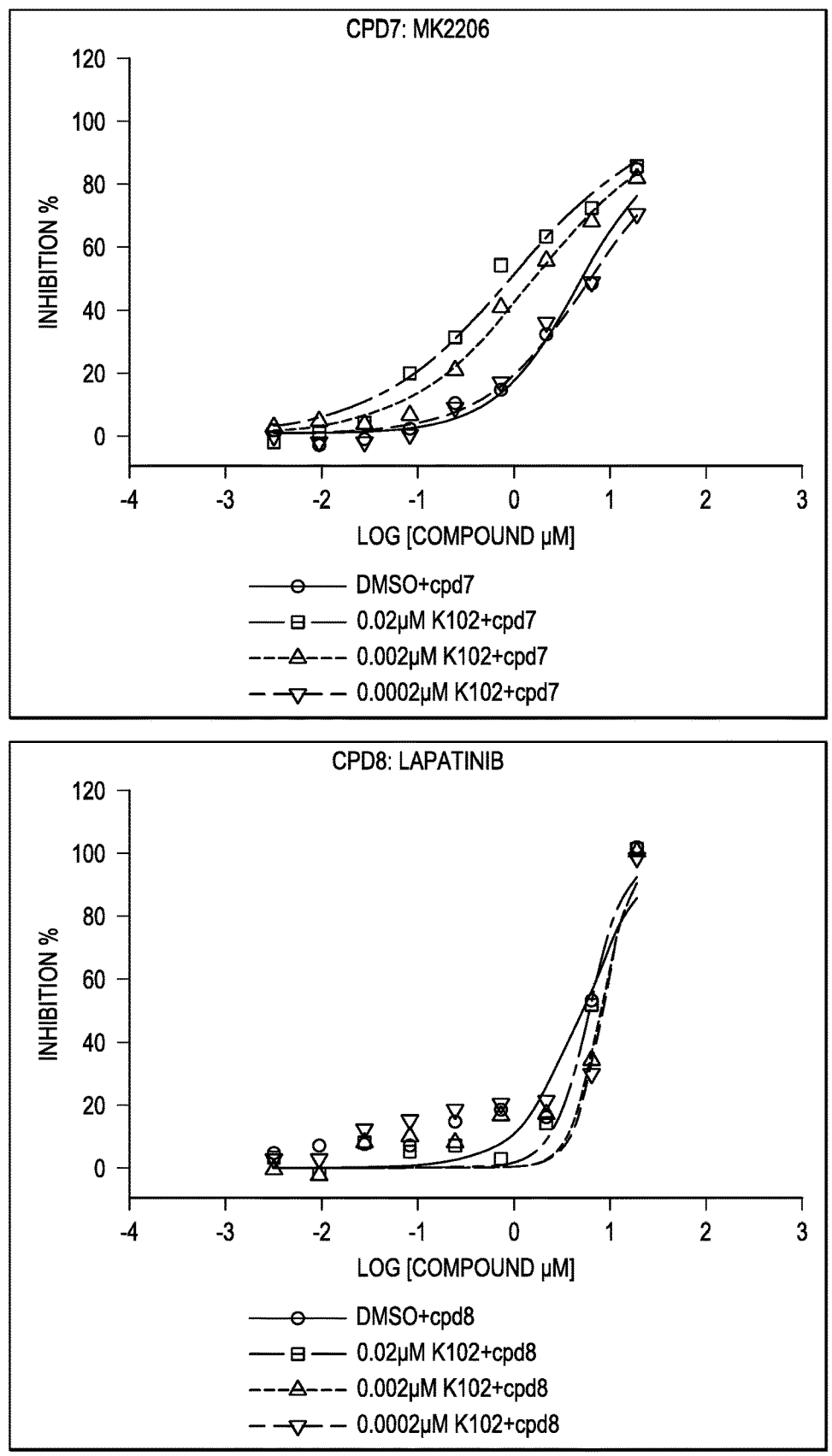
Figure 4E:
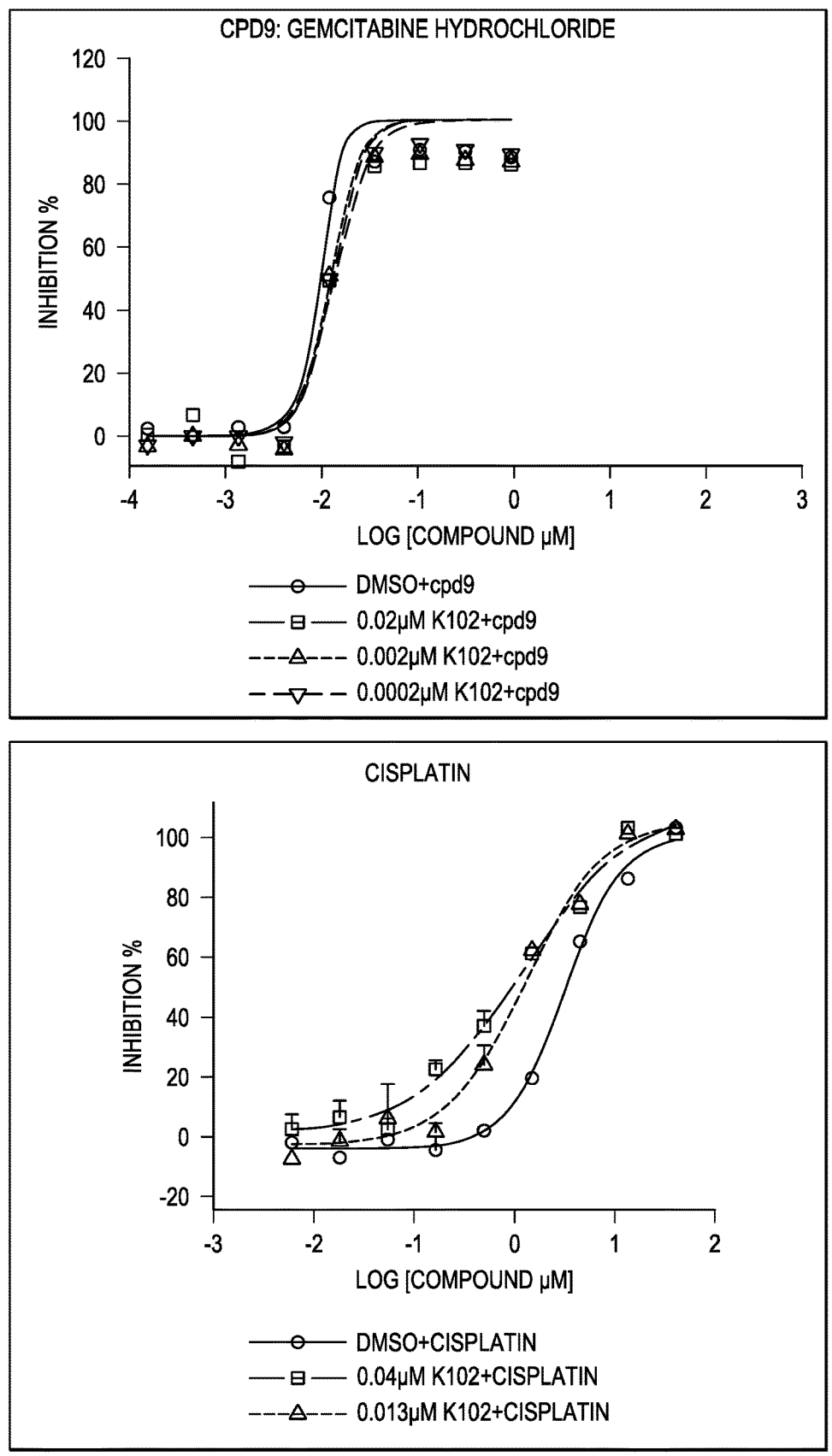
Figure 4F:
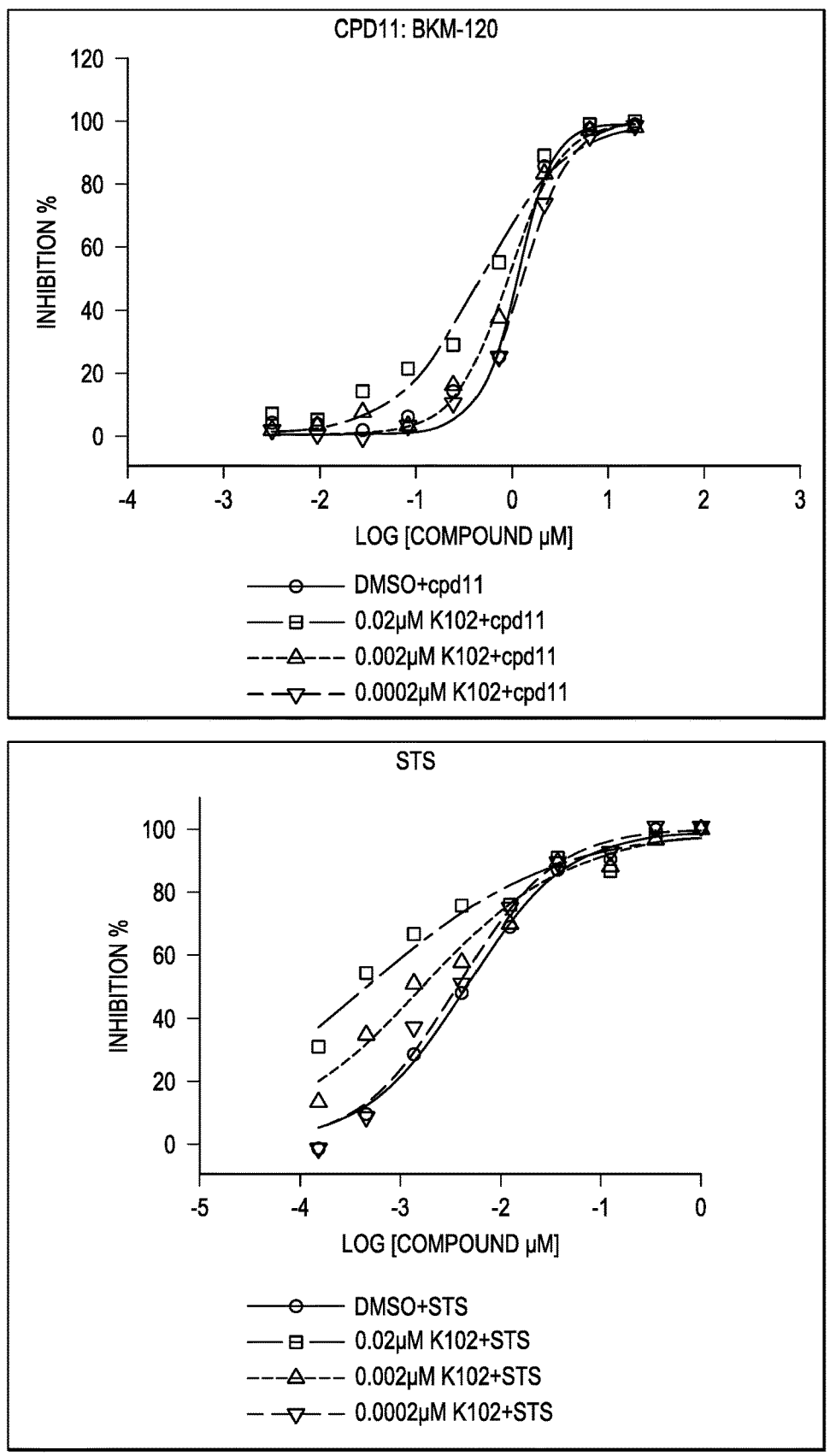
Figure 8:
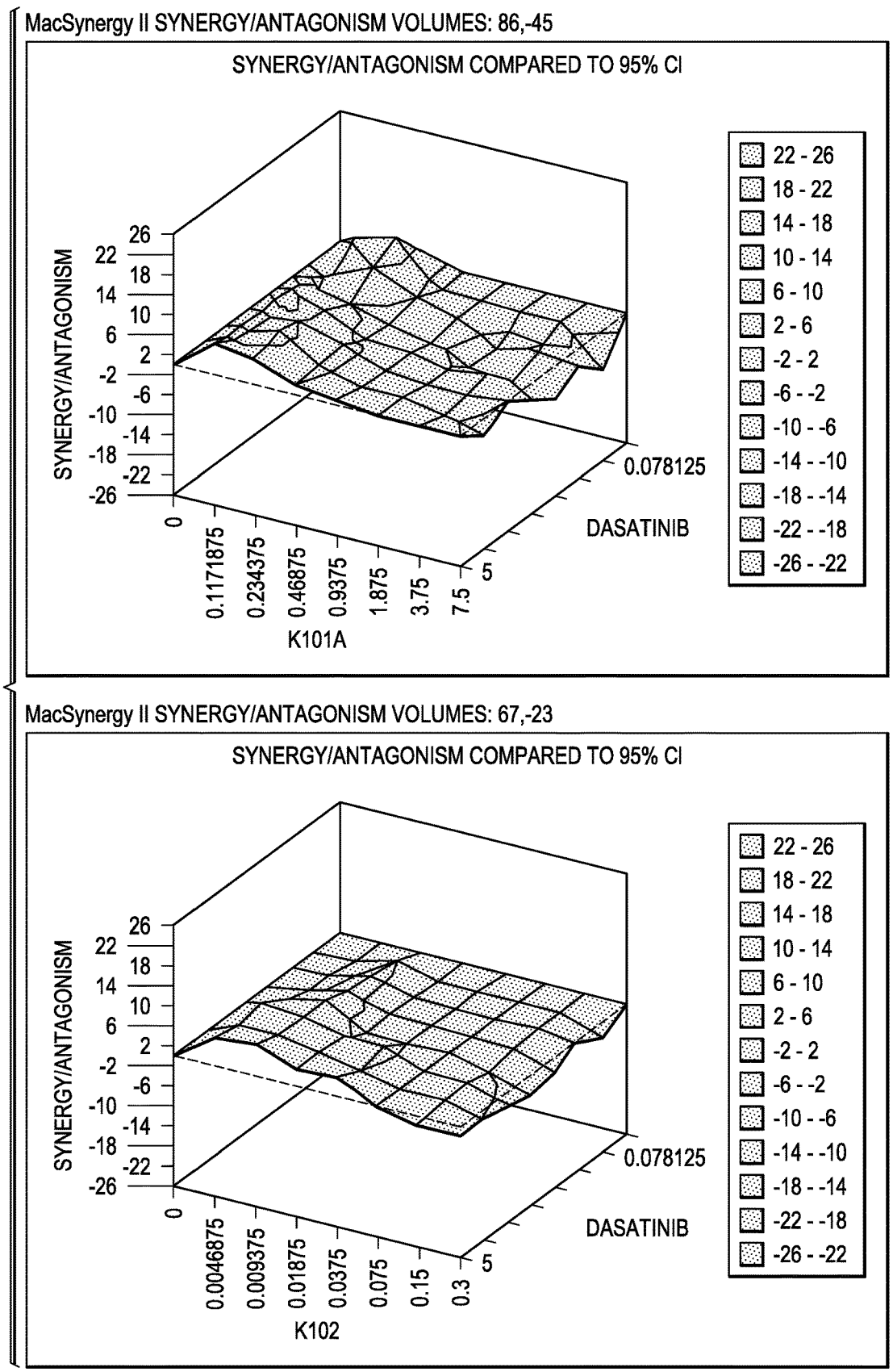
FIG. 8 shows synergism/antagonism plot of PKC activator K101A or K102 in combination with dasatinib on growth of inhibition of lung cancer cell line A549.

Furthermore, synergistic effects were observed when the PKC activator compounds were combined with multiple kinase inhibitors (e.g., staurosporine (STS)) and src-family kinase inhibitors (e.g., dasatinib) (Table 11A, Table 12, and Table 13A; FIG. 2B and FIG. 2F for compound K101A; FIG. 10; FIG. 3B and FIG. 3F for compound K101E; FIG. 4B and FIG. 4F for compound K102). As shown in FIG. 8, moderate synergistic effects were observed when lower concentrations of the PKC activator compounds were combined with dasatinib, whereas minor or insignificant antagonist effects were observed at much higher concentrations of the PKC activator compounds.

Figure 2G:
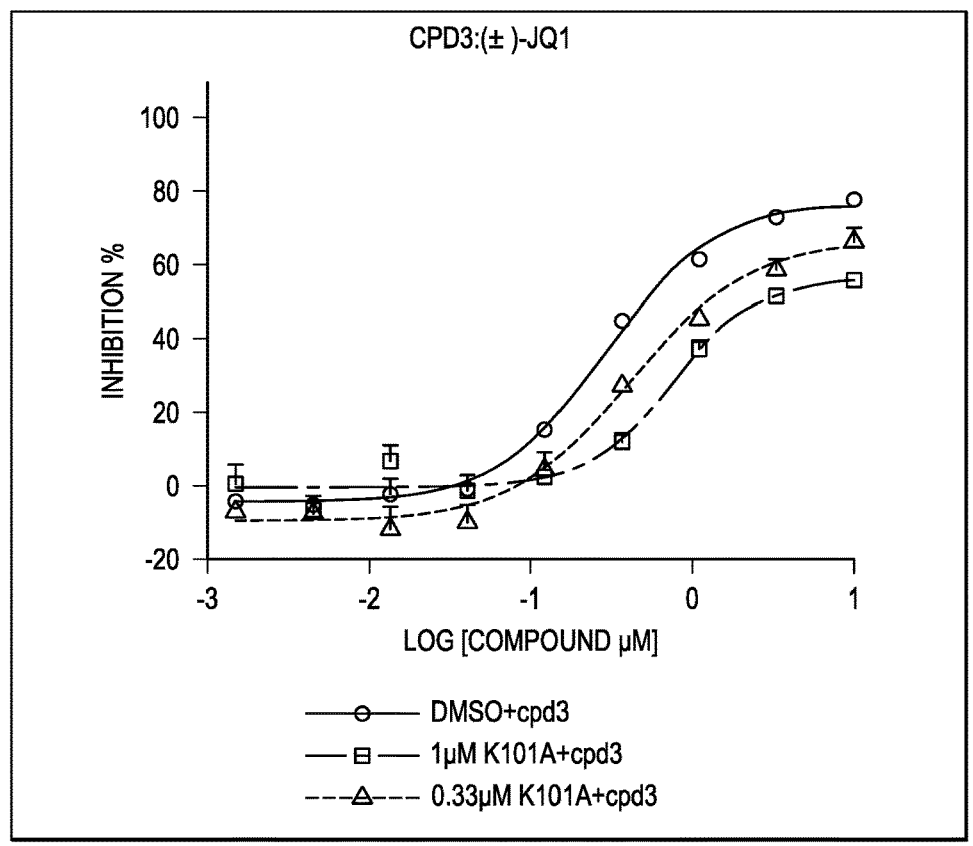
Figure 2G:
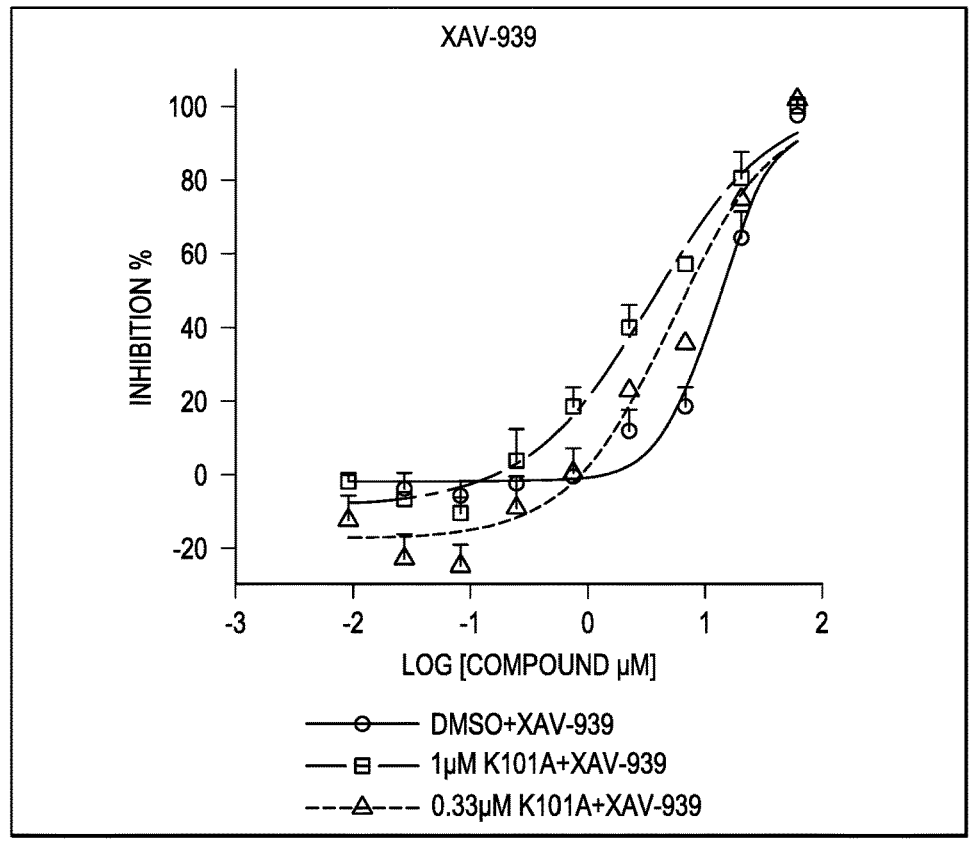
Figure 2H:
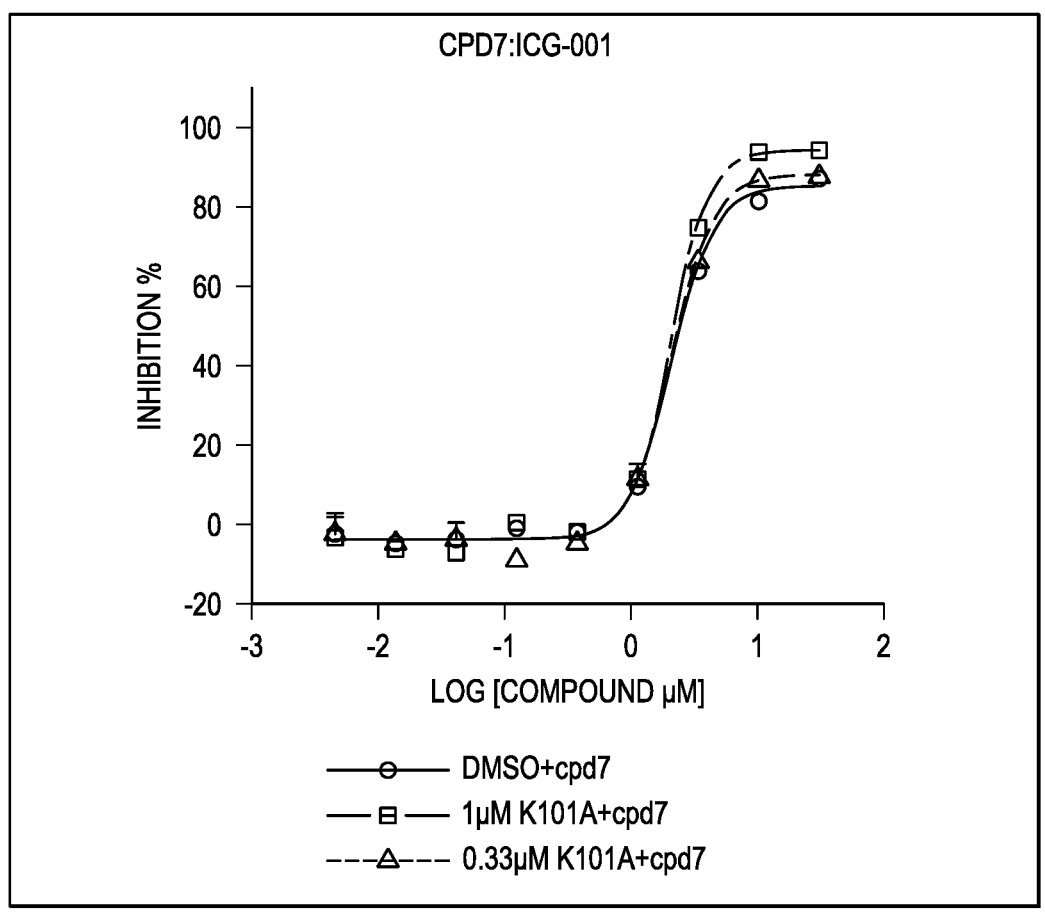
Figure 4G:
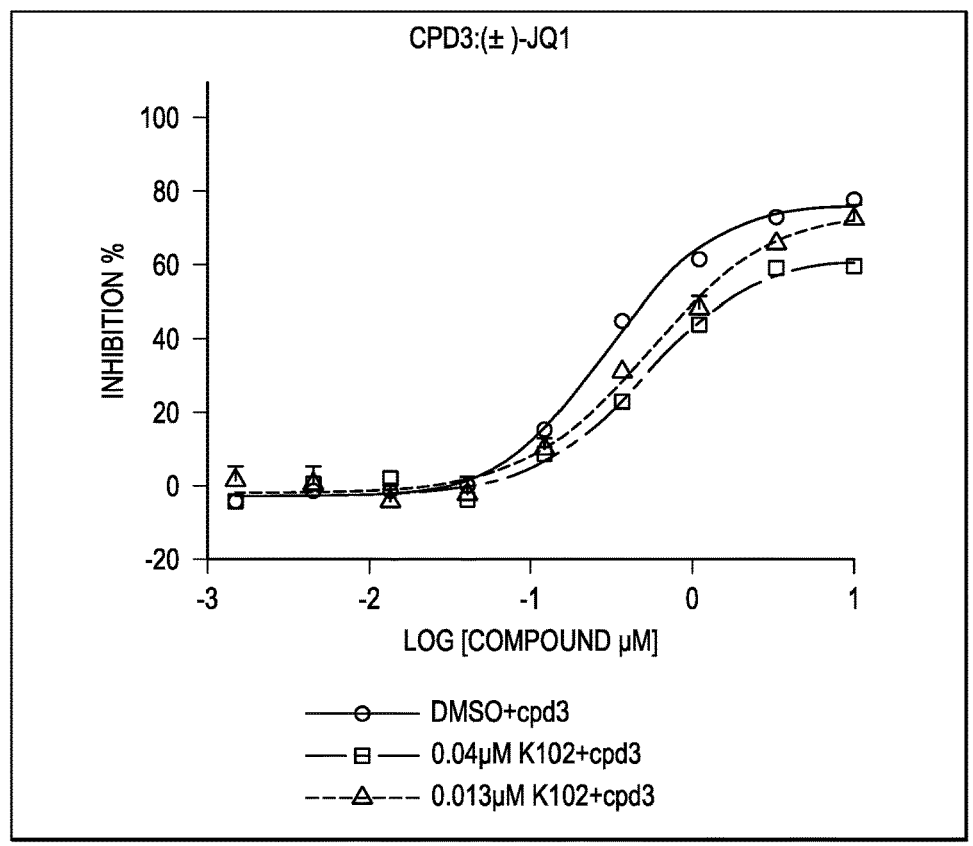
Figure 4G:
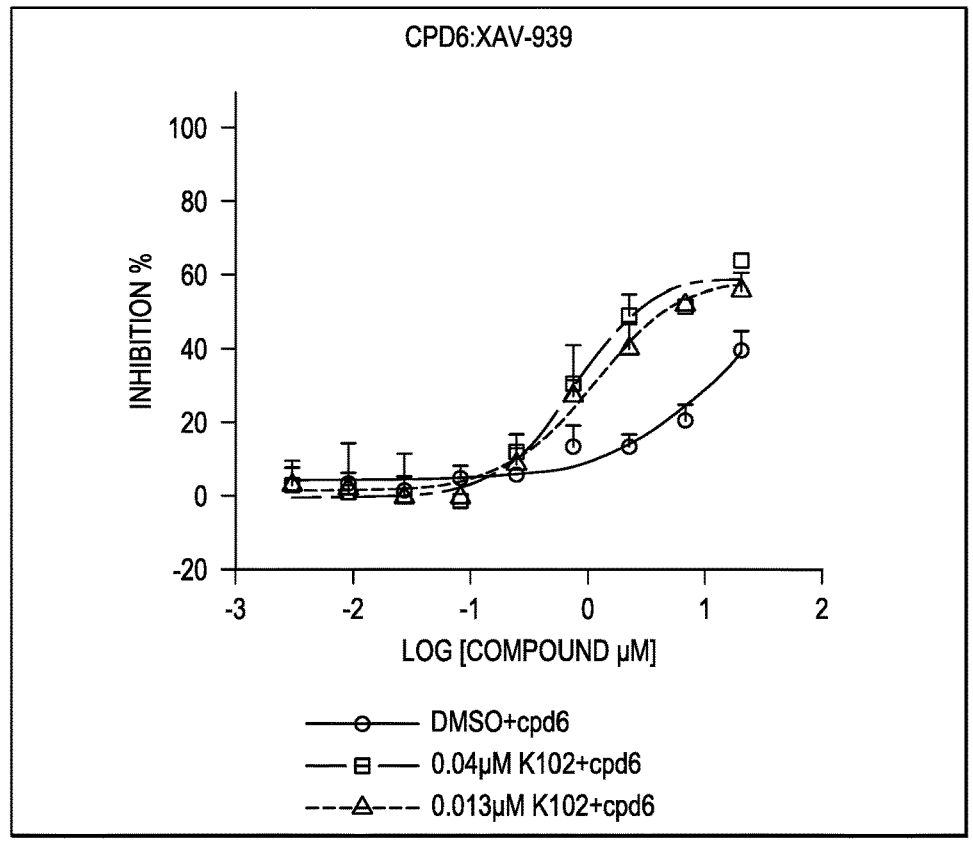
Figure 4H:
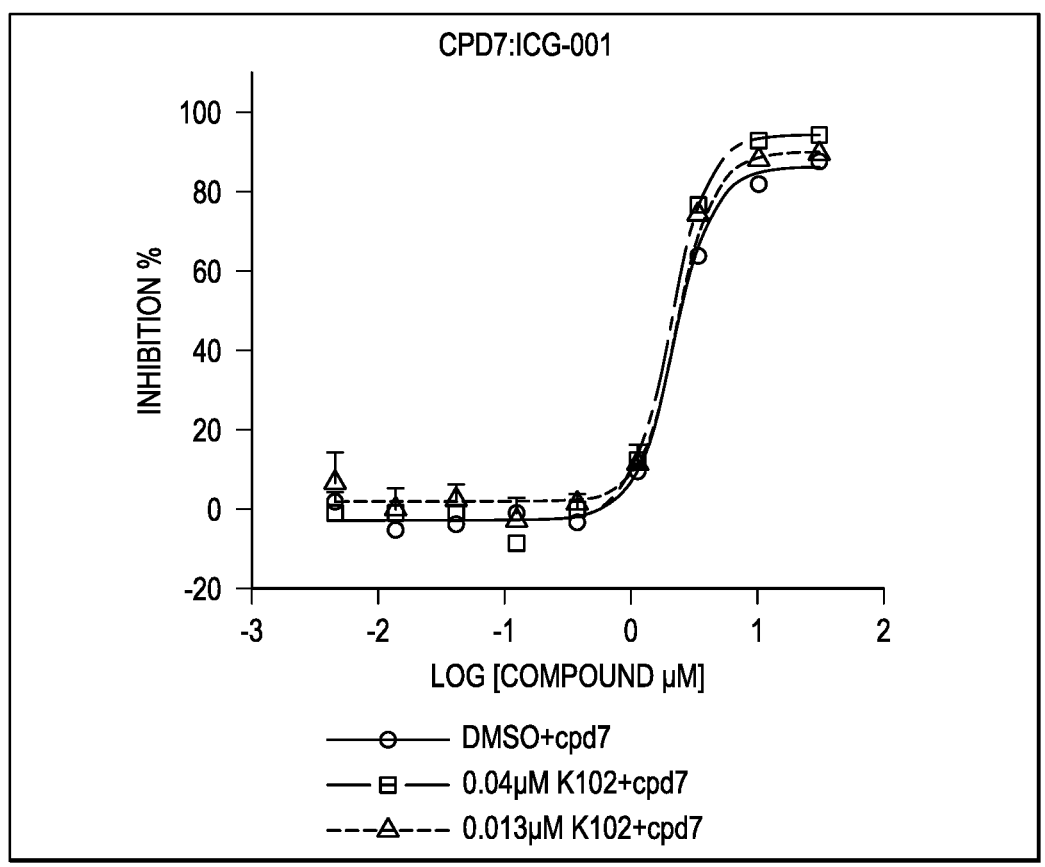

The PKC activator compounds also showed synergistic effect when combined with certain Wnt/β-catenin pathway inhibitors (Table 11B and Table 13B; FIG. 2G and FIG. 2H for compound K101A; FIG. 4G and FIG. 4H for compound K101A). Among these inhibitors, Tankyrase 1/2 inhibitors (e.g., XAV-939) showed strong synergistic effect when combined with K101A or K102. Although IC50 ratio could not be calculated for compound LGK-974, a Wnt/β-catenin pathway inhibitor targeting PORCN, due to low top inhibition in A549, addition of K101A or K102 increased the top inhibition (%) by at least 2-fold, indicating a possible synergistic effect. However, another Wnt/β-catenin pathway inhibitor, ICG-001, targeting CBP, a protein required for TCF/β-catenin-mediated transcription, did not show synergy with K101A or K102. Interestingly, Wnt pathway activation is associated with resistance to cisplatin in the A549 lung cancer cell line (Yang et al., 2013, PloS One. 8(5):e65309; Gao et al., 2013, Cancer Lett. 336(1):231-239).

Figure 5:
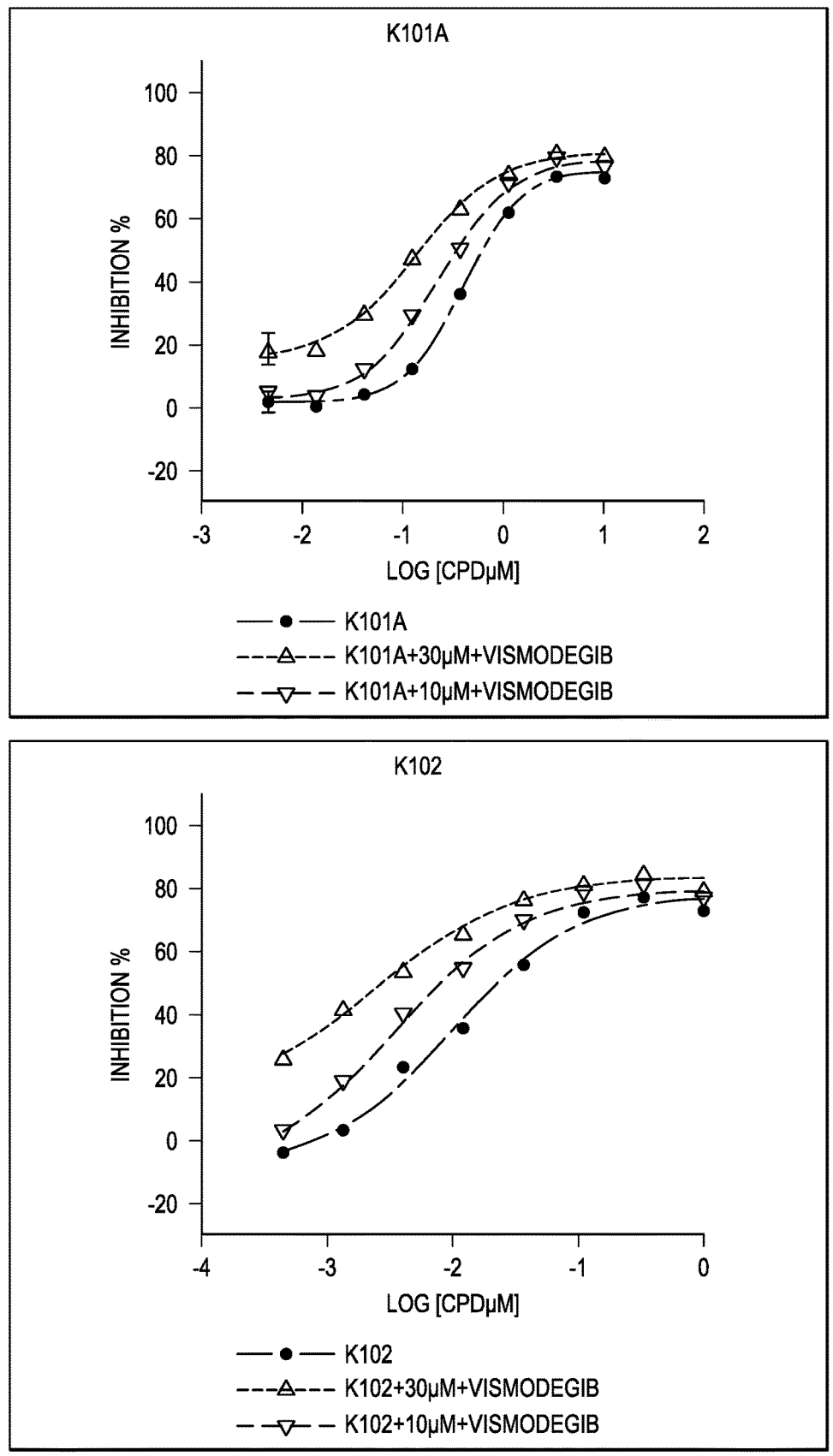
FIG. 5 shows effect of PKC activator K101A or K102 in combination with vismodegib, an antagonist of the Smoothened (SMO), on growth of inhibition of lung cancer cell line A549.

In addition to Wnt pathway, the hedgehog (Hh) signaling pathway also plays vital roles during normal embryonic development, and aberrant activation of Hh signaling has been implicated in a number of cancers, including basal cell carcinoma, medulloblastoma, pancreatic, lung, prostrate, and breast cancers. As shown in FIG. 5, PKC activators showed strong synergy with vismodegib, an inhibitor that blocks the activity of Smoothened protein in the Hh pathway, when tested on A549 cells. Vismodegib alone did not inhibit cell proliferation but potentiated the anti-proliferative effects of K101A or K102 in a concentration-dependent manner.

Figure 10A:
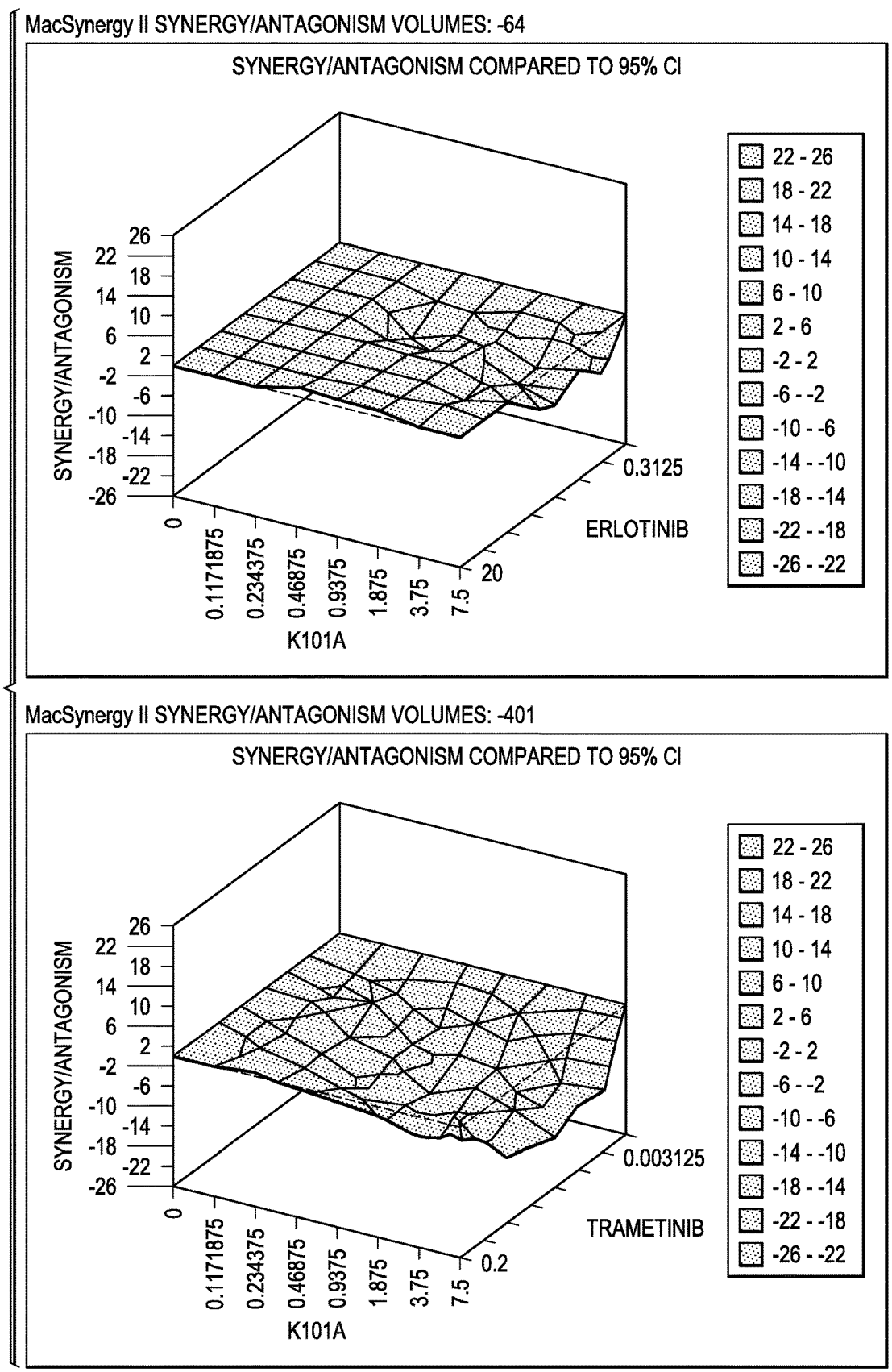
FIGS. 10A and 10B show synergism/antagonism plot of PKC activator K101A or K102 in combination with erlotinib (EFGR inhibitor) and trametinib (MEK inhibitor) on growth of inhibition of lung cancer cell line A549.
Figure 10B:
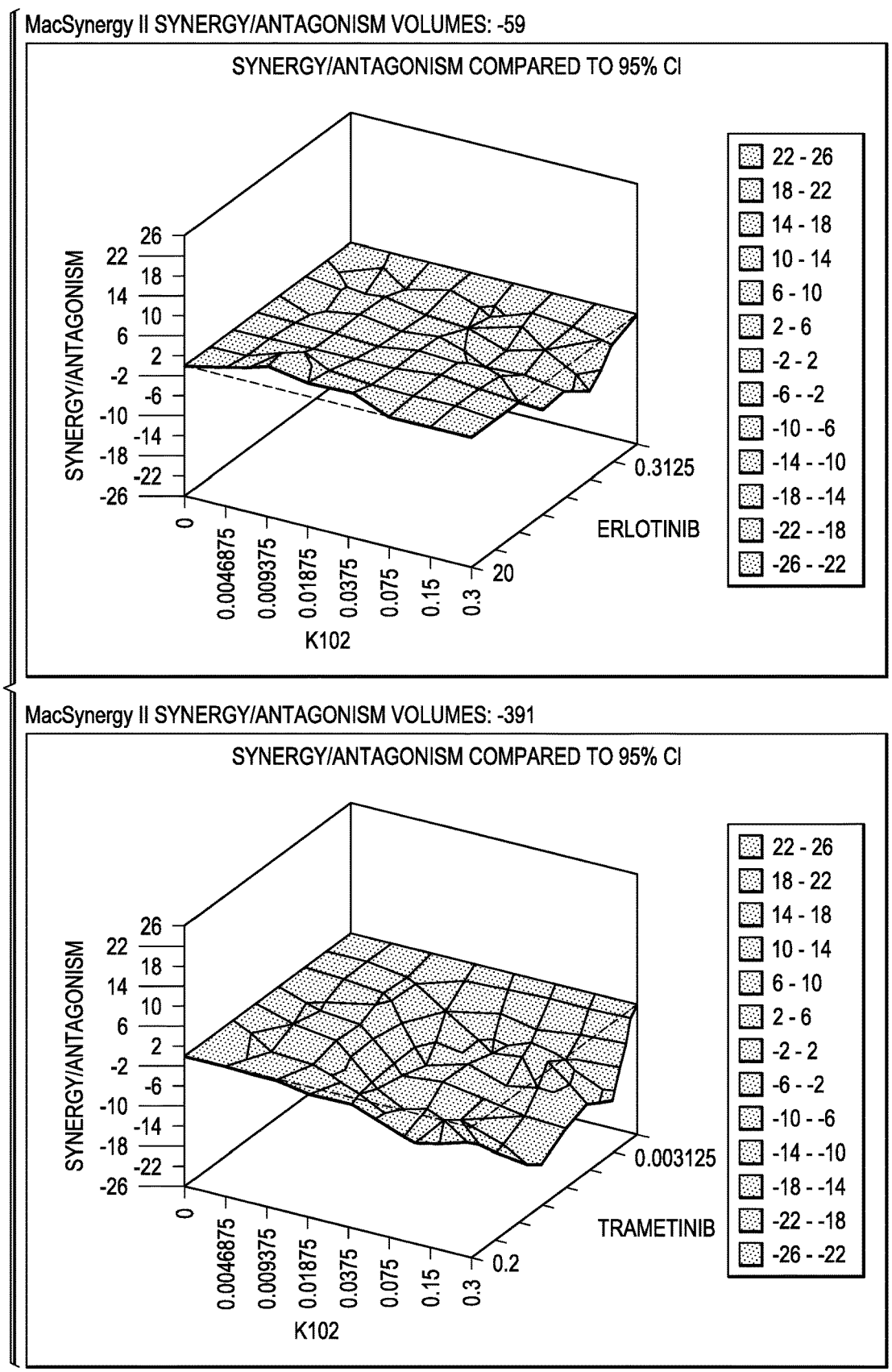

On the other hand, the PKC activator compounds showed antagonistic effect when combined with some therapeutic agents in inhibiting the growth of A549 cells. These included inhibitors targeting growth factor receptor/MAPK pathways (Table 11A, Table 12, and Table 13A; FIG. 2A and FIG. 2D for compound K101A; FIG. 3A and FIG. 3D for compound K101E; FIG. 4A and FIG. 4D for compound K102). For example, K101A, K101E, and K102 demonstrated strong antagonistic effect when combined with MEK inhibitor trametinib. Moderate antagonistic effect was observed in combination with EGFR inhibitor erlotinib. Interestingly, as shown in FIG. 10A and FIG. 10B, the antagonistic effect was detected in the full concentration range tested for trametinib (0.003-0.2 µM) whereas that was only evident in the lower half of the concentration range tested for erlotinib (0.3-2.5 µM). The magnitude of the antagonistic effect appeared to increase as the concentration of the PKC activator compounds increased. The results indicate that activation of MAPK pathway maybe required for anti-proliferative effect mediated by the PKC activator compounds. The PKC activator compounds showed no or insignificant antagonistic effect when combined with a dual EGFR/HER2 inhibitor lapatinib.

Figure 11:
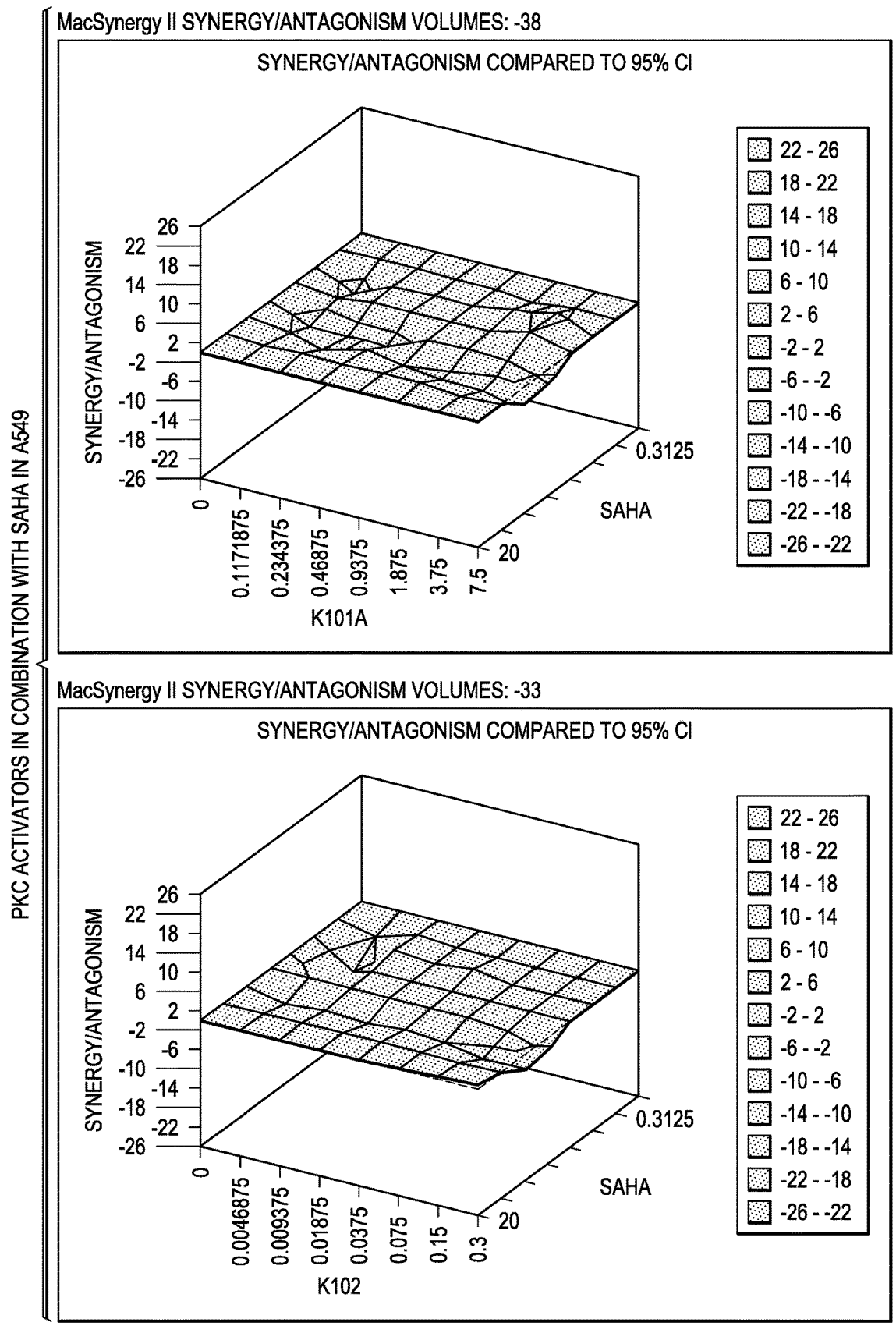
FIG. 11 shows synergism/antagonism plot of PKC activator K101A or K102 in combination with suberoylanilide hydroxamic acid (SAHA), a histone deacetylase inhibitor, on growth of inhibition of lung cancer cell line A549.

Antagonistic effects were also observed when the PKC activator compounds were combined with therapeutic agents targeting chromatin remodeling related to transcriptional regulation (Table 11B and Table 13B; FIG. 2G for compound K101A; FIG. 4G for compound K102; and FIG. 11). Such agents included HDAC inhibitors (e.g., Vorinostat/SAHA) and BET bromodomain (BRD2, BRD3, BRD4 and BRDT) inhibitors (e.g., (±)-JQ1). While K101A or K102 demonstrated strong antagonist effect when combined with JQ1, there was a minor but significant antagonistic effect when combined with SAHA. These results were unexpected since the PKC activator compounds had been shown in the literature to synergize with SAHA or JQ1 to disrupt HIV latency (Margolis et al., 2013, Curr Opin HIV AIDS. 8(3): 230-235; Barton et al., 2013, Clin Pharmacol Ther. 93(1): 46-56; Darcis et al., 2015, PLoS Pathog 11(7):e1005063; Jiang et al., 2015, PLoS Pathog 11 (7):e1005066).

Figure 9:
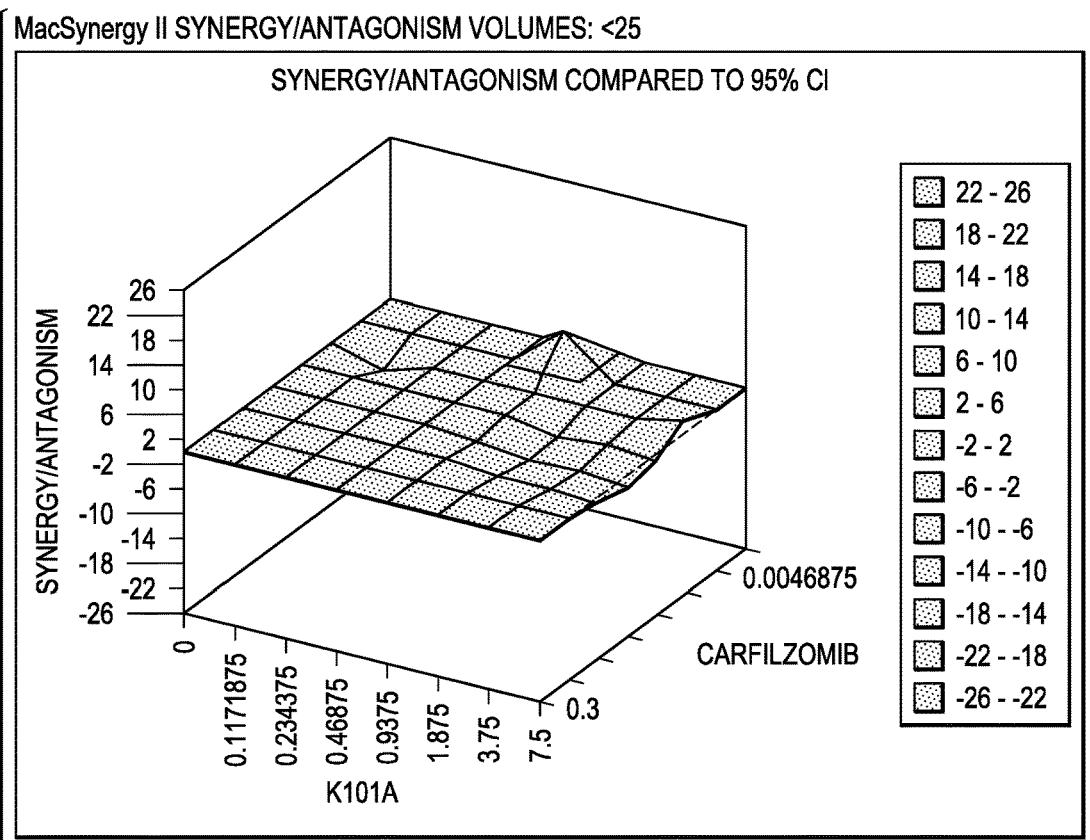
FIG. 9 shows synergism/antagonism plot of PKC activator K101A or K102 in combination with carfilzomib (20S proteasome inhibitor), on growth of inhibition of lung cancer cell line A549.
Figure 9:
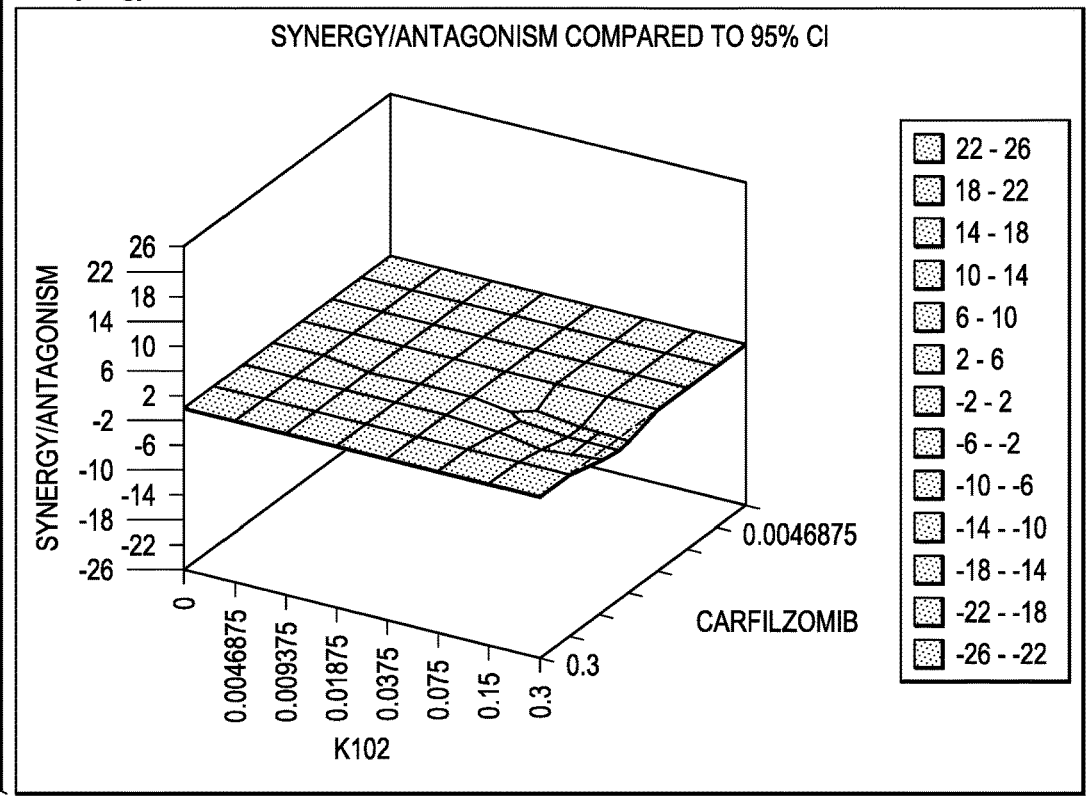

For some therapeutic agents tested, use in a combination with the PKC activator compounds showed insignificant synergism or antagonism when tested on A549 lung cancer cell line. These included chemotherapeutic agents paclitaxel or gemcitabine, proteasome inhibitor carfilzomib, EGFR/HER2 dual inhibitor lapatinib, and CBP inhibitor ICG-001 (Table 11B, Table 11A, Table 11B, Table 12, Table 13A, and Table 13B; FIG. 2C, FIG. 2E, and FIG. 2H for compound K101A; FIG. 3C and FIG. 3E for compound K101E; FIG. 4C, FIG. 4E, and FIG. 4H for compound K102; and FIG. 9).

Example 5: Analysis of Diterpenoid PKC Activators in Combination with Other Chemotherapeutic Agents: Studies with Other Cancer Types The PKC activating agents (e.g., K101A, K101E, and K102) in combination with other chemotherapeutic agents, including standard chemotherapies and certain chemotherapeutic agents targeting certain cell signaling pathways, were also examined on cancer cells other than lung cancer cells. For studies in these other cancer cell lines, the PKC activator compounds K101A or K102 were assayed alone or in combination with a second therapeutic agent in the 384-well viability/proliferation assays or in 96-well MacSynergy II format described above for studies on cell line A549.

Figure 12A:
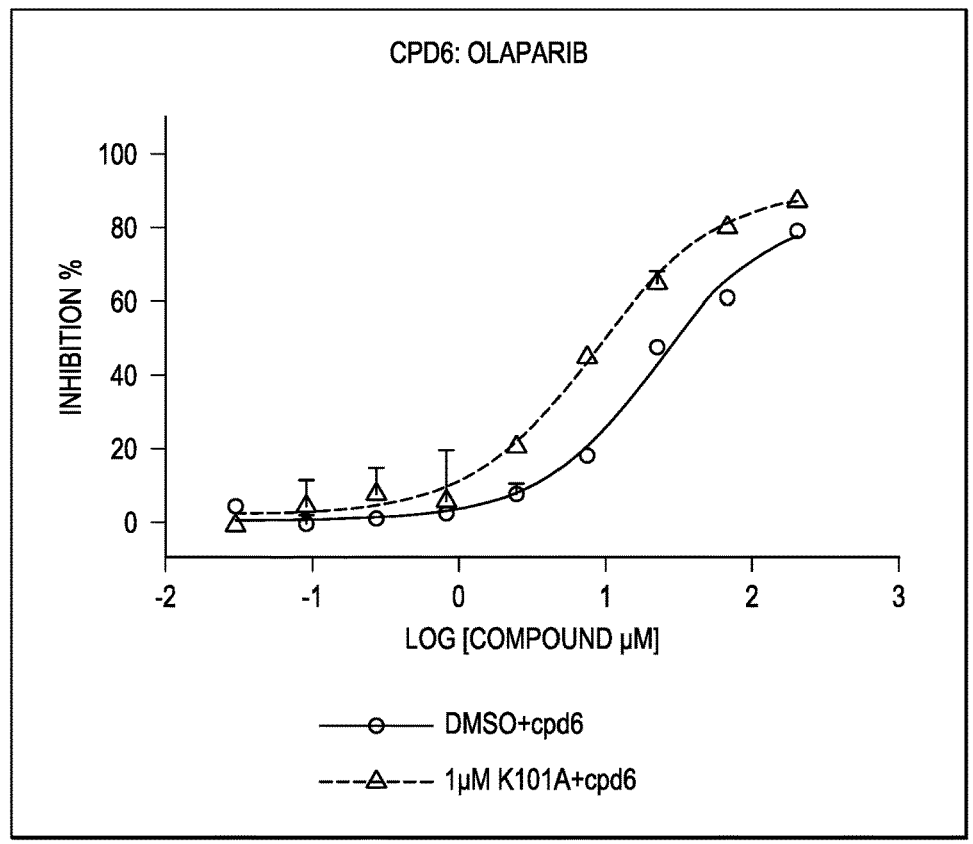
FIGS. 12A and 12B show effect of PKC activator K101A in combination with a second therapeutic agent on growth inhibition of pancreatic cancer cell line Panc2.13.
Figure 12A:
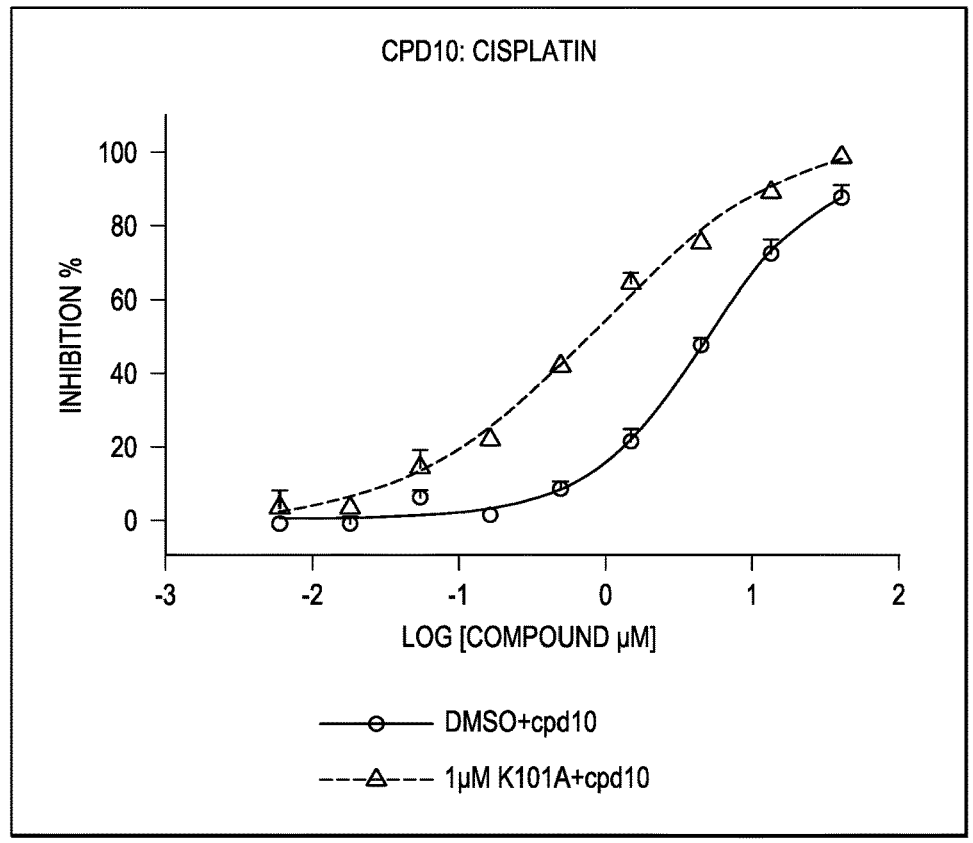
Figure 12B:
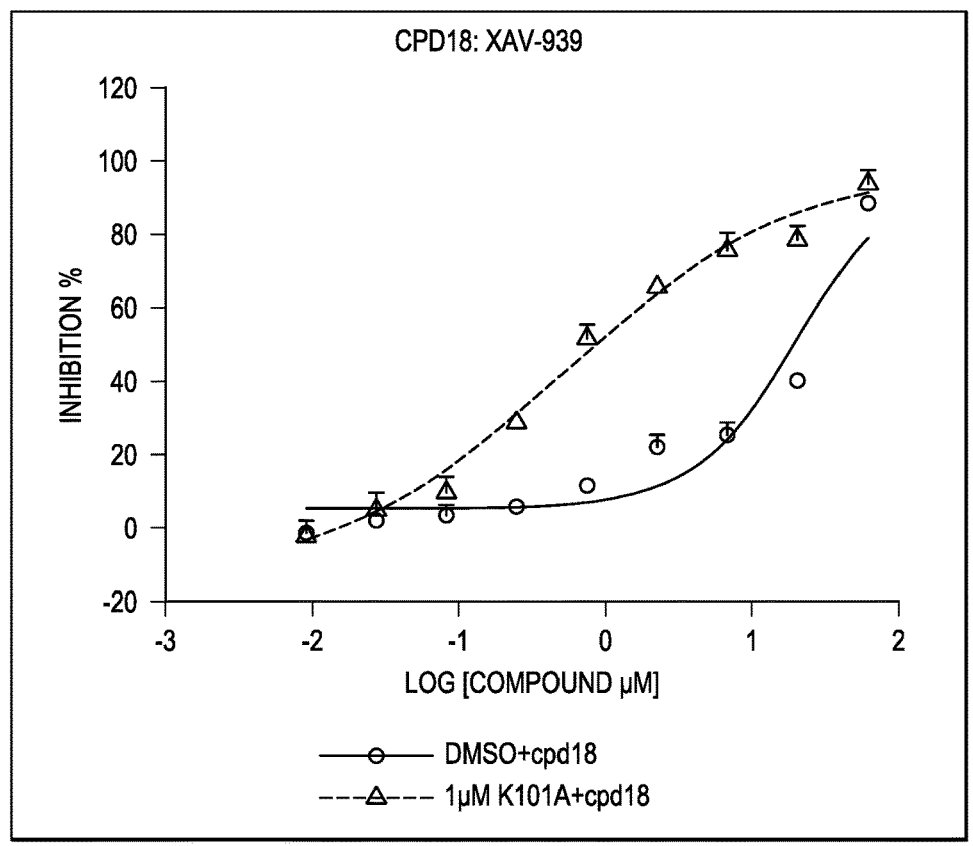
Figure 12B:
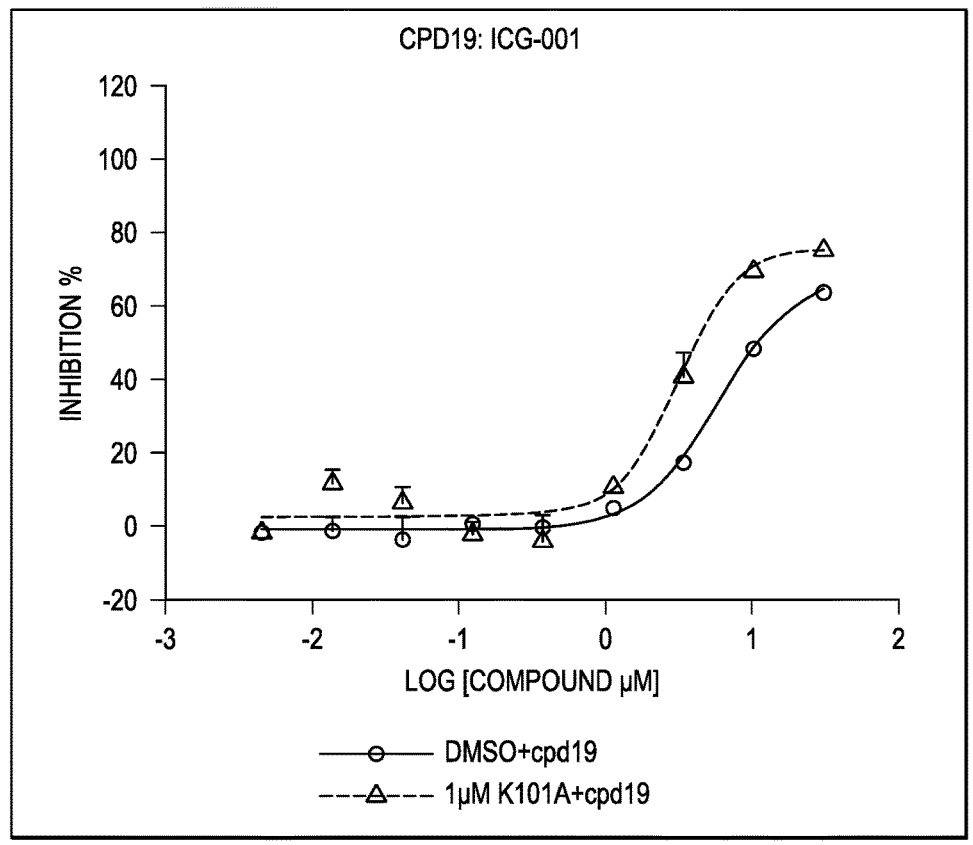
Figure 13A:
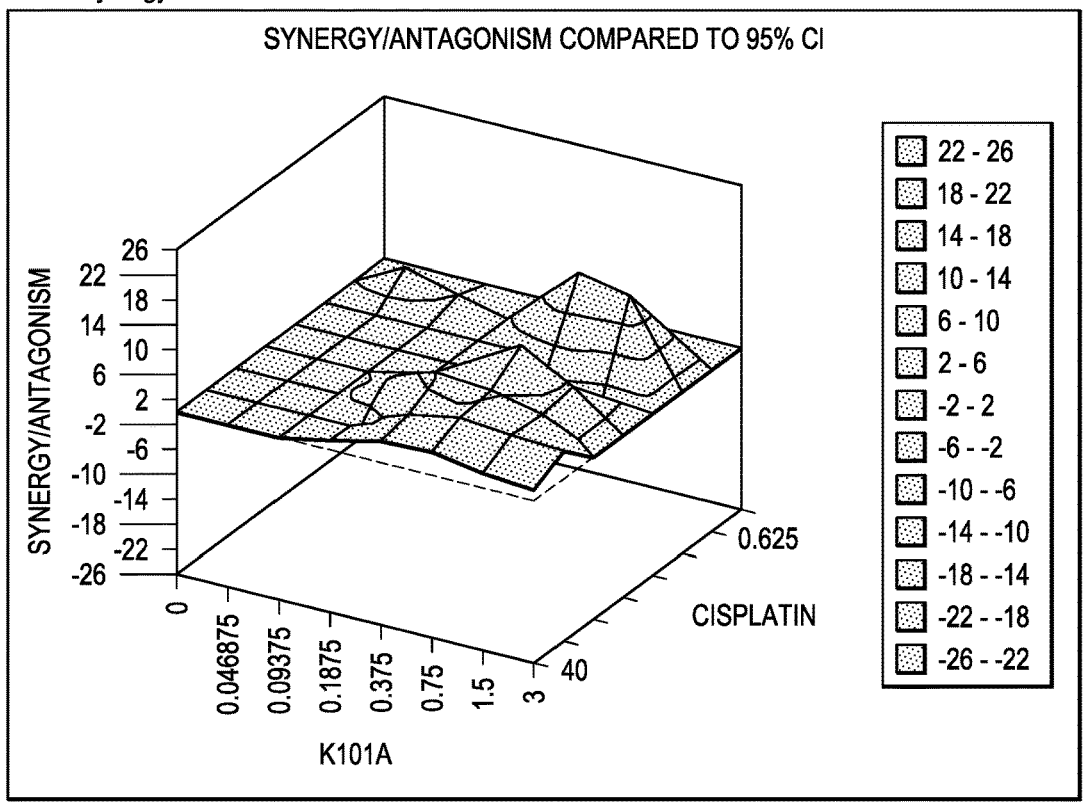
FIGS. 13A and 13B show synergism/antagonism plot of PKC activator K101A in combination with cisplatin, oxaliplatin or MK2206 on growth inhibition of pancreatic cancer cell line MiaPaCa-2.
Figure 13A:
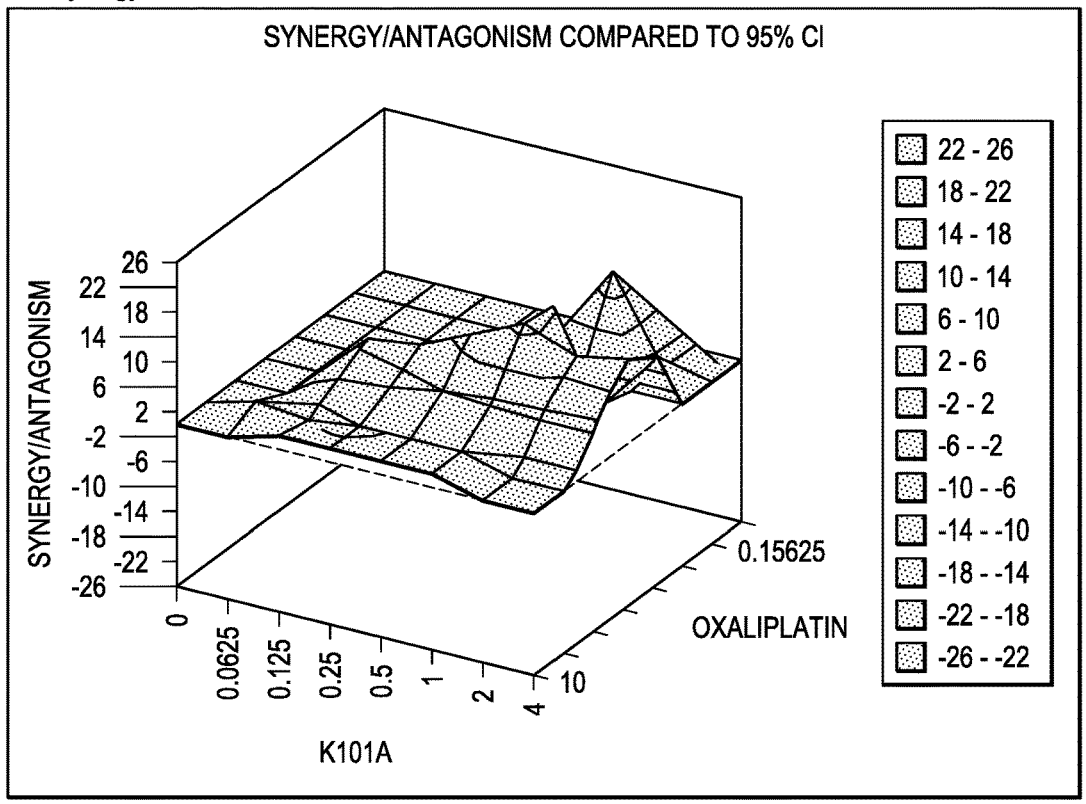
Figure 13B:
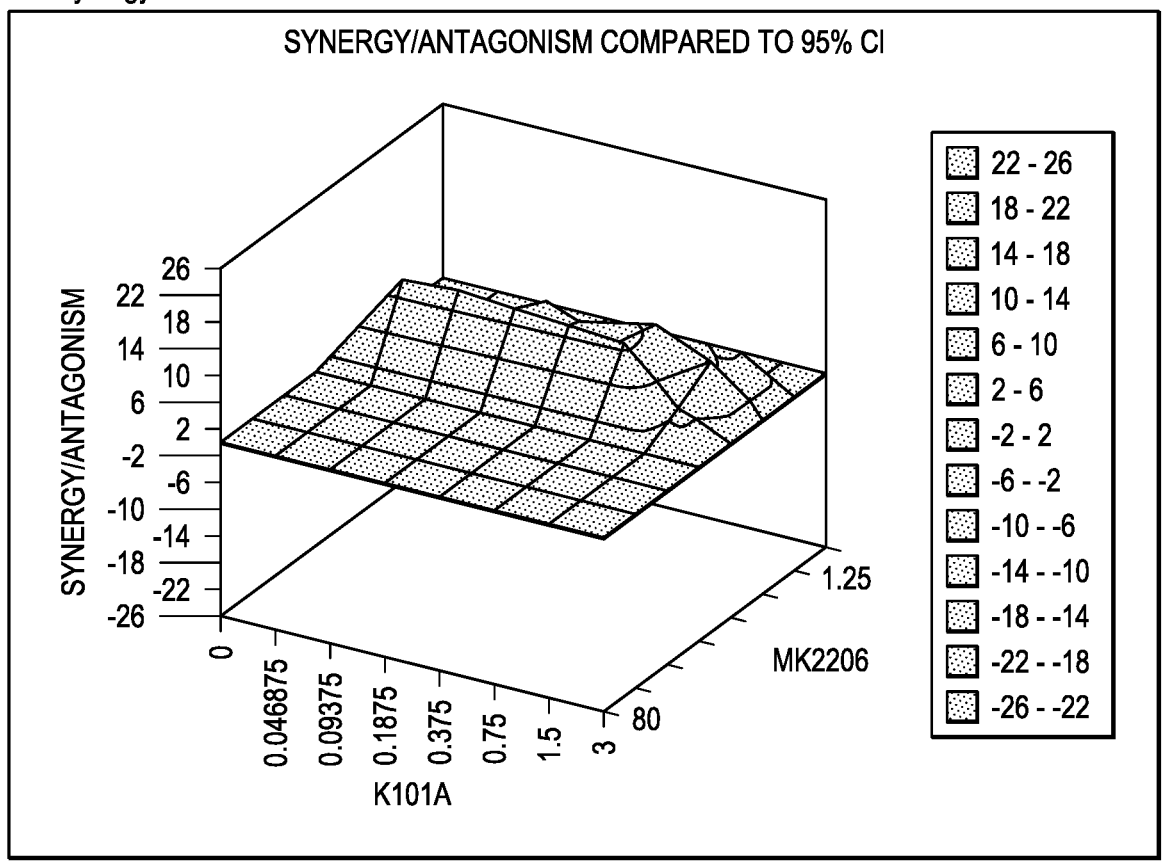
Figure 14A:
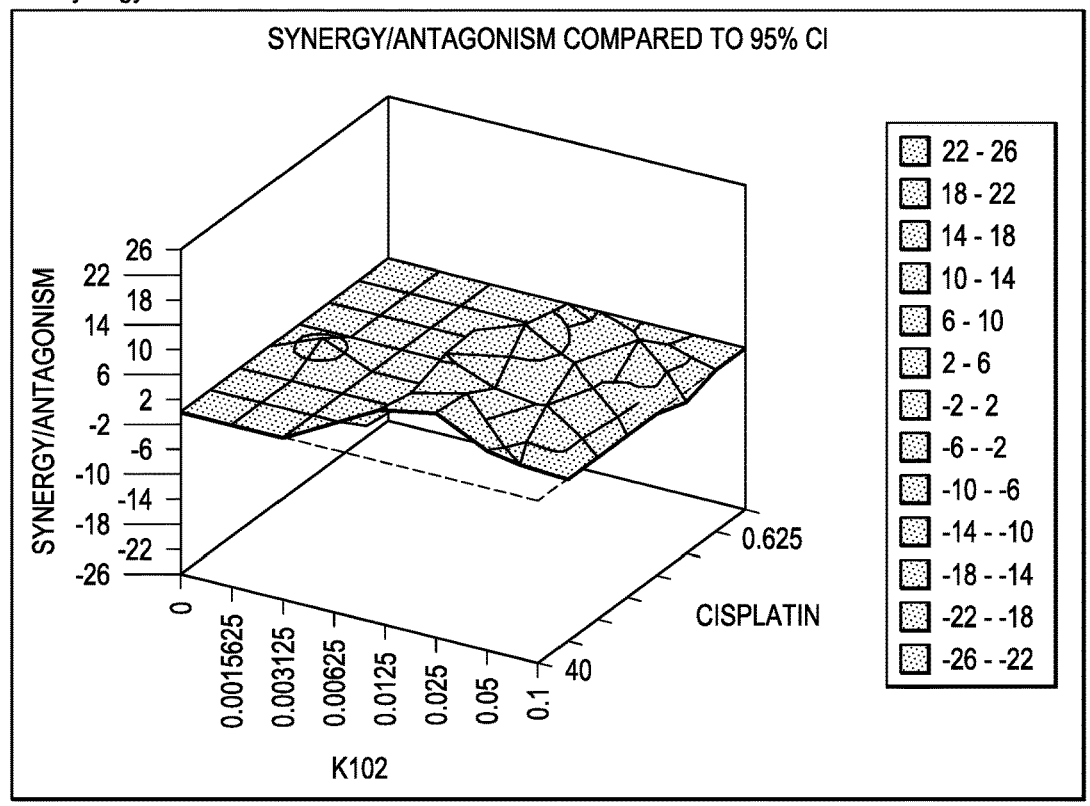
FIGS. 14A and 14B show synergism/antagonism plot of PKC activator K102 in combination with cisplatin, oxaliplatin or MK2206 on growth inhibition of pancreatic cancer cell line MiaPaCa-2.
Figure 14A:
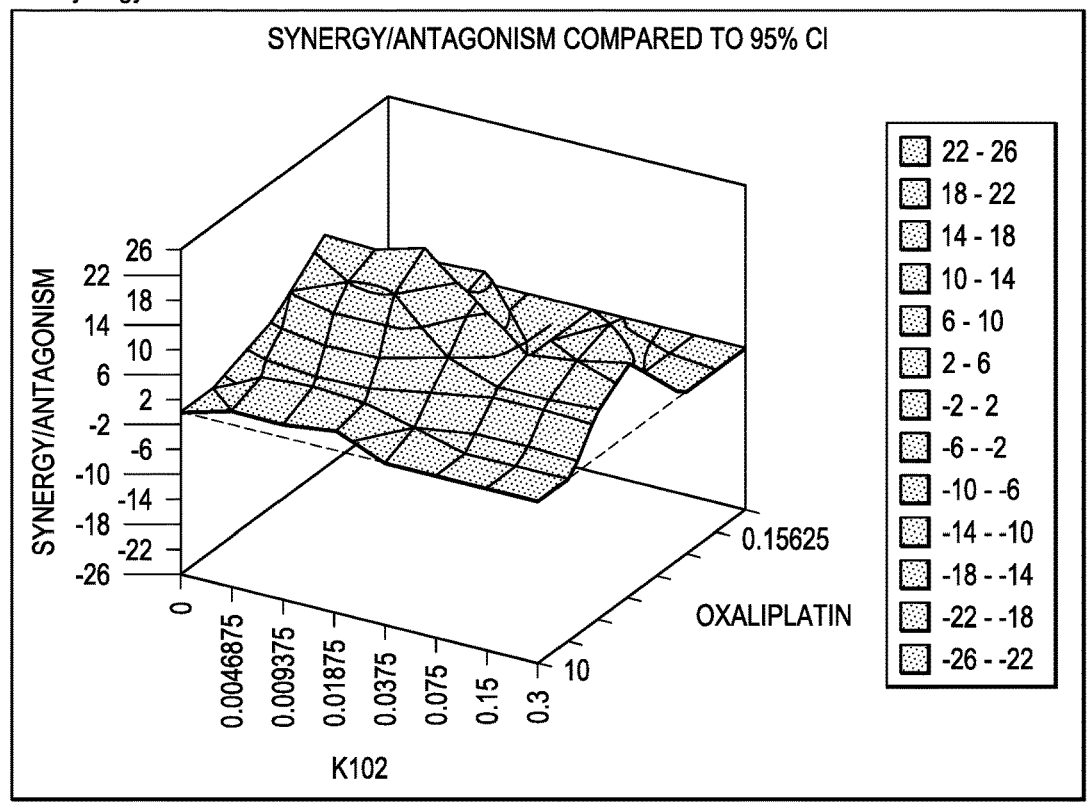
Figure 14B:
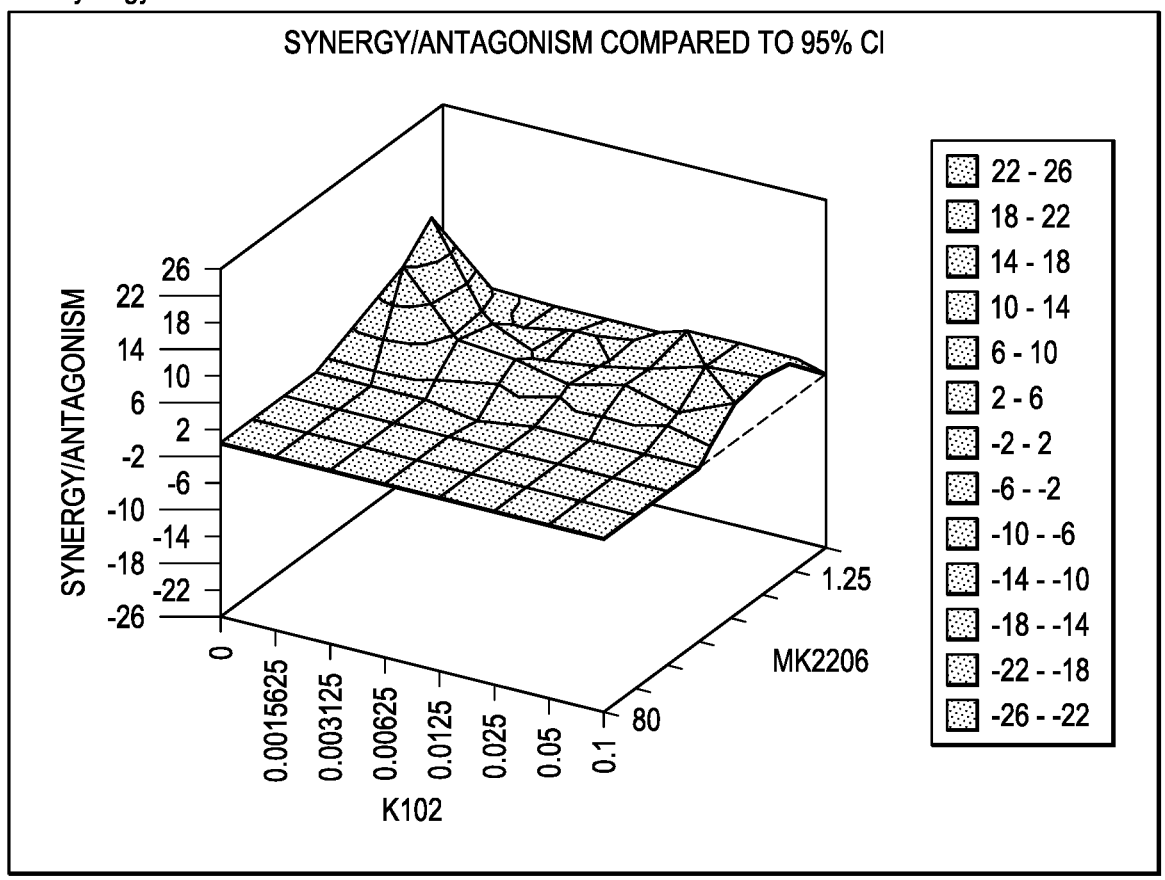
Figure 15:
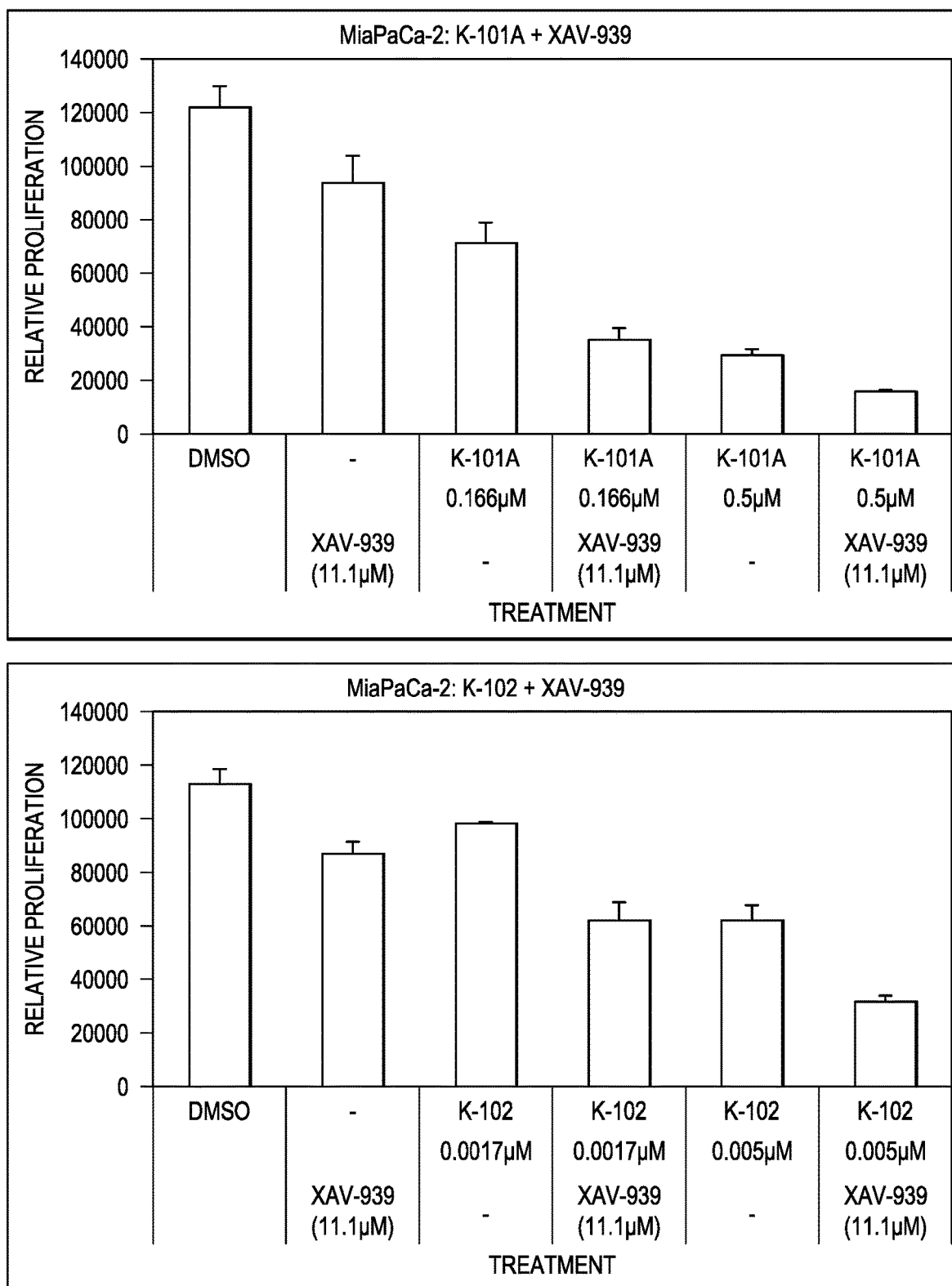
FIG. 15 shows effect of PKC activator K101A or K102 in combination with XAV-939 on growth inhibition of pancreatic cancer cell line MiaPaCa-2.
Figure 16:
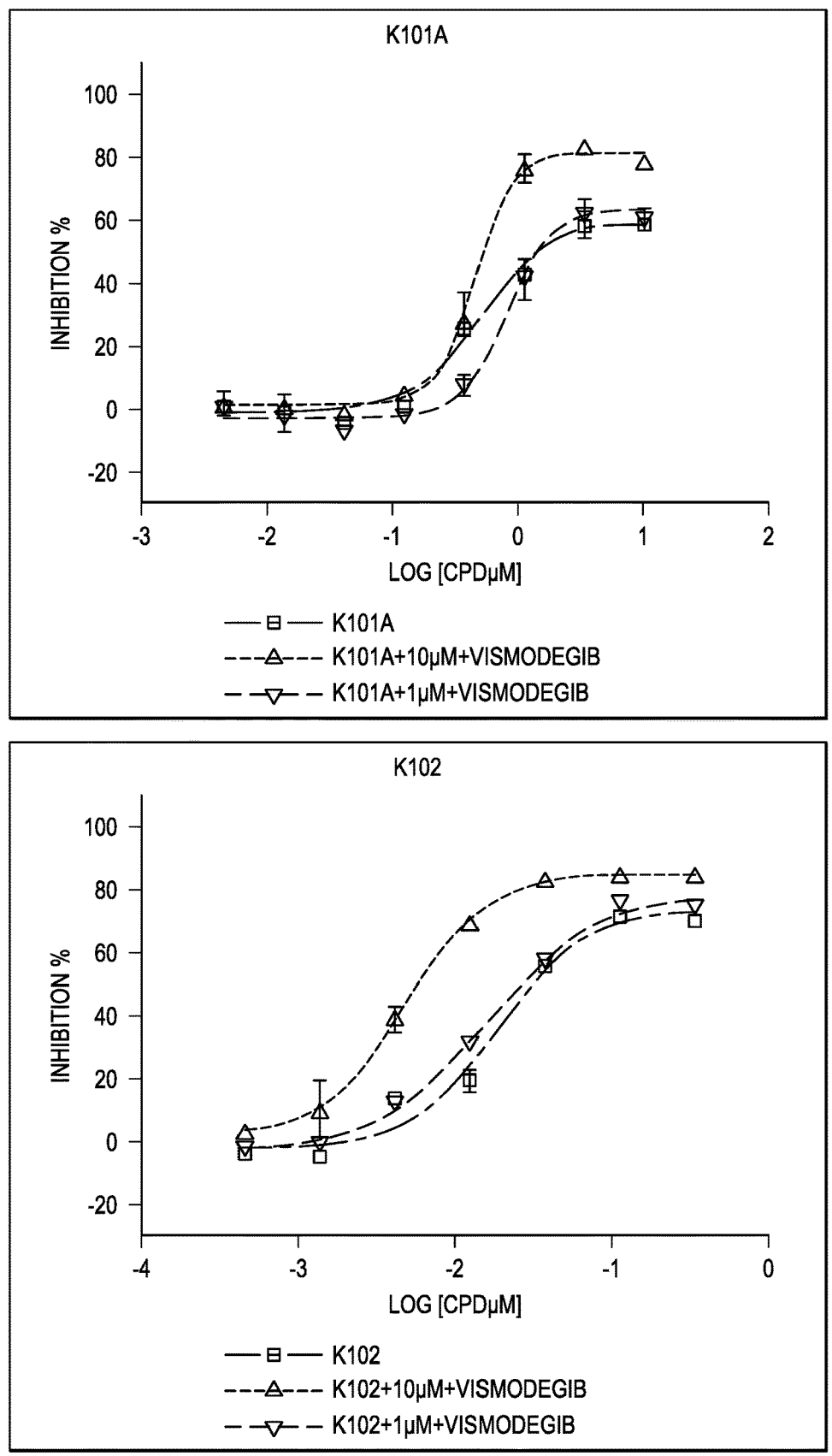
FIG. 16 shows effect of PKC activator K101A or K102 in combination with vismodegib on growth inhibition of pancreatic cancer cell line MiaPaCa-2.

Similar to observations in A549 lung cancer cell line, DNA cross linking agent, PARP inhibitor, AKT inhibitor, Wnt pathway and Hh pathway inhibitors demonstrated synergy with PKC activators K101A or K102 in different pancreatic cancer cell lines (see Table 14). However, MEK inhibitor showed antagonistic effects for the combination treatment. In Panc2.13 cells, K101A at 1 μM (FIG. 12A and FIG. 12B) or at 0.67 μM (data not shown) showed strong synergy with PARP inhibitor (e.g., olaparib), platinum-based drug (e.g., cisplatin), Tankyrase1/2 inhibitor (e.g., XAV-939), and CBP inhibitor (e.g., ICG-001). In MiaPaCa-2 cells, K101A or K102 showed strong synergy with platinum-based drug (e.g. cisplatin and oxaliplatin) and AKT inhibitor (e.g. MK2206), with synergy volumes >100 in the MacSynergy combination experiments (FIG. 13A and FIG. 13B for compound K101A; FIG. 14A and FIG. 14B for compound K102). In most cases, the synergy was observed in lower concentration range for one of the combination agents, indicating that less combination agent could be used to reduce potential toxicity. Although no strong synergy was observed for the combination treatments with XAV-939, additive effects were demonstrated when low doses of K101A (0.166 and 1 μM) or K102 (0.0017 and 0.005 μM) were used with XAV-939, as shown in FIG. 15. In addition, the Hh inhibitor vismodegib showed synergy with K101A or K102 at 10 μM but not at 1 μM (FIG. 16). Vismodegib alone at 10 μM did not inhibit proliferation of MiaPaCa-2.

Figure 17:
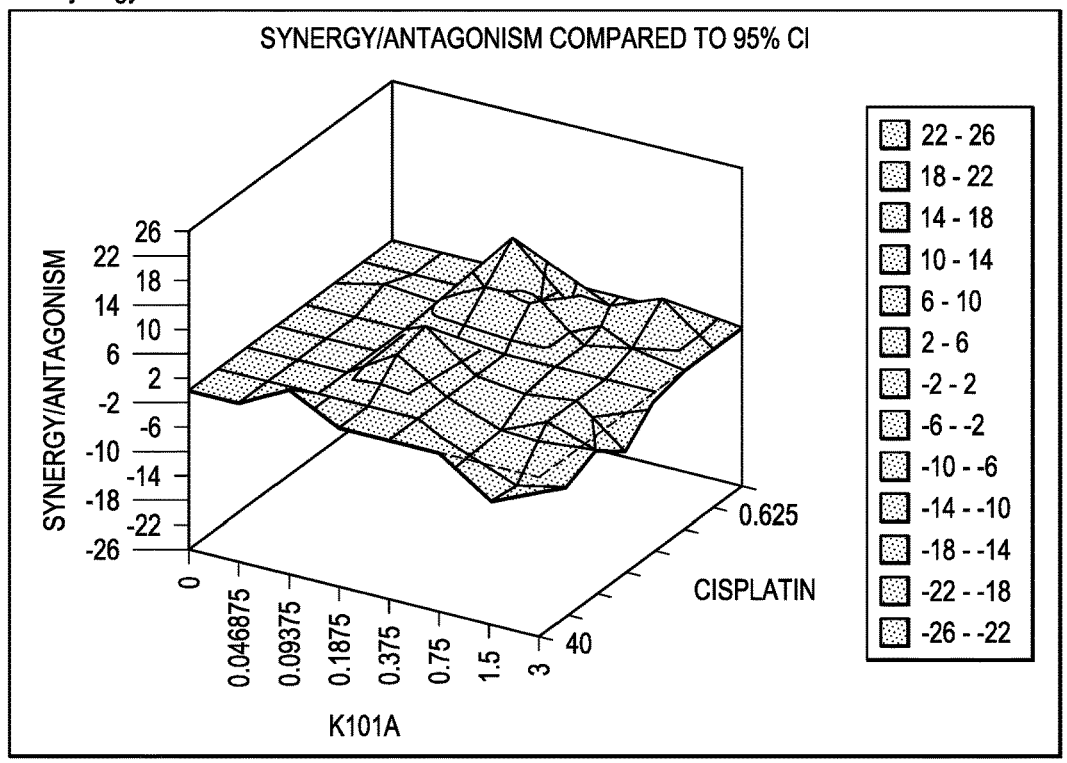
FIG. 17 show synergism/antagonism plot of PKC activator K101A or K102 in combination with cisplatin on growth inhibition of pancreatic cancer cell line Panc1.
Figure 17:
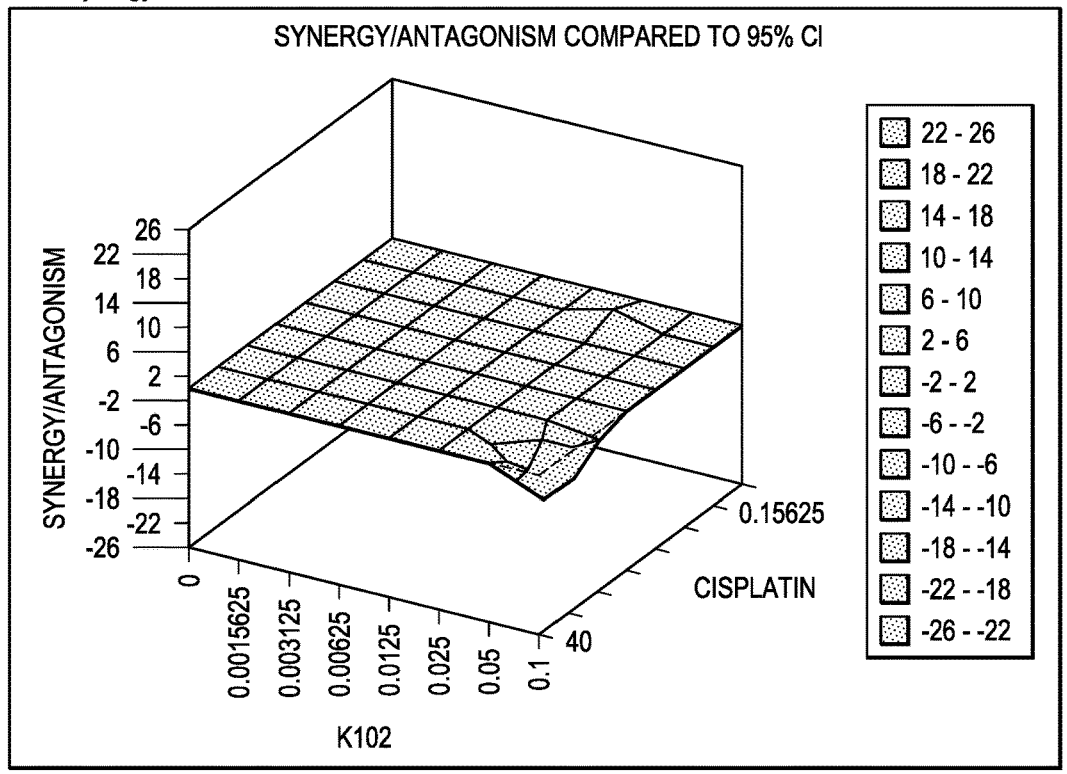

In another pancreatic cell line Panc1, a platinum drug (e.g. cisplatin) synergized moderately with K101A (at lower concentration range of both combination agents) but not with K102 (FIG. 17). Slight antagonism was observed at highest concentrations of combination agents.

TABLE 14

| Compound Name | Class | Panc2.13 K101A | MiaPaCa-2 K101A | MiaPaCa-2 K102 | Panc1 K101A | Panc1 K102 |
|---|---|---|---|---|---|---|
| Trametinib | MEK inhibitor | Antagonism | Antagonism (strong) | Antagonism (strong) | ND | ND |
| Olaparib | PARP inhibitor | Synergism | ND | ND | ND | ND |
| MK2206 | AKT inhibitor | None | Synergism (strong) | Synergism (strong) | ND | ND |
| Cisplatin | DNA cross linking agent | Synergism | Synergism (moderate) | Synergism (moderate/strong) | Synergy (moderate)* | None |
| Oxaliplatin | DNA cross linking agent | ND | Synergism (strong) | Synergism (strong) | ND | ND |
| XAV-939 | Tankyrase 1/2 inhibitor | Synergism (slight-additive) | Synergism (slight-additive) | Synergism (slight-additive) | ND | ND |
| ICG-001 | CBP inhibitor | Synergism | ND | ND | ND | ND |
| Vismodegib | Smoothened inhibitor | ND | Synergism (minor) | Synergism | ND | ND |

PKC activator compounds in combination with platinum-based drugs cisplatin or oxaliplatin were examined on colon cancer cell line Colo205. As shown in Table 15 summarizing the synergy volumes from the MacSynergy combination experiments, minor synergy (synergy volumes ≥25) were observed for the combination of cisplatin with K101A or K102 and the combination of oxaliplatin with K102. Antagonism was observed at high concentration range of combination agents.

TABLE 15

| Compound | Class | Colo205* | |
|---|---|---|---|
| Cisplatin | DNA cross linking agent | 49 | 41 |
| Oxaliplatin | DNA cross linking agent | 11 | 25 |

Figure 18:
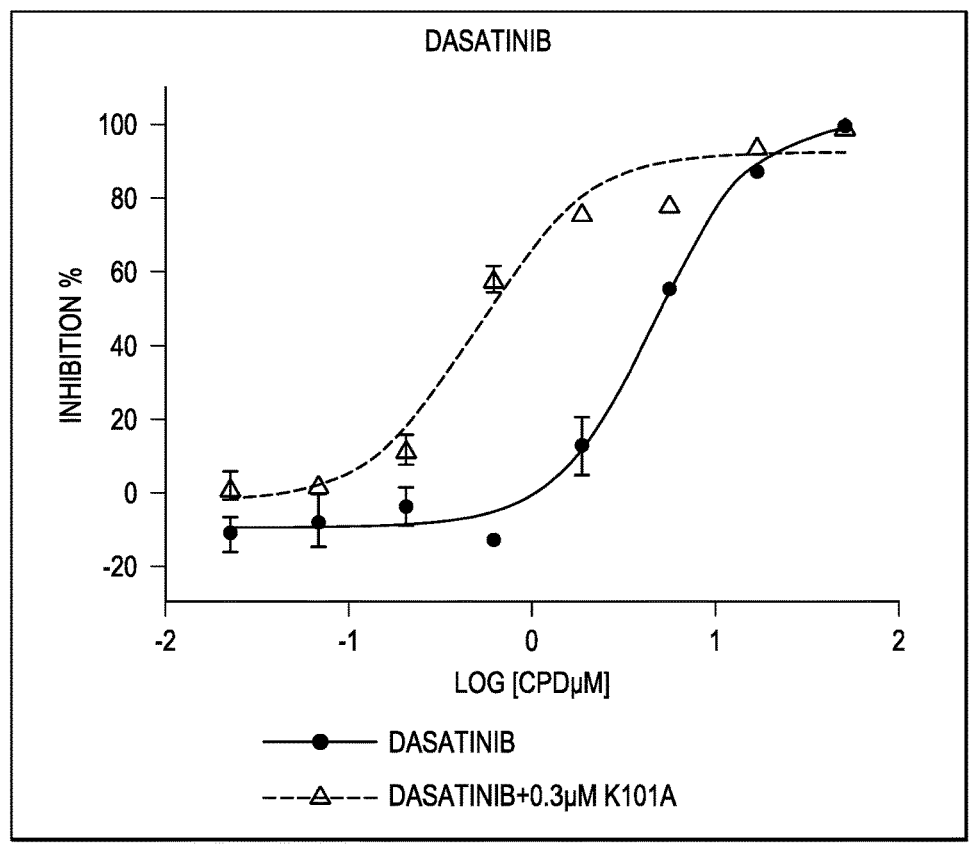
FIG. 18 shows effect of PKC activator K101A or K102 in combination with dasatinib on growth inhibition of human promyelocytic leukemia cell line HL-60.
Figure 18:
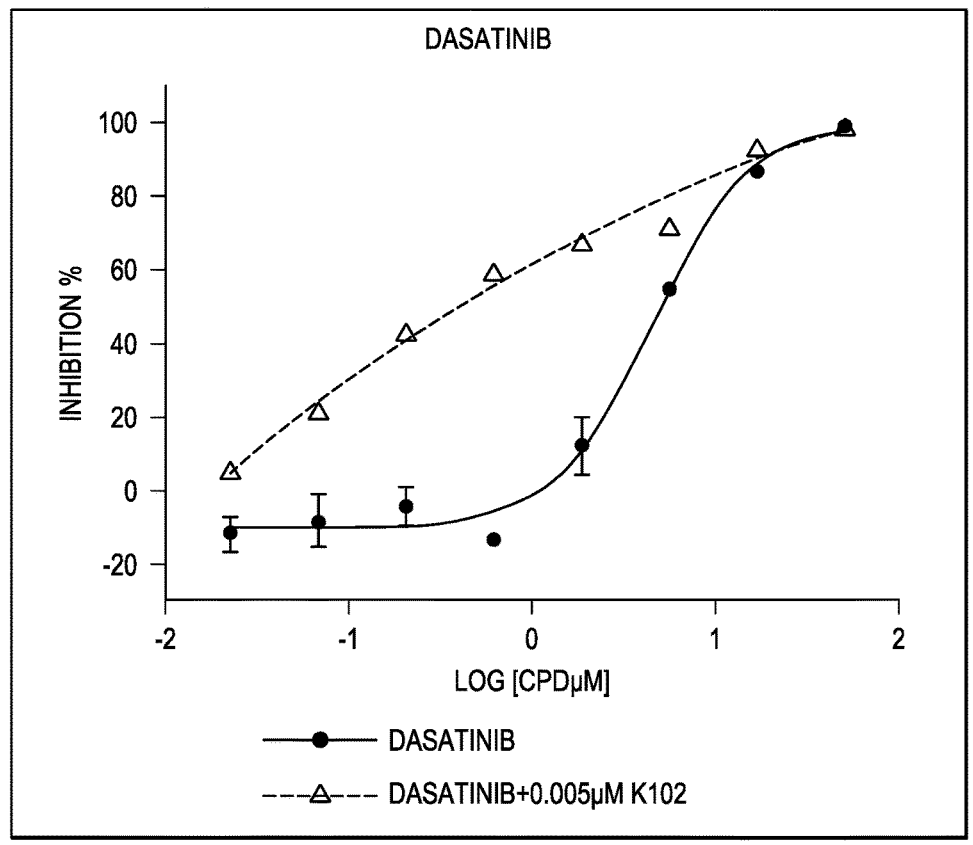
Figure 19:
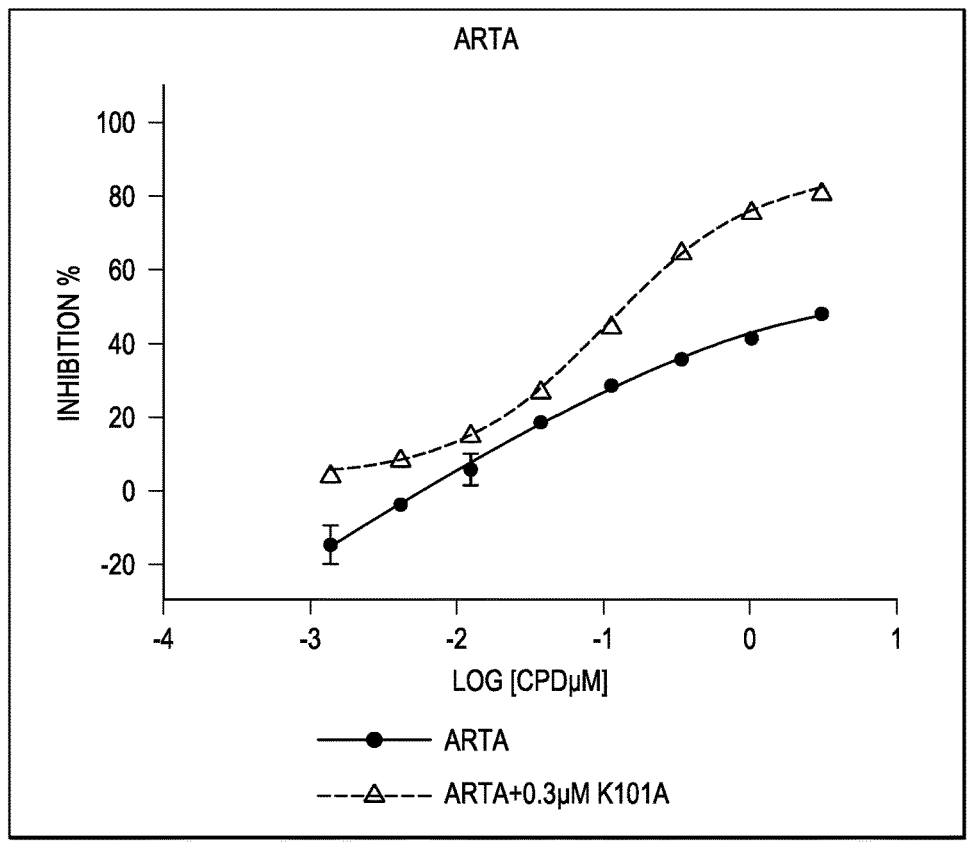
FIG. 19 shows effect of PKC activator K101A or K102 in combination with all-trans retinoic acid (ARTA) on growth inhibition of human promyelocytic leukemia cell line HL-60.
Figure 19:
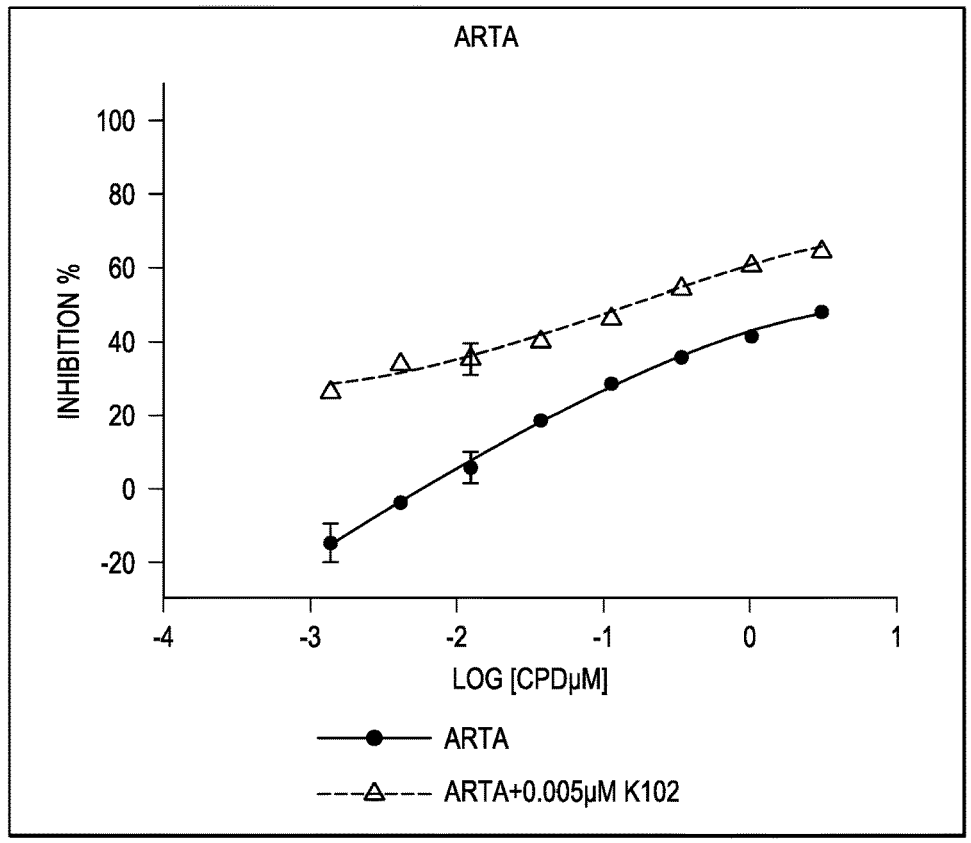
Figure 20:
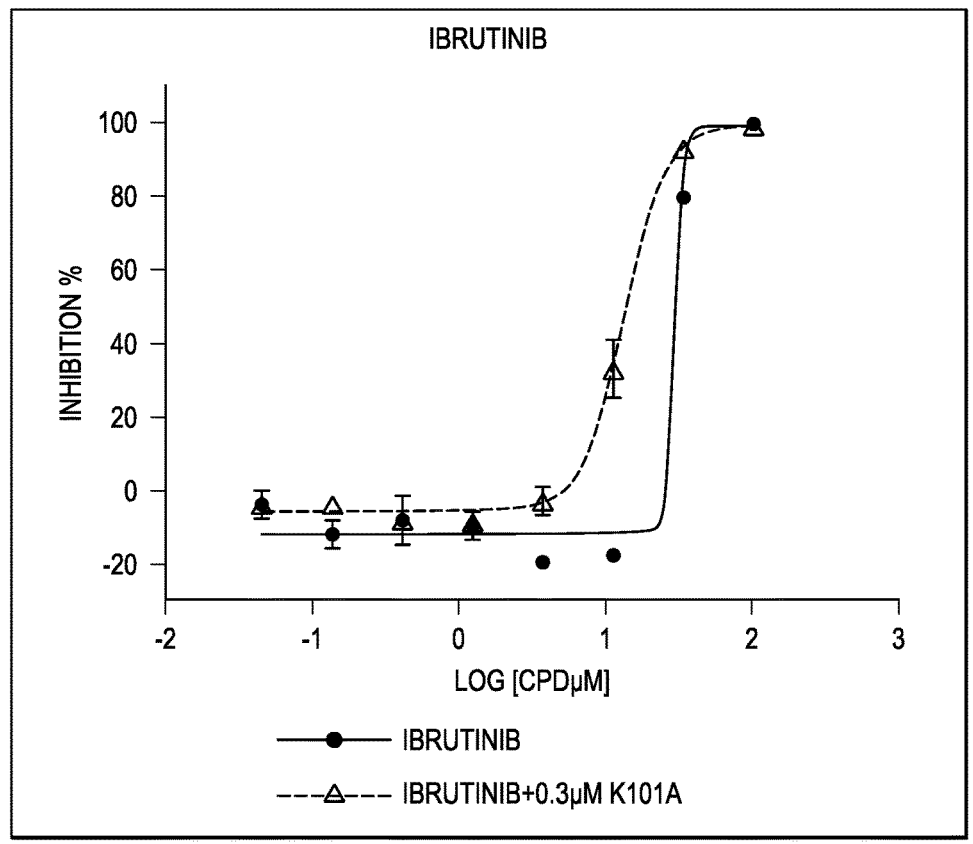
FIG. 20 shows effect of PKC activator K101A or K102 in combination with ibrutinib on growth inhibition of human promyelocytic leukemia cell line HL-60.
Figure 20:
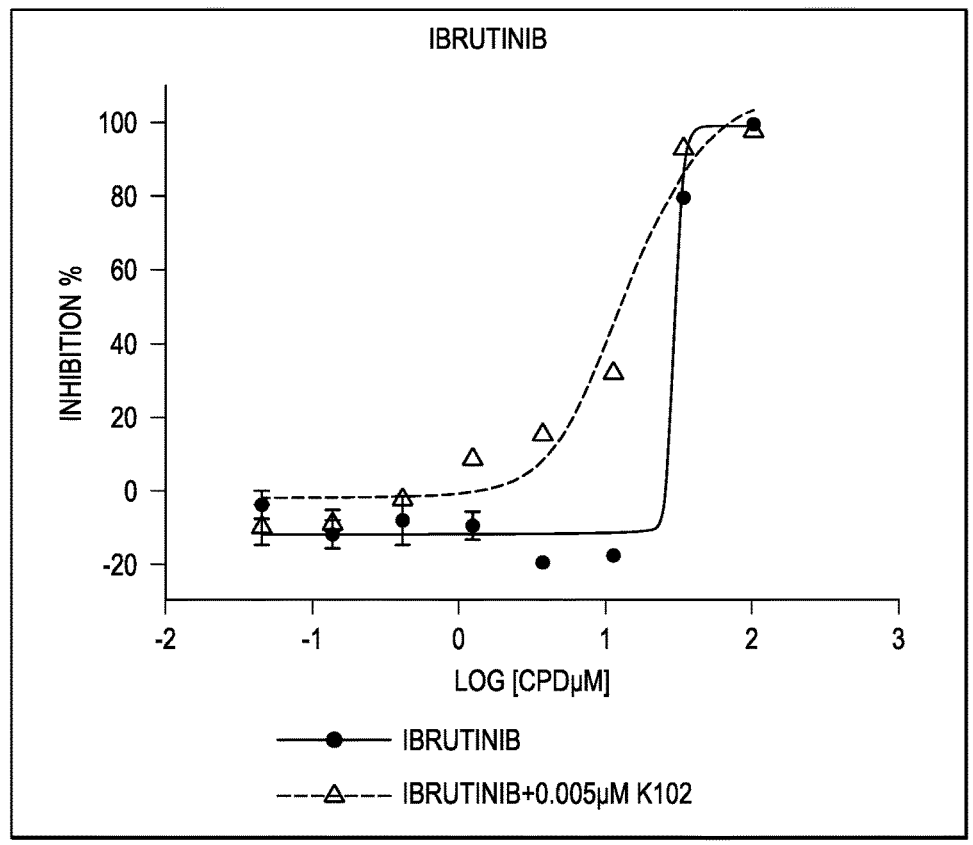
Figure 21:
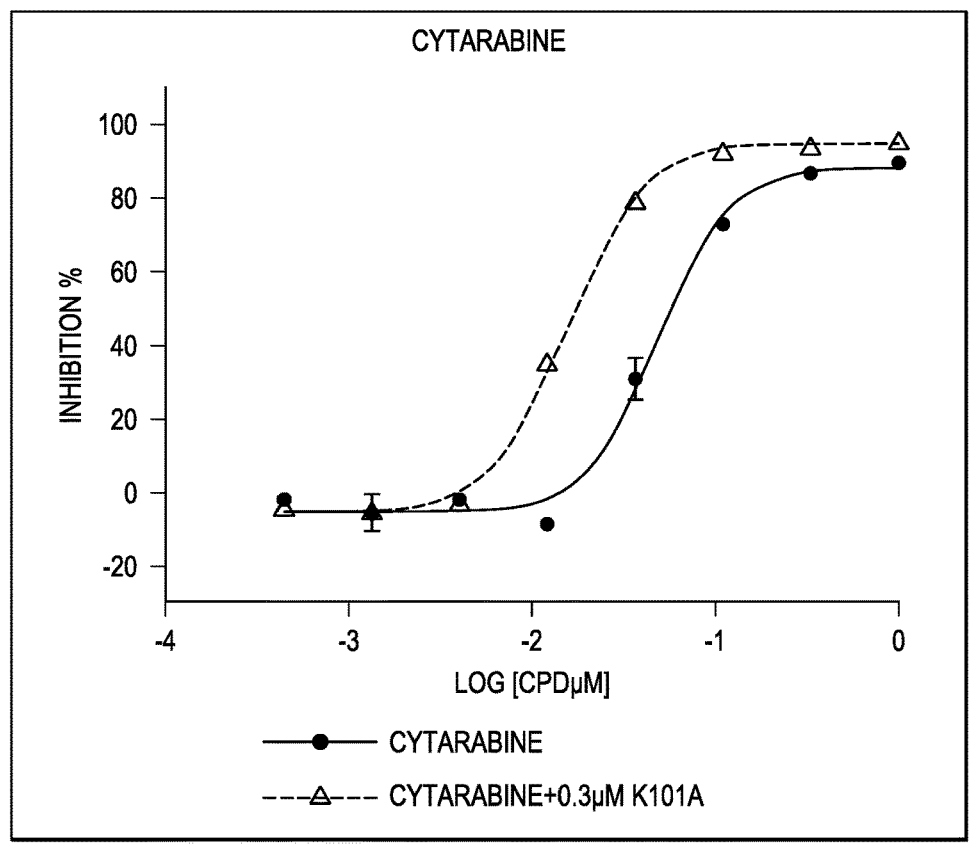
FIG. 21 shows effect of PKC activator K101A or K102 in combination with cytarabine on growth inhibition of human promyelocytic leukemia cell line HL-60.
Figure 21:
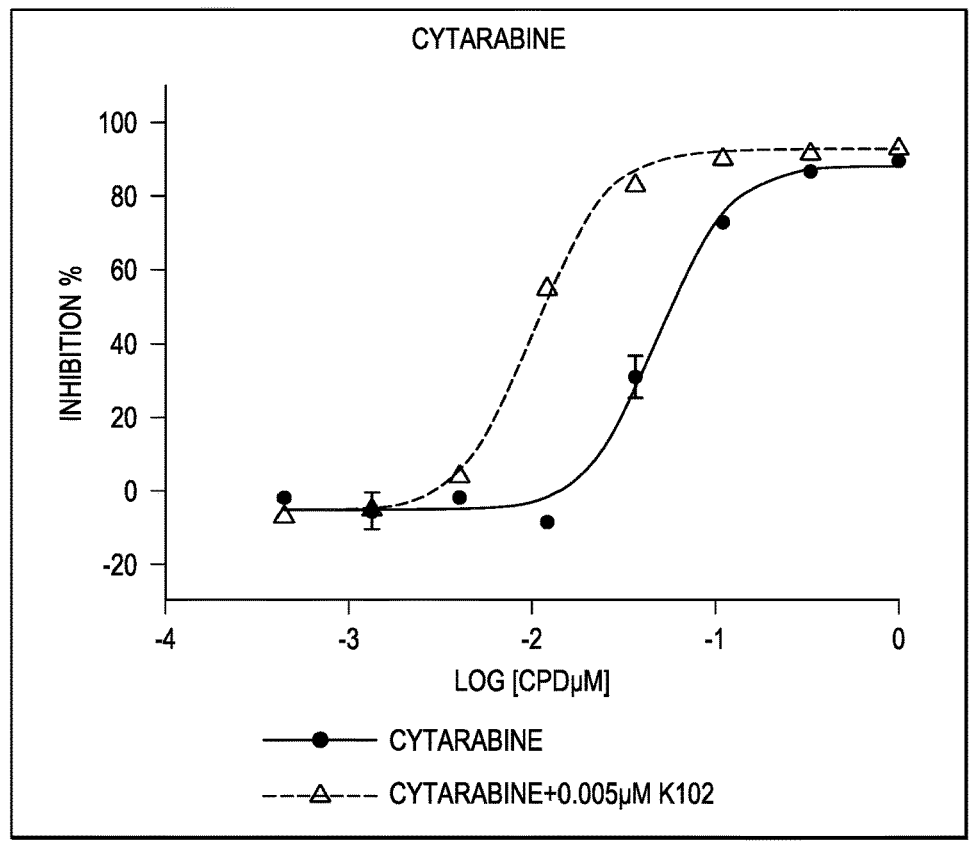
Figure 22:
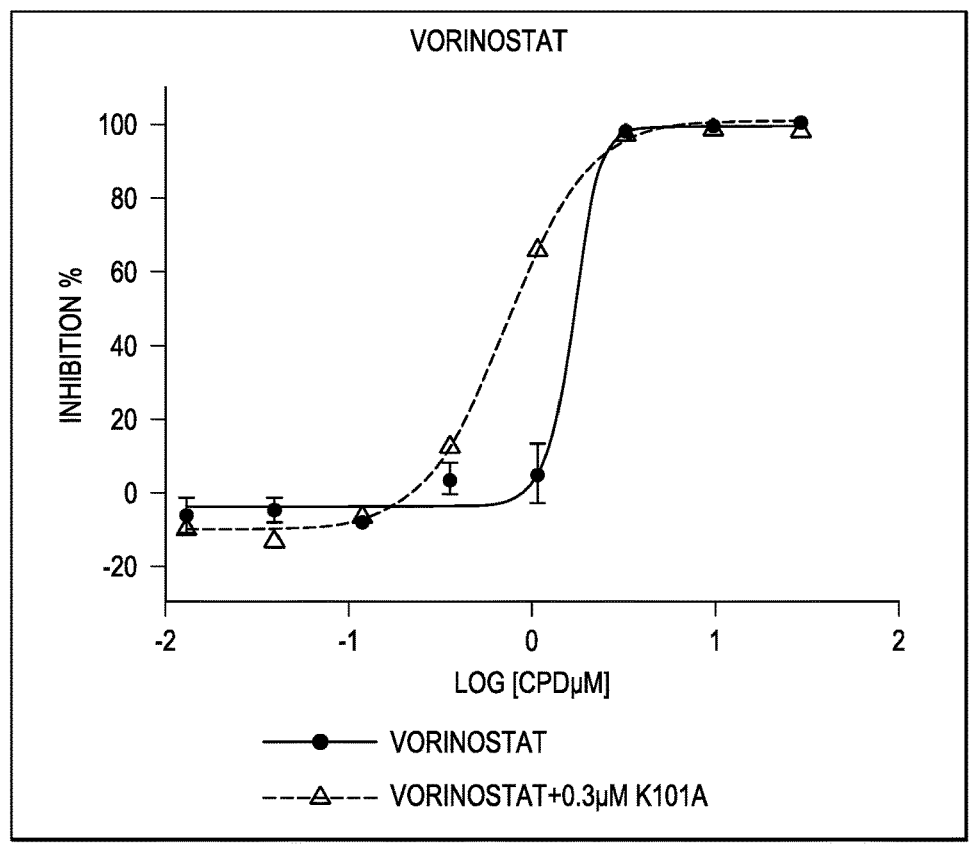
FIG. 22 shows effect of PKC activator K101A or K102 in combination with vorinostat (SAHA) on growth inhibition of human promyelocytic leukemia cell line HL-60.
Figure 22:
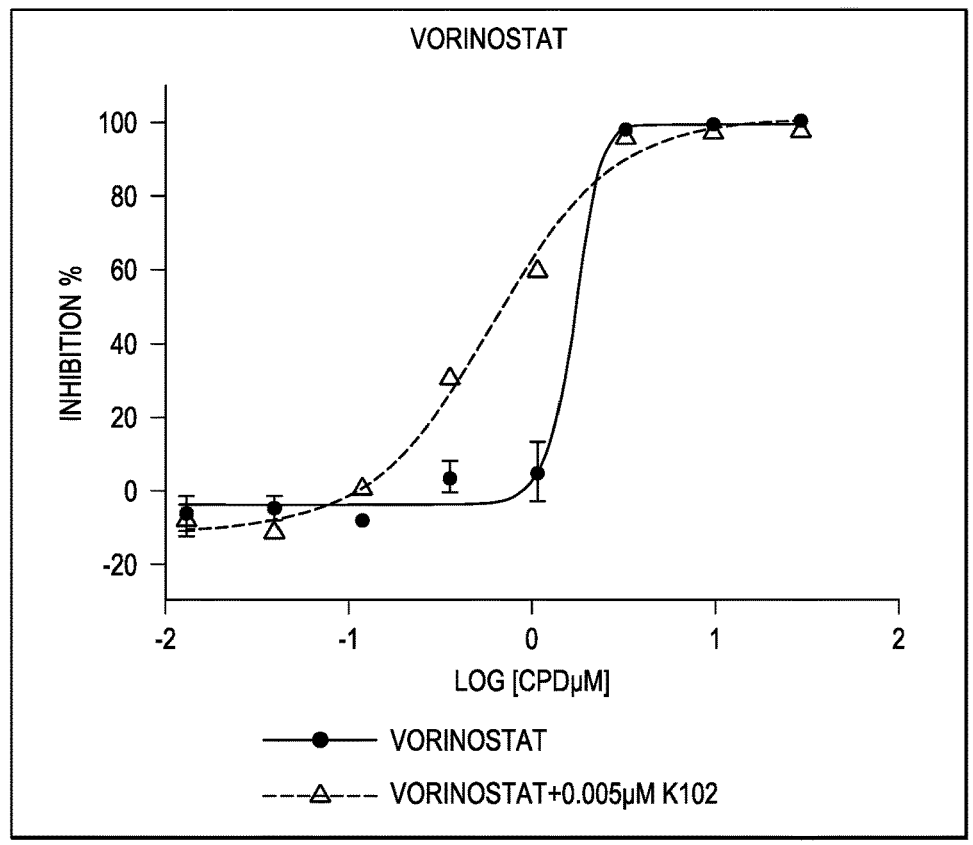
Figure 23:
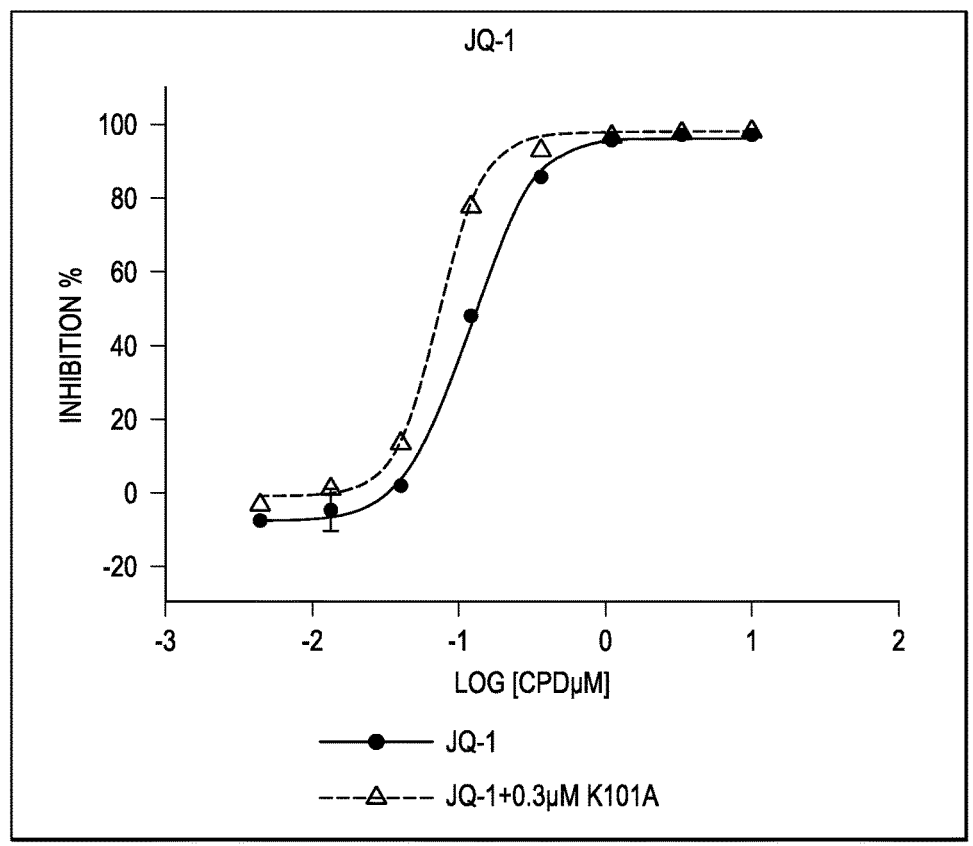
FIG. 23 shows effect of PKC activator K101A or K102 in combination with JQ-1 on growth inhibition of human promyelocytic leukemia cell line HL-60.
Figure 23:
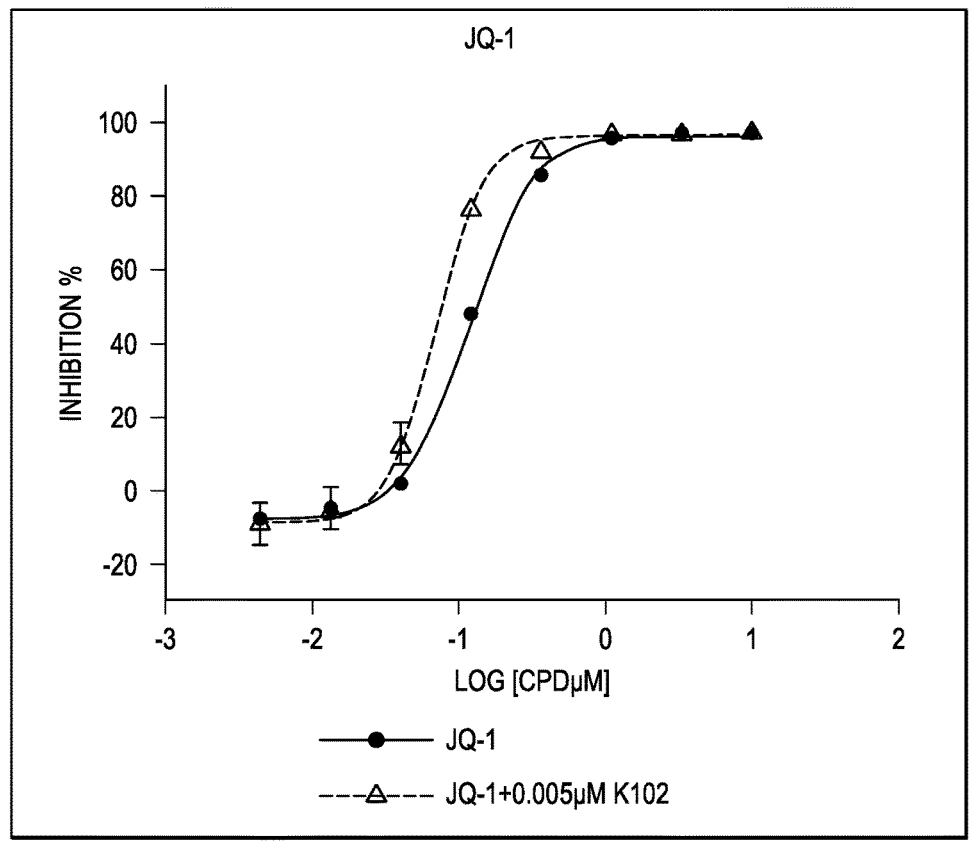

In addition to solid cancers, blood cancers, such as leukemias and lymphomas, were also screened with PKC activator compounds in combination with standard of care drugs for such disorders. In HL-60 human promyelocytic leukemia cells, a src/bcr-able family kinase inhibitor dasatinib showed strong synergy with PKC activating compound K101A and K102 (FIG. 18). Potency of dasatinib in inhibiting growth of HL-60 increased more than 10-fold when combined with K101A (0.3 µM) or K102 (0.005 µM). All-trans retinoic acid (ATRA), a differentiation agent used to treat human promyelocytic leukemia, also showed strong synergy with K101A and K102 (FIG. 19). Addition of K101A (0.3 µM) or K102 (0.005 µM) shifted the ATRA inhibition curve up by 5-40% after subtracting the inhibition by K101A or K102 alone. Ibrutinib, a BTK inhibitor approved to treat certain types of blood cancers, also synergized with K101A or K102 (FIG. 20). Cytarabine, an anti-metabolite chemotherapeutic drug, showed strong synergy with K101A or K102 (FIG. 21). The inhibition curve was shifted half-log or a full-log to the left in combination with K101A (0.3 µM) or K102 (0.005 µM), respectively. Chromatin remodeling agents such as HDAC inhibitor (e.g. SAHA, a.k.a vorinostat) or BET bromodomain inhibitor (e.g. JQ1) showed moderate or minor synergistic/additive effect with PKC activators K101A and K102 (FIG. 22 and FIG. 23) in HL-60 cells. These results are in contrast to those in A549 lung cancer cells where antagonism was observed. In HIV latency assays, SAHA or JQ1 has been shown to cooperate with PKC activators to reactivate HIV LTR-driven transcription and production of viral proteins (Margolis et al., 2013, Curr Opin HIV AIDS. 8(3):230-235; Barton et al., 2013, Clin Pharmacol Ther. 93(1):46-56; Darcis et al., 2015, PLoS Pathog 11(7):e1005063; Jiang et al., 2015, PLoS Pathog 11 (7):e1005066). Thus, synergism or antagonism between PKC activators and chromatin remodeling agents (e.g. SAHA or JQ-1) can be advantageously tested for each cancer or cancer cell line of interest.

Figure 24:
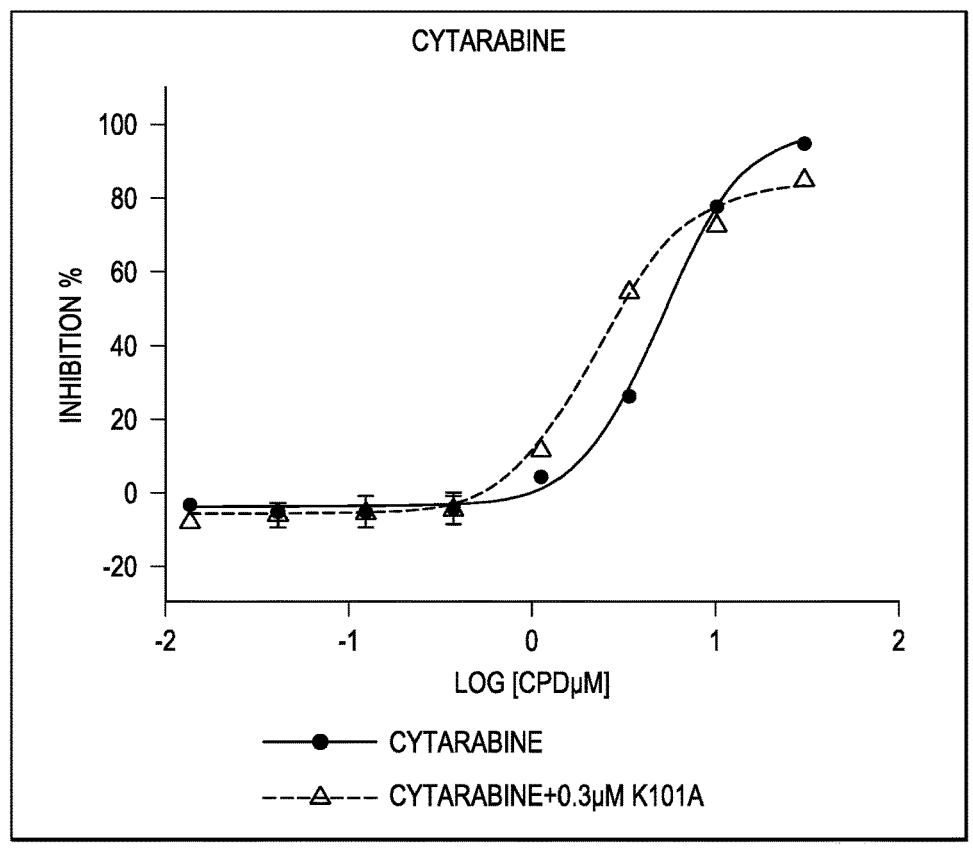
FIG. 24 shows effect of PKC activator K101A or K102 in combination with cytarabine on growth inhibition of human monocytic leukemia cell line THP-1.
Figure 24:
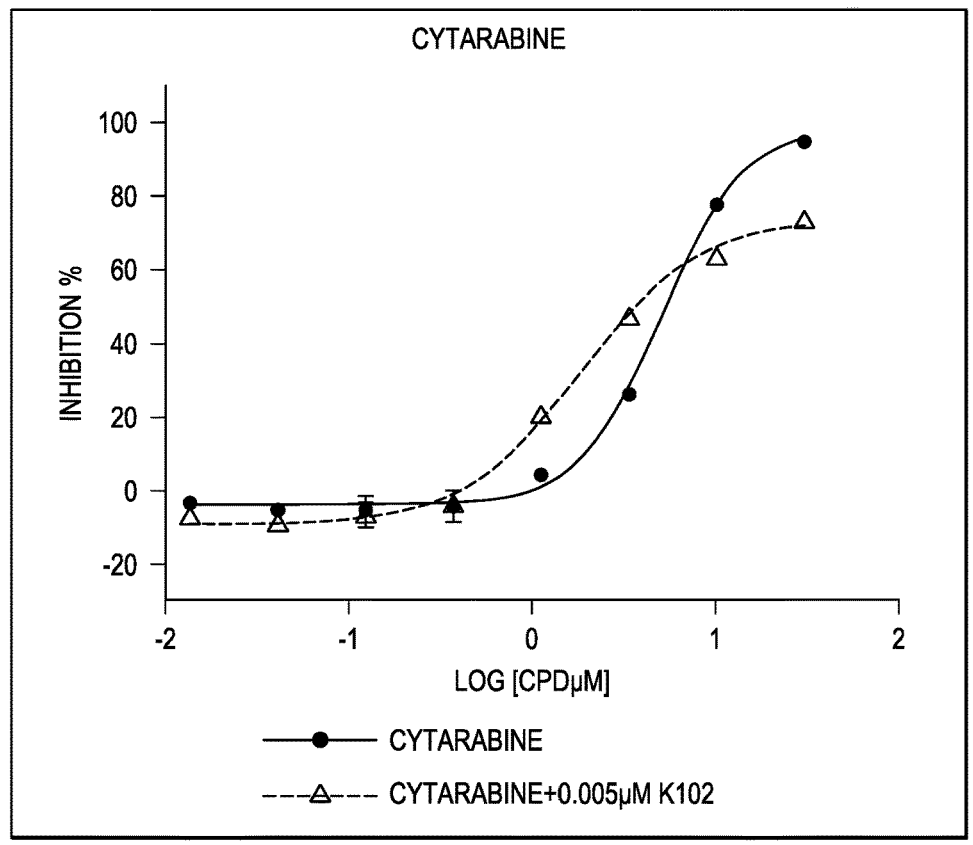

In THP-1 human acute monocytic leukemia cells, nucleoside analog cytarabine also showed synergy with K101A (0.3 µM) and K102 (0.005 µM) (FIG. 24) although the magnitude of synergy was much reduced compared to HL-60.

Figure 25:
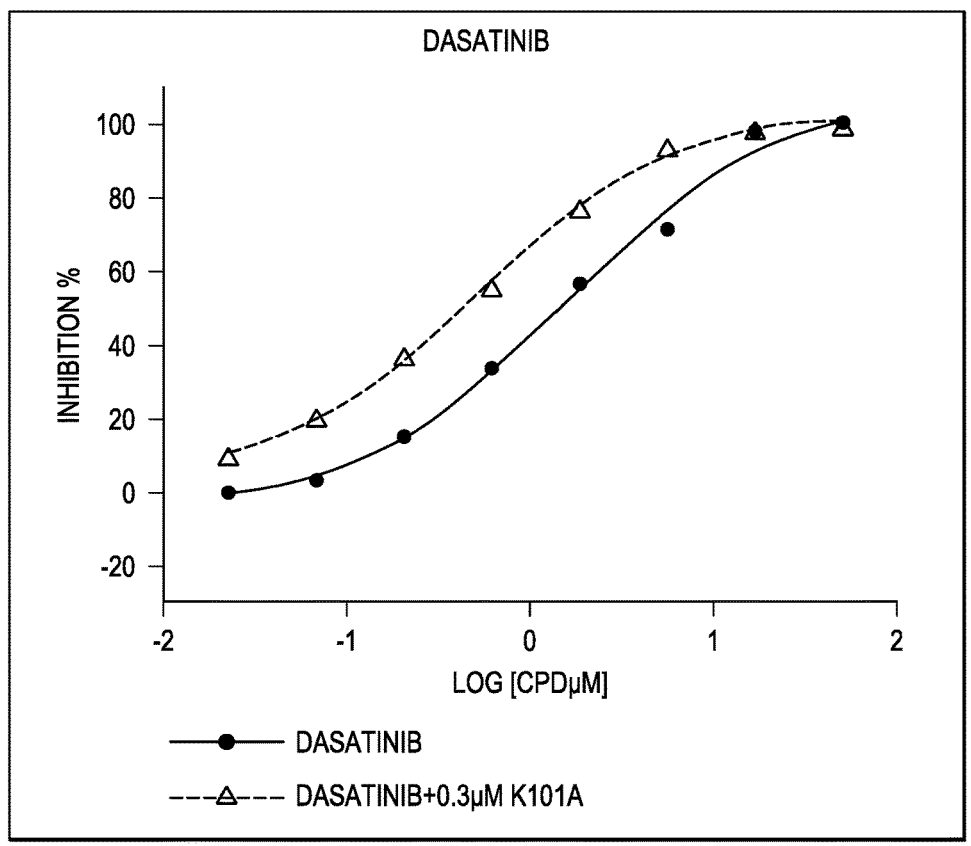
FIG. 25 shows effect of PKC activator K101A or K102 in combination with dasatinib on growth inhibition of human leukemic cell line MV4-11.
Figure 25:
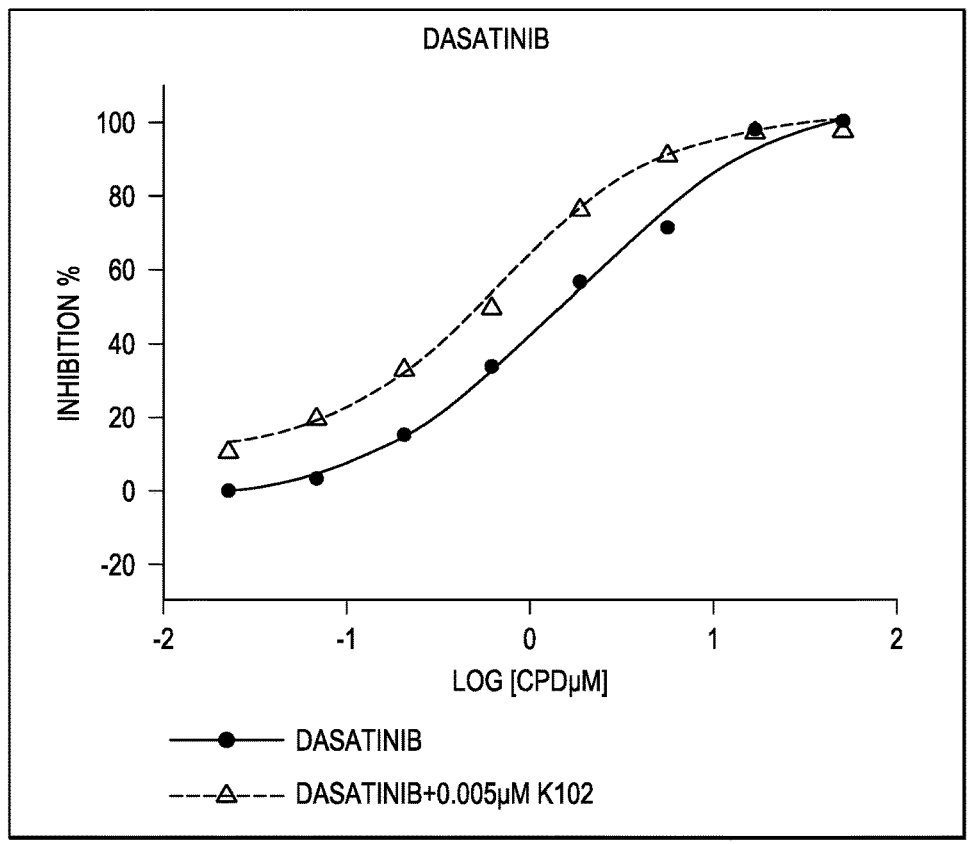
Figure 26:
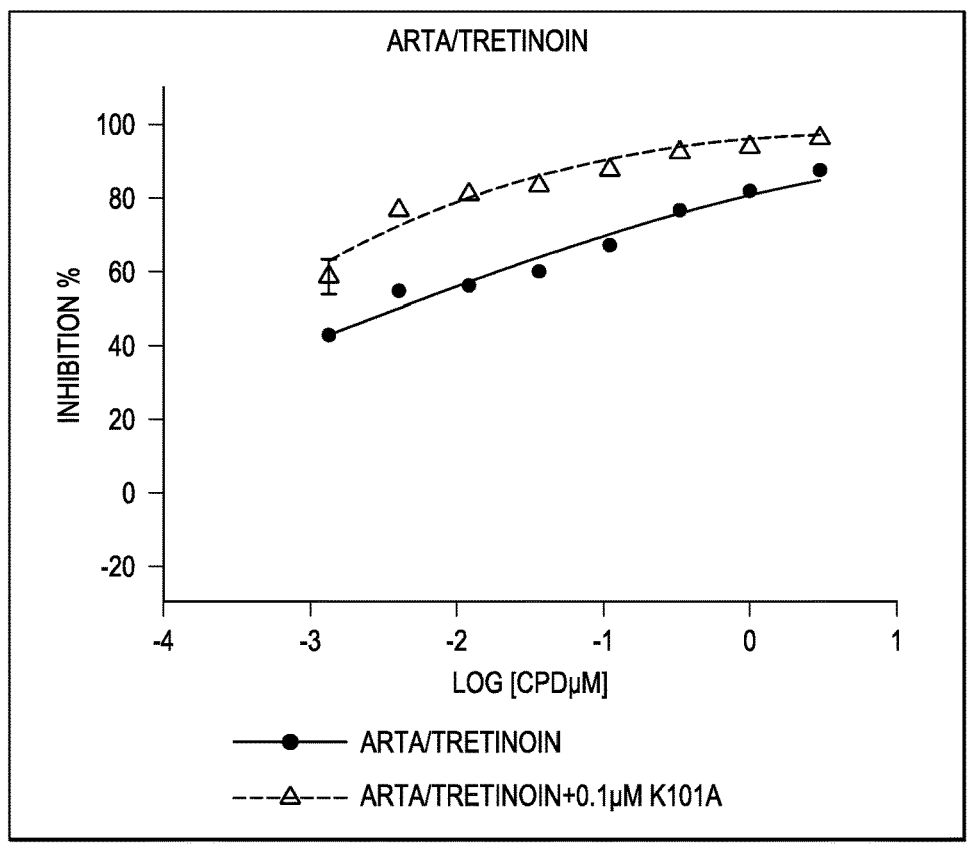
FIG. 26 shows effect of PKC activator K101A or K102 in combination with all-trans retinoic acid (ARTA) on growth inhibition of human leukemic cell line MV4-11.
Figure 26:
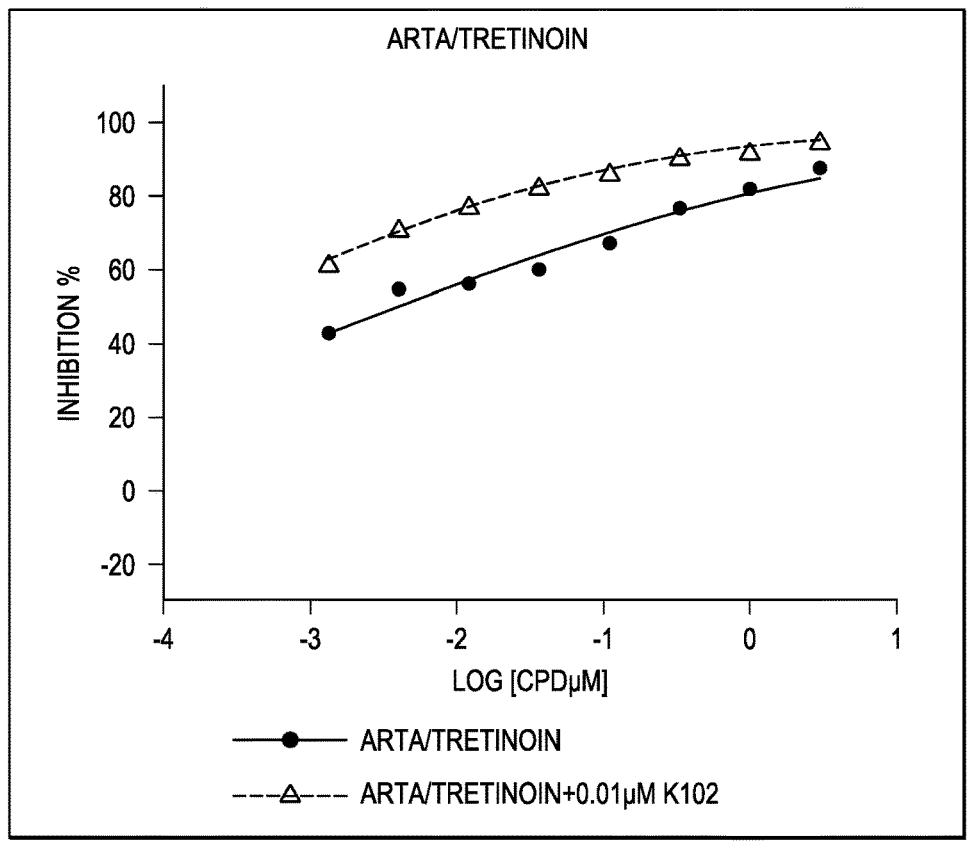

In MV-4-11 human myelomonocytic leukemia, dasatinib synergized moderately with both K101A and K102, as shown in FIG. 25. Quite similar to the effect on HL-60 cells, the combination of K101A (0.1 µM) or K102 (0.01 µM) with ATRA shifted the inhibition curve up by 5-20% in MV-4-11 cells (FIG. 26).

Lymphoma cell lines, such as Mino (Mantle cell lymphoma), Namalwa (Burkitt's lymphoma), SU-DHL-2 (large cell lymphoma; diffuse histiocytic lymphoma), and WSU-DLCL-2 (diffuse large cell lymphoma) represents some subtypes of lymphomas. Diterpenoid PKC activators in combination with PI3K (delta) inhibitors (e.g. idelalisib/CAL-101), BTK inhibitors (e.g. ibrutinib), protease inhibitors (e.g. carfilzomib and bortezomib), thalidomide, chromatin-remodeling agents (e.g. SAHA and JQ-1), and anti-metabolites (e.g. cytarabine) were tested on several of the lymphoma cell lines.

In Mino cells, the combination of PKC activator K101A (0.1 µM) or K102 (0.001 µM) with cytarabine resulted in synergistic anti-proliferative effect, especially at lower concentration range of cytarabine (e.g. below 0.1 µM), where it alone did not exhibit 100% inhibition (data not shown). K101A or K102 alone had less than 10% inhibition on proliferation and the effect was subtracted in calculation for synergy. Thus, lower dose of cytarabine could be used to achieve similar efficacy and to reduce toxicity when combined with PKC activators.

Figure 27:
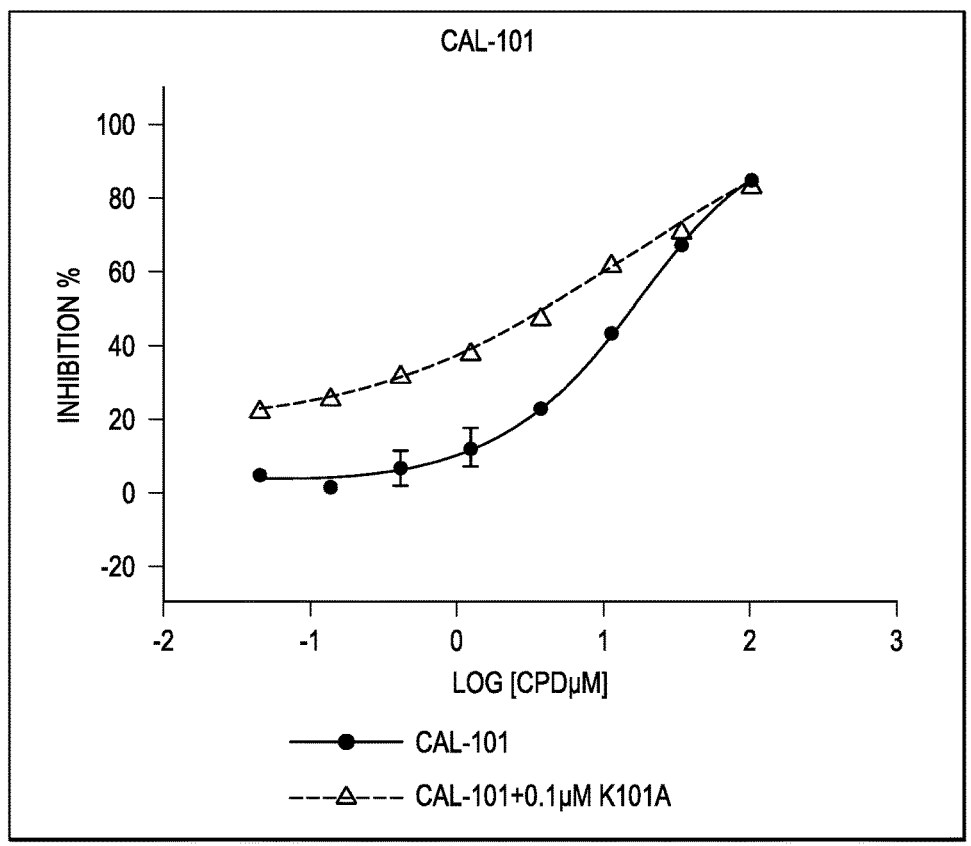
FIG. 27 shows effect of PKC activator K101A or K102 in combination with idelalisib (CAL-101) on growth inhibition of human lymphoma cell line Namalwa.
Figure 27:
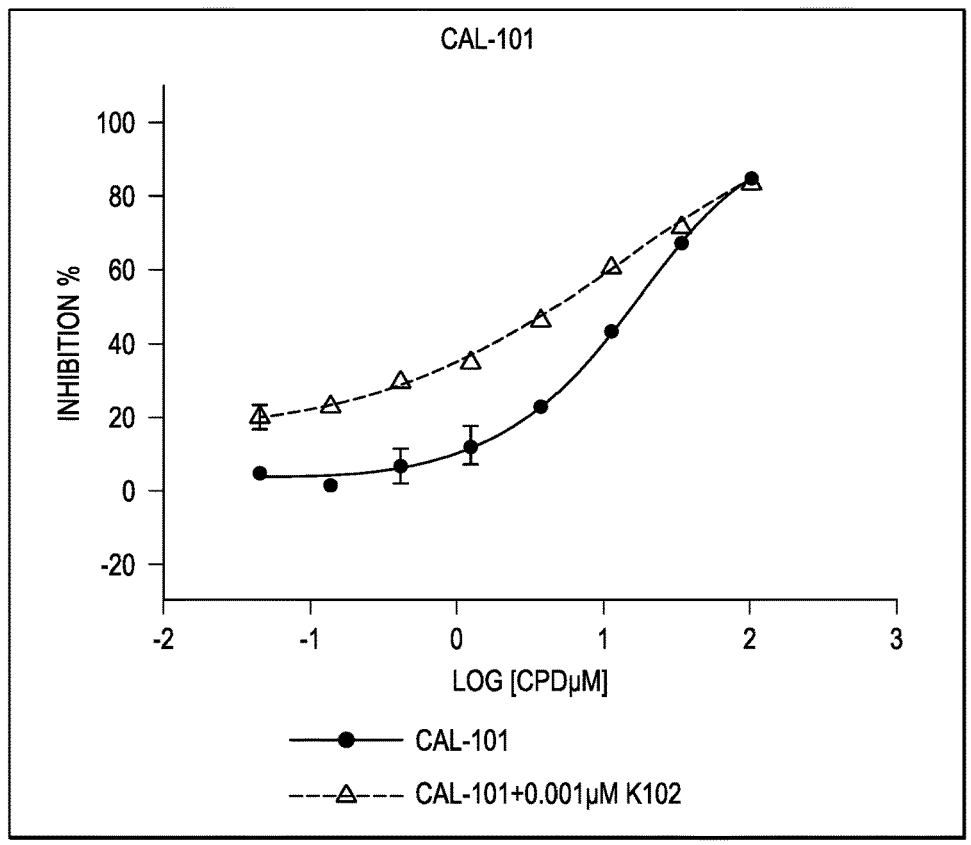
Figure 28:
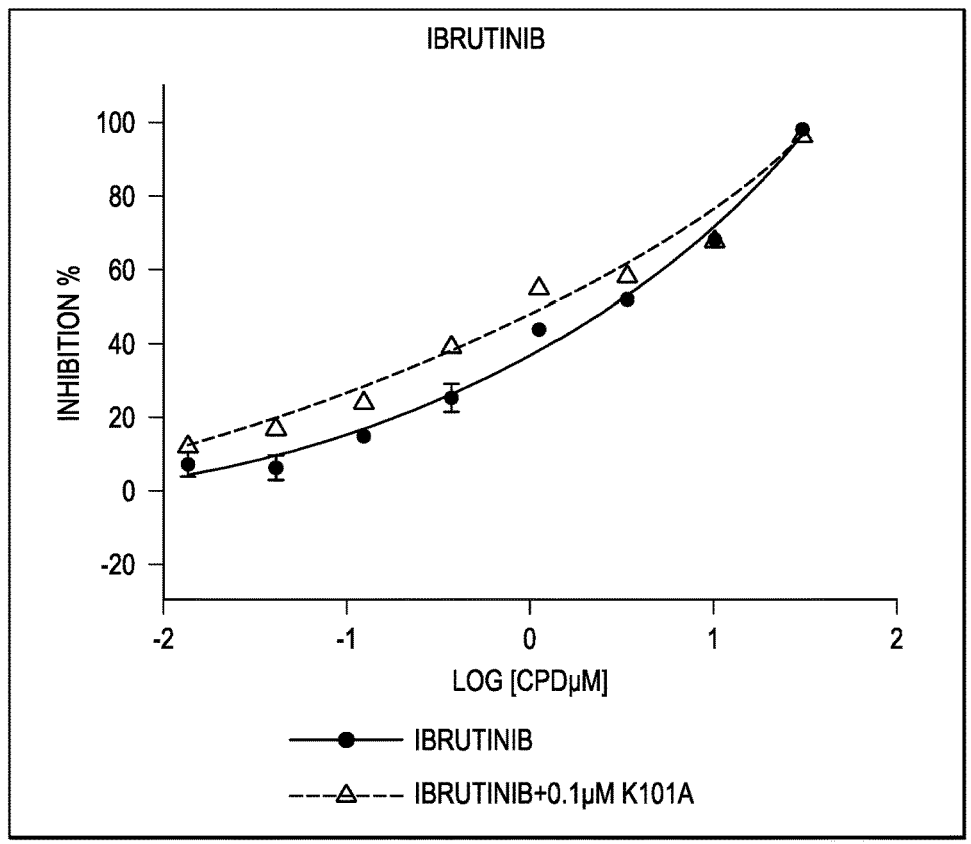
FIG. 28 shows effect of PKC activator K101A or K102 in combination with ibrutinib on growth inhibition of human lymphoma cell line Namalwa.
Figure 28:
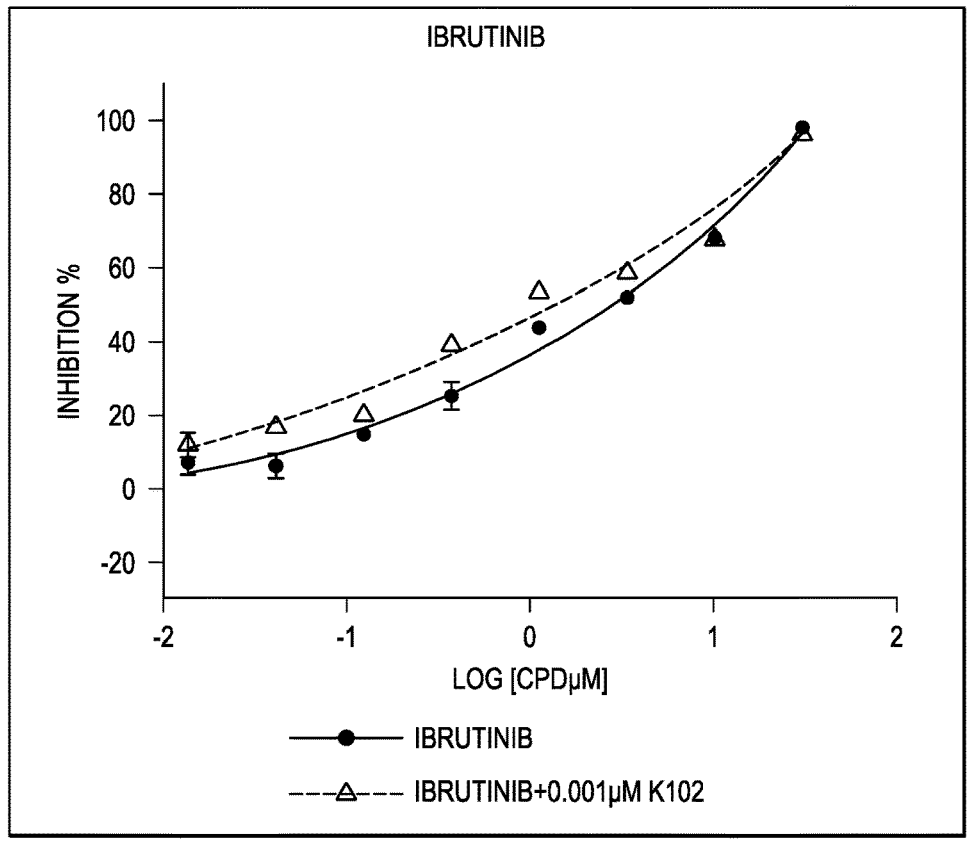

In Namalwa cells, the combination of PKC activator K101A (0.1 µM) or K102 (0.001 µM) with idelalisib (CAL-101 resulted in synergistic anti-proliferative effect, increasing inhibition by at least 20% at concentration range (roughly 0.03-3 µM) of idelalisib/CAL-101 (FIG. 27). Minor synergy was also observed for the combination of PKC activator K101A or K102 with BTK inhibitor ibrutinib (FIG. 28).

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of treating cancer in a subject, comprising administering to a subject in need thereof a therapeutically effective amount of a diterpenoid protein kinase C (PKC) activator, and one or more of a therapeutic agent selected from phosphoinositol-3 kinase (PI3K) inhibitor, AKT inhibitor, mammalian target of rapamycin (mTOR) inhibitor, poly ADP ribose polymerase (PARP) inhibitor, CBP/β-catenin inhibitor, Tankyrase (TNKS) inhibitor, probable protein-cysteine N-palmitoyltransferase (PORCN) inhibitor, scr kinase or bcr-abl kinase inhibitor, Smoothened (SMO) inhibitor, and combinations thereof, wherein the cancer is selected from the group consisting of the cancer of the pancreas, lung, colon, head and neck, stomach (gastric), biliary tract, endometrium, ovary, small intestine, urinary tract, liver, cervix, breast, kidney, renal, and hematologic cancers.

2. A method of treating cancer, comprising administering to a subject in need thereof a therapeutically effective amount of a diterpenoid protein kinase C (PKC) activator, and one or more of an inhibitor of PI3K/AKT/mTOR signaling pathway, wherein the cancer is selected from the group consisting of the cancer of the pancreas, lung, colon, head and neck, stomach (gastric), biliary tract, endometrium, ovary, small intestine, urinary tract, liver, cervix, breast, kidney, renal, and hematologic cancers.

3. The method of claim 2, wherein the one or more of an inhibitor of PI3K/AKT/mTOR signaling pathway is selected from a PI3K inhibitor, AKT inhibitor, mTOR inhibitor, and combinations thereof.

4. A method of treating cancer in a subject, comprising administering to a subject in need thereof a therapeutically effective amount of a diterpenoid protein kinase C activator, and one or more of an inhibitor of Wnt/β-catenin signaling pathway, wherein the cancer is selected from the group consisting of the cancer of the pancreas, lung, colon, head and neck, stomach (gastric), biliary tract, endometrium, ovary, small intestine, urinary tract, liver, cervix, breast, kidney, renal, and hematologic cancers.

5. The method of claim 4, wherein the one or more of an inhibitor of Wnt/β-catenin signaling pathway is selected from CBP/β-catenin inhibitor, TNKS inhibitor, PORCN inhibitor, and combinations thereof.

6. The method of claim 1, wherein the cancer is identified as having an activating or oncogenic K-RAS, N-RAS, or H-RAS activity.

7. The method of claim 1, further comprising measuring the protein kinase C activation potential by assessing the phosphorylation level of one or more of PKC α, β, γ, δ, ε, η, θ, ι/λ, μ and ζ proteins.

8. The method of claim 7, wherein the phosphorylation level is determined following contacting the cancer with the diterpenoid PKC activator.

9. A method of treating a leukemia or lymphoma in a subject, comprising administering to a subject in need thereof a therapeutically effective amount of a diterpenoid PKC activator, and a therapeutic agent selected from a PI3K inhibitor, scr kinase or bcr-abl kinase inhibitor, histone deacetylase (HDAC) inhibitor, Bromodomain and Extra-Terminal motif (BET) inhibitor, all-trans-retinoic acid (ATRA), Bruton's tyrosine kinase (BTK) inhibitor, anticancer nucleoside analog, and combinations thereof.

10. The method of claim 1, wherein the diterpenoid PKC activator is a PKC activating phorbol, deoxyphorbol, ingenol, daphnane, or lathyrane compound, or derivatives, analogs, or prodrugs thereof.

11. The method of claim 10, wherein the PKC activator is a compound of structural formula (PI):

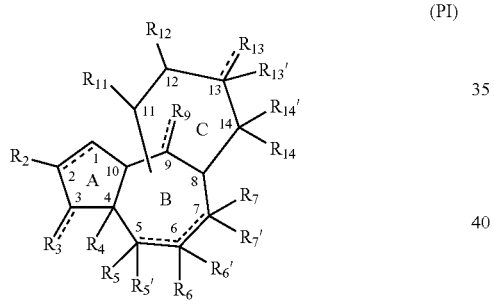

(PI)

or an enantiomer, hydrate, solvate, or pharmaceutically acceptable salt thereof
wherein
Ring C is attached to Ring B at carbon atom 9 or 10;
$R_2$ is selected from H or lower alkyl;
$R_3$ is H, or O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl, —$S(O)_2R_b$, —$S(O)_2OR_b$, or —$P(O)(OR_b)_2$;
$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —$S(O)_2R_b$, —$S(O)_2OR_b$, and —$P(O)(OR_b)_2$;
$R_5'$ and $R_6'$ are H, or $R_5'$ and $R_6'$ together form a bond or are bonded to a common oxygen atom to form an epoxide;
$R_6$ is —$NR_bR_b$, —$NHC(O)R_b$, —$SR_b$, $SOR_b$, —$S(O)_2R_b$, —$S(O)_2OR_b$, —$P(O)(OR_b)_2$, —$SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$C_{1-4}$alkyl-O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, —$S(O)_2R_b$, —$S(O)_2OR_b$, —$P(O)(OR_b)$, or $R_d$ is a promoiety which is hydrolyzable under biological conditions to yield an -alkyl-OH;
$R_6'$ and $R_7'$ are H, or $R_6'$ and $R_7'$ together form a bond or are bonded to a common oxygen atom to form an epoxide;
$R_7$ is H or OH;
$R_9$ is H, oxo, or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl, or $R_9'$, is an O atom which is bonded to an optionally substituted common C atom bonded to $R_{13}'$ and $R_{14}'$, wherein $R_{13}'$ and $R_{14}'$ each is an O atom;
$R_{11}$ is lower alkyl;
$R_{12}$ is H, halo, —$NR_bR_b$, —$NHC(O)R_b$, —$SR_b$, $SOR_b$, —$S(O)_2R_b$, —$S(O)_2OR_b$, —$P(O)(OR_b)_2$, —$SeR_b$, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $R_{12}$ is —OR$_g$, wherein R$_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —S(O)$_2$R$_b$, —S(O)$_2$OR$_b$, and —P(O)(OR$_b$)$_2$;

R$_{13}$ is H, halo, oxo, —NR$_b$R$_b$, —NHC(O)R$_b$, —SR$_b$, SOR$_b$, —S(O)$_2$R$_b$, —S(O)$_2$OR$_b$, —P(O)(OR$_b$)$_2$, —SeR$_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —OR$_h$, wherein R$_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —S(O)$_2$R$_b$, —S(O)$_2$OR$_b$, and —P(O)(OR$_b$)$_2$;

R$_{13}$' and R$_{14}$' are independently H, OH, or are bonded to a common carbon atom to form a cyclopropyl ring, wherein the cyclopropyl ring is optionally mono- or disubstituted with OH, halo, —NR$_b$R$_b$, —NHC(O)R$_b$, —SR$_b$, SOR$_b$, —S(O)$_2$R$_b$, —S(O)$_2$OR$_b$, and —OP(O)(OR$_b$)$_2$, —SeR$_b$, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, carbamate, phosphine, phosphoramide, phosphoramidite, phosphoramidate, phosphonate, sulfonamide, amide, guanidine, urea; or a progroup which is hydrolysable under biological conditions to yield an -alkyl-OH group, or R$_{13}$' and R$_{14}$' are each an O atom which is bonded to an optionally substituted common C atom bonded to R$_9$, wherein R$_9$ is an O atom;

R$_{14}$ is H, OH or optionally substituted alkenyl;

wherein each R$_b$ is independently H, optionally substituted alkyl, optionally substituted alkenyl, alkynyl, optionally substituted aryl, optionally substituted heteroaryl, optionally substituted arylalkyl, or optionally substituted heteroarylalkyl; and the dashed line (- - - - -) represents an optional bond.

12. The method of claim 11, wherein the PKC activator is a compound of structural formula (PII):

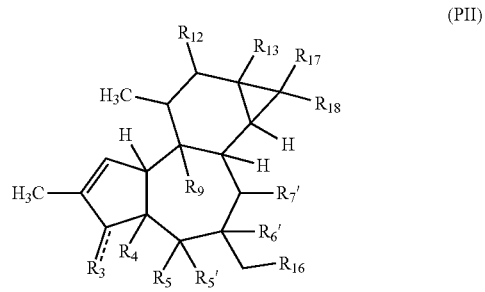

or an enantiomer, hydrate, solvate, or pharmaceutically acceptable salt thereof, wherein R$_3$ is O, S or N double bonded to the ring carbon, or R$_3$ is —OR$_a$, wherein R$_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

R$_4$ and R$_5$ are independently H, halo, cyano, or R$_4$ is —OR$_c$, wherein R$_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

R$_5$' and R$_6$' are H, or R$_5$' and R$_6$' together form a bond or are bonded to a common oxygen atom to form an epoxide;

R$_6$' and R$_7$' are H, or R$_6$' and R$_7$' together form a bond or are bonded to a common oxygen atom to form an epoxide;

R$_9$ is H or —OR$_f$, wherein R$_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{12}$ is H, halo, or —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted aryloxy, optionally substituted arylalkyloxy, optionally substituted alkylcarbonyloxy, optionally substituted alkenylcarbonyloxy, optionally substituted arylcarbonyloxy, optionally substituted arylalkylcarbonyloxy, phosphine, phosphate, phosphoramide, phosphoramidite, phosphoramidate, phosphonate, sulfate, sulfonate, sulfonamide, sulfone, sulfite, amide, guanidine, or urea.

13. The method of claim 11, wherein, the PKC activator is compound of structural formula (PIII):

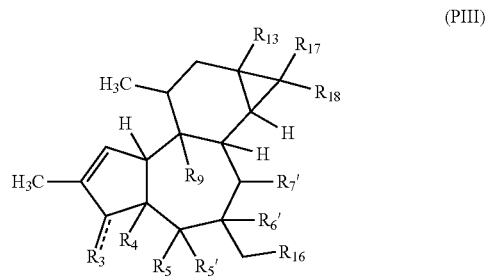

(PIII)

or an enantiomer, hydrate, solvate, or pharmaceutically acceptable salt thereof, wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5'$ and $R_6'$ are H, or $R_5'$ and $R_6'$ together form a bond or are bonded to a common oxygen atom to form an epoxide;

$R_6'$ and $R_7'$ are H, or $R_6'$ and $R_7'$ together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —OR$_h$, wherein R$_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

R$_{16}$ is H, halo, or —O—R$_d$, wherein R$_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or R$_d$ is a promoiety which is hydrolyzable under biological conditions to yield an —OH group at the C20 carbon atom; and R$_{17}$ and R$_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, phosphine, phosphate, phosphoramide, phosphoramidite, phosphoramidate, phosphonate, sulfate, sulfonate, sulfonamide, sulfone, sulfite, amide, guanidine, urea, or a progroup which is hydrolyzable under biological conditions to yield an -alkyl-OH group.

14. The method of claim 13, wherein the PKC activator comprises a compound of formula (PIIIc):

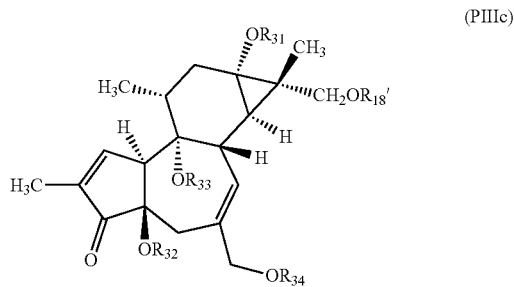

(PIIIc)

or an enantiomer, hydrate, solvate, or pharmaceutically acceptable salt thereof, wherein, R$_{18}$' is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group;

R$_{31}$, R$_{32}$, and R$_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and R$_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_{34}$ is a promoiety which is hydrolyzable under biological conditions to yield an —OH group at the C20 carbon atom.

15. The method of claim 11, wherein the PKC activator comprises a compound of formula (PIV):

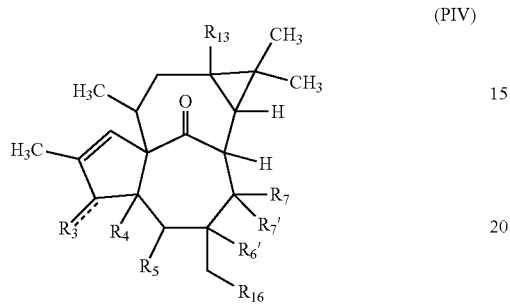

(PIV)

or an enantiomer, hydrate, solvate, or pharmaceutically acceptable salt thereof, wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is –$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_6'$ and $R_7'$ are H, or $R_6'$ and $R_7'$ together form a bond or are bonded to a common oxygen atom to form an epoxide;

$R_7$ is H or OH;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and $R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$.

16. The method of claim 15, wherein the PKC activator comprises a compound of formula (PIVc):

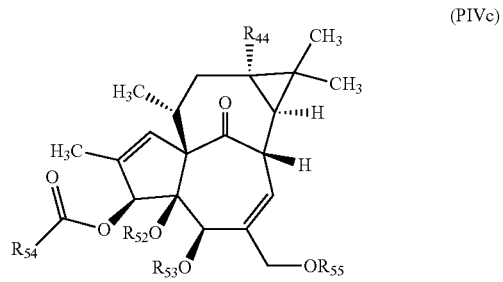

(PIVc)

or an enantiomer, hydrate, solvate, or pharmaceutically acceptable salt thereof, wherein $R_{44}$ is H or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{52}$ and $R_{53}$ are independently H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{54}$ is H, an optionally substituted alkyl, optionally substituted alkenyl, optionally substituted cycloalkyl, optionally substituted aryl, optionally substituted heteroaryl, optionally substituted arylalkyl, optionally substituted arylalkenyl, optionally substituted heteroarylalkyl, optionally substituted heteroarylalkenyl; and $R_{55}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group at the C20 carbon atom.

17. The method of claim 9, wherein the diterpenoid PKC activator is a PKC activating phorbol, deoxyphorbol, ingenol, daphnane, or lathyrane compound, or derivatives, analogs, or prodrugs thereof.

18. The method of claim 17, wherein the PKC activator is a compound of structural formula (PI):

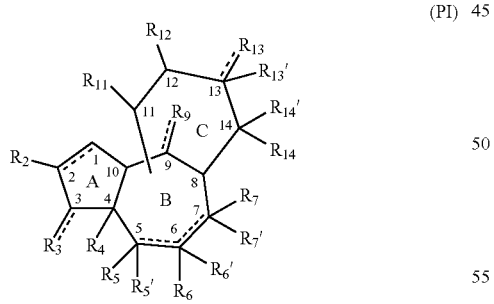

(PI)

or an enantiomer, hydrate, solvate, or pharmaceutically acceptable salt thereof
wherein
Ring C is attached to Ring B at carbon atom 9 or 10;
$R_2$ is selected from H or lower alkyl;
$R_3$ is H, or O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl, —$S(O)_2R_b$, —$S(O)_2OR_b$, or —$P(O)(OR_b)_2$;

$R_4$ and $R_5$ are independently H, halo, cyano, or $R_4$ is —$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —$S(O)_2R_b$, —$S(O)_2OR_b$, and —$P(O)(OR_b)_2$;

$R_5'$ and $R_6'$ are H, or $R_5'$ and $R_6'$ together form a bond or are bonded to a common oxygen atom to form an epoxide;

$R_6$ is —$NR_bR_b$, —$NHC(O)R_b$, —$SR_b$, $SOR_b$, —$S(O)_2R_b$, —$S(O)_2OR_b$, —$P(O)(OR_b)_2$, —$SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$C_{1-4}$alkyl-O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, —$S(O)_2R_b$, —$S(O)_2OR_b$, —$P(O)(OR_b)$, or $R_d$ is a promoiety which is hydrolyzable under biological conditions to yield an -alkyl-OH;

$R_6'$ and $R_7'$ are H, or $R_6'$ and $R_7'$ together form a bond or are bonded to a common oxygen atom to form an epoxide;

$R_7$ is H or OH;

$R_9$ is H, oxo, or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl, or $R_9'$, is an O atom which is bonded to an optionally substituted common C atom bonded to $R_{13}'$ and $R_{14}'$, wherein $R_{13}'$ and $R_{14}'$ each is an O atom;

$R_{11}$ is lower alkyl;

$R_{12}$ is H, halo, —$NR_bR_b$, —$NHC(O)R_b$, —$SR_b$, $SOR_b$, —$S(O)_2R_b$, —$S(O)_2OR_b$, —$P(O)(OR_b)_2$, —$SeR_b$, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or $R_{12}$ is —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —$S(O)_2R_b$, —$S(O)_2OR_b$, and —$P(O)(OR_b)_2$;

$R_{13}$ is H, halo, oxo, —$NR_bR_b$, —$NHC(O)R_b$, —$SR_b$, $SOR_b$, —$S(O)_2R_b$, —$S(O)_2OR_b$, —$P(O)(OR_b)_2$, —$SeR_b$, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, —$S(O)_2R_b$, —$S(O)_2OR_b$, and —$P(O)(OR_b)_2$;

$R_{13}'$ and $R_{14}'$ are independently H, OH, or are bonded to a common carbon atom to form a cyclopropyl ring, wherein the cyclopropyl ring is optionally mono- or disubstituted with OH, halo, —$NR_bR_b$, —$NHC(O)R_b$, —$SR_b$, $SOR_b$, —$S(O)_2R_b$, —$S(O)_2OR_b$, and —$OP(O)(OR_b)_2$, —$SeR_b$, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, carbamate, phosphine, phosphoramide, phosphoramidite, phosphoramidate, phosphonate, sulfonamide, amide, guanidine, urea; or a progroup which is hydrolysable under biological conditions to yield an -alkyl-OH group, or $R_{13}'$ and $R_{14}'$ are each an O atom which is bonded to an optionally substituted common C atom bonded to $R_9$, wherein $R_9$ is an O atom;

$R_{14}$ is H, OH or optionally substituted alkenyl;

wherein each $R_b$ is independently H, optionally substituted alkyl, optionally substituted alkenyl, alkynyl, optionally substituted aryl, optionally substituted heteroaryl, optionally substituted arylalkyl, or optionally substituted heteroarylalkyl; and the dashed line (- - - - -) represents an optional bond.

19. The method of claim 18, wherein the PKC activator is a compound of structural formula (PII):

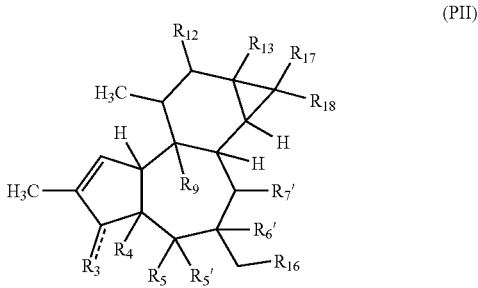

or an enantiomer, hydrate, solvate, or pharmaceutically acceptable salt thereof, wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is –$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5'$ and $R_6'$ are H, or $R_5'$ and $R_6'$ together form a bond or are bonded to a common oxygen atom to form an epoxide;

$R_6'$ and $R_7'$ are H, or $R_6'$ and $R_7'$ together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{12}$ is H, halo, or —$OR_g$, wherein $R_g$ is H, optionally substituted alkyl, optionally substituted alkenyl, optionally substituted alkynyl, optionally substituted cycloalkyl, optionally substituted aryl, optionally substituted heteroaryl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —$OR_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at $R_{16}$; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted aryloxy, optionally substituted arylalkyloxy, optionally substituted alkylcarbonyloxy, optionally substituted alkenylcarbonyloxy, optionally substituted arylcarbonyloxy, optionally substituted arylalkylcarbonyloxy, phosphine, phosphate, phosphoramide, phosphoramidite, phosphoramidate, phosphonate, sulfate, sulfonate, sulfonamide, sulfone, sulfite, amide, guanidine, or urea.

20. The method of claim 18, wherein, the PKC activator is compound of structural formula (PIII):

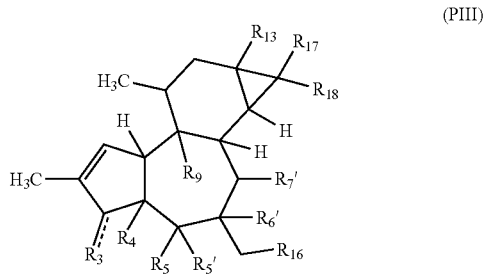
(PIII)

or an enantiomer, hydrate, solvate, or pharmaceutically acceptable salt thereof, wherein $R_3$ is O, S or N double bonded to the ring carbon, or $R_3$ is —$OR_a$, wherein $R_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

$R_4$ and $R_5$ are independently H, halo, cyano, or $R_4$ is –$OR_c$, wherein $R_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_5'$ and $R_6'$ are H, or $R_5'$ and $R_6'$ together form a bond or are bonded to a common oxygen atom to form an epoxide;

$R_6'$ and $R_7'$ are H, or $R_6'$ and $R_7'$ together form a bond or are bonded to a common oxygen atom to form an epoxide;

$R_9$ is H or —$OR_f$, wherein $R_f$ is H, an optionally substituted alkyl, optionally substituted aryl, optionally substituted heteroaryl, optionally substituted alkylcarbonyl; optionally substituted arylcarbonyl, optionally substituted heteroarylcarbonyl, optionally substituted arylalkylcarbonyl, optionally substituted heteroarylalkylcarbonyl, or optionally substituted arylalkyloxycarbonyl;

$R_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

$R_{16}$ is H, halo, or —O—$R_d$, wherein $R_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or $R_d$ is a promoiety which is hydrolyzable under biological conditions to yield an —OH group at the C20 carbon atom; and $R_{17}$ and $R_{18}$ are each independently H, OH, amino, thiol, sulfanyl, sulfinyl, sulfonyl, optionally substituted alkyl, optionally substituted cycloalkyl, optionally substituted heteroalkyl, optionally substituted aryl, optionally substituted heteroaryl, optionally substituted alkyloxy, optionally substituted alkenyloxy, optionally substituted alkynyloxy, optionally substituted cycloalkyloxy, optionally substituted cycloalkenyloxy, optionally substituted heterocycloalkyloxy, optionally substituted aryloxy, optionally substituted heteroaryloxy, optionally substituted arylalkyloxy, optionally substituted arylalkenyloxy, optionally substituted heteroarylalkyloxy, optionally substituted heteroarylalkenyloxy, optionally substituted alkylcarbonyloxy, optionally substituted alkenylcarbonyloxy, optionally substituted alkynylcarbonyloxy, optionally substituted arylcarbonyloxy, optionally substituted heteroarylcarbonyloxy, optionally substituted arylalkylcarbonyloxy, optionally substituted arylalkenylcarbonyloxy, optionally substituted heteroarylalkylcarbonyloxy, optionally substituted heteroarylalkenylcarbonyloxy, optionally substituted carboxyalkylcarbonyloxy, optionally substituted amino acid carbonyloxy, phosphine, phosphate, phosphoramide, phosphoramidite, phosphoramidate, phosphonate, sulfate, sulfonate, sulfonamide, sulfone, sulfite, amide, guanidine, urea, or a progroup which is hydrolyzable under biological conditions to yield an -alkyl-OH group.

21. The method of claim 20, wherein the PKC activator comprises a compound of formula (PIIIc):

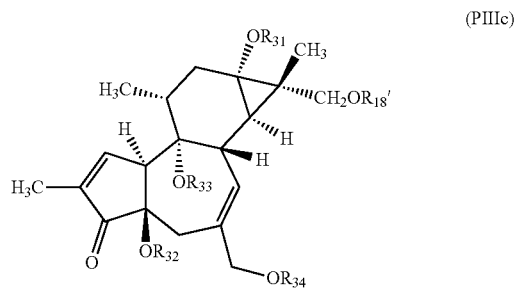

or an enantiomer, hydrate, solvate, or pharmaceutically acceptable salt thereof, wherein, $R_{18}'$ is H, optionally substituted alkyl, optionally substituted cycloalkyl, optionally substituted heteroalkyl, optionally substituted aryl, optionally substituted heteroaryl, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group;

$R_{31}$, $R_{32}$, and $R_{33}$ are each independently H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and R$_{34}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or R$_{34}$ is a promoiety which is hydrolyzable under biological conditions to yield an —OH group at the C20 carbon atom.

22. The method of claim 18, wherein the PKC activator comprises a compound of formula (PIV):

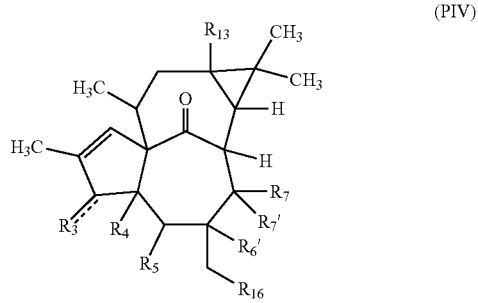

(PIV)

or an enantiomer, hydrate, solvate, or pharmaceutically acceptable salt thereof, wherein R$_3$ is O, S or N double bonded to the ring carbon, or R$_3$ is —OR$_a$, wherein R$_a$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted heteroarylalkylcarbonyl, arylalkenylcarbonyl, optionally substituted heteroarylalkenylcarbonyl;

R$_4$ and R$_5$ are independently H, halo, cyano, or R$_4$ is —OR$_c$, wherein R$_c$ is H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;

R$_6$' and R$_7$' are H, or R$_6$' and R$_7$' together form a bond or are bonded to a common oxygen atom to form an epoxide;

R$_7$ is H or OH;

R$_{13}$ is H, halo, carbamate, phosphine, phosphoramide, phosphoramidite, phosphoramidate, phosphonate, sulfonamide, amide, guanidine, urea, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, or —OR$_h$, wherein R$_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl; and R$_{16}$ is H, halo, or —OR$_d$, wherein R$_d$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or R$_d$ is a promoiety which is hydrolyzable under biological conditions to yield an —OH group at R$_{16}$.

23. The method of claim 22, wherein the PKC activator comprises a compound of formula (PIVc):

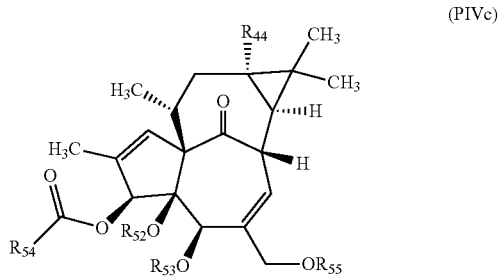

(PIVc)

or an enantiomer, hydrate, solvate, or pharmaceutically acceptable salt thereof, wherein

- $R_{44}$ is H or —$OR_h$, wherein $R_h$ is H, optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;
- $R_{52}$ and $R_{53}$ are independently H, an optionally substituted alkyl, optionally substituted alkenyl, optionally substituted alkynyl, optionally substituted cycloalkyl, optionally substituted aryl, optionally substituted heteroaryl, optionally substituted arylalkyl, optionally substituted heteroarylalkyl, optionally substituted alkylcarbonyl, optionally substituted alkenylcarbonyl, optionally substituted cycloalkylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl;
- $R_{54}$ is H, an optionally substituted alkyl, optionally substituted alkenyl, optionally substituted cycloalkyl, optionally substituted aryl, optionally substituted heteroaryl, optionally substituted arylalkyl, optionally substituted arylalkenyl, optionally substituted heteroarylalkyl, optionally substituted heteroarylalkenyl; and
- $R_{55}$ is H, optionally substituted alkyl, optionally substituted alkenyl, optionally substituted alkynyl, optionally substituted cycloalkyl, optionally substituted cycloalkenyl, optionally substituted heterocycloalkyl, optionally substituted aryl, optionally substituted heteroaryl, optionally substituted arylalkyl, optionally substituted arylalkenyl, optionally substituted heteroarylalkyl, optionally substituted heteroarylalkenyl, optionally substituted alkylcarbonyl, optionally substituted alkenylcarbonyl, optionally substituted alkynylcarbonyl, optionally substituted arylcarbonyl, optionally substituted heteroarylcarbonyl, optionally substituted arylalkylcarbonyl, optionally substituted arylalkenylcarbonyl, optionally substituted heteroarylalkylcarbonyl, optionally substituted heteroarylalkenylcarbonyl, optionally substituted carboxyalkylcarbonyl, optionally substituted amino acid carbonyl, or a promoiety which is hydrolyzable under biological conditions to yield an —OH group at the C20 carbon atom.

24. The method of claim 1, wherein the one or more therapeutic agent is selected from poly ADP ribose polymerase (PARP) inhibitor, scr kinase or bcr-abl kinase inhibitor, Smoothened (SMO) inhibitor, and combinations thereof.

25. The method of claim 9, wherein the therapeutic agent is selected from histone deacetylase (HDAC) inhibitor, Bromodomain and Extra-Terminal motif (BET) inhibitor, and combinations thereof.

26. The method of claim 9, wherein the therapeutic agent is selected from all-trans-retinoic acid (ATRA), Bruton's tyrosine kinase (BTK) inhibitor, and combinations thereof.

27. The method of claim 9, wherein the therapeutic agent is selected from a PI3K inhibitor, scr kinase or bcr-abl kinase inhibitor, and combinations thereof.

* * * * *